(12) United States Patent
Ballou et al.

(10) Patent No.: US 10,548,969 B2
(45) Date of Patent: *Feb. 4, 2020

(54) OIL-IN-WATER EMULSION INFLUENZA VACCINE

(71) Applicant: GLAXOSMITHKLINE BIOLOGICALS SA, Rixensart (BE)

(72) Inventors: William Ripley Ballou, Rixensart (BE); Emmanuel Jules Hanon, Rixensart (BE)

(73) Assignee: GlaxoSmithKline Biologicals SA, Rixensart (BE)

(*) Notice: Subject to any disclaimer, the term of this patent is extended or adjusted under 35 U.S.C. 154(b) by 0 days.

This patent is subject to a terminal disclaimer.

(21) Appl. No.: 16/018,292

(22) Filed: Jun. 26, 2018

(65) Prior Publication Data

US 2018/0339037 A1 Nov. 29, 2018

Related U.S. Application Data

(60) Continuation of application No. 15/446,508, filed on Mar. 1, 2017, now Pat. No. 10,016,495, which is a division of application No. 12/596,202, filed as application No. PCT/EP2008/054614 on Apr. 16, 2008, now Pat. No. 9,597,389.

(30) Foreign Application Priority Data

Apr. 20, 2007 (GB) .................................. 0707697.9
Jun. 12, 2007 (GB) .................................. 0711357.4
Jun. 21, 2007 (GB) .................................. 0712062.9
Oct. 10, 2007 (WO) ................. PCT/EP2007/060743
Dec. 18, 2007 (GB) .................................. 0724651.5

(51) Int. Cl.

| | | |
|---|---|---|
| A61K 39/145 | (2006.01) | |
| A61K 39/12 | (2006.01) | |
| A61K 39/39 | (2006.01) | |
| C12N 7/00 | (2006.01) | |
| A61K 39/00 | (2006.01) | |

(52) U.S. Cl.
CPC .......... *A61K 39/145* (2013.01); *A61K 39/12* (2013.01); *A61K 39/39* (2013.01); *C12N 7/00* (2013.01); *A61K 2039/545* (2013.01); *A61K 2039/55511* (2013.01); *A61K 2039/55566* (2013.01); *A61K 2039/55577* (2013.01); *A61K 2039/70* (2013.01); *C12N 2760/16134* (2013.01); *C12N 2760/16151* (2013.01); *C12N 2760/16234* (2013.01); *C12N 2760/16251* (2013.01); *Y02A 50/41* (2018.01)

(58) Field of Classification Search
None
See application file for complete search history.

(56) References Cited

U.S. PATENT DOCUMENTS

| | | |
|---|---|---|
| 4,235,877 A | 11/1980 | Fullerton et al. |
| 4,454,119 A | 6/1984 | Fukushi et al. |
| 4,652,518 A | 3/1987 | Makela |
| 4,877,611 A | 10/1989 | Cantrell |
| 4,912,094 A | 3/1990 | Myers |
| 5,149,531 A | 9/1992 | Younger |
| 5,278,302 A | 1/1994 | Caruthers et al. |
| 5,376,369 A | 12/1994 | Allison et al. |
| 5,666,153 A | 9/1997 | Copeland et al. |
| 5,667,784 A | 9/1997 | Lammert et al. |
| 5,856,462 A | 1/1999 | Agarwal |
| 5,858,368 A | 1/1999 | Smith |
| 5,969,109 A | 10/1999 | Bona |
| 6,372,223 B1 | 4/2002 | Kistner et al. |
| 6,372,227 B1 | 4/2002 | Garcon et al. |
| 6,451,325 B1 | 9/2002 | Van Nest et al. |
| 6,623,739 B1 | 9/2003 | Momin et al. |
| 6,861,410 B1 | 3/2005 | Ott et al. |
| 9,597,389 B2 * | 3/2017 | Ballou ................. A61K 39/145 |
| 2003/0133944 A1 | 7/2003 | Cohen et al. |
| 2004/0047869 A1 | 3/2004 | Garcon et al. |
| 2004/0071734 A1 | 4/2004 | Garcon et al. |
| 2007/0141078 A1 | 6/2007 | D'Hondt et al. |
| 2008/0014217 A1 | 1/2008 | Hanon et al. |
| 2008/0171063 A1 | 7/2008 | Hanon et al. |

(Continued)

FOREIGN PATENT DOCUMENTS

| | | |
|---|---|---|
| EP | 0113665 | 6/1984 |
| EP | 198474 | 10/1986 |

(Continued)

OTHER PUBLICATIONS

Definition of 'metabolisable', Dorland's Illustrated Medical Dictionary, W.B. Sanders Company, 25th Ed. (1974).
Gluck, Reinhard, "Immunopotentiating reconstituted influenza virosomes (IRIVs) and other adjuvants for improved presentation of small antigens", Vaccine, 10:915-920 (1992).
Rubins, et al., "Pneumolysin in pneumococcal adherence and colonization", Microbial Pathogenesis, 25, 337-342 (1998).
Robbins, et al., "Human tumor antigens recognized by T cells", Current Opinions in Immunology, 8:628-636 (1996).

(Continued)

*Primary Examiner* — Benjamin P Blumel

(57) ABSTRACT

The present invention provides an immunogenic influenza composition in a dose volume suitable for human use, comprising an influenza virus antigen or antigenic preparation thereof and an adjuvant composition comprising an oil-in-water emulsion, wherein said oil-in-water emulsion comprises a metabolisable oil at a level of below 11 mg and an emulsifying agent at a level of below 5 mg and optionally a tocol or a sterol at a level of below 12 mg. Suitably the amount of influenza antigen per strain per dose is 15 μg HA or a low amount such as less than 15 μg HA.

16 Claims, 24 Drawing Sheets

Specification includes a Sequence Listing.

(56) References Cited

U.S. PATENT DOCUMENTS

| | | |
|---|---|---|
| 2008/0181911 A1 | 7/2008 | Hanon et al. |
| 2009/0028903 A1 | 1/2009 | Hanon et al. |
| 2009/0081253 A1 | 3/2009 | Hanon et al. |
| 2009/0136543 A1 | 5/2009 | Hanon et al. |
| 2009/0263422 A1 | 10/2009 | Hanon et al. |
| 2009/0304742 A1 | 12/2009 | Contorni |
| 2010/0183667 A1 | 7/2010 | Ballou et al. |
| 2010/0189741 A1 | 7/2010 | Ballou et al. |
| 2010/0260797 A1 | 10/2010 | Hanon et al. |

FOREIGN PATENT DOCUMENTS

| | | |
|---|---|---|
| EP | 0362278 | 12/1988 |
| EP | 0304578 | 3/1989 |
| EP | 366412 | 10/1989 |
| EP | 468250 | 7/1991 |
| EP | 414374 | 9/1991 |
| EP | 0399843 B | 7/1994 |
| EP | 0870508 | 10/1998 |
| EP | 1092444 | 4/2001 |
| JP | 09-506887 | 7/1997 |
| JP | 11-21253 | 1/1999 |
| WO | WO 90/01496 | 2/1990 |
| WO | WO 90/02562 | 3/1990 |
| WO | WO 90/14837 | 12/1990 |
| WO | WO 1990/014837 | 12/1990 |
| WO | WO 91/13281 | 9/1991 |
| WO | WO 92/16231 | 10/1992 |
| WO | WO 93/10152 | 5/1993 |
| WO | WO 93/19780 | 10/1993 |
| WO | WO 94/19013 | 9/1994 |
| WO | WO 94/21292 | 9/1994 |
| WO | WO 95/11700 | 5/1995 |
| WO | WO 95/17210 | 6/1995 |
| WO | WO 95/22989 | 8/1995 |
| WO | WO 95/26204 | 10/1995 |
| WO | WO 96/025555 | 2/1996 |
| WO | WO 96/26277 | 8/1996 |
| WO | WO 96/33739 | 10/1996 |
| WO | WO 98/50567 | 11/1998 |
| WO | WO 98/56414 | 12/1998 |
| WO | WO 99/11241 | 3/1999 |
| WO | WO 99/12565 | 3/1999 |
| WO | WO 99/17741 | 4/1999 |
| WO | WO 99/33488 | 7/1999 |
| WO | WO 99/34850 | 7/1999 |
| WO | WO 99/56776 | 11/1999 |
| WO | WO 00/15251 | 3/2000 |
| WO | WO 00/47222 | 8/2000 |
| WO | WO 2001/22992 | 4/2001 |
| WO | WO 01/54719 | 8/2001 |
| WO | WO 02/32454 | 4/2002 |
| WO | WO 02/038176 | 5/2002 |
| WO | WO 02/74336 | 9/2002 |
| WO | WO 02/097072 | 12/2002 |
| WO | WO 2002/097072 | 12/2002 |
| WO | WO 03/011223 | 2/2003 |
| WO | WO 03/043572 | 5/2003 |
| WO | WO 03/099195 | 12/2003 |
| WO | WO 04/075829 | 9/2004 |
| WO | WO 05/107797 | 11/2005 |
| WO | WO 06/100109 | 9/2006 |
| WO | WO 2006/100110 | 9/2006 |
| WO | WO 07/006939 | 1/2007 |
| WO | WO 07/052055 | 5/2007 |
| WO | WO 07/52155 | 5/2007 |
| WO | WO 07/080308 | 7/2007 |
| WO | WO 08/009309 | 1/2008 |
| WO | WO 08/043774 | 4/2008 |

OTHER PUBLICATIONS

Van den Eynde, et al., "Tumor antigens recognized by T lymphocytes", International Journal of Clinical & Laboratory Research, 27:81-86 (1997).

Correale, et al., "A novel biweekly pancreatic cancer treatment schedule with gemcitabine, 5-flourouracil and folinic acid", Journal of the National Cancer Institute 89:293 (1997).

Singh, et al., "Recent Advances in Vaccine Adjuvants", Pharmaceutical Research, Jun. 6, 2002, vol. 19, No. 6, pp. 715-728 (2006).

"Immunisation of Mice with RSV antigen preF and fractions of the oil in water emulsion adjuvant AS03": cited to European Patent Office on May 17, 2010 in EP application No. 0782111.7 (2007).

Third party observations submitted on Apr. 8, 2015 to the European Patent Office for European patent application No. 10178205.

Ott, et al., "Enhancement of humoral response against human influenza vaccine with the simple submicron oil/emulsion adjuvant MF59", Vaccine, 13(16):1557-1562 (1995).

Fluad® Datasheet, Jun. 2004.

Third party observations filed in EP application No. 11194315.5, filed Nov. 21, 2014, communicated to Applicants on Dec. 2, 2014.

Fluarix™ product information sheet, Fluarix SH 2005 English, 2005.

Brandenburg, et al., "Phase Diagram of Deep Rough Mutant Lipopolysaccharide from *Salmonella* Minnesota R595", Journal of Structural Biology, 93(2):93-106 (1992).

Fluad® 2004/2005 Datasheet (in German).

Minutello, et al., "Safety and immunogenicity of an inactivated subunit influenza virus vaccine combined with MF59 adjuvant emulsion in elderly subjects, immunized for three consecutive influenza seasons", Vaccine 17:99-104 (1999).

EP Application No. 11194315.5 Third Party Observations under Article 115 EPC, dated Nov. 13, 2013.

Extended European Search Report dated Mar. 26, 2013 for EP App. No. 11194315.

Vaccines for pandemic influenza, summary report. Nov. 11-12, 2004 World Health Organization (WHO).

Ansaldi, et al., "Cross-protection by MF59™-adjuvanted influenza vaccine: Neutralizing and haemagglutination-inhibiting antibody activity against a (H3N2) drifted influenza viruses," Vaccine, vol. 26, pp. 1525-1529 (2008).

Atmar, et al., "Safety and immunogenicity of Nonadjuvanted and MF59-Adjuvanted Influenza A/H9N2 Vaccine Preparations", Clinical Infectious Diseases, 43:1135-1142 (2006).

Banzhoff, et al., "A new MF59-adjuvanted influenza vaccine enhances the immune response in the elderly with chronic diseases: results from an immunogenicity meta-analysis", Gerontology, vol. 49, pp. 177-184, 2003.

Baras, et al., Cross-Protection against Lethal H5N1 Challenge in Ferrets with an Adjuvanted Pandemic Influenza Vaccine:, PLoS One, Issue 1, e1401: 1-4 (2008).

Bardiya, et al., "Influenza vaccines: recent advances in production technologies", Applied Microbiology and Biotechnology, 67:299-305 (2005).

Bernstein, et al., "Effects of Adjuvants on the Safety and Immunogenicity of an Avian Influenza H5N1 Vaccine in Adults", The Journal of Infectious Diseases, vol. 197, pp. 667-675 (2008).

Boger, et al., "Subcutaneous and Intradermal Vaccination with Asian Influenza Vaccine," J.A.M.A., 1957, 165(13): 1687-1689.

Bresson, et al., "Safety and immunogenicity of an inactivated split-virion influenza A/Vietnam/1194/2004 H5N1 vaccine phase I randomized trial", The Lancet. 2006:367 (9523):1657.

Brown, et al., "CD4 cell response to influenza infection," Seminars in Immunology, vol. 16, pp. 171-177, 2004.

Chaloupka, et al., "Comparative Analysis of Six European Influenza Vaccines", Eur. J. Clin. Microbiol. Infect. Dis., 15(2):121-127 (1996).

Cinatl, et al., "The threat of avian influenza A (H5N1). Part IV: Development of vaccines", Medical Microbiology and Immunology, 196:213-225 (2007).

Coller, et al., "Development of Primed Animal Models to Assess the Immunogenicity of Influenza Vaccines", Research and Development, Viral Vaccines, GlaxoSmithKline Biologicals, Rue de l'Institut 89, 1330 Rixensart, Belgium, 1 page.

Couch, et al., "Improvement of Inactivated Influenza Virus Vaccines", The Journal of Infectious Diseases, 176:S38-S44 (1997).

(56) References Cited

OTHER PUBLICATIONS

De Donato, et al., "Safety and immunogenicity of MF59-adjuvanted influenza vaccine in the elderly," Vaccine, vol. 17, pp. 3094-3101, 1999.
Del Giudice, et al., "An MF59-adjuvanted inactivated influenza vaccine containing A/Panama/199 (H3N2) induced broader serological protection against heterovariant influenza virus strain A/Fujian/2002 than a subunit and a split influenza vaccine," Vaccine, vol. 24, pp. 3063-3065, 2006.
Frey, et al., "Comparison of the safety, tolerability and immunogenicity of a MF59-adjuvanted influenza vaccine and a non-adjuvanted influenza vaccine in non-elderly adults," Vaccine, vol. 21, pp. 4234-4237, 2003.
Fukuda, et al., "Inactivated Influenza Vaccines," Vaccines, Fourth Edition, Plotkin, Orenstetin, Chapter 17, pp. 339-370 (2004).
Garcon, et al., "GlaxoSmithKline Adjuvant Systems in Vaccines: Concepts, Achievements and Perspectives", Expert Rev. Vaccines, 6(5): 723-739 (2007).
Gasparini, et al., "Increased immunogenicity of the MF59-adjuvanted vaccine compared to a conventional subunit vaccine in elderly subjects," European J. of Epidemiology, vol. 17, pp. 135-140, 2001.
Gelder, et al., Six unrelated HLA-DR-matched adults recognize identical CD4+ T Cell epitopes from influenza A haemagglutinin that are not simple peptides with high HLA-Dr binding affinites, Int. Immunol. (1998) 10(2):211-22.
Gelder, et al., "Human CD4+ T-cell repertoire of responses to influenza virus hemagglutinin after recent natural infection", J. Virol., 1995 69(12):7497-506.
Gelder, et al., "Human CD4+ T-cell recognition of influenza A virus hemagglutinin after subunit vaccination", J. Virol. 70(7):4787-90 (1996).
Goji, Immune Responses of Healthy Subjects to a Single Dose of Intramuscular Inactivated Influenza A:, Abstract LB-4, 44th Annual Meeting of IDSA, Oct. 12-15, 2006.
Guarnaccia, et al., Comparative Immunogenicity-Reactogenicity dose-response study of influenza vaccine, Annals of Allergy, US, American College of Allergy and Immunology, vol. 65, No. 3, pp. 218-221 (1990).
Hehme, et al., "Immunogenicity of a Monovalent, Aluminum-Adjuvanted Influenza Whole Virus Vaccine for Pandemic Use", Virus Research, 103: 163-171 (2004).
Hehme, et al., "Pandemic Preparedness: Lessons Learnt from H2N2 and H9N2 Candidate Vaccines", Med. Microbiology Immunol., 191: 203-208 (2002).
Hehme, "GSK's Pandemic Flue Vaccine Project: Evaluation of H2N2 and H9N2 Candidate Vaccines" GlaxoSmithKline Biologicals, Who Meeeting on Development and Evaluation of Influenza Pandemic Vaccines, Geneva, 2005, pp. 1-20.
Iorio, et al., "Antibody responses and HIV-1 viral load in HIV-1-seropositive subjects immunized with eithr the MF59-adjuvanted influenza vaccine or a conventional non-adjuvanted subunit vaccine during highly active antiretroviral therapy," Vaccine, vol. 21, pp. 3629-3637, 2003.
Johansen, et al., "Toll-like receptor ligands as adjuvants in allergen-specific immunotherapy", Clin. Exp. Allergy, 35(12): 1591-8 (2005).
Keitel, et al., "Preparing for a possible pandemic: influenza A/H5N1 vaccine development", Current Opinion in Pharmacology, vol. 7 : 484-490 (2007).
Kistner, et al, "Development of a Mammalian Cell (Vero) Derived Candidate Influenza Virus Vaccine", Vaccine, 16(9/10)960-968 (1998).
Kunzel, et al., "Kinetics of humoral antibody response to trivalent inactivated split influenza vaccine in subjects previously vaccinated or vaccinated for the first time," Vaccine, vol. 14, No. 12, 1996.
La Montagne, et al , "Summary of Clinical Trials of Inactivated Influenza Vaccine," Reviews of Infectious Diseases, 1983, 5(4):723-736.
Lee, et al., "CD4 T Cell-Independent antibody response promotes resolution of primary influenza infection and helps to prevent reinfection", J. Immunol, 175:5827-5838 (2005).
Kistner, et al , "Development of a Vero Cell-Derived Influenza Whole Virus Vaccine," Developments in Biological Standardization, 1999, 98:101-110.
Leroux-Roels, et al, "Antigen Sparing and Cross-Reactive Immunity with an Adjuvanted rH5N1 Prototype Pandemic Influenza Vaccine, a Randomized Controlled Trial", The Lancet, 370: 580-589 (2007).
Leroux-Roels, et al, "Broad Clade 2 Cross-Reactive Immunity Induced by an Adjuvanted Clade 1 rH5N1 Pandemic Influenza Vaccine", PLoS One, 3(2) 1-5 (2008).
Lin, et al., "Safety and Immunogenicity of an Inactivated Adjuvanted Whole-Virion Influenza A (H5N1) Vaccine: A Phase I Randomised Controlled Trial," The Lancet, 2006, 368: 991-997.
Lu, et al., "A mouse model for the evaluation of Pathogenesis and immunity to influenza A (H5N1) viruses isolated from humans", Journal of Virology, vol. 73, No. 7, pp. 5903-5911 (1999).
Merten, et al., "Production of Influenza Virus in Cell Cultures for Vaccine Preparation," Advances in Experimental Medicine and Biology, 1996, 397:141-151.
Murasko, et al,, "Role of humoral and cell-mediated immunity in protection from influenza disease after immunization of healthy elderly," Experimental Gerontology, vol. 37, pp. 427-439, 2002.
Nichol, et al., "Vaccines for seasonal and pandemic influenza," J. of Infect. Dis, Vaccines and Prevention of Influenza, vol. 194, pp. S111-1118, 2006.
Nichol, et al., Influenza vaccination and reduction in hospitalizations for cardiac disease and stroke among the elderly, New England Journal of Medicine, 348:1322-1332 (2003).
Nicholson, et al., "Safety and Antigenicity of Non-Adjuvanted and MF59-Adjuvanted Influenza A/Duck/Singapore/97 (H5N3) Vaccine: A Randomized Trial of Two Potential Vaccines Against H5N1 Influenza", The Lancet, 357:1937-1943 (2001).
Nicholson, et al.,"Clinical Studies of Monovalent Inactivated Whole Virus and Subunit A/USSR/77 (H1N1) Vaccine: Serological Responses and Clinical Reactions", Journal of Biological Standardization, 7:123-136 (1979).
Puig-Barbera, et al., "Effectiveness of the MF592004", Vaccine 23, 283-289 (2004).
Paschke, et al, Increased immunogenicity with an MF59-adjuvanted. Journal of Preventive Medicine and Hygiene, 44:78-84 (2003).
Patel et al., "A randomized open-label phase I clinical trial comparing the safety, reactogenicity and immunogenicity of booster immunization with inactivated influenza AIH5N1 vaccine administered by the intradermal (ID) or intramuscular (IM) route among healthy adults", Abstract LB-5, 44th Annual Meeting of IDSA, Oct. 12-15, 2006.
Podda, "The adjuvanted influenza vaccines with novel adjuvants: experience with the MF59-adjuvanted vaccine," Vaccine, vol. 19, pp. 2673-2680, 2001.
Rieberdy, et al., "Protection against a Lethal Avian Influenza A Virus in a Mammalian System", Journal of Virology, 73(2):1453-1459 (1999).
Rimmelzwaan, et al., "ISCOM Vaccine Induced Protection Against a Lethal Challenge with a Human H5N1 Influenza Virus", Vaccine, 17: 1355-1358 (1999).
Ruat et al., "Vaccination of Macaques with Adjuvanted Formula in-Inactivation Influenza A Virus (H5N1) Vaccines: Protection against H5N1 Challenge without Disease Enhancement", Journal of Virology, 2565-2569 (Mar. 2008).
Ruf, et al., "Open, randomized study to compare the immunogenicity and reactogenicity of an influenza split vaccine with an MF59-adjuvanted subunit vaccine and a virosome-based subunit vaccine in elderly," Infection, vol. 32, No. 4, pp. 191-198, 2004.
Rinella, et al., "Effect of Anions on Model Aluminum-Adjuvant-Containing Vaccines," Journal of Colloid and Interface Science, 1995, 172: 121-130.
Squarcione, et al., "Comparison of the reactiogenicity and immunogenicity of a split and a subunit-adjuvanted influenza vaccine in elderly," Vaccine, vol. 21, pp. 1268-1274, 2003.
Stephenson, et al , "Confronting the avian influenza threat: vaccine development for a potential pandemic", Lancet Infectious Disease, 4:499-509 (2004).

(56) References Cited

OTHER PUBLICATIONS

Stephenson, et al,, "Boosting immunity of influenza H5N1 with MF59-adjuvanted H5N3 A/Duck/Singapore/97 vaccine in a primed human population," Vaccine, vol. 21, pp. 1687-1693, 2003.
Stephenson, et al , "Cross-reactivity to highly pathogenic avian influenza H5N1 viruses after vaccination with non-adjuvanted and MF59-adjuvanted influenza A/Duck/Singapore/97 (H5N3) vaccine: a potential priming strategy," J. of Infect. Dis.,vol. 191, pp. 1210-1215, 2005.
Stephenson, et al , "Development of Vaccines Against Influenza H5," The Lancet, 2006, 6:458-460.
Stephenson, et al,, "Safety and antigenicity of whole virus and subunit influenza A/Hong Kong/1073/99 (H9N2) vaccine in healthy adults: phase I randomised trial," Lancet, vol. 362, pp. 1959-1966, 2003.
Stephenson, I., "H5N1 Vaccines: How Prepared are we for a Pandemic?" The Lancet, 2006, 368:965-966.
Tamura, et al, "Mechanisms al Broad Cross-Protection Provided by Influenza Virus Infection and Their Application to Vaccines", Jpn. J. of Infect. Dis., 58: 195-207 (2005).
Thomas, et al., "Cell-mediated protection in influenza infection," Influenza Pathogenesis, vol. 12, No. 1, pp. 48-54, 2006.
Treanor, et al., "Safety and Immunogenicity of an Inactivated Subvirion Influenza A (H5N1) Vaccine", The New England Journal of Medicine, 354(13) :1343-1351(2006).
White, et al., Characterization of Aluminum-Containing Adjuvants, Developmental Biology, 2000, 103:217-228.
Wood et al,, "International collaborative study of single radial diffusion and immunoelectraphoresis techniques for the assay of haemagglutinin antigen of influenza virus", J. Biol. Stand. 9 (1981) 317.
Wood, et al., "A Sensitive, single-radial diffusion autoradiographic zone size enhancement technique from 1he assay of influenza haemagglutinin," J, Gen Viral., vol. 47, pp. 355-363 (1980).
Wood el al,, "An improved single radial immunodiffusion technique for the assay of influenza haemagglutinin antigen: adaptation for potency determinatian of inactivated whole virus and subunit vaccines", J. Biol. Stand. 5 (1977) 237.
Yalamati, et al., "Synthetic monophosphoryl lipid A: A promising TLR 4 ligand," Abstracts of Papers American Chemical Society, vol. 229, No. Part 1, 2005.
Zahn, et al, "CD4 Help-Independent Induction of Cytotoxic CDS Cells to Allogeneic P815 Tumor Cells is absolutely dependent on costimulation", J. Immunol., 165:3612-3619 (2000).
Yin, "Early Trial Show H5N1 Influenza Vaccine Safe and Effective in Humans at Low Doses," *The Lancet Press Release*, 2006.
Dalsgaard, et al, "Saponin adjuvants", Archiv. fur die gesamte Virusforschung, vol. 44, Springer Verlag, Berlin, p. 243-254 (1974).
Edwards, et al., "Safety, Efficacy, and Use of inactivated influenza vaccine in children", Advanced Studies in Medicine, 2:301-305 (2002).
GLAXOSMITHKLINE, "Briefing document: GSK's strategy against pandemic threat: Pre-pandemic and pandemic vaccines", May 2006.
Nakajima, et al., "Genetic Relationship between the HA genes of type A influenza viruses isolated in off-seasons and later epidemic seasons", Epidemiol. Infect. 106, 383-395 (1991).
Sabroe, et al, "Tool-Like Receptors in Health and Disease: Complex Questions Remain", J. lmmunol., p. 1630 (2003).
Iinuma, et al., "Characteristics of cytotoxic T lymphocytes directed to influenza virus haemagglutinin elicited by immunization with muramyldipeptide-influenza liposome vaccine", Scand J lmmunol., Jan.; 41(1):1-10 (1995) Abstract Only.
Levandowski, et al., "Cross-Reactive Antibodies Induced by a Monovalent Influenza B Virus Vaccine", 1991, Journal of Clinical Microbiology, vol. 29, No. 7, pp. 1530-1532.

\* cited by examiner

FIG. 9A

Anti A/H5N1 ELISA midpoint: Ig response

Bar chart, y-axis: ELISA Midpoint (GMT +/- IC95), 0 to 125000. Groups: H5N1 split plain (1.5 μg), H5N1 split 2x AS03 (1.5 μg), H5N1 split AS03 (1.5 μg), H5N1 split AS03/2 (1.5 μg), H5N1 split AS03/5 (1.5 μg), PBS.

FIG. 9B

Anti A/H5N1 ELISA midpoint: Ig response

Bar chart, y-axis: ELISA Midpoint (GMT +/- IC95), 0 to 150000. Groups: H5N1 split plain (0.38 μg), H5N1 split 2x AS03 (0.38 μg), H5N1 split AS03 (0.38 μg), H5N1 split AS03/2 (0.38 μg), H5N1 split AS03/5 (0.38 μg), PBS.

FIG. 9E

Anti A/H5N1 ELISA midpoint: IgG2b response

[Bar chart: ELISA Midpoint (GMT +/- IC95) on y-axis from 0 to 20000]

- H5N1 split plain (1.5 µg)
- H5N1 split 2x AS03 (1.5 µg)
- H5N1 split AS03 (1.5 µg)
- H5N1 split AS03/2 (1.5 µg)
- H5N1 split AS03/5 (1.5 µg)
- PBS

FIG. 9F

Anti A/H5N1 ELISA midpoint: IgG2b response

[Bar chart: ELISA Midpoint (GMT +/- IC95) on y-axis from 0 to 30000]

- H5N1 split plain (0.38 µg)
- H5N1 split 2x AS03 (0.38 µg)
- H5N1 split AS03 (0.38 µg)
- H5N1 split AS03/2 (0.38 µg)
- H5N1 split AS03/5 (0.38 µg)
- PBS

FIG. 10A

Anti A/H5N1 A/Vietnam - HI titers

HI titers (GMT +/- IC95), y-axis 0–8000 x-axis categories: H5N1 split plain (1.5 μg), H5N1 split 2x AS03 (1.5 μg), H5N1 split AS03 (1.5 μg), H5N1 split AS03/2 (1.5 μg), H5N1 split AS03/5 (1.5 μg), PBS

FIG. 10B

Anti A/H5N1 A/Vietnam - HI titers

HI titers (GMT +/- IC95), y-axis 0–8000 x-axis categories: H5N1 split plain (0.38 μg), H5N1 split 2x AS03 (0.38 μg), H5N1 split AS03 (0.38 μg), H5N1 split AS03/2 (0.38 μg), H5N1 split AS03/5 (0.38 μg), PBS

FIG. 11B

| | H5N1 split plain | H5N1 split 2x AS03 | H5N1 split AS03 | H5N1 split AS03/2 | H5N1 split AS03/5 | PBS |
|---|---|---|---|---|---|---|
| CD4+IL2+ | 0.03 | 0.64 | 0.45 | 0.48 | 0.42 | 0.01 |
| CD4+IL2+INFg+ | 0.03 | 0.03 | 0.05 | 0.03 | 0.03 | 0.01 |
| CD4+INFg+ | 0.03 | 0.03 | 0.03 | 0.03 | 0.03 | 0.03 |

ICS on spleen (6 days Post II) - restimulation with split A/Vietnam 3 µg HA/ml 0.38 µg HA % Flu-specific CD4+ T cells \* Group with statistically significant difference compared to the plain.

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Synthetic sequence, unmethylated CG containing
      sequence

<400> SEQUENCE: 1
tccatgacgt tcctgacgtt                                                    20

<210> SEQ ID NO 2
<211> LENGTH: 18
<212> TYPE: DNA
<213> ORGANISM: Artificial Sequence
<220> FEATURE:
<223> OTHER INFORMATION: Synthetic sequence, unmethylated CG containing
      sequence

<400> SEQUENCE: 2
tctcccagcg tgcgccat                                                      18

<210> SEQ ID NO 3
<211> LENGTH: 30
<212> TYPE: DNA
<213> ORGANISM: Artificial Sequence
<220> FEATURE:
<223> OTHER INFORMATION: Synthetic sequence, unmethylated CG containing
      sequence

<400> SEQUENCE: 3
accgatgacg tcgccggtga cggcaccacg                                         30

<210> SEQ ID NO 4
<211> LENGTH: 24
<212> TYPE: DNA
<213> ORGANISM: Artificial Sequence
<220> FEATURE:
<223> OTHER INFORMATION: Synthetic sequence, unmethylated CG containing
      sequence

<400> SEQUENCE: 4
tcgtcgtttt gtcgttttgt cgtt                                               24

<210> SEQ ID NO 5
<211> LENGTH: 20
<212> TYPE: DNA
<213> ORGANISM: Artificial Sequence
<220> FEATURE:
<223> OTHER INFORMATION: Synthetic sequence, unmethylated CG containing
      sequence

<400> SEQUENCE: 5
tccatgacgt tcctgatgct                                                    20

<210> SEQ ID NO 6
<211> LENGTH: 22
<212> TYPE: DNA
<213> ORGANISM: Artificial Sequence
```

```
<220> FEATURE:
<223> OTHER INFORMATION: Synthetic sequence, unmethylated CG containing
      sequence

<400> SEQUENCE: 6
tcgacgtttt cggcgcgcgc cg                                            22
```

OIL-IN-WATER EMULSION INFLUENZA VACCINE

TECHNICAL FIELD

The present invention relates to influenza immunogenic compositions and vaccination regimes for immunising humans against influenza disease, their use in medicine, in particular their use in augmenting immune responses to various antigens, and to methods of preparation. In particular, the invention relates to influenza vaccines comprising an influenza virus antigen or antigenic preparation in combination with an oil-in-water emulsion adjuvant, wherein said oil-in-water emulsion adjuvant comprises a metabolisable oil and an emulsifying agent, and optionally a tocol and/or a sterol.

TECHNICAL BACKGROUND

Influenza viruses are one of the most ubiquitous viruses present in the world, affecting both humans and livestock. Influenza results in an economic burden, morbidity and even mortality, which are significant.

The influenza virus is an RNA enveloped virus with a particle size of about 125 nm in diameter. It consists basically of an internal nucleocapsid or core of ribonucleic acid (RNA) associated with nucleoprotein, surrounded by a viral envelope with a lipid bilayer structure and external glycoproteins. The inner layer of the viral envelope is composed predominantly of matrix proteins and the outer layer mostly of host-derived lipid material. Influenza virus comprises two surface antigens, glycoproteins neuraminidase (NA) and haemagglutinin (HA), which appear as spikes, 10 to 12 nm long, at the surface of the particles. It is these surface proteins, particularly the haemagglutinin that determine the antigenic specificity of the influenza subtypes. Virus strains are classified according to host species of origin, geographic site and year of isolation, serial number, and, for influenza A, by serological properties of subtypes of HA and NA. 16 HA subtypes (H1-H16) and nine NA subtypes (N1-N9) have been identified for influenza A viruses [Webster R G et al. Evolution and ecology of influenza A viruses. *Microbiol. Rev.* 1992; 56:152-179; Fouchier R A et al. Characterization of a Novel Influenza A Virus Hemagglutinin Subtype (H16) Obtained from Black-Headed Gulls. *J. Virol.* 2005; 79:2814-2822). Viruses of all HA and NA subtypes have been recovered from aquatic birds, but only three HA subtypes (H1, H2, and H3) and two NA subtypes (N1 and N2) have established stable lineages in the human population since 1918. Only one subtype of HA and one of NA are recognised for influenza B viruses.

Influenza A viruses evolve and undergo antigenic variability continuously [Wiley D, Skehel J. The structure and the function of the hemagglutinin membrane glycoprotein of influenza virus. *Ann. Rev. Biochem.* 1987; 56:365-394]. A lack of effective proofreading by the viral RNA polymerase leads to a high rate of transcription errors that can result in amino-acid substitutions in surface glycoproteins. This is termed "antigenic drift". The segmented viral genome allows for a second type of antigenic variation. If two influenza viruses simultaneously infect a host cell, genetic reassortment, called "antigenic shift" may generate a novel virus with new surface or internal proteins. These antigenic changes, both 'drifts' and 'shifts' are unpredictable and may have a dramatic impact from an immunological point of view as they eventually lead to the emergence of new influenza strains and that enable the virus to escape the immune system causing the well known, almost annual, epidemics. Both of these genetic modifications have caused new viral variants responsible for pandemic in humans.

Influenza B virus antigenic drift is less frequent than that in the A strains and antigenic shift is unknown. Although antigenically distinct lineages (usually two, e.g. B/Yamagata and B/Victoria) of influenza B may occasionally co-circulate, with proportions varying from year to year and country to country, it is usual for influenza vaccines to contain only one influenza B strain.

HA is the most important antigen in defining the serological specificity of the different influenza strains. This 75-80 kD protein contains numerous antigenic determinants, several of which are in regions that undergo sequence changes in different strains (strain-specific determinants) and others in regions which are common to many HA molecules (common to determinants).

Influenza viruses cause epidemics almost every winter, with infection rates for type A or B virus as high as 40% over a six-week period. Influenza infection results in various disease states, from a sub-clinical infection through mild upper respiratory infection to a severe viral pneumonia. Typical influenza epidemics cause increases in incidence of pneumonia and lower respiratory disease as witnessed by increased rates of hospitalization or mortality. The severity of the disease is primarily determined by the age of the host, his immune status and the site of infection.

Elderly people, 65 years old and over, are especially vulnerable, accounting for 80-90% of all influenza-related deaths in developed countries. Individuals with underlying chronic diseases or with an impaired immune response are also most likely to experience such complications. Young infants also may suffer severe disease. These groups in particular therefore need to be protected. Besides these 'at risk'-groups, the health authorities are also recommending to vaccinate health care providers.

Vaccination plays a critical role in controlling annual influenza epidemics. Currently available influenza vaccines are either inactivated or live attenuated influenza vaccine. Inactivated flu vaccines are composed of three possible forms of antigen preparation: inactivated whole virus, subvirions where purified virus particles are disrupted with detergents or other reagents to solubilise the lipid envelope (so-called "split" vaccine) or purified HA and NA (subunit vaccine). These inactivated vaccines are given intramuscularly (i.m.), subcutaneously (s.c), or intranasally (i.n.).

Influenza vaccines for interpandemic use, of all kinds, are usually trivalent vaccines. They generally contain antigens derived from two influenza A virus strains and one influenza B strain. A standard 0.5 ml injectable dose in most cases contains (at least) 15 µg of haemagglutinin antigen component from each strain, as measured by single radial immunodiffusion (SRD) (J. M. Wood et al.: An improved single radial immunodiffusion technique for the assay of influenza haemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of haemagglutinin antigen of influenza virus. J. Biol. Stand. 9 (1981) 317-330). Quadrivalent vaccines have also been reported, containing, in addition to the three classical strains, an additional B strain (Commun Dis Intel) 2006, 30, 350-357) or an additional H3N2 strain (Vaccine 1992, 10, 506-511).

Interpandemic influenza virus strains to be incorporated into influenza vaccine each season are determined by the World Health Organisation in collaboration with national health authorities and vaccine manufacturers. Interpandemic Influenza vaccines currently available are considered safe in all age groups (De Donato et al. 1999, Vaccine, 17, 3094-3101).

Vaccine efficacy is however affected by the age and immune status of recipients and the match between vaccine and circulating influenza strains. There is little evidence that current influenza vaccines work in small children under two years of age. Furthermore, reported rates of vaccine efficacy for prevention of typical confirmed influenza illness are 23-72% for the elderly, which are significantly lower than the 60-90% efficacy rates reported for younger adults (Govaert, 1994, J. Am. Med. Assoc., 21, 166-1665; Gross, 1995, Ann Intern. Med. 123, 523-527). The effectiveness of an influenza vaccine has been shown to correlate with serum titres of hemagglutination inhibition (HI) antibodies to the viral strain, and several studies have found that older adults exhibit lower HI titres after influenza immunisation than do younger adults (Murasko, 2002, Experimental gerontology, 37, 427-439).

By way of background, during interpandemic periods, influenza viruses that circulate are related to those from the preceding epidemic. The viruses spread among people with varying levels of immunity from infections earlier in life. Such circulation, over a period of usually 2-3 years, promotes the selection of new strains that have changed enough to cause an epidemic again among the general population; this process is termed 'antigenic drift'. 'Drift variants' may have different impacts in different communities, regions, countries or continents in any one year, although over several years their overall impact is often similar. Typical influenza epidemics cause increases in incidence of pneumonia and lower respiratory disease as witnessed by increased rates of hospitalisation or mortality. The elderly or those with underlying chronic diseases are most likely to experience such complications, but young infants also may suffer severe disease.

At unpredictable intervals, novel influenza viruses emerge with a key surface antigen, the haemagglutinin, of a totally different subtype from strains circulating the season before. Here, the resulting antigens can vary from 20% to 50% from the corresponding protein of strains that were previously circulating in humans. This phenomenon, called "antigenic shift" can result in virus escaping 'herd immunity' and establishing pandemics. In other words, an influenza pandemics occurs when a new influenza virus appears against which the human population has no immunity. It is thought that at least the past pandemics have occurred when an influenza virus from a different species, such as an avian or a porcine influenza virus, has crossed the species barrier. If such viruses have the potential to spread from human to human, they may spread worldwide within a few months to a year, resulting in a pandemic. For example, in 1957 (Asian Flu pandemic), viruses of the H2N2 subtype replaced H1N1 viruses that had been circulating in the human population since at least 1918 when the virus was first isolated. The H2 HA and N2 NA underwent antigenic drift between 1957 and 1968 until the HA was replaced in 1968 (Hong-Kong Flu pandemic) by the emergence of the H3N2 influenza subtype, after which the N2 NA continued to drift along with the H3 HA (Nakajima et al., 1991, Epidemiol. Infect. 106, 383-395).

Several clinical studies have been performed to evaluate safety and immunogenicity in unprimed populations, with monovalent candidate vaccines containing a pandemic strain such as the non-circulating H2N2 or H9N2 strains. Studies have investigated split or whole virus formulations of various HA concentrations (1.9, 3.8, 7.5 or 15 µg HA per dose), with or without alum adjuvantation. Influenza viruses of the H2N2 subtype circulated from 1957 until 1968 when they were replaced by H3N2 strains during the 'Hong Kong pandemic'. Today, individuals that were born after 1968 are immunologically naïve to H2N2 strains. These vaccine candidates have been shown to be immunogenic and well tolerated. Results are reported in Hehme, N et al. 2002, Med. Microbiol. Immunol. 191, 203-208; in Hehme N. et al. 2004, Virus Research 103, 163-171; and two studies were reported with H5N1 (Bresson J L et al. *The Lancet.* 2006:367 (9523):1657-1664; Treanor J J et al. *N Engl J Med.* 2006; 354:1343-1351). Other studies have reported results with MF59 adjuvanted influenza vaccines. One study has reported that two doses of an H5N3 influenza vaccine adjuvanted with MF59 was boosting immunity to influenza H5N1 in a primed population (Stephenson et al., Vaccine 2003, 21, 1687-1693) and another study has reported cross-reactive antibody responses to H5N1 viruses obtained after three doses of MF59-adjuvanted influenza H5N3 vaccine (Stephenson et al., J. Infect. Diseases 2005, 191, 1210-1215).

Persons at risk in case of an influenza pandemic may be different from the defined risk-groups for complications due to seasonal influenza. According to the WHO, 50% of the human cases caused by the avian influenza strain H5N1 occurred in people below 20 years of age, 90% occurred among those aged <40. (WHO, weekly epidemiological record, 30 Jun. 2006).

During a pandemic, antiviral drugs may not be sufficient or effective to cover the needs and the number of individuals at risk of influenza will be greater than in interpandemic periods, therefore the development of a suitable vaccine with the potential to be produced in large amounts and with efficient distribution and administration potential is essential. One way would be to free rapidly some production capacity for the production of pandemic influenza vaccine. However since the mass vaccination would only start after the onset of the pandemic, this would anyway result in important delays caused by the time needed to identify the strain and to produce the first lot. Moreover there will be a fixed and therefore limited weekly output by the vaccines manufacturers. This means that the current approach will almost certainly leave large parts of the population, globally unprotected when the pandemic strikes. The vaccine would be available too late for large parts of the population and mortality is anticipated to be high with an estimated 180-360 million deaths globally.

One way to address this current dilemma is to generate a pandemic vaccine in advance of a pandemic, and to design a monovalent vaccine with the "best candidate pandemic strain" instead of trivalent vaccines in an attempt to reduce vaccine volume, primarily as two doses of vaccine may be necessary in order to achieve protective antibody levels in immunologically naïve recipients (Wood J M et al. Med Mircobiol Immunol. 2002; 191:197-201. Wood J M et al. Philos Trans R Soc Lond B Biol Sci. 2001; 356:1953-1960). This vaccine could then be used for stockpiling or for priming of the population during the interpandemic period.

Unfortunately since current production facilities are entirely consumed year-round with the production of seasonal trivalent vaccines for annual vaccination in the Northern and Southern hemispheres, both approaches mentioned above are not feasible because there is no additional production capacity to produce that "best candidate pandemic strain". In addition, it should be noted that there is an urgent need to find a solution to cope with shortages of interpandemic influenza vaccines which are regularly encountered during the annual influenza seasons. One solution could be to build additional production capacities, this would however require several years of construction, which is anyway an inadequate approach should a pandemic strike within the next years.

At present, the sole way to rapidly gain additional capacity would be to shorten the production time for the annual trivalent vaccine. Recurrent shortages of influenza vaccines occur each season in most of the countries which precludes an optimal coverage of the population regarded as high risk for developing severe influenza disease and complications. As antigen production is the rate-limiting factor in influenza vaccines production, alternative antigen sparing strategies have to be explored.

Some approaches rely on adjuvantation, the aim of which is to increase immunogenicity of the vaccine in order to be able to decrease the antigen content (antigen sparing) and thus increase the number of vaccine doses available. The use of an adjuvant may also overcome the potential weak immunogenicity of the antigen in a naïve population. Several approaches have been published. Examples have been shown using whole inactivated H2N2 or H9N2 virus adjuvanted with aluminium salt (N. Hehme et al. Virus Research 2004, 103, 163-171) or using a plain subvirion H5N1 vaccine or aluminium hydroxide adjuvanted split virus H5N1 vaccine (Bresson J L et al. The Lancet. 2006:367 (9523):1657-1664; Treanor J J et al. N Engl J Med. 2006; 354:1343-1351). The results of this last trial indicate that both plain and adjuvanted H5N1 virus vaccines are safe up to an antigen dose of 90 μg (tested only as plain subvirion vaccine). Using such a high dose of antigen is however not compatible with an antigen-sparing strategy rendered essential in the case of a pandemic. A sub-unit influenza vaccine adjuvanted with the adjuvant MF59, in the form of an oil-in-water emulsion is commercially available for the elderly and at risk population, and has demonstrated its ability to induce a higher antibody titer than that obtained with the non-adjuvanted sub-unit vaccine (De Donato et al. 1999, Vaccine, 17, 3094-3101). However, in a later publication, the same vaccine has not demonstrated its improved profile compared to a non-adjuvanted split vaccine (Puig-Barbera et al., 2004, Vaccine 23, 283-289).

New vaccines which are effective whilst addressing the antigen-sparing considerations are therefore still needed. These new vaccines will have an acceptable if not improved immunogenicity, in particular against weakly or non-immunogenic pandemic strains or for the immuno-compromised individuals such as the elderly population. These new vaccines will also ideally have a cross-protection potential, such that they could be used as pre-pandemic or stockpiling vaccines to prime an immunologically naive population against a pandemic strain before or upon declaration of a pandemic.

STATEMENT OF THE INVENTION

The present inventors have discovered that, in order to improve the supply of influenza vaccines, novel effective immunogenic influenza formulations could be developed, which contain an adjuvant thus allowing for a lower amount of influenza antigen to be used. Novel adjuvanted compositions are hereby provided which allow an antigen sparing formulation affording sufficient protection of all age groups, in terms of cellular mediated immune response and/or humoral response.

The inventors have in particular discovered that it could be relied on immunogenic influenza compositions characterised in that each or all of the individual components of the adjuvant within the immunogenic composition is/are at a lower level than previously thought useful. This carries the advantage maintaining the level of immunogenicity against an antigen whilst the reactogenicity within the host recipient is reduced.

Accordingly, in first aspect of the present invention, there is provided an immunogenic influenza composition, in particular a vaccine, in a dose volume suitable for human use comprising an influenza virus antigen or antigenic preparation in combination with an oil-in-water emulsion adjuvant, wherein said oil-in-water emulsion adjuvant comprises a metabolisable oil and an emulsifying agent, and optionally a tocol and/or a sterol, and wherein said metabolisable oil is present in said human dose at a level of below 11 mg, and said emulsifying agent is present in said human dose at a level of below 5 mg. Said tocol and/or sterol when present is present in said human dose at a level of below 12 mg. Suitably the amount of influenza antigen per strain per dose is 15 μg HA or a low amount such as less than 15 μg HA.

In another aspect the present invention provides for a vaccine kit comprising an influenza virus antigen component or an influenza virus antigenic preparation component, optionally a low amount antigen component, and further comprising for concomitant or sequential administration an adjuvant as herein defined.

In a third aspect, the invention provides a method for the production of an influenza immunogenic composition for a pandemic situation, a pre-pandemic situation or an interpandemic (seasonal) situation which method comprises admixing an influenza virus antigen or antigenic preparation thereof with an oil-in-water emulsion adjuvant as herein defined. In particular the invention provides a method for the production of an influenza vaccine which method comprises a step of mixing the adjuvanted immunogenic with a pharmaceutically acceptable excipient, and providing vaccine units which contain no more than 15 μg influenza haemagglutinin antigen per dose. The influenza virus may be egg-derived, plant-derived, cell-culture derived, or may be recombinantly produced. Suitably the influenza virus antigen is egg-derived or cell culture-derived.

In a fourth aspect, there is provided an immunogenic composition or a vaccine as herein defined for use in the treatment or prevention of disease caused by influenza infection. In a related aspect the invention provides for the use of a influenza virus antigen or antigenic preparation thereof and an oil-in-water emulsion as herein defined in the manufacture of an immunogenic composition, e.g. a vaccine, for the protection against infection or disease caused by an influenza virus.

In yet another aspect there is provided the use of (a) a low amount, as herein defined, of influenza virus antigen or antigenic preparation thereof from influenza strain, and (b) an oil-in-water emulsion adjuvant as herein defined, in the manufacture of an immunogenic composition, or a kit, for inducing at least one of i) an improved CD4 T-cell immune response, ii) an improved B cell memory response, iii) an improved humoral response, against said virus antigen or antigenic composition in a human, compared to the response obtained with the non-adjuvanted composition.

In a further aspect, there is provided a method or use as hereinabove defined, for protection against infection or disease caused by an influenza virus which is a variant of the virus from which the antigen in the immunogenic composition is derived. In another embodiment, there is provided a method or use as hereinabove defined for protection against influenza infections or disease caused by a pathogen which comprises an antigen which is a variant of that antigen in the immunogenic composition.

The invention also relates to a method of vaccination comprising delivery of an antigen and an oil-in-water emulsion adjuvant as defined herein.

Other aspects and advantages of the present invention are described further in the following detailed description of the preferred embodiments thereof.

BRIEF DESCRIPTION OF FIGURES

FIG. 9A: Mice study: H5N1-specific serum Ig ELISA titers on day 14 post-immunization (GMT+/−IC95) for 1.5 μg.

FIG. 9B: Mice study: H5N1-specific serum Ig ELISA titers on day 14 post-immunization (GMT+/−IC95) for 0.38 μg.

FIG. 9E: Mice study: Anti-H5N1 IgG2b isotypic responses on day 14 post-immunization (GMT+/−IC95) for 1.5 μg.

FIG. 9F: Mice study: Anti-H5N1 IgG2b isotypic responses on day 14 post-immunization (GMT+/−IC95) for 0.38 μg.

FIG. 10A: Mice study: Hemagglutination inhibition test (GMT+/−IC95) on day 21 post-immunization (GMT+/−IC95) for 1.5 μg.

FIG. 10B: Mice study: Hemagglutination inhibition test (GMT+/−IC95) on day 21 post-immunization (GMT+/−IC95) for 0.38 μg.

FIG. 11B: Mice study: Cellular immune response (CD4+ T cell) in naïve C57BI/6 mice immunized with different dose of H5N1 vaccine (1.5 or 0.38 μg) adjuvanted with dose range AS03: 0.38 μg HA Ag (antigen).

DETAILED DESCRIPTION

Figure 1:
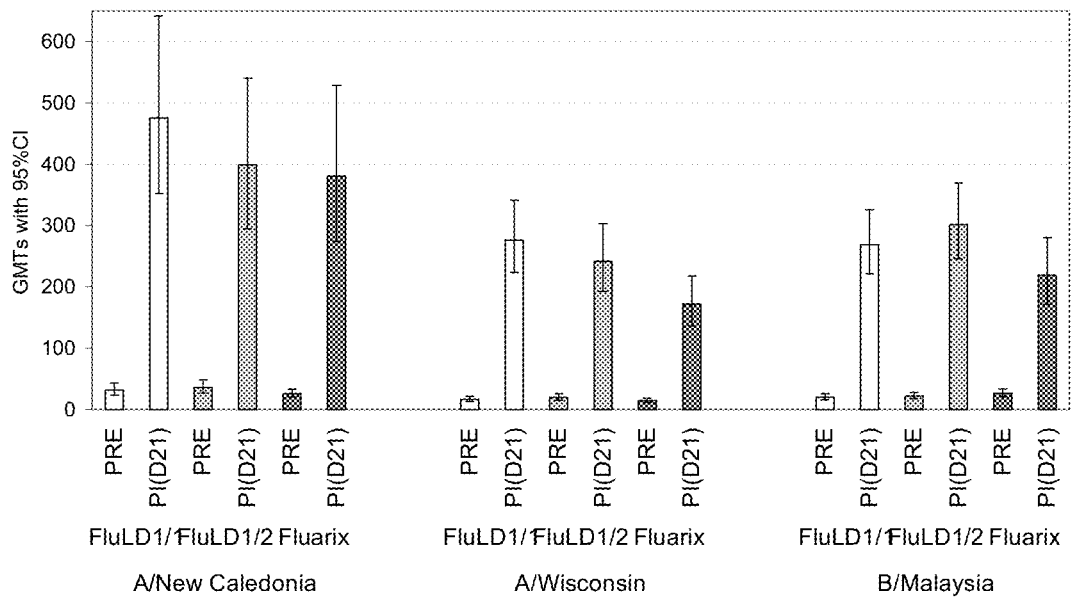
FIG. 1: Clinical trial: Geometric mean titers (GMTs) for anti-HA antibody at different timepoints (ATP cohort for immunogenicity).

The present inventors have discovered that an adjuvant composition, which comprises a metabolisable oil and an emulsifying agent, and optionally a tocol and/or a sterol, where each component is present at a lower level per human vaccine dose than used before, can improve immune responses to an influenza preparation, whilst at the same time having lower reactogenicity than some of the prior art formulations where the adjuvant components were present at higher levels (suitably 2-fold higher or more) per human dose.

The present inventors have further found that an influenza formulation comprising an influenza virus or antigenic preparation thereof together with an adjuvant as herein defined, and optionally additionally with immunostimulants such as with a lipid A derivative such as 3D-MPL, was capable of i) improving the CD4 T-cell immune response and/or the humoral immune response against said antigen or antigenic composition compared to that obtained with the un-adjuvanted virus or antigenic preparation thereof, and/or ii) generating a CD4 T-cell immune response and/or humoral immune response against said antigen or antigenic composition comparable to that obtained with the composition adjuvanted with an adjuvant where each component is present at a higher (suitably 2-fold higher or more) level. The formulations adjuvanted with the adjuvant are advantageously used to induce anti-influenza CD4-T cell responses capable of detecting influenza epitopes presented by MHC class II molecules. The present applicant has found that it is effective to target the cell-mediated immune system in order to increase responsiveness against homologous and drift influenza strains (upon vaccination and infection).

It is a specific embodiment of the present invention that the compositions for use in the present invention may be able to provide, in humans either or both of (i) a better sero-protection against influenza following revaccination compared with the un-adjuvanted composition, and (ii) a comparable sero-protection against influenza following revaccination compared with an adjuvanted composition where each component is present at a higher level, as assessed by the number of human subjects meeting any, several or all of the influenza correlates of protection (i.e. seroconversion rate, conversion factor, protection rate). Furthermore, it is another specific embodiment that the composition for use in the present invention will also be able to induce either or both of (i) a higher B cell memory response following the first vaccination of a human subject, and a higher humoral response following revaccination, compared to the non-adjuvanted composition, and (ii) a comparable B cell memory response following the first vaccination of a human subject, and a comparable humoral response following revaccination, compared to the adjuvanted composition where each component is present at a higher (suitably 2-fold higher or more) level.

The adjuvanted influenza compositions according to the invention have several advantages. These advantages can be assessed by comparison to the equivalent non-adjuvanted compositions, or by comparison to the adjuvanted composition where each adjuvant component is present at a higher level:

1) An improved immunogenicity compared to the non-adjuvanted composition, thereby allowing any or all of the following: i) improving weak immune response to less immunogenic influenza strains to a level higher than those obtained with the non-adjuvanted formulations; ii) restoring weak immune response in specific populations such as in the elderly people (over 50 years of age, typically over 65 years of age) to levels seen in young people (antibody and/or T cell responses);
2) The use of adjuvants can overcome the potential weak immunogenicity of the antigen in a naïve population or in young infants (between 6 months to 4 years, in particular children below 1 year of age) and induce priming and protection;
3) In addition to affording an at least equivalent protection against the vaccine strains as compared to a classical vaccine (e.g. a commercially available split vaccine), they may confer an additional layer of protection against drift strains by leading to an improved cross-protection profile: increased cross-reactivity, cross-protection against variant (drifted) influenza strains allowing the set-up of a cross-priming strategy; this is of special interest where they can be used as pre-pandemic vaccines further allowing only one dose of a pandemic vaccine to be required to enhance the protection against the (circulating) pandemic strain; this is also of interest as it may address the problem of H3N2 drifts which tend to appear more quickly than in the other interpandemic A strain H1N1;
4) a reduced reactogenicity profile of the adjuvanted composition compared to that profile abotained with a composition where each component is present at a higher (suitably 2-fold higher or more) level, whilst maintaining a satisfactory immunogenic potential.

By further reaching any or all of these advantages with a reduced antigen dosage (typically below 15 μg/strain/dose) and a reduced adjuvant dosage, they will ensure an increased capacity in case of emergency or for preparedness of a pandemic situation (antigen-sparing in the pandemic situation) and offering a possibility of higher number of vaccine doses available to the population during the interpandemic vaccination season.

By relying on a combination of a reduced antigen dosage and/or a reduced adjuvant dosage they will allow the development of more complex influenza compositions, such as a quadrivalent vaccine, comprising a fourth strain which can be a second influenza B strain or a pandemic influenza strain to be added to the standard trivalent vaccine. In another aspect of the invention, the adjuvanted immunogenic composition as defined herein demonstrates immunogenicity results for both antibody production and post-vaccination frequency of influenza-specific (optionally cross-reactive) CD4 which are greater than or equivalent to those generated with non-adjuvanted vaccine or with the vaccine adjuvanted with an adjuvant where the adjuvant components are present at a higher level, respectively. This effect is in particular of value in the paediatric population or the elderly population allowing higher efficacy than the currently commercial vaccines, whilst showing lower or fewer reactogenicity symptoms compared to the group receiving the adjuvanted vaccine wherein the adjuvant components are at a higher (suitably 2-fold higher) amount.

Oil-in-Water Emulsion Adjuvant

The adjuvant according to the present invention is an emulsion, in particular, an oil-in-water emulsion, and may optionally comprise other immunostimulants. In particular, the oil phase of the emulsion system comprises a metabolisable oil. The meaning of the term metabolisable oil is well known in the art. Metabolisable can be defined as "being capable of being transformed by metabolism" (Dorland's Illustrated Medical Dictionary, W.B. Sanders Company, 25th edition (1974)). The oil may be any vegetable oil, fish, oil, animal or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. A particularly suitable metabolisable oil is squalene. Squalene (2,6,10,15,19, 23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is an oil for use in this invention. Squalene is a metabolisable oil by virtue of the fact that it is an intermediate in the biosynthesis of cholesterol (Merck index, $10^{th}$ Edition, entry no. 8619).

Oil-in-water emulsions per se are well known in the art, and have been suggested to be useful as adjuvant compositions (EP399843B); also combinations of oil-in-water emulsions and other active agents have been described as adjuvants for vaccines: WO95/17210; WO98/56414; WO99/12565; WO99/11241; WO2006/100109; WO 2006/100110; WO 2006/100111 which disclose emulsion adjuvants based on squalene, α-tocopherol, and TWEEN 80, optionally formulated with the immunostimulants QS21 and/or 3D-MPL). Other oil-in-water emulsion-based adjuvants have been described, such as those disclosed in WO90/14837; WO00/50006; WO2007/080308; WO2007/006939, all of which form oil emulsion systems (in particular when based on squalene) to form alternative adjuvants and compositions of the present invention.

In a specific embodiment, the oil-in-water emulsion comprises a metabolisable, non-toxic oil, such as squalane or squalene, optionally a tocol such as tocopherol in particular alpha tocopherol (and optionally both squalene and alpha tocopherol) and an emulsifier (or surfactant) such as the non-ionic surfactant TWEEN80™ or Polysorbate 80. In a specific embodiment the oil emulsion further comprises a sterol such as cholesterol.

Tocols (e.g. vitamin E) are also often used in oil emulsions adjuvants (EP0382271B1; U.S. Pat. No. 5,667,784; WO95/17210). Tocols used in the oil emulsions (optionally oil-in-water emulsions) of the invention may be formulated as described in EP0382271B1, in that the tocols may be dispersions of tocol droplets, optionally comprising an emulsifier, of optionally less than 1 micron in diameter. Alternatively, the tocols may be used in combination with another oil, to form the oil phase of an oil emulsion. Examples of oil emulsions which may be used in combination with the tocol are described herein, such as the metabolisable oils described above.

The method of producing oil-in-water emulsions is well known to the person skilled in the art. Commonly, the method comprises mixing the oil phase with a surfactant such as a PBS/TWEEN80™ solution, followed by homogenisation using a homogenizer, it would be clear to a man skilled in the art that a method comprising passing the mixture twice through a syringe needle would be suitable for homogenising small volumes of liquid. Equally, the emulsification process in microfluidiser (M110S Microfluidics machine, maximum of 50 passes, for a period of 2 minutes at maximum pressure input of 6 bar (output pressure of about 850 bar)) could be adapted by the man skilled in the art to produce smaller or larger volumes of emulsion. The adaptation could be achieved by routine experimentation comprising the measurement of the resultant emulsion until a preparation was achieved with oil droplets of the required diameter.

In an oil-in-water emulsion, the oil and emulsifier should be in an aqueous carrier. The aqueous carrier may be, for example, phosphate buffered saline.

The size of the oil droplets found within the stable oil-in-water emulsion are optionally less than 1 micron, may be in the range of substantially 30-600 nm, optionally substantially around 30-500 nm in diameter, and optionally substantially 150-500 nm in diameter, and in particular about 150 nm in diameter as measured by photon correlation spectroscopy. In this regard, 80% of the oil droplets by number should be within the ranges, optionally more than 90% and optionally more than 95% of the oil droplets by number are within the defined size ranges.

A key aspect of the present invention is the fact that the components present in the adjuvant of the immunogenic compositions are at lower amounts than had previously been thought useful, suitably at below 11 mg metabolisable oil (such as squalene), for example between 0.5-11 mg, 0.5-10 mg or 0.5-9 mg, and at below 5 mg emulsifying agent (suitably such as polyoxyethylene sorbitan monooleate), for example between 0.1-5 mg, per human dose of the immunogenic composition. Suitably tocol (e.g. alpha-tocopherol) where present is at below 12 mg, for example between 0.5-12 mg. The adjuvant composition of the invention comprises an oil-in-water emulsion adjuvant, suitably said emulsion comprises a metabolisable oil in an amount of between 0.5-10 mg, and an emulsifying agent in an amount of between 0.4-4 mg, and optionally a tocol in an amount of between 0.5-11 mg. Suitably said emulsion has oil droplets of which at least 70%, suitably at least 80% by intensity have diameters of less than 1 μm.

The invention therefore provides a human dose of an adjuvanted immunogenic composition wherein said adjuvant comprises an oil-in-water emulsion adjuvant comprising a metabolisable oil, suitably squalene, at a level lower than 11 mg per human dose, suitably between 0.5-11, 0.5-10, 0.5-9, 1-10, 1-11, 2-10, 4-8, or 4.5-5.5 (e.g. 2-3, 5-6, or 9-10 mg) metabolisable oil per human dose. In another embodiment the invention provides a human dose of an adjuvanted immunogenic composition wherein said adjuvant comprises an oil-in-water emulsion adjuvant comprising an emulsifying agent, suitably a polyoxyethylene sorbitan monooleate (such as Tween 80 or Polysorbate 80™), at a level lower than 5 mg per human dose, suitably between 0.1-5, 0.2-5, 0.3-5, 0.4-5, 0.5-4, 1-2 or 2-3 mg (e.g. 0.4-1.2, 2-3 or 4-5 mg) emulsifying agent per human dose. In still another embodiment the invention provides a human dose of an adjuvanted immunogenic composition wherein said adjuvant further comprises a tocol, suitably alpha-tocopherol, at a level lower than 12 mg per human dose, suitably between 0.5-12, 10-11, 1-11, 2-10, 4-9, 5-7 mg (e.g. 10-11, 5-6, 2.5-3.5, 1-2 or 1-3 mg) tocol per human dose.

Suitably a human dose of an adjuvant immunogenic composition according to the invention is where the oil-in-water emulsion adjuvant comprises 4.5-5.5 or 5-6 mg metabolisable oil (suitably squalene), 5-7 mg tocol (suitably alpha-tocopherol) and 2-3 mg emulsifying agent, which can be a non-ionic surfactant (suitably a polyoxyethylene sorbitan monooleate such as Tween 80™ or Polysorbate 80™). According to another suitable embodiment, a human dose of an adjuvant immunogenic composition according to the invention is where the oil-in-water emulsion adjuvant comprises 2-3 mg metabolisable oil (suitably squalene), 2.5-3.5 mg tocol (suitably alpha-tocopherol) and 1-1.5 mg emulsifying agent (suitably a polyoxyethylene sorbitan monooleate such as Tween 80™ or Polysorbate 80™). In still another embodiment, a human dose of an adjuvant immunogenic composition according to the invention is where the oil-in-water emulsion adjuvant comprises 0.5-1.5 mg metabolisable oil (suitably squalene), 0.5-1.5 mg tocol (suitably alpha-tocopherol) and 0.25-0.75 mg emulsifying agent (suitably a polyoxyethylene sorbitan monooleate such as Tween80™ or Polysorbate 80™). In some cases it may be advantageous that the vaccines of the present invention will further contain a stabiliser.

By the term "human dose" is meant a influenza composition dose (after mixing the adjuvant and the antigen components) which is delivered in a volume suitable for human use. Generally this is between 0.25 and 1.5 ml. In one embodiment, a human dose is about 0.5 ml. In a further embodiment, a human dose is higher than 0.5 ml, for example about 0.6, 0.7, 0.8, 0.9 or about 1 ml. In a further embodiment, a human dose is between 1 ml and 1.5 ml. In another embodiment, in particular when the immunogenic composition is for the paediatric population, a human dose may be less than 0.5 ml, for example between 0.25 and 0.5 ml or exactly 0.1 ml, 0.2 ml, 0.25 ml, 0.3 ml or 0.4 ml. The invention is characterised in that each or all of the individual components of the adjuvant within the immunogenic composition is/are at a lower level than previously thought useful and is/are typically as recited above. Particularly suitable compositions comprise the following o/w adjuvant components in the following amounts in the final volume of human dose (suitably of about 0.5 ml or about 0.7 ml) (Table 1):

TABLE 1 specific o/w emulsion-based adjuvants according to the invention

A

| | Adjuvant A | Adjuvant B | Adjuvant E | Adjuvant F | Adjuvant C | Adjuvant H | Adjuvant G | Adjuvant D |
|---|---|---|---|---|---|---|---|---|
| o/w emulsion* Components: | 125 µl | 100 µl | 83.33 µl | 62.5 µl | 50 µl | 41.67 µl | 31.25 µl | 25 µl |
| Tocopherol (mg) | 5.94 (5.6-6.2) | 4.75 (4.5-5.0) | 3.96 (3.8-4.2) | 2.97 (2.8-3.1) | 2.38 (2.3-2.5) | 1.98 (1.9-2.1) | 1.49 (1.4-1.6) | 1.19 (1.1-1.25) |
| Squalene (mg) | 5.35 (5.1-5.6) | 4.28 (4.1-4.5) | 3.57 (3.4-3.75) | 2.68 (2.5-2.8) | 2.14 (2.0-2.25) | 1.78 (1.7-1.9) | 1.34 (1.3-1.4) | 1.07 (1.0-1.1) |
| Polysorbate 80 or Tween 80 (mg) | 2.43 (2.3-2.6) | 1.94 (1.8-2.0) | 1.62 (1.5-1.7) | 1.21 (1.1-1.3) | 0.97 (0.9-1.0) | 0.81 (0.8-0.9) | 0.61 (0.58-0.64) | 0.49 (0.47-0.51) |

*suitable o/w volumes are given for illustration but are not limiting
( ) between brackets are suitable ranges (+/-5%) around the above value

B

| Components: | Adjuvant I | Adjuvant J | Adjuvant K | Adjuvant L | Adjuvant M | Adjuvant N | Adjuvant O | Adjuvant P |
|---|---|---|---|---|---|---|---|---|
| Span 85 (mg) | 0.59 (0.56-0.62) | 0.47 (0.45-0.49) | 0.39 (0.37-0.41) | 0.29 (0.28-0.3) | 0.24 (0.23-0.25) | 0.2 (0.19-0.21) | 0.15 (0.14-0.16) | 0.12 (0.11-0.13) |
| Squalene (mg) | 4.88 (4.6-5.1) | 3.9 (3.7-4.1) | 3.25 (3.1-3.4) | 2.44 (2.3-2.6) | 1.95 (1.85-2.05) | 1.63 (1.55-1.7) | 1.22 (1.2-1.3) | 0.98 (0.9-1.1) |
| Polysorbate 80 or Tween 80 (mg) | 0.59 (0.56-0.62) | 0.47 (0.45-0.49) | 0.39 (0.37-0.41) | 0.29 (0.28-0.3) | 0.24 (0.23-0.25) | 0.2 (0.19-0.21) | 0.15 (0.14-0.16) | 0.12 (0.11-0.13) |

| Components: | Adjuvant Q | Adjuvant R | Adjuvant S | Adjuvant T | Adjuvant U | Adjuvant V | Adjuvant W | Adjuvant X |
|---|---|---|---|---|---|---|---|---|
| Span 85 (mg) | 0.84 (0.8-0.9) | 0.67 (0.64-0.7) | 0.56 (0.53-0.6) | 0.42 (0.4-0.44) | 0.34 (0.32-0.36) | 0.28 (0.27-0.3) | 0.21 (0.2-0.22) | 0.17 (0.16-0.18) |
| Squalene (mg) | 4.88 (4.6-5.1) | 3.9 (3.7-4.1) | 3.25 (3.1-3.4) | 2.44 (2.3-2.6) | 1.95 (1.85-2.05) | 1.63 (1.55-1.7) | 1.22 (1.2-1.3) | 0.98 (0.9-1.1) |
| Polysorbate 80 or Tween 80 (mg) | 0.84 (0.8-0.9) | 0.67 (0.64-0.7) | 0.56 (0.53-0.6) | 0.42 (0.4-0.44) | 0.34 (0.32-0.36) | 0.28 (0.27-0.3) | 0.21 (0.2-0.22) | 0.17 (0.16-0.18) |

( ) between brackets are suitable ranges (+/-5%) around the above value (+/-5%)

All numerical values given (e.g. in % or in mg) including those in Table 1 should be undertood to allow for a 5% variation, i.e. 4.88 mg squalene should be understood to mean between 4.64-5.12 mg.

A pre-dilution of each component (o/w emulsion and antigen) may be performed to produce an adjuvanted vaccine that delivers the required HA amount and the required adjuvant component amount.

In one aspect of the invention, the o/w emulsion of the adjuvanted vaccine of the invention (whether pre-diluted or not) may be added in a volume not exceeding, or suitably lower than, a half of the total dose volume. By way of illustration, suitable volumes (e.g. ranging from 125 µl to 25 µl) are given for the emulsion component of formulations A-H illustrated in Table 1A. Accordingly in one aspect of the invention, there is provided a method for making an adjuvanted influenza vaccine comprising a step of admixing a first volume of an oil-in-water emulsion and a second volume of an aqueous suspension comprising an influenza virus or antigenic preparation thereof, wherein the second volume is greater than the second volume. Suitably the first volume of o/w emulsion is obtained after dilution of a concentrated emulsion.

Alternatively, substantially equal volumes (whether after pre-dilution or not) of o/w emulsion and antigen suspension are mixed to produce the adjuvanted vaccine compositions of the invention. The respective volume of each component will typically then be at a maximum excess of 10% that of the other component (i.e. adjuvant emulsion:antigen suspension ratio of 1:1.1 to 1.1:1), suitably at a maximum excess of 5% (i.e. o/w emulsion:antigen suspension ratio of 1:1.05 to 1.05:1), suitably at a maximum excess of 2.5% (i.e. adjuvant emulsion:antigen suspension ratio of 1:1.025 to 1.025:1). Accordingly in another aspect of the invention, there is provided a method for making an adjuvanted influenza vaccine comprising a step of admixing substantially equal volumes of an oil-in-water emulsion and of an aqueous suspension comprising an influenza virus or antigenic preparation thereof. Suitably the first volume of o/w emulsion is obtained after dilution of a concentrated emulsion.

Still in another embodiment, the o/w emulsion adjuvant of the adjuvanted vaccine of the invention is added in a volume exceeding a half of the total dose volume. Accordingly in another aspect of the invention, there is provided a method for making an adjuvanted influenza vaccine comprising a step of admixing a first volume of an oil-in-water emulsion and a second volume of an aqueous suspension comprising an influenza virus or antigenic preparation thereof, wherein the first volume is greater than the second volume. Suitably the first volume of o/w emulsion is obtained after dilution of a concentrated emulsion.

In all three methods, the amounts of emulsion components and optionally HA in the final human dose volume are lower than was previously thought useful and are as claimed herein. Suitably they are in the specific amounts as claimed herein.

The amount of each individual component within the vaccine can be expressed a percentage of the total vaccine composition, i.e. in % (v/v) or in % (w/v). The following conversion figures will be known by the skilled person and can be applied: squalene 0.855 g/ml, alpha-tocopherol 0.949 g/ml, polysorbate 80 1.080 g/ml, and Span 85 0.94 g/ml.

Accordingly, the metabolisable oil (suitably squalene) is present in the vaccine composition in an amount of 0.5% to 2%, suitably 0.25-2, or 0.25-1.75, or 0.5-1.65, or 0.6-1.5, or 0.8-1.4 or 1-1.25% (w/v) oil of the total vaccine volume. In another specific embodiment, the metabolisable oil (suitably squalene) is present in a final amount of about 1.25%, or about 0.6% (w/v) of the total volume of the vaccine composition. In another specific embodiment, the metabolisable oil is present in a final amount of 0.25% (w/v) of the total vaccine volume.

The amount of tocol may also be expressed as a percentage of the total vaccine composition volume. Suitably tocol is present in the vaccine composition in an amount 0.25% to 2% (w/v) of the total volume of the immunogenic composition, for instance, 0.25-2 comprises 0.25-2, or 0.25-1.75, or 0.5-1.65, or 0.6-1.5, or 0.8-1.4 or 1-1.25% (w/v) tocol of the total vaccine volume. In one embodiment of the invention, tocol is present in an amount of between 0.2% and 2% (v/v) of the total volume of the vaccine composition, or at an amount of 1.25% (v/v) in a 0.5 ml vaccine dose volume. In a specific embodiment, the tocol is present in a final amount of about 1.25% of the total volume of the immunogenic composition. In another specific embodiment, the tocol is present in a final amount of 0.25% (v/v) of the total vaccine volume or 1.25% (v/v) in 0.5 ml vaccine dose volume or 0.9% (v/v), in 0.7 ml vaccine dose volume, or 0.5% (v/v) in 0.5 ml vaccine dose or 0.35-0.37%, or 0.36% in 0.7 ml vaccine dose.

In one embodiment of the invention, the emulsifying agent is present in an amount of 0.1-5, 0.2-5, 0.3-5, 0.4-5, 0.4-1.2, 0.5-4, 1-2, 2-3 or 4-5 mg, per human dose. When more than one emulsifying agent is present, such as when Tween80 and Span85 are both present, the claimed amount is understood to be the total amount of emulsifying agent. The amount of emulsifying agent may be expressed as a percentage of the total vaccine composition volume. Suitably the emulsifying agent is present in the vaccine composition in an amount 0.125-0.8% (w/v) of the total volume of the immunogenic composition, such as at 0.08-0.05, or 0.1-0.7, or 0.2-0.6, or 0.25-0.55, or 0.3-0.52 or 0.4-0.5% (w/v) of the total vaccine volume. In a specific embodiment the emulsifying agent is present in an amount of 1%, 0.5% or 0.2% (w/v) of the total vaccine composition volume.

In a specific embodiment, a 0.5 ml vaccine dose volume contains 0.5% (w/w) Tween 80, and a 0.7 ml vaccine dose volume contains 0.35% (w/w) Tween 80. In another specific embodiment 1 0.5 ml vaccine dose contains 0.2% (w/w) emulsifying agent and a 0.7 ml vaccine dose contains 0.14% (w/w) emulsifying agent. Span 85 (Sorbitan trioleate) may also be present at a level of 0.1 to 1% in the emulsions used in the invention, suitably at about 0.5% or less. In a specific embodiment, Span 85 when present is added to the composition at a percentage identical to that of polysorbate 80.

In some cases it may be advantageous that the immunogenic compositions and vaccines of the present invention will further contain a stabiliser, for example other emulsifiers/surfactants, including caprylic acid (merck index $10^{th}$ Edition, entry no. 1739), for example Tricaprylin.

The invention further provides an adjuvant composition comprising the individual components as defined herein above and in the amount defined above, for example but not exclusively as illustrated in Table 1. Typically such an adjuvant composition will be in a human dose suitable volume. Where the adjuvant is in a liquid form to be combined with a liquid form of an antigenic composition, the adjuvant composition will be in a human dose suitable volume which is a fraction of the intended final volume of the human dose, such as for example approximately half of the intended final volume of the human dose, for example a 360 µl volume for an intended human dose of 0.7 ml, or a 250 µl volume for an intended human dose of 0.5 ml. If the human vaccine dose is increased it is intended that the amount (in mg) of the adjuvant components remain unchanged by this increase of dose volume, simply becoming more dilute. The adjuvant composition is diluted as needed when combined with the antigen composition to provide the final human dose of vaccine. The final volume of such dose will of course vary dependent on the initial volume of the adjuvant composition and the volume of antigen composition added to the adjuvant composition.

In an alternative embodiment, liquid adjuvant is used to reconstitute a lyophilised antigen composition. In this embodiment, the human dose suitable volume of the adjuvant composition is approximately equal to the final volume of the human dose. The liquid adjuvant composition is added to the vial containing the lyophilised antigen composition. The final human dose can vary between 0.5 and 1.5 ml. In a particular embodiment the human dose is about 0.5 ml or about 0.7 ml, in this embodiment the vaccine composition of the invention will comprise a level of metabolisable oil less than 11 mg or in the amounts defined above, for example between suitably between 0.5-11, 1-11, 2-10, 4-8, or 5-6 mg (e.g. 2-3, 5-6, or 9-10 mg per 0.5 ml human dose, furthermore in this embodiment an adjuvant composition of the invention will comprise a level of metabolisable oil less than 11 mg or in the amounts defined above, for example between suitably between 0.5-11, 1-11, 2-10, 4-8, or 5-6 mg (e.g. 2-3, 5-6, or 9-10 mg) or metabolisable oil, per 250 µl of adjuvant composition, or per 500 µl of adjuvant composition dependent on whether the adjuvant composition is intended to be combined with a liquid or lyophilised antigen composition respectively. Likewise, in the particular embodiment where the human dose is 0.5 ml, in this embodiment the vaccine composition of the invention will comprise a level of emulsifying agent, suitably a polyoxyethylene sorbitan monooleate (such as Tween 80™ or Polysorbate 80™), at a level lower than 5 mg per human dose, suitably between 0.1-5, 0.2-5, 0.3-5, 0.4-5, 0.5-4, or 2-3 mg (e.g. 0.4-1.2, 2-3 or 4-5 mg) of emulsifying agent per 0.5 ml human dose, furthermore in this embodiment an adjuvant composition of the invention will comprise a level of emulsifying agent, suitably a polyoxyethylene sorbitan monooleate (such as Tween80™ or Polysorbate 80™), at a level lower than 5 mg per human dose, suitably between 0.1-5, 0.2-5, 0.3-5, 0.4-5, 0.5-4, or 2-3 mg (e.g. 0.4-1.2, 2-3 or 4-5 mg) of emulsifying agent per 250 µl of adjuvant composition, or per 500 µl of adjuvant composition dependent on whether the adjuvant composition is intended to be combined with a liquid or lyophilised antigen composition respectively. Similarly, in the particular embodiment where the human dose is 0.5 ml, in this embodiment the vaccine composition of the invention will comprise a level of tocol, suitably alpha-tocopherol, at a level lower than 12 mg per human dose, suitably between 0.5-12, 1-11, 2-10, 4-9, 5-7 mg (e.g. 10-11, 5-6, 2.5-3.5, or 1-3 mg) tocol per 0.5 ml human dose, furthermore in this embodiment an adjuvant composition of the invention will comprise a level of tocol, suitably alpha-tocopherol, at a level lower than 12 mg per human dose, suitably between 0.5-12, 1-11, 2-10, 4-9, 5-7 mg (e.g. 10-11, 5-6, 2.5-3.5, or 1-3 mg) of tocol per 250 µl of adjuvant composition, or per 500 µl of adjuvant composition dependent on whether the adjuvant composition is intended to be combined with a liquid or lyophilised antigen composition respectively.

Optionally the ratio of oil (e.g. squalene): tocol (e.g. α-tocopherol) is equal or less than 1 as this provides a more stable emulsion.

In some cases it may be advantageous that the vaccines of the present invention will further contain a stabiliser.

The dose of the components at which the adjuvant is operated in the immunogenic composition is suitably able to enhance an immune response to an antigen in a human. In particular a suitable amount of metabolisable oil, tocol and polyoxyethylene sorbitan monooleate is that which improves the immunological potential of the composition compared to the unadjuvanted composition, or is that which gives an immunological potential similar to that obtained with the composition adjuvanted with an adjuvant comprising another—higher—amount of said components, in a target human population, whilst being acceptable from a reactogenicity profile.

Optional Immunostimulants

In a specific embodiment according to the invention, the adjuvant is an oil-in-water emulsion adjuvant comprising a metabolisable oil such as squalene, a tocol such as alpha-tocopherol and a surfactant such as polysorbate 80, in the amounts defined above, and does not contain any additional immunostimulants(s), in particular it does not contain a non-toxic lipid A derivative (such as 3D-MPL) or a saponin (such as QS21).

In another embodiment of the invention there is provided a vaccine composition comprising an antigen or antigen composition and an adjuvant composition comprising an oil-in-water emulsion and optionally one or more further immunostimulants, wherein said oil-in-water emulsion comprises 0.5-10 mg metabolisable oil (suitably squalene), 0.5-11 mg tocol (suitably alpha-tocopherol) and 0.4-4 mg emulsifying agent.

In a specific embodiment the oil-in-water emulsion adjuvant optionally comprises one or more additional adjuvants or immunostimulants other than QS21 and/or MPL.

In another specific embodiment, the oil-in-water emulsion adjuvant and immunogenic composition further comprises an additional immunostimulant which is a lipopolysaccharide, suitably a non-toxic derivative of lipid A, particularly monophosphoryl lipid A or more particularly 3-Deacylated monophoshoryl lipid A (3D-MPL). 3D-MPL is sold under the name MPL by GlaxoSmithKline Biologicals N.A. and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-g (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present invention small particle 3D-MPL may be used. Small particle 3D-MPL has a particle size such that it may be sterile-filtered through a 0.22 µm filter. Such preparations are described in WO94/21292.

Said lipopolysaccharide, such as 3D-MPL, can be used at amounts between 1 and 50 µg, per human dose of the immunogenic composition. Such 3D-MPL can be used at a level of about 25 µg, for example between 20-30 µg, suitably between 21-29 µg or between 22 and 28 µg or between 23 and 27 µg or between 24 and 26 µg, or 25 µg. In another embodiment, the human dose of the immunogenic composition comprises 3D-MPL at a level of about 10 µg, for example between 5 and 15 µg, suitably between 6 and 14 µg, for example between 7 and 13 µg or between 8 and 12 µg or between 9 and 11 µg, or 10 µg.

In a further embodiment, the human dose of the immunogenic composition comprises 3D-MPL at a level of about 5 µg, for example between 1 and 9 µg, or between 2 and 8 µg or suitably between 3 and 7 µg or 4 and 6 µg, or 5 µg.

In another embodiment, synthetic derivatives of lipid A are used as optional additional immunostimulant, some being described as TLR-4 agonists, and include, but are not limited to:

OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026)

OM 294 DP (3S, 9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO99/64301 and WO 00/0462)

OM 197 MP-Ac DP (3S-, 9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127)

Other TLR4 ligands which may be used are alkyl Glucosaminide phosphates (AGPs) such as those disclosed in WO9850399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR4 agonists, and some are TLR4 antagonists. Both are thought to be useful as adjuvants.

Other suitable TLR-4 ligands, capable of causing a signalling response through TLR-4 (Sabroe et al, JI 2003 p1630-5) are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides and b-defensin-2, muramyl dipeptide (MDP) or F protein of respiratory syncitial virus. In one embodiment the TLR agonist is HSP 60, 70 or 90. Other suitable TLR-4 ligands are as described in WO 2003/011223 and in WO 2003/099195 such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057, ER804058, ER804059, ER804442, ER804680, and ER804764. Suitably said TLR-4 ligand is ER804057.

Toll-like receptors (TLRs) are type I transmembrane receptors, evolutionarily conserved between insects and humans. Ten TLRs have so far been established (TLRs 1-10) (Sabroe et al, JI 2003 p1630-5). Members of the TLR family have similar extracellular and intracellular domains; their extracellular domains have been shown to have leucine—rich repeating sequences, and their intracellular domains are similar to the intracellular region of the interleukin-1 receptor (IL-1R). TLR cells are expressed differentially among immune cells and other cells (including vascular epithelial cells, adipocytes, cardiac myocytes and intestinal epithelial cells). The intracellular domain of the TLRs can interact with the adaptor protein Myd88, which also posses the IL-1R domain in its cytoplasmic region, leading to NF-KB activation of cytokines; this Myd88 pathway is one way by which cytokine release is effected by TLR activation. The main expression of TLRs is in cell types such as antigen presenting cells (eg dendritic cells, macrophages etc).

Activation of dendritic cells by stimulation through the TLRs leads to maturation of dendritic cells, and production of inflammatory cytokines such as IL-12. Research carried out so far has found that TLRs recognise different types of agonists, although some agonists are common to several TLRs. TLR agonists are predominantly derived from bacteria or viruses, and include molecules such as flagellin or bacterial lipopolysaccharide (LPS). By "TLR agonist" it is meant a component which is capable of causing a signalling response through a TLR signalling pathway, either as a direct ligand or indirectly through generation of endogenous or exogenous ligand (Sabroe et al, JI 2003 p1630-5).

In another embodiment, other natural or synthetic agonists of TLR molecules are used as optional additional immunostimulants. These could include, but are not limited to agonists for TLR2, TLR3, TLR7, TLR8 and TLR9.

Accordingly, in one embodiment, the adjuvant and immunogenic composition further comprises an additional immunostimulant which is selected from the group consisting of: a TLR-1 agonist, a TLR-2 agonist, TLR-3 agonist, a TLR-4 agonist, TLR-5 agonist, a TLR-6 agonist, TLR-7 agonist, a TLR-8 agonist, TLR-9 agonist, or a combination thereof.

In one embodiment of the present invention, a TLR agonist is used that is capable of causing a signalling response through TLR-1 (Sabroe et al, JI 2003 p1630-5). Suitably, the TLR agonist capable of causing a signalling response through TLR-1 is selected from: Tri-acylated lipopeptides (LPs); phenol-soluble modulin; *Mycobacterium tuberculosis* LP; S-(2,3-bis(palmitoyloxy)-(2-RS)-propyl)-N-palmitoyl-(R)-Cys-(S)-Ser-(S)-Lys(4)-OH, trihydrochloride (Pam$_3$Cys) LP which mimics the acetylated amino terminus of a bacterial lipoprotein and OspA LP from *Borrelia burgdorferi*.

In an alternative embodiment, a TLR agonist is used that is capable of causing a signalling response through TLR-2 (Sabroe et al, JI 2003 p1630-5). Suitably, the TLR agonist capable of causing a signalling response through TLR-2 is one or more of a lipoprotein, a peptidoglycan, a bacterial lipopeptide from *M tuberculosis, B burgdorferi. T pallidum*; peptidoglycans from species including *Staphylococcus aureus*; lipoteichoic acids, mannuronic acids, *Neisseria* porins, bacterial fimbriae, Yersina virulence factors, CMV virions, measles haemagglutinin, and zymosan from yeast.

In an alternative embodiment, a TLR agonist is used that is capable of causing a signalling response through TLR-3 (Sabroe et al, JI 2003 p1630-5). Suitably, the TLR agonist capable of causing a signalling response through TLR-3 is double stranded RNA (dsRNA), or polyinosinic-polycytidylic acid (Poly IC), a molecular nucleic acid pattern associated with viral infection.

In an alternative embodiment, a TLR agonist is used that is capable of causing a signalling response through TLR-5 (Sabroe et al, JI 2003 p1630-5). Suitably, the TLR agonist capable of causing a signalling response through TLR-5 is bacterial flagellin.

In an alternative embodiment, a TLR agonist is used that is capable of causing a signalling response through TLR-6 (Sabroe et al, JI 2003 p1630-5). Suitably, the TLR agonist capable of causing a signalling response through TLR-6 is mycobacterial lipoprotein, di-acylated LP, and phenol-soluble modulin. Further TLR6 agonists are described in WO2003043572.

In an alternative embodiment, a TLR agonist is used that is capable of causing a signalling response through TLR-7 (Sabroe et al, JI 2003 p1630-5). Suitably, the TLR agonist capable of causing a signalling response through TLR-7 is a single stranded RNA (ssRNA), loxoribine, a guanosine analogue at positions N7 and C8, or an imidazoquinoline compound, or derivative thereof. In one embodiment, the TLR agonist is imiquimod. Further TLR7 agonists are described in WO02085905.

In an alternative embodiment, a TLR agonist is used that is capable of causing a signalling response through TLR-8

(Sabroe et al, JI 2003 p1630-5). Suitably, the TLR agonist capable of causing a signalling response through TLR-8 is a single stranded RNA (ssRNA), an imidazoquinoline molecule with anti-viral activity, for example resiquimod (R848); resiquimod is also capable of recognition by TLR-7. Other TLR-8 agonists which may be used include those described in WO2004071459.

In an alternative embodiment, a TLR agonist is used that is capable of causing a signalling response through TLR-9 (Sabroe et al, JI 2003 p1630-5). In one embodiment, the TLR agonist capable of causing a signalling response through TLR-9 is HSP90. Alternatively, the TLR agonist capable of causing a signalling response through TLR-9 is bacterial or viral DNA, DNA containing unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462. Suitably, CpG nucleotides are CpG oligonucleotides. Suitable oligonucleotides for use in the immunogenic compositions of the present invention are CpG containing oligonucleotides, optionally containing two or more dinucleotide CpG motifs separated by at least three, suitably at least six or more nucleotides. A CpG motif is a Cytosine nucleotide followed by a Guanine nucleotide. The CpG oligonucleotides of the present invention are typically deoxynucleotides. In a specific embodiment the internucleotide in the oligonucleotide is phosphorodithioate, or suitably a phosphorothioate bond, although phosphodiester and other internucleotide bonds are within the scope of the invention. Also included within the scope of the invention are oligonucleotides with mixed internucleotide linkages. Methods for producing phosphorothioate oligonucleotides or phosphorodithioate are described in U.S. Pat. Nos. 5,666,153, 5,278, 302 and WO95/26204. Examples of preferred oligonucleotides have the following sequences. The sequences may contain phosphorothioate modified internucleotide linkages:

```
OLIGO 1 (SEQ ID NO: 1):
TCC ATG ACG TTC CTG ACG TT (CpG 1826)

OLIGO 2 (SEQ ID NO: 2):
TCT CCC AGC GTG CCC CAT (CpG 1758)

OLIGO 3 (SEQ ID NO: 3):
ACC GAT GAC GTC GCC GGT GAC CCC ACC ACG

OLIGO 4 (SEQ ID NO: 4):
TCG TCG TTT TGT CGT TTT GTC GTT (CpG 2006 or 7909)

OLIGO 5 (SEQ ID NO: 5):
TCC ATG ACG TTC CTG ATG CT (CpG 1668)

OLIGO 6 (SEQ ID NO: 6):
TCG ACG TTT TCG CCC CCC GCC G (CpG 5456)
```

Suitably the phosphorothioate backbone CpG7909 (SEQ ID NO:4) is used. Alternative CpG oligonucleotides may comprise the specified sequences above in that they have inconsequential deletions or additions thereto. The CpG oligonucleotides utilised in the present invention may be synthesized by any method known in the art (for example see EP 468520). Conveniently, such oligonucleotides may be synthesized utilising an automated synthesizer.

In another embodiment, the adjuvant and immunogenic composition further comprises a saponin adjuvant. A particularly suitable saponin for use in the present invention is Quil A and its derivatives. Quil A is a saponin preparation isolated from the South American tree *Quillaja Saponaria Molina* and was first described by Dalsgaard et al. in 1974 ("Saponin adjuvants", Archiv. für die gesamte Virusforschung, Vol. 44, Springer Verlag, Berlin, p 243-254) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria Molina*, which induces CD8+ cytotoxic T cells (CTLs), Th1 cells and a predominant IgG2a antibody response and is a preferred saponin in the context of the present invention. In a suitable form of the present invention, the saponin adjuvant within the immunogenic composition is a derivative of *saponaria molina* quil A, such as an immunologically active fraction of Quil A, such as QS-17 or QS-21, suitably QS-21. In one embodiment the compositions of the invention contain the immunologically active saponin fraction in substantially pure form. In one embodiment, the compositions of the invention contain QS21 in substantially pure form, that is to say, the QS21 is at least 90% pure, for example at least 95% pure, or at least 98% pure.

Other useful saponins are derived from the plants *Aesculus hippocastanum* or *Gyophilla struthium*. Other saponins which have been described in the literature include Escin, which has been described in the Merck index (12$^{th}$ ed: entry 3737) as a mixture of saponins occuring in the seed of the horse chestnut tree, Lat: *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190). Fractions of escin have been purified and shown to be biologically active (Yoshikawa M, et al. (Chem Pharm Bull (Tokyo) 1996 August; 44(8):1454-1464)). Sapoalbin from *Gypsophilla struthium* (R. Vochten et al., 1968, J. Pharm. Belg., 42, 213-226) are also an option.

Said immunologically active saponin, such as QS21, can be used in amounts of between 1 and 50 µg, per human dose of the immunogenic composition. Advantageously QS21 is used at a level of about 25 µg, for example between 20-30 µg, suitably between 21-29 µg or between 22-28 µg or between 23-27 µg or between 24-26 µg, or 25 µg. In another embodiment, the human dose of the immunogenic composition comprises QS21 at a level of about 10 µg, for example between 5 and 15 µg, suitably between 6-14 µg, for example between 7-13 µg or between 8-12 µg or between 9-11 µg, or 10 µg. In a further embodiment, the human dose of the immunogenic composition comprises QS21 at a level of about 5 µg, for example between 1-9 µg, or between 2-8 µg or suitably between 3-7 µg or 4-6 µg, or 5 µg.

The dose of 3D-MPL and/or QS21 is suitably able to enhance an immune response to an antigen in a human. In particular a suitable 3D-MPL and/or QS21 amount is that which improves the immunological potential of the composition compared to the unadjuvanted composition, or compared to the composition adjuvanted with another 3D-MPL or QS21 amount, whilst being acceptable from a reactogenicity profile. Typically for human administration the saponin (e.g. QS21) and/or LPS derivative (e.g. 3D-MPL) will be present in a human dose of immunogenic composition in the range of 1 µg-200 µg, such as 10-50 µg, or 1 µg-25 µg per dose.

In a specific embodiment, the adjuvant and immunogenic compositions according to the invention comprise a saponin (e.g. QS21) and/or an LPS derivative (e.g. 3D-MPL) in an oil emulsion described above, together with a sterol (e.g.

cholesterol). These sterols are well known in the art, for example cholesterol is disclosed in the Merck Index, 11th Edn., page 341, as a naturally occurring sterol found in animal fat. Additionally the oil emulsion (in particular the oil-in-water emulsion) may contain Span 85 and/or lecithin and/or tricaprylin. Adjuvants comprising an oil-in-water emulsion, a sterol and a saponin are described in WO 99/12565. Examples of further immunostimulants are described herein and in "Vaccine Design—The Subunit and Adjuvant Approach" 1995, Pharmaceutical Biotechnology, Volume 6, Eds. Powell, M. F., and Newman, M. J., Plenum Press, New York and London, ISBN 0-306-44867-X.

Where squalene and a saponin (optionally QS21) are included, it is of benefit to also include a sterol (optionally cholesterol) to the formulation as this allows a reduction in the total level of oil in the emulsion. This leads to a reduced cost of manufacture, improvement of the overall comfort of the vaccination, and also qualitative and quantitative improvements of the resultant immune responses, such as improved IFN-γ production. Accordingly, the adjuvant system of the present invention typically comprises a ratio of metabolisable oil:saponin (w/w) in the range of 200:1 to 300:1, also the present invention can be used in a "low oil" form the optional range of which is 1:1 to 200:1, optionally 20:1 to 100:1, or substantially 48:1, this vaccine retains the beneficial adjuvant properties of all of the components, with a much reduced reactogenicity profile. Accordingly, some embodiments have a ratio of squalene:QS21 (w/w) in the range of 1:1 to 250:1, or 20:1 to 200:1, or 20:1 to 100:1, or substantially 48:1. Optionally a sterol (e.g. cholesterol) is also included present at a ratio of saponin:sterol as described herein.

Adjuvants wherein an additional immunostimulant is optionally included are particularly suitable for infant and/or elderly vaccine formulations.

The oil-in-water emulsion adjuvant according to the present invention may thus optionally further comprise 5-60, 10-50, or 20-30 µg (e.g. 5-15, 40-50, 10, 20, 30, 40 or 50 µg) lipid A derivative (for instance 3D-MPL). The oil-in-water adjuvant may optionally contain 0.025-2.5, 0.05-1.5, 0.075-0.75, 0.1-0.3, or 0.125-0.25 mg (e.g. 0.2-0.3, 0.1-0.15, 0.25 or 0.125 mg) sterol (for instance cholesterol), 1-60, 10-50, or 20-30 µg (e.g. 1-10, 5-15, 40-50, 10, 20, 30, 40 or 50 µg) lipid A derivative (for instance 3D-MPL or any synthetic derivative of lipid A), and 1-60, 10-50, or 20-30 µg (e.g. 1-10, 5-15, 40-50, 10, 20, 30, 40 or 50 µg) saponin (for instance QS21).

Influenza Viral Strains and Influenza Antigens, Vaccination Regimes, Dosing and Efficacy Criteria Said influenza virus or antigenic preparation thereof may be egg-derived or cell-culture derived. For example, the influenza virus antigen or antigenic preparations thereof according to the invention may be derived from the conventional embryonated egg method, by growing influenza virus in eggs and purifying the harvested allantoic fluid. Eggs can be accumulated in large numbers at short notice. Alternatively, they may be derived from any of the new generation methods using cell or cell culture to grow the virus or express recombinant influenza virus surface antigens. Suitable cell substrates for growing the virus include for example dog kidney cells such as MDCK or cells from a clone of MDCK, MDCK-like cells, monkey kidney cells such as AGMK cells including Vero cells, suitable pig cell lines, or any other mammalian cell type suitable for the production of influenza virus for vaccine purposes. Suitable cell substrates also include human cells e.g. MRC-5 cells or the Per.C6 cell line. Suitable cell substrates are not limited to cell lines; for example primary cells such as chicken embryo fibroblasts and avian cell lines such as chicken or duck cell lines (e.g. EBx cell line such as EB14 or EB24 derived from chicken or duck embryonic stem cells respectively) are also included. Suitable insect cells are Sf9 or Hi5.

In one embodiment, an influenza virus or antigenic preparation thereof for use according to the present invention may be a split influenza virus or split virus antigenic preparation thereof. In an alternative embodiment the influenza preparation may contain another type of inactivated influenza antigen, such as inactivated whole virus or purified HA and NA (subunit vaccine), or an influenza virosome. In a still further embodiment, the influenza virus may be a live attenuated influenza preparation.

A split influenza virus or split virus antigenic preparation thereof for use according to the present invention is suitably an inactivated virus preparation where virus particles are disrupted with detergents or other reagents to solubilise the lipid envelope. Split virus or split virus antigenic preparations thereof are suitably prepared by fragmentation of whole influenza virus, either infectious or inactivated, with solubilising concentrations of organic solvents or detergents and subsequent removal of all or the majority of the solubilising agent and some or most of the viral lipid material. By split virus antigenic preparation thereof is meant a split virus preparation which may have undergone some degree of purification compared to the split virus whilst retaining most of the antigenic properties of the split virus components. For example, when produced in eggs, the split virus may be depleted from egg-contaminating proteins, or when produced in cell culture, the split virus may be depleted from host cell contaminants. A split virus antigenic preparation may comprise split virus antigenic components of more than one viral strain. Vaccines containing split virus (called 'influenza split vaccine') or split virus antigenic preparations generally contain residual matrix protein and nucleoprotein and sometimes lipid, as well as the membrane envelope proteins. Such split virus vaccines will usually contain most or all of the virus structural proteins although not necessarily in the same proportions as they occur in the whole virus. Examples of commercially available split vaccines are for example FLUARIX™, FIUSHIELD™, or FLUZONE™.

Alternatively, the influenza virus may be in the form of a whole virus vaccine. This may prove to be an advantage over a split virus vaccine for a pandemic situation as it avoids the uncertainty over whether a split virus vaccine can be successfully produced for a new strain of influenza virus. For some strains the conventional detergents used for producing the split virus can damage the virus and render it unusable. Although there is always the possibility to use different detergents and/or to develop a different process for producing a split vaccine, this would take time, which may not be available in a pandemic situation. In addition to the greater degree of certainty with a whole virus approach, there is also a greater vaccine production capacity than for split virus since considerable amounts of antigen are lost during additional purification steps necessary for preparing a suitable split vaccine.

In another embodiment, the influenza virus preparation is in the form of a purified sub-unit influenza vaccine. Sub-unit influenza vaccines generally contain the two major envelope proteins, HA and NA, and may have an additional advantage over whole virion vaccines as they are generally less reactogenic, particularly in young vaccinees. Sub-unit vaccines can be produced either recombinantly or purified from disrupted viral particles. Examples of commercially available sub-unit vaccines are for example AGRIPPAL™, or FLUVIRIN™. In a specific embodiment, sub-unit vaccines are prepared from at least one major envelope component such as from haemagglutinin (HA), neuraminidase (NA), or M2, suitably from HA. Suitably they comprise combinations of two antigens or more, such as a combination of at least two of the influenza structural proteins HA, NA, Matrix 1 (M1) and M2, suitably a combination of both HA and NA, optionally comprising M1. Suitably, the influenza components are produced by recombinant DNA technology, i.e. results from, or is expressed from, a nucleic acid resulting from recombinant DNA manipulations, including live recombinant vector (vaccinia) or recombinant subunit protein (baculovirus/insect cells, mammalian cells, avian cells, yeast, plants or bacteria). Suitable insect cells are *Spodoptera frugiperda* (Sf9) insect cells or High Five (Hi5) insect cells developed from *Trichoplusia ni* (Invitrogen) and suitable baculovirus are *Autographa californica* nuclear polyhedrosis virus (AcNPV) (Baculogold, Becton Dickinson, PharMingen) or the so-called Bacmid system.

In one embodiment, the influenza virus preparation is in the form of a virosome. Virosomes are spherical, unilamellar vesicles which retain the functional viral envelope glycoproteins HA and NA in authentic conformation, intercalated in the virosomes' phospholipids bilayer membrane. Examples of commercially available virosomal vaccines are for example INFLEXAL V™, or INVAVAC™.

In another embodiment, the sub-unit influenza components are expressed in the form of virus-like-particles (VLP) or capsomers, suitably plant-made or insect cells-made VLPs. VLPs present the antigens in their native form. The VLP sub-unit technology may be based entirely on influenza proteins, or may rely on other virus such as the murine leukaemia virus (MLV) and may therefore comprise a non-influenza antigen such as MLV gag protein. A suitable VLP comprises at least one, suitably at least two influenza proteins, optionally with other influenza or non-influenza proteins, such as M1 and HA, HA and NA, HA, NA and M1 or HA, NA and MLV gag. It may be produced either in plant cells or insect cells. VLPs can also carry antigens from more than one influenza strain, such as VLPs made from two seasonal strains (e.g. H1N1 and H3N2) or from one seasonal and one pandemic strain (e.g. H3N2 and H5N1) for example.

Accordingly, in one embodiment the immunogenic composition of the invention comprises an influenza virus antigen or antigenic preparation thereof from influenza virus grown on eggs or on cell culture. In another embodiment, said influenza virus antigen or antigenic preparation thereof comprises a whole virus, a split virus, a virosome or one or more purified antigen chosen from: HA, NA, M1, M2. In another embodiment, said purified antigen(s) are prepared from influenza virus grown in mammalian, avian or insect cells. Specifically, said purified antigen(s) are recombinantly produced. They can be in the form of a Virus-like-particle.

The influenza virus antigen or antigenic preparation thereof may be produced by any of a number of commercially applicable processes, for example the split flu process described in patent no. DD 300 833 and DD 211 444, incorporated herein by reference. Traditionally split flu was produced using a solvent/detergent treatment, such as tri-n-butyl phosphate, or diethylether in combination with Tween™ (known as "Tween-ether" splitting) and this process is still used in some production facilities. Other splitting agents now employed include detergents or proteolytic enzymes or bile salts, for example sodium deoxycholate as described in patent no. DD 155 875, incorporated herein by reference. Detergents that can be used as splitting agents include cationic detergents e.g. cetyl trimethyl ammonium bromide (CTAB), other ionic detergents e.g. laurylsulfate, taurodeoxycholate, or non-ionic detergents such as the ones described above including Triton X-100 (for example in a process described in Lina et al, 2000, Biologicals 28, 95-103) and Triton N-101, or combinations of any two or more detergents.

The preparation process for a split vaccine may include a number of different filtration and/or other separation steps such as ultracentrifugation, ultrafiltration, zonal centrifugation and chromatography (e.g. ion exchange) steps in a variety of combinations, and optionally an inactivation step eg with heat, formaldehyde or β-propiolactone or U.V. which may be carried out before or after splitting. The splitting process may be carried out as a batch, continuous or semi-continuous process. A preferred splitting and purification process for a split immunogenic composition is described in WO 02/097072.

Preferred split flu vaccine antigen preparations according to the invention comprise a residual amount of Tween 80 and/or Triton X-100 remaining from the production process, although these may be added or their concentrations adjusted after preparation of the split antigen. In one embodiment of both Tween 80 and Triton X-100 are present. The preferred ranges for the final concentrations of these non-ionic surfactants in the vaccine dose, arising from the antigenic preparation, are:

Tween 80: 0.01 to 1%, or about 0.1% (v/v)
Triton X-100: 0.001 to 0.1 (% w/v), or 0.005 to 0.02% (w/v).

In a specific embodiment, the final concentration for Tween 80 arising from the antigenic preparation, ranges from 0.025%-0.09% w/v. In another specific embodiment, the antigen is provided as a 2 fold concentrated mixture, which has a Tween 80 concentration ranging from 0.025%-0.2% (w/v) and has to be diluted two times upon final formulation with the adjuvanted (or the buffer in the control formulation).

In another specific embodiment, the final concentration for Triton X-100 ranges from 0.004%-0.017% w/v. In another specific embodiment, the antigen is provided as a 2 fold concentrated mixture, which has a Triton X-100 concentration ranging from 0.005%-0.034% (w/v) and has to be diluted two times upon final formulation with the adjuvanted (or the buffer in the control formulation).

In one embodiment, the influenza preparation is prepared in the presence of low level of thiomersal, or in the absence of thiomersal. In another embodiment, the resulting influenza preparation is stable in the absence of organomercurial preservatives, in particular the preparation contains no residual thiomersal. In particular the influenza virus preparation comprises a haemagglutinin antigen stabilised in the absence of thiomersal, or at low levels of thiomersal (generally 5 μg/ml or less). Specifically the stabilization of B influenza strain is performed by a derivative of alpha tocopherol, such as alpha tocopherol succinate (also known as vitamin E succinate, i.e. VES). Such preparations and methods to prepare them are disclosed in WO 02/097072.

A preferred composition contains three inactivated split virion antigens prepared from the WHO recommended strains of the appropriate influenza season.

In one embodiment, the influenza virus or antigenic preparation thereof and the adjuvant according to the invention are contained in the same container. It is referred to as 'one vial approach'. In another embodiment, the vial is a pre-filled syringe. In an alternative embodiment, the influenza virus or antigenic preparation thereof and adjuvant according to the invention are contained in separate containers or vials and admixed shortly before or upon administration into the subject. It is referred to as 'two vials approach'. Suitably the 2 component vaccine consists of 0.5 ml of concentrated inactivated split virion antigens presented in a type I glass vial (antigen container) and of a pre-filled type I glass syringe containing 0.5 ml of the adjuvant (adjuvant container). Alternatively the vaccine is a 2 components vaccine presented in 2 vials (one for the antigen one for the adjuvant, of 10 doses each) for mixture prior to the administration to the first patient within 24 hours at room temperature and subsequent storage at 4° C. for a short period of time (e.g. up to one week) for subsequent administration. At the time of injection, the content of the multi-dose vial or the syringe containing the adjuvant is injected into the vial that contains the concentrated split virion antigen. After mixing the content is withdrawn into the syringe and the needle is replaced by an intramuscular needle. One dose of the reconstituted adjuvanted influenza candidate vaccine corresponds to 0.5 ml.

In one embodiment, each human dose of the immunogenic composition contains a 15 μg of HA per influenza strain per dose, as determined by SRID. This is particularly useful for the elderly population.

An important aspect of the present invention is the fact that the influenza antigen(s) can be used at lower amounts than had previously been thought useful, suitably at a level of less than 15 μg HA per strain of virus, for example between 1 and 10 μg HA per strain, per human dose of the immunogenic composition.

Accordingly, in one embodiment, each human dose of the immunogenic composition contains a low dose of haemagglutinin (HA), defined as an amount of less than 15 μg of HA per dose, suitably less than 10 μg, as measured by single radial immunodiffusion (SRD) (J. M. Wood et al.: J. Biol. Stand. 5 (1977) 237-247; J. M. Wood et al., J. Biol. Stand. 9 (1981) 317-330). In a specific embodiment, the human dose of the immunogenic composition comprises a dose of haemagglutinin (HA) per strain at a level of about 10 μg, for example between 5 and 15 μg, suitably between 6 and 14 μg, for example between 7 and 13 μg or between 8 and 12 μg or between 9 and 11 μg, or 10 μg. In a further embodiment, the human dose of the immunogenic composition comprises a dose of haemagglutinin (HA) per strain at a level of about 5 μg, for example between 1 and 9 μg, or between 2 and 8 μg or suitably between 3 and 7 μg or 4 and 6 μg, or 5 μg. Suitable amounts are 1.9 μg, 2.5 μg, 3.8 μg, 5.0 μg, 7.5 μg, or 10 μg HA or any suitable amount of HA lower than 15 μg which would have be determined such that the vaccine composition meets the efficacy criteria as defined herein. Advantageously an HA dose of 1 μg of HA or even less such as 0.5 μg of HA that would allow meeting the regulatory criteria defined in Tables 2 may be used. A suitable amount of HA is for example any of 1, 2, 3, 4, 5, 6, 7, 8, 9, 10, 11, 12, 13, 14, μg (w/v) per influenza strain per human dose of the immunogenic composition. Said low amount of HA may be as low as practically feasible provided that it allows to formulate a vaccine which meets the international e.g. EU or FDA criteria for efficacy, as detailed below (see Table 2 and the specific parameters as set forth).

A vaccine dose of 0.5 ml is suitably used. A vaccine dose of 1 ml (0.5 ml adjuvant plus 0.5 ml antigen preparation) is also suitable. Advantageously, a vaccine dose according to the invention, in particular a low HA amount vaccine, may be provided in a smaller volume than the conventional injected split flu vaccines, which are generally about 0.5, 0.7 or 1 ml per dose. The low volume doses according to the invention are suitably below 500 μl, typically below 300 μl and suitably not more than about 200 μl or less per dose. Slight adaptation of the dose volume will be made routinely depending on the HA concentration in the original bulk sample, or depending on the delivery route with smaller doses being given by the intranasal or intradermal route, or depending on the target population (for example infants may receive half of an adult human dose).

Suitably the influenza virus strain or strains to be included in the immunogenic or vaccine composition is/are interpandemic (seasonal) strain(s), or strain(s) being associated with a pandemic outbreak or having the potential to be associated with a pandemic outbreak, or suitably, in a multivalent composition, a mixture of these strains.

Interpandemic strains are for example strains which circulate globally during interpandemic periods such as but not limited to: H1N1, H1N2, H3N2 or B. Commercially available influenza vaccines are a trivalent combination including one influenza B strain and two influenza A strains (H1N1, H3N2).

The features of an influenza virus strain that give it the potential to cause a pandemic or an outbreak of influenza disease associated with pandemic influenza strains are: it contains a new haemagglutinin compared to the haemagglutinin in the currently circulating strains and therefore nearly all people are immunologically naive; it is capable of being transmitted horizontally in the human population; and it is pathogenic for humans. A new haemagglutinin may be one which has not been evident in the human population for an extended period of time, probably a number of decades, such as H2. Or it may be a haemagglutinin that has not been circulating in the human population before, for example H5, H9, H7 or H6 which are found in avian species (birds). In either case the majority, or at least a large proportion of, or even the entire population has not previously encountered the antigen and is immunologically naive to it. At present, the influenza A virus that has been identified by the WHO as one that potentially could cause a pandemic in humans is the highly pathogenic H5N1 avian influenza virus. Therefore, the pandemic vaccine according to the invention will suitably comprise H5N1 virus. Two other suitable strains for inclusion into the claimed composition are H9N2 or H7N1.

Certain parties are generally at an increased risk of becoming infected with influenza in a pandemic situation. The elderly, the chronically ill and small children are particularly susceptible but many young and apparently healthy people are also at risk. For H2 influenza, the part of the population born after 1968 is at an increased risk. It is important for these groups to be protected effectively as soon as possible and in a simple way.

Another group of people who are at increased risk are travelers. People travel more today than ever before and the regions where most new viruses emerge, China and South East Asia, have become popular travel destinations in recent years. This change in travel patterns enables new viruses to reach around the globe in a matter of weeks rather than months or years.

Thus for these groups of people there is a particular need for vaccination to protect against influenza in a pandemic situation or a potential pandemic situation. Suitable strains are, but not limited to: H5N1, H5N8, H5N9, H7N4, H9N2, H7N7, H7N3, H2N2 and H7N1. Other pandemic strains in human: H7N3 (2 cases reported in Canada), H10N7 (2 cases reported in Egypt) and H5N2 (1 case reported in Japan) and H7N2. An influenza strain which is a pandemic strain or a strain susceptible to be associated with a pandemics will be referred to in short in this document as a "pandemic strain".

The influenza medicament of the invention suitably meets certain international criteria for vaccines. Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). *Note for harmonization of requirements for influenza vaccines,* 1997. CHMP/BWP/214/96 circular No 96-0666:1-22) for clinical trials related to annual licensing procedures of influenza vaccines (Table 2). The requirements are different for adult populations (18-60 years) and elderly populations (>60 years) (Table 2). For interpandemic influenza vaccines, at least one of the assessments (seroconversion factor, seroconversion rate, seroprotection rate) should meet the European requirements, for all strains of influenza included in the vaccine. The proportion of titres equal or greater than 1:40 is regarded most relevant because these titres are expected to be the best correlate of protection [Beyer W et al. 1998. Clin Drug Invest.; 15:1-12].

As specified in the "Guideline on dossier structure and content for pandemic influenza vaccine marketing authorisation application. (CHMP/VEG/4717/03, Apr. 5, 2004, or more recently EMEA/CHMP/VWP/263499/2006 of 24 Jan. 2007 entitled 'Guidelines on flu vaccines prepared from viruses with a potential to cause a pandemic', available on www.emea.eu.int), in the absence of specific criteria for influenza vaccines derived from non circulating strains, it is anticipated that a pandemic candidate vaccine should (at least) be able to elicit sufficient immunological responses to meet suitably all three of the current standards set for existing vaccines in unprimed adults or elderly subjects, after two doses of vaccine. The EMEA Guideline describes the situation that in case of a pandemic the population will be immunologically naive and therefore it is assumed that all three CHMP criteria for seasonal vaccines will be fulfilled by pandemic candidate vaccines. No explicit requirement to prove it in pre-vaccination seronegative subjects is required.

The compositions of the present invention suitably meet at least one such criteria for the pandemic strain included in the composition (one criteria is enough to obtain approval), suitably at least two, or typically at least all three criteria for protection as set forth in Table 2A.

TABLE 2A (CHMP criteria)

|  | 18-60 years | >60 years |
| --- | --- | --- |
| Seroconversion rate* | >40% | >30% |
| Conversion factor** | >2.5 | >2.0 |
| Protection rate*** | >70% | >60% |

*Seroconversion rate is defined as the proportion of subjects in each group having a protective post-vaccination titre ≥1:40. The seroconversion rate simply put is the % of subjects who have an HI titre before vaccination of <1:10 and ≥1:40 after vaccination. However, if the initial titre is ≥1:10 then there needs to be at least a fourfold increase in the amount of antibody after vaccination.
**Conversion factor is defined as the fold increase in serum HI geometric mean titres (GMTs) after vaccination, for each vaccine strain.
***Protection rate is defined as the proportion of subjects who were either seronegative prior to vaccination and have a (protective) post-vaccination HI titre of ≥1:40 or who were seropositive prior to vaccination and have a significant 4-fold increase in titre post-vaccination; it is normally accepted as indicating protection.

A 70% seroprotection rate is defined by the European health regulatory authority (CHMP—Committee for Medicinal Products for Human Use) is one of three criteria normally required to be met for an annual seasonal influenza vaccine and which CHMP is also expecting a pandemic candidate vaccine to meet. However, mathematical modelling has indicated that a vaccine that is, at the population level, only 30% efficient against certain drifted strains may also be of benefit in helping to reduce the magnitude of a pandemic and that a pandemic vaccination campaign using a (pre-pandemic) vaccine with 30% efficacy against the pandemic strain (cross-protection of 30%) could effectively reduce the clinical attack rate by 75% and consequently morbidity/mortality within the population (Ferguson et al, Nature 2006).

FDA has published a draft guidance (CBER draft criteria) (available from the Office of Communication, Training and Manufacturers Assistance (HFM-40), 1401 Rockville Pike, Suite 200N, Rockville, Md. 20852-1448, or by calling 1-800-835-4709 or 301-827-1800, or from the Internet at http://www.fda.gov/cber/guidelines.htm) on Clinical Data Needed to Support the Licensure of Pandemic Influenza Vaccines, and the proposed criteria are also based on the CHMP criteria. FDA uses slightly different age cut-off points. Appropriate endpoints similarly include: 1) the percent of subjects achieving an HI antibody titer 1:40, and 2) rates of seroconversion, defined as a four-fold rise in HI antibody titer post-vaccination. The geometric mean titer (GMT) should be included in the results, but the data should include not only the point estimate, but also the lower bound of the 95% confidence interval of the incidence rate of seroconversion, and the day 42 incidence rate of HI titers 1:40 must exceed the target value. These data and the 95% confidence intervals (CI) of the point estimates of these evaluations should therefore be provided. FDA draft guidance requires that both targets be met. This is summarised in Table 2B.

TABLE 2B (CBER draft criteria)

|  | 18-64 years | >64 years |
| --- | --- | --- |
| Seroconversion rate * | >40% | >30% |
| Rate of HI titers ≥1:40 | >70% | >60% |

* The seroconversion rate is is defined as: a) for subjects with a baseline titer ≥1:10, a 4-fold or greater rise; or b) for subjects with a baseline titer <1:10, a rise to ≥1:40. These criteria must be met at the lower bound of the 95% CI for the true value.

Accordingly, in one aspect of the invention, it is provided for a composition, method or use as claimed herein wherein said immune response or protection induced by the administration of the contemplated influenza composition meets all three EU regulatory criteria for influenza vaccine efficacy. Suitably at least one, suitably two, or three of following criteria are met for the strain or each strain of the composition:

a seroconversion rate of >50%, of >60%, of >70%, suitably of >80% or >90% in the adult population (aged 18-60), and/or suitably also in the elderly population (aged >60 years);

a protection rate of >75%, of >80%, of >85%, suitably of >90% in the adult population (aged 18-60), and/or suitably also in the elderly population (aged >60 years);

a conversion factor of >4.0, of >5.0, of >6.0, of >7.0, of >8.0, of >9.0 or of 10 or above 10 in the adult population (aged 18-60), and/or suitably also in the elderly population (aged >60 years).

In a specific embodiment the composition according to the invention will meet both a seroconversion rate of >60%, or >70%, or suitably >80% and a protection rate of >75%, suitably of >80% in the adult population. In another specific embodiment the composition according to the invention will meet both a conversion factor of >5.0, or >7.0 or suitably >10.0 and a seroconversion rate of >60%, or >70%, or suitably >80% in the adult population. In another specific embodiment, the composition according to the invention will meet both a conversion factor of >5.0, or >7.0 or suitably >10.0, and a protection rate of >75%, suitably >80% in the adult population. In still another specific embodiment the composition according to the invention will meet both a conversion factor of 10.0 or above, a seroconversion rate of 80% or above, and a protection rate of 80% or above.

In another embodiment, the claimed vaccine, suitably a pre-pandemic vaccine containing a pandemic strain or a strain susceptible to be associated with a pandemic, will have 30% efficacy against the circulating pandemic strain (cross-protection of 30%). In particular the claimed vaccine will meet a seroprotection rate of at least 30% against drifted strains, suitably of at least 40%, or >50% or >60% against drifted strains. Suitably the seroprotection rate will be >70%, or suitably >80% against drift strains. Said pre-pandemic vaccine, capable of conferring cross-protection, will be able to reduce substantially the overall infection attack rate, by at least 50%, or suitably at least 75%, and consequently morbidity/mortality within the population.

In still another embodiment, the claimed adjuvanted vaccine is able to induce neutralizing antibodies in at least 50% of subjects, at least 60%, suitable at least 70%, or suitably in more than 75% of subjects against a drifted strain or a strain from a different clade. Suitably this effect is achieved with a low dose of antigen, such as with 7.5 µg HA or even a lower antigen dose such as 3.8 µg or 1.9 µg of HA.

Suitably any or all of such criteria are also met for other populations, such as in children and in any immuno-compromised population.

In one aspect of the invention, the human dose of the immunogenic composition contains an haemagglutinin (HA) from a single influenza strain, and is referred to as a "monovalent" influenza composition. In another aspect of the invention, the human dose of the immunogenic composition comprises haemagglutinin (HA) from more than one influenza strain, and is referred to as a "multivalent" influenza composition. A suitable multivalent composition according to the invention is a bivalent composition (comprising haemagglutinin (HA) from two influenza virus strains such as but not exclusively two strains associated to a pandemics or susceptible to be associated with a pandemic, e.g. H5=H2), a trivalent composition (comprising haemagglutinin (HA) from three influenza virus strains, optionally from two A strains, and one B strain such as but not limited to B/yamagata or B/Victoria), a quadrivalent composition (comprising haemagglutinin (HA) from four influenza virus strains) or a pentavalent composition (comprising haemagglutinin (HA) from five influenza virus strains). A suitable quadrivalent composition comprises haemagglutinin from two A strains and two B strains from different lineage (such as B/yamagata or B/Victoria). Alternatively a quadrivalent composition comprises haemagglutinin from three A strains (optionally H1N1, H3N2, and one A strain associated to a pandemic or susceptible to be associated to a pandemic) and one B strain (such as B/yamagata or B/Victoria). Another alternative quadrivalent composition comprises haemagglutinin from four A strains from a strain associated to a pandemic or susceptible to be associated to a pandemic, such as avian strains such as H5+H2+H7+H9. Specifically a multivalent adjuvanted pandemic composition such as a pandemic bi-valent (e.g. H5+H2) or trivalent or quadrivalent (e.g. H5+H2+H7+H9) offers the advantage of a pre-emptive immunisation against pandemic influenza A threats subtypes and durable priming against threat subtypes. Typically two doses are given from 6 weeks of age using a convenient schedule (e.g., 6-12 months apart), and optionally a periodic booster foreseen (e.g., 10 yrs). Optionally, such a pandemic vaccine may be combined with a seasonal vaccine.

A multivalent composition can also comprise more than 5 influenza strains such as 6, 7, 8, 9 or 10 influenza strains.

When two B strains are used in a multivalent seasonal composition, they can be from two different lineages (optionally from B/Victoria and B/Yamagata). At least one of said B strain, suitably both B strains, will be from a circulating lineage. Such a composition is particularly suitable for children. Suitably when the multivalent composition for use in children includes two B strains the quantity of antigen normally allotted to the B strain is divided among the two B strains. Specifically, the adjuvanted quadrivalent (H1+H3+ both B lineages) influenza vaccine offers the advantage of enhanced prophylaxis for naïve children as its superior efficacy compared to unadjuvanted vaccines (in terms of both homologous and drift protection, and its efficacy against two circulating B lineages) and of possible year-round immunization based on age. One dose or two doses are suitably administered as early as from the age of 6 weeks, or between 6 to 35 months.

In a specific embodiment, the human dose of the immunogenic composition is a trivalent immunogenic or vaccine composition comprising haemagglutinin (HA) from two A strains (optionally H1N1, H3N2) and one B strain. Suitably the HA per strain is a low amount of HA (optionally 10 µg HA per strain or below) and is as defined above. Suitably the HA per strain is at about or below 5 µg, at about 2.5 µg or below. The adjuvant is as defined herein and in particular as defined in Table 1. Suitably the adjuvant composition is an oil-in-water emulsion comprising squalene, alpha-tocopherol, and polysorbate 80 at an amount of between 5-6 mg, between 5-6 mg and between 2-3 mg per dose, respectively. Alternatively, the adjuvant composition is an oil-in-water emulsion comprising squalene, alpha-tocopherol, and polysorbate 80 at an amount of between 2.5-3.5 mg, between 2-3 mg and between 1-2 mg per dose, respectively. These adjuvanted immunogenic compositions or vaccines are particularly suitable for the adult (18-60 years) or older children (3-17 years) population, and may provide cross-protection against H3N2 drift variants and against B strain from a different lineage.

In another specific embodiment, the human dose of the immunogenic composition is a quadrivalent immunogenic or vaccine composition comprising haemagglutinin (HA) from two A strains (optionally H1N1, H3N2) and two B strains (optionally from a different lineage, such as from B/Victoria and B/Yamagata). Suitably the HA per strain per dose is at about 15 µg. Suitably the HA per strain is a low amount of HA (optionally at about 10 µg HA per strain per dose or below, so as to achieve a maximum of 40-45 µg HA per dose) and is as defined above. Suitably the HA per strain is at about or below 5 µg, at about 2.5 µg or below. The adjuvant is as defined herein and in particular as defined in Table 1. Suitably the adjuvant composition is an oil-in-water emulsion comprising squalene, alpha-tocopherol, and polysorbate 80 at an amount of between 5-6 mg, between 5-6 mg and between 2-3 mg per dose, respectively. Alternatively, the adjuvant composition is an oil-in-water emulsion comprising squalene, alpha-tocopherol, and polysorbate 80 at an amount of between 2.5-3.5 mg, between 2-3 mg and between 1-2 mg per dose, respectively. Such a composition comprising a second B strain is particularly suitable for very young children especially where prior exposure or priming is important. The adjuvant will provide the advantage to deliver to this population an increased protection. The human dose of the immunogenic composition for the children population is suitably a half of an adult human dose, and will suitably comprise 2.5 µg HA per strain, and an oil-in-water emulsion comprising squalene, alpha-tocopherol, and polysorbate 80 at an amount of between 2.5-3.5 mg, between 2-3 mg and between 1-2 mg per dose.

Alternatively said additional B strain, suitably with the characteristics and at the amount defined above in respect of the quadrivalent composition, may be added in the form of a monovalent composition to a trivalent composition as described above. Using a low amount of HA such as at or below 10 µg, or at or below 5 µg, or, optionally for young children, at or below 2.5 µg would have the advantage to limit the impact of an addition influenza strain on the global vaccine supply. Suitably when two B strains are included in the vaccine composition the quantity of antigen normally allotted to the B strain is divided among the two B strains.

In another specific embodiment, the human dose of the immunogenic composition is a quadrivalent immunogenic or vaccine composition comprising haemagglutinin (HA) from two interpandemic A strains (optionally H1N1, H3N2), one B strain and one A strain associated with a pandemic or susceptible to be associated with a pandemic (optionally H5N1, H9N2, H7N7, H5N8, H5N9, H7N4, H7N3, H2N2, H10N7, H5N2, H7N2 and H7N1). Suitably the HA per strain is a low amount of HA (optionally 10 µg HA per strain or below) and is as defined above. Suitably the HA per strain is at about or below 5 µg, at about 2.5 µg or below. The adjuvant is as defined herein and in particular as defined in Table 1. Suitably the adjuvant composition is an oil-in-water emulsion comprising squalene, alpha-tocopherol, and polysorbate 80 at an amount of between 5-6 mg, between 5-6 mg and between 2-3 mg per dose, respectively. Alternatively, the adjuvant composition is an oil-in-water emulsion comprising squalene, alpha-tocopherol, and polysorbate 80 at an amount of between 2.5-3.5 mg, between 2-3 mg and between 1-2 mg per dose, respectively.

In another specific embodiment, the human dose of the immunogenic composition is a quadrivalent immunogenic or vaccine composition comprising haemagglutinin (HA) from three interpandemic A strains (optionally H1N1, and two H3N2 strains) and one B strain. Suitably the HA per strain is a low amount of HA (optionally 10 µg HA per strain or below) and is as defined above. Suitably the HA per strain is at about or below 5 µg, at about 2.5 µg or below. The adjuvant is as defined herein and in particular as defined in Table 1. Suitably the adjuvant composition is an oil-in-water emulsion comprising squalene, alpha-tocopherol, and polysorbate 80 at an amount of between 5-6 mg, between 5-6 mg and between 2-3 mg per dose, respectively. Alternatively, the adjuvant composition is an oil-in-water emulsion comprising squalene, alpha-tocopherol, and polysorbate 80 at an amount of between 2.5-3.5 mg, between 2-3 mg and between 1-2 mg per dose, respectively. Such a composition comprising a third seasonal A strain is particularly suitable for very young children. Suitably, two of the three interpandemic strains are H3N2 strain, the second H3N2 strain being of a proximate, or a distant, clade compared to the first H3N2 strain. The adjuvant will provide the advantage to deliver to this population an increased protection. The human dose of the immunogenic composition for the children population is suitably a half of an adult human dose, and will suitably comprise 2.5 µg HA per strain, and an oil-in-water emulsion comprising squalene, alpha-tocopherol, and polysorbate 80 at an amount of between 2.5-3.5 mg, between 2-3 mg and between 1-2 mg per dose.

In another specific embodiment, the human dose of the immunogenic composition is a pentavalent immunogenic or vaccine composition comprising haemagglutinin (HA) from two interpandemic A strains (optionally H1N1, H3N2), two B strains (optionally from a different lineage, such as from B/Victoria and B/Yamagata) and one A strain associated to a pandemic or susceptible to be associated with a pandemic (optionally H5N1, H9N2, H5N8, H5N9, H7N4, H7N7, H7N3, H2N2, H10N7, H5N2 and H7N1). Suitably the HA per strain per dose is at about 15 µg. Suitably the HA per strain is a low amount of HA (optionally at about 10 µg HA per strain per dose or below, so as to achieve a maximum of 40-45 µg HA per dose) and is as defined above. Suitably the HA per strain is at about or below 5 µg, at about 2.5 µg or below. The adjuvant is as defined herein and in particular as defined in Table 1. Suitably the adjuvant composition is an oil-in-water emulsion comprising squalene, alpha-tocopherol, and polysorbate 80 at an amount of between 5-6 mg, between 5-6 mg and between 2-3 mg per dose, respectively. Alternatively, the adjuvant composition is an oil-in-water emulsion comprising squalene, alpha-tocopherol, and polysorbate 80 at an amount of between 2.5-3.5 mg, between 2-3 mg and between 1-2 mg per dose, respectively.

In another specific embodiment, the human dose of the immunogenic composition is a pentavalent immunogenic or vaccine composition comprising haemagglutinin (HA) from three interpandemic A strains (optionally H1N1, and two H3N2 strains) and two B strains (optionally from a different lineage, such as from B/Victoria and B/Yamagata). Suitably the HA per strain is a low amount of HA (optionally 10 µg HA per strain or below) and is as defined above. Suitably the HA per strain is at about or below 5 µg, at about 2.5 µg or below. The adjuvant is as defined herein and in particular as defined in Table 1. Suitably the adjuvant composition is an oil-in-water emulsion comprising squalene, alpha-tocopherol, and polysorbate 80 at an amount of between 5-6 mg, between 5-6 mg and between 2-3 mg per dose, respectively. Alternatively, the adjuvant composition is an oil-in-water emulsion comprising squalene, alpha-tocopherol, and polysorbate 80 at an amount of between 2.5-3.5 mg, between 2-3 mg and between 1-2 mg per dose, respectively.

Accordingly in a specific embodiment the invention provides an influenza immunogenic composition comprising squalene and HA wherein the weight ratio squalene:total amount of HA (all influenza strains included) is in the range of between about 50-150 or about 150-400 (e.g. 200-300). Such compositions are suitably but not exclusively for use in the elderly population and best balances reactogenicity and immunogenicity. In another embodiment, the invention provides an influenza immunogenic composition comprising squalene and HA wherein the weight ratio squalene:total amount of HA (all influenza strains included) is between about 50-400, e.g. about 50-100, 75-150, 75-200, 75-400, 100-200, 100-250 or 200-400. The ratio will suitably be such that at least two, suitably all three criteria (Table 2) for protection will be met for a specific population. A TLR agonist, suitably a TLR-4 (e.g. chosen from: 3D-MPL, MPL; an AGP molecule such as RC527 or RC529, or ER804057) or TLR-9 (suitably a CpG oligonucleotide e.g. CpG7909) agonist may be included. Suitable weight ratios squalene:TLR-4 are of between about 100-450, e.g. 50-250, 50-150, 100-250, 200-250, 350-450. Suitable weight ratios squalene:TLR-9 are of between about 50-1000, e.g. 50-500, 100-1000, 100-400, 400-600. The HA can be from seasonal influenza strains. Such compositions are suitably but not exclusively for use in the adult or pediatric populations and best balance reactogenicity and immunogenicity. Suitably the HA is from at least three, at least four influenza strains. Suitably three seasonale (e.g. H1N1, H3N2, B) strains are present. Suitably when four strains are present they are from the group of: four seasonal strains (e.g. H1N1, H3N2, two B strains; or H1N1, B, two H3N2 strains) or the group of one pandemic (e.g. avian) strain plus three seasonal strains (e.g. H1N1, H3N2, B).

All the claimed adjuvanted immunogenic compositions or vaccine can advantageously rely on the adjuvant to provide a persistent immune response, over a period of time exceeding 6 months, suitably 12 months after the vaccination.

Suitably the above response(s) is(are) obtained after one dose, or typically after two doses administered during the same on-going primary immune response. It is a particular advantage of the claimed composition that the immune response is obtained after only one dose of adjuvanted composition or vaccine. It is also suitable that two doses are administered during the same on-going primary immune response, suitably for naïve or immuno-compromised populations or individuals. Suitably, two doses might be needed in children, in particular below the age of 6 years or 9-10 years, not previously vaccinated.

Accordingly, there is provided in one aspect of the invention the use of a non-live pandemic influenza virus antigen preparation, in particular a split influenza virus or antigenic preparation thereof, in the manufacture of a vaccine composition for a one-dose or a two-doses vaccination against influenza, wherein the one-dose or the two-doses vaccination generates an immune response which meets at least one, suitably two or three, international regulatory requirements for influenza vaccines. In another particular embodiment said one-dose vaccination also or additionally generates a CD4 T cell immune response and/or a B cell memory response which is higher than that obtained with the non adjuvanted vaccine. In a particular embodiment said immune response is a cross-reactive antibody response or a cross-reactive CD4 T cell response or both. In a specific embodiment the human patient is immunologically naïve (i.e. does not have pre-existing immunity) to the vaccinating strain. Specifically the vaccine composition contains a low HA antigen amount and an oil-in-water emulsion adjuvant with components at a level lower than what had previously been thought useful, and which amounts are as defined herein. Specifically the vaccine composition is as defined herein. In particular the immunogenic properties of the vaccine composition are as defined herein. Suitably the vaccine is administered intramuscularly.

Immunogenic Properties of the Immunogenic Composition Used for the Vaccination (Optionally the First Vaccination) of the Present Invention In the present invention the adjuvanted immunogenic composition is suitably capable of inducing an improved CD4+ T-cell immune response against the or against at least one of the component antigen(s) or antigenic composition compared to the CD4+ T-cell immune response obtained with the corresponding composition which is non-adjuvanted, i.e. does not contain any exogeneous adjuvant (herein also referred to as "plain composition"). In a specific embodiment, where the immunogenic influenza composition is from several influenza strains, one of which being either a second B strain, or a third interpandemic A strain, or a pandemic strain, said improved CD4+ T-cell immune response is against at least one of these strains. In another embodiment, the adjuvanted immunogenic composition, where the adjuvant component(s) are at a lower level than previously thought useful and is/are typically as defined above, is suitably capable of inducing a CD4+ T-cell immune response against the or against at least one of the component antigen(s) or antigenic composition, at least comparable to that obtained with compositions adjuvanted with some of the prior art adjuvants. This characteristic will be referred to as "comparable CD4+ T-cell immune response" in the text below.

By "improved CD4+ T-cell immune response" is meant that a higher CD4+ response is obtained in a human patient after administration of the adjuvanted immunogenic composition as herein defined than that obtained after administration of the same composition without adjuvant. For example, a higher CD4+ T-cell response is obtained in a human patient upon administration of an immunogenic composition comprising an influenza virus or antigenic preparation thereof together with an oil-in-water emulsion adjuvant comprising a metabolisable oil (optionally squalene), a tocol (optionally alpha tocopherol), and an emulsifying agent (optionally a polyoxyethylene sorbitan monooleate such as Tween 80™ or Polysorbate 80™), compared to the response induced after administration of an immunogenic composition comprising an influenza virus or antigenic preparation thereof which is non-adjuvanted. Such adjuvanted formulation will advantageously be used to induce anti-influenza CD4+ T-cell response capable of detection of influenza epitopes presented by MHC class II molecules.

Suitably said immunological response induced by an adjuvanted split influenza composition for use in the present invention is higher than the immunological response induced by any other non-adjuvanted influenza conventional vaccine, such as sub-unit influenza vaccine or whole influenza virus vaccine.

In particular but not exclusively, said "improved CD4+ T-cell immune response" or "comparable CD4+ T-cell immune response" is obtained in an immunologically unprimed patient, i.e. a patient who is seronegative to said influenza virus or antigen. This seronegativity may be the result of said patient having never faced such virus or antigen (so-called 'naive' patient) or, alternatively, having failed to respond to said antigen once encountered. Suitably said improved CD4+ T-cell immune response is obtained in an immunocompromised subject such as an elderly, typically at least 50 years of age, typically 65 years of age or above, or an adult below 65 years of age with a high risk medical condition ('high risk' adult), or a child under the age of two.

The (improved) CD4+ T-cell immune response may be assessed by measuring the number of cells producing any of the following cytokines:

- cells producing at least two different cytokines (CD40L, IL-2, IFNγ, TNFα)
- cells producing at least CD40L and another cytokine (IL-2, TNFα, IFNγ)
- cells producing at least IL-2 and another cytokine (CD40L, TNFα, IFNγ)
- cells producing at least IFNγ and another cytokine (IL-2, TNFα, CD40L)
- cells producing at least TNFα and another cytokine (IL-2, CD40L, IFNγ)

There will be "improved" CD4+ T-cell immune response when cells producing any of the above cytokines will be in a higher amount following administration of the adjuvanted composition compared to the administration of the non-adjuvanted composition. Typically at least one, suitably two of the five conditions mentioned herein above will be fulfilled. In a particular embodiment, the cells producing all four cytokines will be present at a higher amount in the adjuvanted group compared to the un-adjuvanted group. There will be a "comparable" CD4+ T-cell immune response when there will be no significant, optionally no statistically significant decrease in the response obtained with the adjuvanted immunogenic composition, where the adjuvant component(s) are at a lower level than previously thought useful and is/are typically as defined herein, compared to that obtained with compositions adjuvanted with some of the prior art adjuvants (i.e. with the same component(s) at a high level).

In a specific embodiment, an improved CD4 T-cell immune response may be conferred by the adjuvanted influenza composition of the present invention and may be ideally obtained after one single administration. The single dose approach will be extremely relevant for example in a rapidly evolving outbreak situation. In certain circumstances, especially for the elderly population, or in the case of young children (below 9 years of age) who are vaccinated for the first time against influenza, or in the case of a pandemic, it may be beneficial to administer two doses of the same composition for that season. The second dose of said same composition (still considered as 'composition for first vaccination') may be administered during the on-going primary immune response and is adequately spaced. Typically the second dose of the composition is given a few weeks, or about one month, e.g. 2 weeks, 3 weeks, 4 weeks, 5 weeks, or 6 weeks after the first dose, to help prime the immune system in unresponsive or poorly responsive individuals. In a specific aspect, the primo-vaccination is followed by a subsequent vaccination course of adjuvanted vaccine product containing a heterologous influenza strain.

In a specific embodiment, the administration of said immunogenic composition alternatively or additionally induces an improved B-memory cell response in patients administered with the adjuvanted immunogenic composition compared to the B-memory cell response induced in individuals immunized with the un-adjuvanted composition. An improved B-memory cell response is intended to mean an increased frequency of peripheral blood B lymphocytes capable of differentiation into antibody-secreting plasma cells upon antigen encounter as measured by stimulation of in-vitro differentiation (see Example sections, e.g. methods of Elispot B cells memory). In another embodiment, the adjuvanted immunogenic composition, where the adjuvant component(s) are at a lower level than previously thought useful and is/are typically as defined above, is suitably capable of inducing a B-memory cell response against the or against at least one of the component antigen(s) or antigenic composition, comparable (i.e. not significantly, or optionally statistically significantly inferior) to that obtained with compositions adjuvanted with some of the prior art adjuvants. This characteristic will be referred to as "comparable B-memory cell response" in the text.

In a still further specific embodiment, the vaccination with the composition for the first vaccination, adjuvanted, has no measurable impact on the CD8 response.

Suitably, the claimed composition comprising an influenza virus or antigenic preparation thereof formulated with an oil-in-water emulsion adjuvant, in particular an oil-in-water emulsion adjuvant comprising a metabolisable oil (optionally qualene), a tocol (optionally alpha-tocopherol), and an emulsifying agent (optionally a polyoxyethylene sorbitan monooleate such as Tween 80™ or Polysorbate 80™) in the low amounts such as defined herein, will be effective in promoting T cell responses in an immuno-compromised or immunologically naïve human population. Suitably, the administration of a single dose of the adjuvanted immunogenic composition for first vaccination, as described in the invention will be capable of providing better sero-protection, as assessed by the correlates of protection for influenza vaccines, following revaccination against influenza, than does the vaccination with an non-adjuvanted influenza vaccine. The claimed adjuvanted formulation will also advantageously induce an improved CD4 T-cell immune response against influenza virus compared to that obtained with the non-adjuvanted formulation. This property can be associated with an increased responsiveness upon vaccination or infection vis-à-vis influenza antigenic exposure. Furthermore, this may also be associated with a cross-responsiveness, i.e. a higher ability to respond against variant influenza strains. This qualitatively and/or quantitatively improved response may be beneficial in all populations in the case of pandemics, and especially in an immuno-compromised human population such as the elderly population (65 years of age and above) and in particular the high risk elderly population. This may also be of benefit to the mostly naïve infant population (below 5 years, suitably below 2 years of age). When the composition comprises at least one pandemic strain, this improved response will be of benefit for usage for priming, e.g. from stockpiled vaccine containing a drift variant, before or at onset of pandemic outbreak. This may result in reducing the overall morbidity and mortality rate and preventing emergency admissions to hospital for pneumonia and other influenza-like illness. Furthermore it allows inducing a CD4 T cell response which is more persistent in time, e.g. still present one year after the first vaccination, compared to the response induced with the non-adjuvanted formulation. All these advantages could be obtained with the claimed adjuvant composition, whilst reducing the overall reactogenicity compared to adjuvant having higher component(s) amount(s).

Suitably the CD4 T-cell immune response, such as the "improved" or "comparable" CD4 T-cell immune response obtained in an unprimed subject, involves the induction of a cross-reactive CD4 T helper response. In particular, the amount of cross-reactive CD4 T cells is increased. By 'cross-reactive' CD4 response is meant CD4 T-cell targeting shared epitopes between influenza strains, optionally from different clades or lineages.

Usually, available influenza vaccines are effective only against infecting strains of influenza virus that have haemagglutinin of similar antigenic characteristics. When the infecting (circulating) influenza virus has undergone minor changes (such as a point mutation or an accumulation of point mutations resulting in amino acid changes in the surface glycoproteins in particular haemagglutinin (antigenic drift variant virus strain) the vaccine may still provide some protection, although it may only provide limited protection as the newly created variants may escape immunity induced by prior influenza infection or vaccination. Antigenic drift is responsible for annual epidemics that occur during interpandemic periods (Wiley & Skehel, 1987, Ann. Rev. Biochem. 56, 365-394). The induction of cross-reactive CD4 T cells provides an additional advantage to the composition of the invention, in that it may provide also cross-protection, in other words protection against heterologous infections, i.e. infections caused by a circulating influenza strain which is a variant (e.g. a drift) of the influenza strain contained in the immunogenic composition. This may be advantageous when the circulating strain is difficult to propagate in eggs or to produce in cell culture, rendering the use of a drifted strain a working alternative. This may also be advantageous when the subject received a first and a second vaccination several months or a year apart, and the influenza strain in the immunogenic composition used for a second immunization is a drift variant strain of the strain used in the composition used for the first vaccination.

The adjuvanted influenza immunogenic composition as herein defined has therefore a higher ability to induce sero-protection and cross-reactive CD4 T cells in vaccinated elderly or yound children subjects. This characteristic may be associated with a higher ability to respond against a variant strain of the strain present in the immunogenic composition. This may prove to be an important advantage in a pandemic situation. For example an immunogenic influenza composition comprising at least one pandemic strain, optionally any of H5, a H2, a H9, H7 or H6 strain(s), may provide a higher ability to respond against a pandemic variant, i.e. a drift strain of said pandemic strain(s), either upon subsequent vaccination with or upon infection by said drift strain. For example, the adjuvanted vaccine composition comprises a A/Indonesian strain and is capable of geneting a cross-protective and/or cross-reactive immune response against one, suitable more than one of drift strains, such as A/Hong Kong, A/Turkey, A/Vietnam and/or A/Anhui strain(s).

Detection of Cross-Reactive CD4 T-Cells Following Vaccination with Influenza Vaccine Following classical trivalent Influenza vaccine administration (3 weeks), there is a substantial increase in the frequency of peripheral blood CD4 T-cells responding to antigenic strain preparation (whole virus or split antigen) that is homologous to the one present in the vaccine (H3N2: A/Panama/2007/99, H1N1: N New Caledonia/20/99, B: B/Shangdong/7/97) (see Example III). A comparable increase in frequency can be seen if peripheral blood CD4 T-cells are restimulated with influenza strains classified as drifted strains (H3N2: A/Sydney/5/97, H1N1: A/Beijing/262/95, B: B/Yamanashi/166/98). In contrast, if peripheral blood CD4 T-cells are restimulated with influenza strains classified as shift strains (H2N2: A/Singapore/1/57, H9N2: A/Hongkong/1073/99) by expert in the field, there is no observable increase following vaccination.

CD4 T-cells that are able to recognize both homologous and drifted Influenza strains have been named in the present document "cross-reactive". The adjuvanted influenza compositions as described herein have been capable to show heterosubtypic cross-reactivity since there is observable cross-reactivity against drifted Influenza strains. As said above, the ability of a vaccine formulation comprising at least one pandemic strain to be effective against drift pandemic strain(s) may prove to be an important characteristic in the case of pandemic.

Consistently with the above observations, CD4 T-cell epitopes shared by different Influenza strains have been identified in human (Gelder C et al. 1998, Int Immunol. 10(2):211-22; Gelder C M et al. 1996 J Virol. 70(7):4787-90; Gelder C M et al. 1995 J Virol. 1995 69(12):7497-506).

Due to its immunogenic properties, the claimed composition may be able to establish a proactive vaccination strategy against the threat of a human influenza pandemic, including the stockpiling of pre-pandemic vaccine in order to better prepare against the onset of a pandemic. It may also be able to establish a proactive vaccination strategy against circulating strains that might not exactly match the strain(s) present in the vaccine composition. In a specific embodiment, the adjuvanted composition may offer the additional benefit of providing better protection against circulating strains which have undergone a major change (such as gene recombination for example, between two different species) in the haemagglutinin (antigenic shift) against which currently available vaccines have no efficacy.

Specifically, the pre-pandemic vaccine is one that comprises at least one pandemic strain (optionally H5N1 (avian flu)) similar to the ones currently circulating in the bird population and has been produced, for example through to the use of reverse genetics. The immunity developed in response to the pre-pandemic vaccine may allow the immune system to be 'primed' or 'educated' in readiness and thereby allowing for more rapid development of protective immune responses after encountering the actual pandemic virus strain leading to a decreased susceptibility to a related pandemic strain of the influenza. Once a pandemic has been declared by WHO and the final pandemic strain identified (which may be or not be a drift strain), the pre-pandemic vaccine will also allow a more rapid immune response to the pandemic vaccine when the latter becomes available.

Revaccination and Composition Used for Revaccination (Boosting Composition)

In one aspect of the present invention, there is provided the use of:
  (a) an influenza virus or antigenic preparation thereof, from a first influenza strain, and
  (b) an oil-in-water emulsion adjuvant as herein defined
in the manufacture of an immunogenic composition as herein defined, for protection against influenza infections caused by a influenza strain which is a variant of said first influenza strain.

Also provided is an immunogenic composition comprising an influenza virus or antigenic preparation thereof, from a first influenza strain, and an oil-in-water emulsion adjuvant as herein defined, for use in the protection of a human or a human population against influenza infections caused by a influenza strain which is a variant of said first influenza strain.

An aspect of the present invention provides the use of an influenza antigen in the manufacture of an influenza immunogenic composition for revaccination of humans previously vaccinated (with one or two doses) with an adjuvanted influenza composition as defined herein. Also provided is an immunogenic composition comprising an influenza virus or antigenic preparation thereof, optionally with an oil-in-water emulsion adjuvant as herein defined, for use in the revaccination of humans previously vaccinated (with one or two doses) with an adjuvanted influenza composition as defined herein.

In an embodiment, the immunogenic composition for revaccination contains an influenza virus or antigenic preparation thereof which shares common CD4 T-cell epitopes with the influenza virus or antigenic preparation thereof used for the first vaccination. A common CD4 T cell epitope is intended to mean peptides/sequences/epitopes from different antigens which can be recognised by the same CD4 cell (see examples of described epitopes in: Gelder C et al. 1998, Int Immunol. 10(2):211-22; Gelder C M et al. 1996 J Virol. 70(7):4787-90; Gelder C M et al. 1995 J Virol. 1995 69(12):7497-506).

In one aspect of the present invention, there is provided the use of an influenza virus or antigenic preparation thereof, from a first influenza (optionally a pandemic) strain, in the manufacture of an adjuvanted immunogenic composition as herein defined for protection against influenza infections caused by a influenza strain which is a variant of said first influenza (optionally a pandemic) strain. Also provided is an adjuvanted immunogenic composition comprising an influenza virus or antigenic preparation thereof, from a first influenza (optionally a pandemic) strain, and an adjuvant as herein defined, for use in the protection against influenza infections caused by a influenza strain which is a variant of said first influenza (optionally a pandemic) strain.

In another aspect, the invention provides for the use of an influenza virus or antigenic preparation thereof in the manufacture of an influenza immunogenic composition for revaccination of humans previously vaccinated with an adjuvanted influenza composition as claimed herein or with an adjuvanted influenza composition comprising a variant influenza strain, the adjuvant being as defined herein. Also provided is an influenza immunogenic composition comprising an influenza virus or antigenic preparation thereof, optionally with an oil-in-water emulsion adjuvant as herein defined, for use in the revaccination of humans previously vaccinated with an adjuvanted influenza composition as claimed herein or with an adjuvanted influenza composition comprising a variant influenza strain, the adjuvant being as defined herein.

In another aspect the present invention provides for a method of vaccinating a human population or individual against one influenza virus strain followed by revaccination of said human or population against a variant influenza virus strain, said method comprising administering to said human (i) a first composition comprising an influenza virus or antigenic preparation thereof from a first influenza virus strain and an adjuvant as herein defined, and (ii) a second immunogenic composition comprising a influenza virus strain variant of said first influenza virus strain. In a specific embodiment said first strain is associated with a pandemic or has the potential to be associated with a pandemic outbreak. In another specific embodiment said variant strain is associated with a pandemic or has the potential to be associated with a pandemic. In particular, the revaccination is made with an influenza composition comprising at least one strain which is a circulating pandemic strain. In another embodiment said variant strain is a drift variant, optionally from a proximal or suitably distant clade of H3N2 used as the first strain. In another embodiment said variant strain is a B strain of a different lineage than that of the first B strain (such as B/yamagata or B/Victoria, belonging to different lineages). Both the priming composition and the boosting composition can be monovalent or suitably multivalent, i.e. can contain at least two influenza virus strains, such as a bivalent, trivalent, quadrivalent or pentavalent vaccine. When the composition(s) is (are) multivalent, at least one strain is suitably selected from the group consisting of: a pandemic strain, a B strain (such as B/yamagata or B/Victoria), a H3N2 strain, and is optionally a drift variant of the strain present in the vaccine used for the first vaccination.

The first vaccination can suitably comprises two doses, administered within a few weeks during the same on-going immune response, as defined above. Typically revaccination is made several months after the first vaccination, suitably at least three months, or 4 months after the first vaccination, suitably 8 to 14 months after, suitably at about 10 to 12 months after or even longer. Suitably revaccination is made at least 6 months after the first vaccination(s). Suitably revaccination is made close to or at the next influenza season, e.g. approximately one year after the first immunogenic composition. The boosting composition may also be given every subsequent year (third, fourth, fifth vaccination and so forth).

Accordingly, in one embodiment, the invention provides for a vaccination scheme (or a composition for use in said scheme) comprising (i) a primary vaccination made with an adjuvanted composition according to the invention, given in one or two doses (suitably spaced, e.g. 3 to 6 weeks apart, or 3-4 weeks apart), at any time in the year (i.e. outside the influenza season), followed by (ii) a boost vaccination administered at least 6 weeks to one year after the first vaccination. When two doses are administered at the primary vaccination, the first can be with a adjuvanted trivalent or quadrivalent seasonal vaccine, followed by a second dose of a pandemic (e.g. monovalent) adjuvanted vaccine. Suitably the boost is administered at least 6 weeks after the first vaccination and at any time within the routine immunisation calendar (e.g. for children), or at the next influenza season. The boost composition can be with any commercially approved influenza vaccine (e.g. a classical trivalent unadjuvanted or adjuvanted vaccine such as FluAd™), or with an adjuvanted composition according to the invention (an adjuvanted trivalent or quadrivalent composition for example). Suitably the boost composition comprises the circulating seasonal strains for that season, which may be drift variant from the strains present in the primary vaccine. This vaccination scheme is suitable for the pediatric population which could be primed early in life (e.g. at an age of under 6 months, or under 2 months) with the vaccine available then, and boosted with a composition comprising the circulating strains, which may be drift variant from the strains present in the primary composition.

The immunogenic composition for revaccination (the boosting composition) may contain any type of antigen preparation, either inactivated or live attenuated. It may contain the same type of antigen preparation e.g. a split influenza virus or antigenic preparation thereof, a whole virion, or a purified HA and NA (sub-unit) vaccine, as the immunogenic composition used for the first vaccination. The boosting composition may contain the same subtype of influenza antigen(s) than that used for the first vaccination. For example, when the first vaccination is made at the declaration of a pandemic and revaccination is made later, the revaccination is made with a vaccine comprising an influenza strain (e.g. H5N1 Vietnam) which is of the same subtype as that used for the first vaccination (e.g. H5N1 Vietnam). Alternatively the boosting composition may contain a drift strain of the same subtype of influenza antigen(s) than that used for the first vaccination, for example H5N1 Indonesia. In another embodiment, said influenza strain used for the revaccination is a shift strain, i.e. is different from that used for the first vaccination, e.g. it has a different HA or NA subtype, such as H5N2 (same HA subtype as H5N1 but different NA subtype) or H7N1 (different HA subtype from H5N1 but same NA subtype). For example the vaccine composition for the first immunisation comprises a A/Indonesian strain and the boosting composition comprises A/Hong Kong, A/Turkey, A/Vietnam and/or A/Anhui strain(s).

In one embodiment, a split virus is used. The boosting composition may be adjuvanted or non-adjuvanted. The non-adjuvanted boosting composition may be Fluarix™/α-Rix®/Influsplit® given intramuscularly, which contains three inactivated split virion antigens prepared from the WHO recommended strains of the appropriate influenza season. In particular, the influenza viral strains or antigenic preparation thereof are selected according to the reference material distributed by the World Health Organisation such that they are adapted to the influenza strain which is circulating on the year of the revaccination. The adjuvanted boosting composition may suitably comprises an oil-in-water emulsion adjuvant as herein defined, optionally with an additional immunostimulant such as TLR-4 ligand such as 3D-MPL or a saponin.

Suitably revaccination made with a composition comprising an adjuvant as herein defined induces any, suitably two or all, of the following: (i) an improved CD4+ T-cell immune response against the influenza virus or antigenic preparation thereof, or (ii) an improved B cell memory response or (iii) an improved humoral response, compared to the equivalent response induced after a first vaccination with the non-adjuvanted influenza virus or antigenic preparation thereof. Suitably revaccination made with a composition comprising an adjuvant as herein defined induces any, suitably two or all, of the following: (i) a comparable CD4+ T-cell immune response against the influenza virus or antigenic preparation thereof, or (ii) a comparable B cell memory response or (iii) a comparable humoral response, compared to the equivalent response induced after a first vaccination with the influenza virus or antigenic preparation thereof adjuvanted with an adjuvant where the component's) are present at a higher level.

In one aspect according to the invention, the revaccination of the subjects with a boosting composition comprising an influenza virus and an oil-in-water emulsion adjuvant comprising a metabolisable oil (optionally squalene), a tocol (optionally alpha-tocopherol), and an emulsifying agent (optionally a polyoxyehtylene sorbitan monooleate), at the amounts as defined above, will show higher antibody titers than the corresponding values in the group of people first vaccinated with the non-adjuvanted composition and boosted with the non-adjuvanted composition. The effect of the adjuvant in enhancing the antibody response to revaccination is especially of importance in the elderly population or in young children which are known to have a low response to vaccination or infection by influenza virus. In particular, the adjuvanted composition-associated benefit will also be marked in terms of improving the CD4 T-cell response following revaccination.

The adjuvanted composition for revaccination will be capable of inducing a better cross-responsiveness against drifted strain (the influenza strain from the next influenza season) compared to the protection conferred by the control vaccine. Said cross-responsiveness has shown a higher persistence compared to that obtained with the un-adjuvanted formulation. The effect of the adjuvant in enhancing the cross-responsiveness against drifted strain is of important in a pandemic situation.

In a further embodiment the invention relates to a vaccination regime in which the first vaccination is made with an influenza composition, suitably a split influenza composition, containing an influenza strain that could potentially cause a pandemic and the revaccination is made with a composition, either monovalent or multivalent, comprising at least one circulating strain, either a pandemic strain or a classical strain.

In a specific embodiment, the human dose of the immunogenic composition for revaccination is adjuvanted with an oil-inwater emulsion adjuvant. Suitably but not exclusively this adjuvant comprises a tocol. Suitably the HA per strain per dose is at about 15 µg. In a specific embodiment the HA per strain is a low amount of HA (optionally at about 10 µg HA per strain per dose or below, so as to achieve a maximum of 40-45 µg HA per dose) and is as defined above. Suitably the HA per strain is at about or below 5 µg, at about 2.5 µg or below. Suitably the adjuvant composition is an oil-in-water emulsion comprising squalene, alpha-tocopherol, and polysorbate 80 at an amount of between 5-6 mg, between 5-6 mg and between 2-3 mg per dose, respectively. Alternatively, the adjuvant composition is an oil-in-water emulsion comprising squalene, alpha-tocopherol, and polysorbate 80 at an amount of between 2.5-3.5 mg, between 2-3 mg and between 1-2 mg per dose, respectively. The human dose of the immunogenic composition for revaccination suitably comprises an oil-in-water emulsion adjuvant which comprises half of the components present in the composition used for the primary vaccination, and will suitably comprise an oil-in-water emulsion comprising squalene, alpha-tocopherol, and polysorbate 80 at an amount of between 2.5-3.5 mg, between 2-3 mg and between 1-2 mg per dose. In a specific embodiment said revaccination dose is given about one year or about two years after the primary vaccination.

CD4 Epitope in HA

This antigenic drift mainly resides in epitope regions of the viral surface proteins haemagglutinin (HA) and neuraminidase (NA). It is known that any difference in CD4 and B cell epitopes between different influenza strains, being used by the virus to evade the adaptive response of the host immune system, will play a major role in influenza vaccination.

CD4 T-cell epitopes shared by different Influenza strains have been identified in human (see for example: Gelder C et al. 1998, Int Immunol. 10(2):211-22; Gelder C M et al. 1996 J Virol. 70(7):4787-90; and Gelder C M et al. 1995 J Virol. 1995 69(12):7497-506).

In a specific embodiment, the revaccination is made by using a boosting composition which contains an influenza virus or antigenic preparation thereof which shares common CD4 T-cell epitopes with the influenza virus antigen or antigenic preparation thereof used for the first vaccination. The invention thus relates to the use of the immunogenic composition comprising a pandemic influenza virus or antigenic preparation thereof and an oil-in-water emulsion adjuvant as defined above, in the manufacture of a first vaccination-component of a multi-dose vaccine, the multi-dose vaccine further comprising, as a boosting dose, an influenza virus or antigenic preparation thereof which shares common CD4 T-cell epitopes with the pandemic influenza virus antigen or virus antigenic preparation thereof of the dose given at the first vaccination.

Vaccination Means

The composition of the invention may be administered by any suitable delivery route, such as intradermal, mucosal e.g. intranasal, oral, intramuscular or subcutaneous. Other delivery routes are well known in the art.

The intramuscular delivery route is particularly suitable for the adjuvanted influenza composition. The composition according to the invention may be presented in a monodose container, or alternatively, a multidose container, particularly suitable for a pandemic vaccine. In this instance an antimicrobial preservative such a thiomersal is typically present to prevent contamination during use. Thiomersal concentration may be at 25 µg/0.5 ml dose (i.e. 50 µg/mL). A thiomersal concentration of 5 µg/0.5 ml dose (i.e. 10 µg/ml) or 10 µg/0.5 ml dose (i.e. 20 µg/ml) is suitably present. A suitable IM delivery device could be used such as a needle-free liquid jet injection device, for example the Biojector 2000 (Bioject, Portland, Oreg.). Alternatively a pen-injector device, such as is used for at-home delivery of epinephrine, could be used to allow self administration of vaccine. The use of such delivery devices may be particularly amenable to large scale immunization campaigns such as would be required during a pandemic.

Intradermal delivery is another suitable route. Any suitable device may be used for intradermal delivery, for example a short needle device. Intradermal vaccines may also be administered by devices which limit the effective penetration length of a needle into the skin, such as those described in WO99/34850 and EP1092444, incorporated herein by reference, and functional equivalents thereof. Also suitable are jet injection devices which deliver liquid vaccines to the dermis via a liquid jet injector or via a needle which pierces the stratum corneum and produces a jet which reaches the dermis. Also suitable are ballistic powder/particle delivery devices which use compressed gas to accelerate vaccine in powder form through the outer layers of the skin to the dermis. Additionally, conventional syringes may be used in the classical mantoux method of intradermal administration.

Another suitable administration route is the subcutaneous route. Any suitable device may be used for subcutaneous delivery, for example classical needle. Suitably, a needle-free jet injector service is used. Suitably said device is pre-filled with the liquid vaccine formulation.

Alternatively the vaccine is administered intranasally. Typically, the vaccine is administered locally to the nasopharyngeal area, suitably without being inhaled into the lungs. It is desirable to use an intranasal delivery device which delivers the vaccine formulation to the nasopharyngeal area, without or substantially without it entering the lungs.

Suitable devices for intranasal administration of the vaccines according to the invention are spray devices. Suitable commercially available nasal spray devices include Accuspray™ (Becton Dickinson). Nebulisers produce a very fine spray which can be easily inhaled into the lungs and therefore does not efficiently reach the nasal mucosa. Nebulisers are therefore not preferred.

Suitable spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO91/13281 and EP311863B and EP516636, incorporated herein by reference. Such devices are commercially available from Pfeiffer GmbH and are also described in Bommer, R. Pharmaceutical Technology Europe, September 1999.

Suitable intranasal devices produce droplets (measured using water as the liquid) in the range 1 to 200 μm, suitably 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Bi-dose delivery is a further suitable feature of an intranasal delivery system for use with the vaccines according to the invention. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a monodose device may be used for administering the vaccines according to the invention.

Alternatively, the epidermal or transdermal vaccination route is also contempletd in the present invention.

In one aspect of the present invention, the adjuvanted immunogenic composition for the first administration may be given intramuscularly, and the boosting composition, either adjuvanted or not, may be administered through a different route, for example intradermal, subcutaneous or intranasal. In a specific embodiment, the composition for the first administration contains a HA amount of less than 15 μg for the pandemic influenza strain, and the boosting composition may contain a standard amount of 15 μg or, suitably a low amount of HA, i.e. below 15 μg, which, depending on the administration route, may be given in a smaller volume.

Although the vaccine of the invention may be administered as a single dose, components thereof may also be co-administered together at the same time or at different times (for instance influenza antigens could be administered separately, suitably at the same time as the administration of the adjuvant). In addition to a single route of administration, 2 different routes of administration may be used when two injections are administered. For example, the first administration (e.g. priming dose) of adjuvanted influenza antigens may be administered IM (or ID) and the second administration (e.g. booster dose) may be administered IN (or ID). In addition, the vaccines of the invention may be administered IM for priming doses and IN for booster doses.

The content of influenza antigens in the vaccine will typically be in the range 0.1-15 μg HA per influenza strain, suitably 1-$10_4$, most typically in the range 1-8 μg. A suitable content of influenza antigens will be less than or exactly 5 μg HA per influenza strain included in the vaccine. Following an initial vaccination, subjects may receive one or several booster immunizations adequately spaced.

Populations to Vaccinate

The target population to vaccinate is the entire population, e.g. healthy young adults (e.g. aged 18-50 or 18-60), elderly (typically aged above 60) or infants/children. The target population may in particular be immuno-compromised. Immuno-compromised humans generally are less well able to respond to an antigen, in particular to an influenza antigen, in comparison to healthy adults.

In one aspect according to the invention, the target population is a population which is unprimed against influenza, either being naïve (such as vis à vis a pandemic strain), or having failed to respond previously to influenza infection or vaccination. Suitably the target population is elderly persons suitably aged at least 60, or at least 65 years and over, younger high-risk adults (i.e. between 18 and 60 years of age) such as people working in health institutions, or those young adults with a risk factor such as cardiovascular and pulmonary disease, or diabetes. Another target population is all children from birth, or aged 2 months and over, or aged 6 months of age and over, especially children 6-23 months of age who experience a relatively high influenza-related hospitalization rate. Another target population is younger children from birth to 6 months of age.

The teaching of all references in the present application, including patent applications and granted patents, are herein fully incorporated by reference. Any patent application to which this application claims priority is incorporated by reference herein in its entirety in the manner described herein for publications and references.

For the avoidance of doubt the terms 'comprising', 'comprise' and 'comprises' herein is intended by the inventors to be optionally substitutable with the terms 'consisting of', 'consist of', and 'consists of', respectively, in every instance. Embodiments herein relating to "vaccine compositions" of the invention are also applicable to embodiments relating to "immunogenic compositions" of the invention, and vice versa. The term "about" (or "around") in all numerical values allows for a 5% variation, i.e. a value of about 1.25% would mean from between 1.19%-1.31%.

The invention will be further described by reference to the following, non-limiting, examples:

Example I describes immunological read-out methods used in mice, ferrets, pigs and human studies.

Example II describes the preparation of the oil-in-water emulsion and adjuvant formulations used in the studies exemplified.

Example III shows a clinical trial in an adult population aged 18-59 years with a vaccine containing a split influenza antigen preparation and two doses of AS03 adjuvant Example IV shows a preclinical evaluation of adjuvanted and non-adjuvanted split influenza vaccines (comprising various doses of AS03 adjuvant) in primed BALB/c mice Example V shows a preclinical evaluation of adjuvanted and non-adjuvanted split influenza vaccines (comprising various doses of AS03 adjuvant) in primed C57BI/6 mice Example VI shows a preclinical evaluation of adjuvanted and non-adjuvanted split influenza vaccines (comprising various doses of AS03 adjuvant and low dose antigen) in primed C57BI/6 mice Example VII shows a preclinical evaluation of adjuvanted and non-adjuvanted split H5N1 vaccines (comprising various doses of AS03 adjuvant and antigen) in naïve C57BI/6 mice Example VIII shows a preclinical evaluation of adjuvanted and non-adjuvanted influenza vaccines in primed Large White pigs Example IX shows a preclinical evaluation of adjuvanted and non-adjuvanted split TIV and QIV seasonal vaccines (comprising various doses of AS03 adjuvant and antigen) in naïve and primed C57BI/6 mice Example X shows a clinical trial in an adult population aged 18-64 years with a vaccine containing a split influenza antigen preparation and various doses of AS03 adjuvant Example XI shows a clinical trial in an elderly population aged 65+ years with a vaccine containing a split influenza antigen preparation and various adjuvants Example I—Immunological Read-Out Methods I.1. Mice Methods I.1.1. Hemagglutination Inhibition Test Test Principle (Classical Procedure).

Anti-Hemagglutinin antibody titers to the three (seasonal) influenza virus strains are determined using the hemagglutination inhibition test (HI). The principle of the HI test is based on the ability of specific anti-Influenza antibodies to inhibit hemagglutination of red blood cells (RBC) by influenza virus hemagglutinin (HA). Heat inactivated sera are treated by Kaolin and RBC to remove non-specific inhibitors. After pretreatment, two-fold dilutions of sera are incubated with 4 hemagglutination units of each influenza strain. Red blood cells are then added and the inhibition of agglutination is scored. The titers are expressed as the reciprocal of the highest dilution of serum that completely inhibited hemagglutination. As the first dilution of sera is 1:20, an undetectable level is scored as a titer equal to 10.

Adaptation for H5N1 (Specific Description of HI Using Horse Erythrocytes):

As the classical HI assay for determining anti-HA antibodies was documented to not well function for the H5N1 strain, and adapted protocol using horse RBC was used. Erythrocytes of horses are used for the H5N1 Pandemic strains. 0.5% (end concentration) horse red blood cell suspension in phosphate buffer containing 0.5% BSA (bovine serum albumin, end concentration). This suspension is prepared every day by washing red blood cell with the same phosphate buffer and a subsequent centrifugation step (10 min, 2000 rpm). This washing step has to be repeated once. After the addition of the horse red blood cells to the reaction mix of sera and virus suspension; the plates have to be incubated at room temperature (RT, 20° C.+/−2° C.) for two hours due to the low sedimentation rate of the horse red blood cells.

Statistical Analysis

Statistical analysis were performed on post vaccination HI titers using UNISTAT. The protocol applied for analysis of variance can be briefly described as follow:

Log transformation of data

Shapiro-Wilk test on each population (group) in order to verify the normality of groups distribution Cochran test in order to verify the homogenicity of variance between the different populations (groups)

Analysis of variance on selected data.

Test for interaction of two-way ANOVA

Tukey-HSD Test for multiple comparisons

I.1.2. Intracellular Cytokine Staining

This technique allows a quantification of antigen specific T lymphocytes on the basis of cytokine production: effector T cells and/or effector-memory T cells produce IFN-γ and/or central memory T cells produce IL-2. PBMCs are harvested at day 7 post-immunization.

Lymphoid cells are re-stimulated in vitro in the presence of secretion inhibitor (Brefeldine).

These cells are then processed by conventional immunofluorescent procedure using fluorescent antibodies (CD4, CD8, IFN-γ and IL-2). Results are expressed as a frequency of cytokine positive cell within CD4/CD8 T cells. Intracellular staining of cytokines of T cells was performed on PBMC 7 days after the second immunization. Blood was collected from mice and pooled in heparinated medium RPMI+ Add. For blood, RPMI+Add-diluted PBL suspensions were layered onto a Lympholyte-Mammal gradient according to the recommended protocol (centrifuge 20 min at 2500 rpm and R.T.). The mononuclear cells at the interface were removed, washed 2× in RPMI+ Add and PBMCs suspensions were adjusted to $2 \times 10^6$ cells/ml in RPMI 5% fetal calf serum.

In vitro antigen stimulation of PBMCs was carried out at a final concentration of $1 \times 10^7$ cells/ml (tube FACS) with Whole FI (1 µgHA/strain) and then incubated 2 hrs at 37° C. with the addition of anti-CD28 and anti-CD49d (1 µg/ml for both).

Following the antigen restimulation step, PBMC are incubated overnight at 37° C. in presence of Brefeldin (1 µg/ml) at 37° C. to inhibit cytokine secretion.

IFN-γ/IL-2/CD4/CD8 staining was performed as follows: Cell suspensions were washed, resuspended in 50 µl of PBS 1% FCS containing 2% Fc blocking reagent (1/50; 2.4G2). After 10 min incubation at 4° C., 50 µl of a mixture of anti-CD4-PE (2/50) and anti-CD8 perCp (3/50) was added and incubated 30 min at 4° C. After a washing in PBS 1% FCS, cells were permeabilized by resuspending in 200 µl of Cytofix-Cytoperm (Kit BD) and incubated 20 min at 4° C. Cells were then washed with Perm Wash (Kit BD) and resuspended with 50 µl of a mix of anti-IFN-γ APC (1/50)+ anti-IL-2 FITC (1/50) diluted in Perm Wash. After an incubation min 2 h max overnight at 4° C., cells were washed with Perm Wash and resuspended in PBS 1% FCS+1% paraformaldehyde. Sample analysis was performed by FACS. Live cells were gated (FSC/SSC) and acquisition was performed on ~20,000 events (lymphocytes) or 35,000 events on CD4+ T cells. The percentages of IFN-γ+ or IL2+ were calculated on CD4+ and CD8+ gated populations.

I.1.3. Anti-H5N1 ELISA

Quantitation of anti-H5N1 Ig, IgG1 and IgG2b antibody titers was performed by ELISA using split H5N1 as coating. Virus and antibody solutions were used at 100 μl per well. Split virus H5N1 was diluted at a final concentration of 1 μg/ml in PBS and was adsorbed overnight at 4° C. to the wells of 96 wells microtiter plates (Maxisorb Immunoplate Nunc 439454). The plates were then incubated for 1 hour at 37° C. with 200 μl per well of PBS containing 1% BSA and 0.1% Tween 20 (saturation buffer). Twelve two-fold dilutions of sera in saturation buffer were added to the H5N1-coated plates and incubated for 1 h 30 at 37° C. The plates were washed four times with PBS 0.1% Tween 20. Biotinilated-conjugated anti-mouse Ig (Prozan-E0413) diluted 1/500 or Biotinilated-conjugated anti-mouse IgG1(Imtech 1070-08), or a biotynilated anti-mouse IgG2b (Imtech 1090-08) dimuated 1/4000 in PBS 1% BSA 0.1% Tween 20 was added to each well and incubated for 1.30 hour at 37° C.; after a washing step, plates were incubated 30 min with a Streptavidine-Biotine-Preoxidase conjugated (Prozan P0397) diluated 1/10000 in PBS 1% BSA Tween 20.

For the colorimetric revelation, plates were incubated 20 min at 22° C. with a solution of o-phenyldiamine (Sigma P4664) 0.04% H2O2 0.03% in 0.1 M citrate buffer pH 4.2. The reaction was stopped with $H_2SO_4$ 2N and micoplates were read at 490-630 nm.

I.2. Ferrets Methods

I.2.1. Hemagglutination Inhibition Test (HI)

Test Procedure.

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pre-treatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:10, an undetectable level was scored as a titer equal to 5.

Statistical Analysis.

Statistical analysis were performed on HI titers (Day 41, before challenge) using UNISTAT. The protocol applied for analysis of variance can be briefly described as followed:

Log transformation of data.

Shapiro-wilk test on each population (group) in ordetr to verify the normality of groups distribution.

Cochran test in order to verify the homogenicity of variance between the different populations (groups).

Test for interaction of one-way ANOVA.

Tuckey-HSD Test for multiple comparisons.

I.2.2. Body Temperature Monitoring

Individual temperatures were monitored during the challenge period with the transmitters and by the telemetry recording. All implants were checked and refurbished and a new calibration was performed by DSI (Data Sciences International, Centaurusweg 123, 5015 TC Tilburg, The Netherlands) before placement in the intraperitoneal cavity. All animals were individually housed in single cage during these measurements.

Temperatures were recorded every 15 minutes 4 days before challenge until 7 days Post-challenge.

I.2.3. Nasal Washes

The nasal washes were performed by administration of 5 ml of PBS in both nostrils in awoke animals. The inoculum was collected in a Petri dish and placed into sample containers on dry ice.

Viral Titration in Nasal Washes

All nasal samples were first sterile filtered through Spin X filters (Costar) to remove any bacterial contamination. 50 μl of serial ten-fold dilutions of nasal washes were transferred to microtiter plates containing 50 μl of medium (10 wells/dilution). 100 μl of MDCK cells ($2.4\times10^5$ cells/ml) were then added to each well and incubated at 35° C. for 5-7 days.

After 5-7 days of incubation, the culture medium is gently removed and 100 μl of a 1/20 WST-1 containing medium is added and incubated for another 18 hrs.

The intensity of the yellow formazan dye produced upon reduction of WST-1 by viable cells is proportional to the number of viable cells present in the well at the end of the viral titration assay and is quantified by measuring the absorbance of each well at the appropriate wavelength (450 nanometers). The cut-off is defined as the OD average of uninfected control cells—0.3 OD (0.3 OD correspond to +/−3 StDev of OD of uninfected control cells). A positive score is defined when OD is <cut-off and in contrast a negative score is defined when OD is >cut-off. Viral shedding titers were determined by “Reed and Muench” and expressed as Log TCID50/ml.

I.3. Pig Methods

I.3.1. Hemagglutination Inhibition Test (HI)

Test Procedure.

Anti-Hemagglutinin antibody titers to the three influenza virus strains were determined using the hemagglutination inhibition test (HI). The principle of the HI test is based on the ability of specific anti-Influenza antibodies to inhibit hemagglutination of chicken red blood cells (RBC) by influenza virus hemagglutinin (HA). Sera were first treated with a 25% neuraminidase solution (RDE) and were heat-inactivated to remove non-specific inhibitors. After pre-treatment, two-fold dilutions of sera were incubated with 4 hemagglutination units of each influenza strain. Chicken red blood cells were then added and the inhibition of agglutination was scored. The titers were expressed as the reciprocal of the highest dilution of serum that completely inhibited hemagglutination. As the first dilution of sera was 1:10, an undetectable level was scored as a titer equal to 5.

Statistical Analysis.

Statistical analysis were performed on HI titers (Day 41, before challenge) using UNISTAT. The protocol applied for analysis of variance can be briefly described as followed:

Log transformation of data.

Shapiro-wilk test on each population (group) in ordetr to verify the normality of groups distribution.

Cochran test in order to verify the homogenicity of variance between the different populations (groups).

Test for interaction of one-way ANOVA.

Tuckey-HSD Test for multiple comparisons.

I.4. Assays for Assessing the Immune Response in Humans

I.4.1. Hemagglutination Inhibition Assay

The immune response was determined by measuring HI antibodies using the method described by the WHO Collaborating Centre for influenza, Centres for Disease Control, Atlanta, USA (1991).

Antibody titre measurements were conducted on thawed frozen serum samples with a standardised and comprehensively validated micromethod using 4 hemagglutination-inhibiting units (4 HIU) of the appropriate antigens and a 0.5% fowl erythrocyte suspension. Non-specific serum inhibitors were removed by heat treatment and receptor-destroying enzyme.

The sera obtained were evaluated for HI antibody levels. Starting with an initial dilution of 1:10, a dilution series (by a factor of 2) was prepared up to an end dilution of 1:20480. The titration end-point was taken as the highest dilution step that showed complete inhibition (100%) of hemagglutination. All assays were performed in duplicate.

I.4.2. Neuraminidase Inhibition Assay

The assay was performed in fetuin-coated microtitre plates. A 2-fold dilution series of the antiserum was prepared and mixed with a standardised amount of influenza A H3N2, H1N1 or influenza B virus. The test was based on the biological activity of the neuraminidase which enzymatically releases neuraminic acid from fetuin. After cleavage of the terminal neuraminic acid β-D-glactose-N-acetyl-galactosamin was unmasked. Horseradish peroxidase (HRP)-labelled peanut agglutinin from *Arachis hypogaea*, which binds specifically to the galactose structures, was added to the wells. The amount of bound agglutinin can be detected and quantified in a substrate reaction with tetra-methylbenzidine (TMB) The highest antibody dilution that still inhibits the viral neuraminidase activity by at least 50% was indicated is the NI titre.

I.4.3. Neutralising Antibody Assay

Neutralising antibody measurements were conducted on thawed frozen serum samples. Virus neutralisation by antibodies contained in the serum was determined in a microneutralization assay. The sera were used without further treatment in the assay. Each serum was tested in triplicate. A standardised amount of virus was mixed with serial dilutions of serum and incubated to allow binding of the antibodies to the virus. A cell suspension, containing a defined amount of MDCK cells was then added to the mixture of virus and antiserum and incubated at 33° C. After the incubation period, virus replication was visualised by hemagglutination of chicken red blood cells. The 50% neutralisation titre of a serum was calculated by the method of Reed and Muench.

I.4.4. Cell-Mediated Immunity was Evaluated by Cytokine Flow Cytometry (CFC)

Peripheral blood antigen-specific CD4 and CD8 T cells can be restimulated in vitro to produce IL-2, CD40L, TNF-alpha and IFN if incubated with their corresponding antigen. Consequently, antigen-specific CD4 and CD8 T cells can be enumerated by flow cytometry following conventional immunofluorescence labelling of cellular phenotype as well as intracellular cytokines production. In the present study, Influenza vaccine antigen as well as peptides derived from specific influenza protein were used as antigen to restimulate Influenza-specific T cells. Results were expressed as a frequency of cytokine(s)-positive CD4 or CD8 T cell within the CD4 or CD8 T cell sub-population.

I.4.5. Statistical Methods

I.4.5.1. Primary Endpoints

Percentage, intensity and relationship to vaccination of solicited local and general signs and symptoms during a 7 day follow-up period (i.e. day of vaccination and 6 subsequent days) after vaccination and overall.

Percentage, intensity and relationship to vaccination of unsolicited local and general signs and symptoms during a 21 day follow-up period (i.e. day of vaccination and 20 subsequent days) after vaccination and overall.

Occurrence of serious adverse events during the entire study.

I.4.5.2. Secondary Endpoints

For the Humoral Immune Response:
Observed Variables:
At days 0 and 21: serum hemagglutination-inhibition (HI) and NI antibody titres, tested separately against each of the three influenza virus strains represented in the vaccine (anti-H1N1, anti-H3N2 & anti-B-antibodies).
At days 0 and 21: neutralising antibody titres, tested separately against each of the three influenza virus strains represented in the vaccine
Derived Variables (with 95% Confidence Intervals):
Geometric mean titres (GMTs) of serum HI antibodies with 95% confidence intervals (95% CI) pre and post-vaccination
Seroconversion rates* with 95% CI at day 21
Conversion factors** with 95% CI at day 21
Seroprotection rates*** with 95% CI at day 21
Serum NI antibody GMTs' (with 95% confidence intervals) at all timepoints.
Seroconversion rate defined as the percentage of vaccinees who have at least a 4-fold increase in serum HI titres on day 21 compared to day 0, for each vaccine strain.
Conversion factor defined as the fold increase in serum HI GMTs on day 21 compared to day 0, for each vaccine strain.
Protection rate defined as the percentage of vaccinees with a serum HI titre=40 after vaccination (for each vaccine strain) that usually is accepted as indicating protection.
It should be understood, that for some of the clinical trials, reactogenicity/safety may be secondary endpoints, and immunogenicity may be the primary endpoint.
For the Cell Mediated Immune (CMI) Response
Observed Variable At days 0 and 21: frequency of cytokine-positive CD4/CD8 cells per $10^6$ in different tests. Each test quantifies the response of CD4/CD8 T cell to:
  Peptide Influenza (pf) antigen (the precise nature and origin of these antigens needs to be given/explained
  Split Influenza (sf) antigen
  Whole Influenza (wf) antigen.
  Derived Variables:
  cells producing at least two different cytokines (CD40L, IL-2, IFNγ, TNFα)
  cells producing at least CD40L and another cytokine (IL-2, TNFα, IFNγ)
  cells producing at least IL-2 and another cytokine (CD40L, TNFα, IFNγ)
  cells producing at least IFNγ and another cytokine (IL-2, TNFα, CD40L)
  cells producing at least TNFα and another cytokine (IL-2, CD40L, IFNγ)

I.3.5.3. Analysis of Immunogenicity

The immunogenicity analysis was based on the total vaccinated cohort. For each treatment group, the following parameters (with 95% confidence intervals) were calculated:
  Geometric mean titres (GMTs) of HI and NI antibody titres at days 0 and 21
  Geometric mean titres (GMTs) of neutralising antibody titres at days 0 and 21.
  Conversion factors at day 21.
  Seroconversion rates (SC) at day 21 defined as the percentage of vaccinees that have at least a 4-fold increase in serum HI titres on day 21 compared to day 0.
  Protection rates at day 21 defined as the percentage of vaccinees with a serum HI titre=1:40.
  The frequency of CD4/CD8 T-lymphocytes secreting in response was summarised (descriptive statistics) for each vaccination group, at each timepoint (Day 0, Day 21) and for each antigen (Peptide influenza (pf), split influenza (sf) and whole influenza (wf)).
  Descriptive statistics in individual difference between timepoint (Post-Pre) responses fore each vaccination group and each antigen (pf, sf, and wf) at each 5 different tests.
  A non-parametric test (Kruskall-Wallis test) was used to compare the location differences between the 3 groups and the statistical p-value was calculated for each antigen at each 5 different tests. All significance tests were two-tailed. P-values less than or equal to 0.05 were considered as statistically significant.

Example II—Preparation of the Oil-in-Water Emulsion and Adjuvant Formulations Unless otherwise stated, the oil/water emulsion used in the subsequent examples is composed an organic phase made of 2 oils (alpha-tocopherol and squalene), and an aqueous phase of PBS containing Tween 80™ or Polysorbate 80™ as emulsifying agent. Unless otherwise stated, the oil-in-water emulsion adjuvant formulations used in the subsequent examples were made comprising the following oil-in-water emulsion component (final concentrations given): 2.5% squalene (v/v), 2.5% alpha-tocopherol (v/v), 0.9% polyoxyethylene sorbitan monooleate (v/v) (Tween 80, see WO 95/17210. This emulsion, termed AS03 in the subsequent examples, was prepared as followed as a two-fold concentrate.

II.1. Preparation of Emulsion SB62

This method was used in the studies reported in the clinical and pre-clinical examples sections. The preparation of the SB62 emulsion is made by mixing under strong agitation of an oil phase composed of hydrophobic components (DL-α-tocopherol and squalene) and an aqueous phase containing the water soluble components (the anionic detergent Tween 80 and PBS mod (modified), pH 6.8). While stirring, the oil phase (1/10 total volume) is transferred to the aqueous phase (9/10 total volume), and the mixture is stirred for 15 minutes at room temperature. The resulting mixture then subjected to shear, impact and cavitation forces in the interaction chamber of a microfluidizer (15000 PSI-8 cycles, or 3 cycles in the adjuvant used in the clinical trial reported in Example III) to produce submicron droplets (distribution between 100 and 200 nm). The resulting pH is between 6.8±0.1. The SB62 emulsion is then sterilised by filtration through a 0.22 μm membrane and the sterile bulk emulsion is stored refrigerated in Cupac containers at 2 to 8° C. Sterile inert gas (nitrogen or argon) is flushed into the dead volume of the SB62 emulsion final bulk container for at least 15 seconds.

The final composition of the SB62 emulsion is as follows: Tween 80: 1.8% (v/v) 19.4 mg/ml; Squalene: 5% (v/v) 42.8 mg/ml; α-tocopherol: 5 (v/v) 47.5 mg/ml; PBS-mod: NaCl 121 mM, KCl 2.38 mM, Na2HPO4 7.14 mM, KH2PO4 1.3 mM; pH 6.8±0.1.

Example III—Clinical Trial in an Adult Population Aged 18-59 Years with a Vaccine Containing a Split Influenza Antigen Preparation and Two Doses of AS03 Adjuvant (Flu-LD-004)

III.1. Introduction

A phase II, controlled, randomized, single blind study was conducted in an adult population aged 18-59 years old in 2006 in order to evaluate the immunogenicity, safety and reactogenicity of the GlaxoSmithKline Biologicals low dose influenza candidate vaccine (i.e. containing 5 μg HA per strain) with two doses of AS03 adjuvant. The humoral immune response (i.e. anti-hemagglutinin) was measured 21 days after intramuscular administration of one dose of an AS03 adjuvanted vaccine. Fluarix™ was used as reference.

III.2. Study Design

Three groups of subjects in parallel received the following vaccine intramuscularly:
  one group of 100 subjects receiving one injection of the low dose split virus influenza vaccine containing 5 μg HA adjuvanted with AS03 (FluLD1/1)
  one group of 100 subjects receiving one injection of the low dose split virus influenza vaccine containing 5 μg HA adjuvanted with a half dose of AS03 (AS03½) (FluLD½)
  one group of 100 subjects receiving one dose of Fluarix™ (Fluarix)

Schedule: one IM injection of influenza vaccine at day 0, study site visits at day 0 and day 21 with a blood sample collection (HI antibody determination) and an additional phone contact at day 30 (study conclusion).

The standard trivalent split influenza vaccine—Fluarix™ used in this study, is a commercial vaccine from the year 2006/2007 Northern Hemisphere developed and manufactured by GlaxoSmithKline Biologicals.

III.3. Study Objectives

III.3.1. Primary Objective

To evaluate the humoral immune response induced by the study vaccines in term of antihaemagglutinin antibody titers:
Observed Variables at Days 0 and 21: Serum Heamagglutination-Inhibition Antibody Titers.
Derived Variables (with 95% Confidence Intervals):
Geometric mean titers (GMTs) of serum antibodies at days 0 and 21
Seroconversion rates* at day 21
Seroconversion factors** at day 21
Seroprotection rates*** at days 0 and 21
Seroconversion rate for Haemagglutinin antibody response is defined as the percentage of vaccinees who have either a prevaccination titer <1:10 and a post-vaccination titer ≥1:40 or a prevaccination titer 1:10 and at least a fourfold increase in post-vaccination titer
Seroconversion factor defined as the fold increase in serum HI GMTs post-vaccination compared to day 0;
Seroprotection rate defined as the percentage of vaccinees with a serum HI titer ≥40 after vaccination that usually is accepted as indicating protection.

III.3.2. Secondary Objective

To evaluate the safety and reactogenicity of the study vaccines in term of solicited local and general adverse events, unsolicited adverse events and serious adverse events:
1. Occurence, intensity and relationship to vaccination of solicited local and general signs and symptoms during a 7-day follow-up period (i.e. day of vaccination and 6 subsequent days) after each vaccination in each group.
2. Occurence, intensity and relationship to vaccination of unsolicited local and general signs and symptoms during a 30-day follow-up period (i.e. day of vaccination and 29 subsequent days) after the vaccination in each group.
3. Occurrence and relationship of serious adverse events during the entire study period in each group.

III.4. Vaccine Composition and Administration

III.4.1. Vaccine Preparation

The non-adjuvanted influenza vaccine is a trivalent split virion, inactivated influenza vaccine consisting of three monovalent viral antigen bulks (prepared from respectively influenza strains A/H1N1, A/H3N2 and B). The antigens present in this vaccine are the same as in the licensed Fluarix™ vaccine which is available on the market as Fluarix™ (α-Rix®) since 1992 and contain 15 μg HA/strain per dose. The influenza strains included in the FluLD clinical lots are the strains that were chosen for the 2006/2007 Northern Hemisphere:
A/New Caledonia/20/99 (H1N1)-like strain: A/New Caledonia/20/99 (H1N1) IVR-116
A/Wisconsin/67/2005 (H3N2)-like strain: A/Wisconsin/67/2005 (H3N2) NYMCX-161
B/Malaysia/2506/2004.
The antigens are derived from egg-grown viruses. Splitting is carried out with sodium deoxycholate prior to the inactivation step, which is performed through the subsequent action of sodium deoxycholate and formaldehyde.

The AS03 adjuvanted low dose influenza (FluLD) vaccine (clinical lots) is based on the commercially available Fluarix™ vaccine (prepared from respectively influenza strains A/H1N1, A/H3N2 and B), but with a lower antigen content and adjuvanted with GSK adjuvant system AS03. AS03 consists of an oil-in-water emulsion (SB62) that contains two biodegradable oils, squalene and α-tocopherol (Vitamin E), and a surfactant, polysorbate 80 (Tween 80). Influenza antigens are incorporated in the aqueous phase of the adjuvant system by simple mixing with the emulsion. Two formulations have been tested, differing by the amount of adjuvant introduced with the Flu antigens in the vaccine lot. The adjuvanted vaccines contain 5 μg haemagglutinin (HA) of each influenza virus strain per dose, combined with a full dose (AS03) or half a dose (AS03 ½) of the adjuvant system AS03. The excipients are the following: polysorbate 80 (Tween 80), octoxynol 10 (Triton X-100), alpha-tocopheryl hydrogen succinate, sodium chloride, disodium hydrogen phosphate, potassium dihydrogen phosphate, potassium chloride, water for injection. The AS03 adjuvanted low dose influenza vaccines (FluLD, full or half dose of AS03) are preservative-free vaccines. However, they contain trace amounts of thiomersal (<1.25 μg of Hg per dose) from the early stages of the manufacturing process. They are both presented as monodose vaccines in glass (Type I) pre-filled syringes at a volume of 0.5 ml/dose.

III.4.1.1. Composition of AS03 Adjuvanted Influenza Vaccine

One dose of FluLD (full or half dose of AS03) corresponds to 0.5 ml. The composition is provided in Table 3. The HA content per dose is 5 μg for both formulations, the sole difference being the amount of AS03 present in the final containers.

TABLE 3

Composition of AS03 adjuvanted low dose influenza vaccine (full and half dose of AS03)

| Component | Quantity per dose (0.5 ml) |
|---|---|
| Inactivated split virions | |
| A/New Caledonia/20/99 (H1N1) IVR-116 | 5 μg HA |
| A/Wisconsin/67/2005 (H3N2) NYMCX-161 | 5 μg HA |
| B/Malaysia/2506/2004 | 5 μg HA |
| Adjuvant (Full Dose/HalfDose) | |
| SB62 emulsion (Total Volume) | 0.250 mL |
| squalene | 10.70 mg/5.35 mg |
| DL-α-tocopherol | 11.88 mg/5.94 mg |
| Polysorbate 80 (Tween 80) | 4.85 mg/2.425 mg |
| Polysorbate 80 (Tween 80) | 0.122 mg |
| Octoxynol 10 (Triton X-100) | 0.0283 mg |
| αTocopheryl hydrogen succinate | 0.01665 mg |
| Sodium chloride | 4 mg |
| Disodium phosphate | 0.575 mg |
| Potassium dihydrogen phosphate | 0.100 mg |
| Potassium chloride | 0.101 mg |
| Water for injection | ad 0.50 ml |

Abbreviations: HA = Haemagglutinin.
The total content in Polysorbate 80 corresponds to 4.972 mg per dose when AS03 full dose is used, and 2.547 mg per dose when AS03 half dose is used.

III.4.1.2. Production of Split Inactivated Influenza Antigen Preparation

The influenza antigens are identical to those included in Fluarix™ (Influenza Virus Vaccine). The monovalent bulks consist of purified inactivated split viruses that are prepared from working seeds of the three strains of influenza virus, type A (H1N1 and H3N2) and type B, which are grown individually in embryonated hens' eggs. These working seeds are derived from strains that are received from a WHO collaborating center following the annual WHO recommendations. For the process for preparing the antigens reference is, by way of illustration, given to WO 02/097072. The volumes of the three monovalent bulks are based on the HA content measured in each monovalent bulk prior to the formulation and on the target manufacturing volume.

A 10-times concentrated phosphate buffered saline (pH 7.4 when 1 time concentrated) and a pre-mixture of Tween 80 and α-tocopheryl hydrogen succinate are diluted in water for injection, followed by stirring during 5-30 minutes at room temperature. The three concentrated monovalent bulks are then successively diluted in the resulting phosphate buffered saline/Tween 80-α-tocopheryl hydrogen succinate solution to a concentration of 20 µg HA of each A monovalent bulk (H1N1, H3N2)

23.32 µg HA of B monovalent bulk per mL of intermediate trivalent bulk (5 µg HA of each A monovalent bulk and 5.83 µg HA of B/500 µl trivalent final bulk).

Between the additions of each monovalent bulk, the mixture is stirred for 10-30 minutes at room temperature and for 15-30 minutes after addition of the last monovalent bulk. This intermediate trivalent bulk also referred to as "prepool" can be held at +2-+8° C. or further processed to the final formulation step on the same day. The final volume of pre-pool is 250 µl per dose.

III.4.1.3. Preparation of the Vaccine Compositions with AS03 Adjuvant

Adjuvanted Vaccine: LD AS03 1/1 (Table 4)

PBS mod 10 fold concentrated (pH 7.4 when one fold concentrated; 137 mM NaCl, 2.7 mM KCl, 8.1 mM $Na_2HPO_4$, 1.47 mM $KH_2PO_4$, pH 7.4) as well as a mixture containing Tween80, Triton X-100 and VES (quantities taking into account the detergent present in the strains) are added to water for injection. After 5 to 30 minutes stirring, 20 µg HA per ml of each strain H1N1 and H3N2 and 23.32 µg HA per ml of B strain are added with 10 to 30 minutes stirring between each addition. After 15 to 30 minutes stirring, a small volume of the so called "intermediate bulk" are discarded for analysis and stored between +2 and +8° C. The intermediate bulk is in PBS mod 1 fold concentrated. The target's detergents concentration are 488 µg Tween 80 per ml, 73.6 µg Triton X-100 per ml and 66.6 µg VES per ml.

The final formulation is then prepared: an equal volume of SB62 (see preparation in Example II) is added to each 250 µl of pre-pool intermediate bulk and mixed during 30 to 60 minutes at room temperature. pH is checked to range between 6.8 and 7.5. Formulation is flushed with nitrogen and then stored between +2 and 8° C. prior to filling.

TABLE 4

AS03 adjuvanted low dose vaccine

| Component | Concentration | Volume (ml) |
|---|---|---|
| Step 1: Prepool | | |
| A/New Caledonia monovalent bulk | 104 µg/ml | 302.88 |
| A/Wisconsin monovalent bulk | 85 µg/ml | 370.59 |
| B/Malaysia monovalent bulk | 110 µg/ml | 333.90 |
| PBS mod(1) | See footnote | 56.76 |
| Tween 80 | 48000 µg/ml | 5.24 |
| Triton X-100 | | Residual from H3N2 strain |
| α-tocopheryl hydrogen succinate | 26480 µg/ml | 1.2 |
| Filtrated water | | 504.43 |
| Total volume = 1575(ml) | | |
| 75 ml of prepool samples are retrieved for testing | | |
| Remaining prepool volume = 1500(ml) | | |
| Step 2: added to prepool | | |
| Emulsion | | 1500 |
| Total volume of final bulk = 3000(ml) | | |

(1)The buffer final bulk composition is: 137 mM NaCl, 2.7 mM KCl, 8.1 mM $Na_2HPO_4$, 1.47 mM $KH_2PO_4$, pH 7.4

Adjuvanted Vaccine: LD AS03 ½ (Table 5)

PBS mod 10 fold concentrated (pH 7.4 when one fold concentrated—see composition above) as well as a mixture containing Tween 80, Triton X-100 and VES (quantities taking into account the detergent present in the strains) are added to water for injection. After 5 to 30 minutes stirring, 20 µg HA per ml of each strain H1N1 and H3N2 and 23.32 µg HA per ml of B strain are added with 10 to 30 minutes stirring between each addition. After 15 to 30 minutes stirring, a small volume of the so called "intermediate bulk" are discarded for analysis and stored between +2 and +8° C. PBS mod is 1 fold concentrated in the intermediate bulk. The target's detergents concentration are 488 µg Tween 80 per ml, 73.6 µg Triton X-100 per ml and 66.6 µg VES per ml Final formulation is then prepared: SB62 is first diluted with the PBS mod buffer and stirred for 15-30 minutes at RT. An equal volume of this diluted SB62 is then added to each 250 µl of pre-pool of intermediate bulk. After 30 to 60 minutes stirring at RT, pH is checked to range between 6.8 and 7.5. Formulation is flushed with nitrogen and then stored between +2 and 8° C. prior to filling.

The final volume of both formulation is 500 µl per dose and the final HA concentration is 10 µg of each A monovalent bulk and 11.66 µg of B monovalent bulk per ml of trivalent final bulk. Final Tween 80, Triton X-100 (residual from H3N2 monobulk manufacturing) and α-tocopheryl hydrogen succinate (α-tocopheryl hydrogen succinate is an ester form of RRR (D isomer)-α-tocopherol) target concentrations are 244 µg/ml, 58.6 µg/ml and 33.3 µg/ml, respectively.

TABLE 5

AS03 adjuvanted low dose vaccine (half-dose of adjuvant)

| Component | Concentration | Volume (ml) |
|---|---|---|
| Step 1: Prepool | | |
| Step 1: Prepool | | |
| A/New Caledonia monovalent bulk | 104 µg/ml | 300.96 |
| A/Wisconsin monovalent bulk | 85 µg/ml | 368.24 |
| B/Malaysia monovalent bulk | 110 µg/ml | 331.78 |
| PBS mod(1) | See legend | 56.4 |
| Tween 80 | 48000 µg/ml | 5.2 |
| Triton X-100 | | Residual from H3N2 strain |
| α-tocopheryl hydrogen succinate | 26480 µg/ml | 1.2 |
| Filtrated water | | 501.22 |
| Total volume = 1565(ml) | | |
| 65 ml of prepool samples are retrieved for testing | | |
| Remaining prepool volume = 1500(ml) | | |
| Step 2: added to prepool | | |
| Emulsion SB62 | | 750 |
| PBS mod(1) | See legend | 75 |
| Filtrated water | | 675 |
| Total volume of final bulk = 3000(ml) | | |

(1)The buffer final bulk composition is: 137 mM NaCl, 2.7 mM KCl, 8.1 mM Na$_2$HPO$_4$, 1.47 mM KH$_2$PO$_4$, pH 7.4

III.4.2. Vaccine Administration

The vaccine is filled into 1.25-ml sterile Type I (Ph. Eur.) glass syringes. Each syringe is filled to a target of 0.57 ml (range: 0.54-0.60 ml). The vaccines were administered intramuscularly in the deltoid region of the non-dominant arm. All vaccines were presented as pre-filled syringes (0.5 ml). In order to ensure proper IM injection of the vaccine, a needle of at least 25G and at least 2.5 cm in length was used.

III.5 Study Population Results

A total of 300 subjects were enrolled in this study: 100 subjects in each of the 3 groups. The mean age of the total vaccinated cohort at the time of vaccination was 36.7 years with a standard deviation of 13.67 years. The mean age and gender distribution of the subjects across the 3 vaccine groups was similar.

III.6 Immunogenicity Results

Analysis of immunogenicity was performed on the ATP cohort for immunogenicity (297 subjects).

Humoral Immune Response

In order to evaluate the humoral immune response induced by the low dose influenza candidate vaccine adjuvanted with AS03, the following parameters (with 95% confidence intervals) were calculated for each treatment group:

Geometric mean titres (GMTs) of HI antibody titres at days 0 and 21;
Seroconversion rates (SC) at days 21;
Conversion factors at day 21;
Protection rates at day 0 and 21.

III.6.1 HI Geometric Mean Titres (GMT)

The GMTs for HI antibodies with 95% CI are shown in Table 6 and FIG. 1. Adjusted GMT ratios between groups are shown in Table 7.

Pre-vaccination GMTs of HI antibodies for all 3 vaccine strains were within the same range in the 3 treatment groups. The observed GMTs at day 21 for adjuvanted groups tends to be higher than Fluarix group for all 3 strains with a statistical difference (no overlapping of 95% CIs and adjusted GMT ratio did not contain the value 1) between FluLD1/1 and Fluarix for the A/Wisconsin vaccine strain. A statistical difference (adjusted GMT ratio did not contain the value 1) was observed also between FluLD½ and Fluarix for the B/Malaysia vaccine strain.

TABLE 6

Seropositivity rates and Geometric mean titers (GMTs) for anti-HA antibody at day 0 and 21 (ATP cohort for immunogenicity)

| | | | | | ≥10 1/DIL | | | GMT | | | | |
|---|---|---|---|---|---|---|---|---|---|---|---|---|
| | | | | | | 95% CI | | | 95% CI | | | |
| Antibody | Group | Timing | N | n | % | LL | UL | 1/DL | LL | UL | Min | Max |
| A/New Caledonia | FluLD1/1 | PRE | 99 | 80 | 80.8 | 71.7 | 88.0 | 31.9 | 23.5 | 43.4 | <10.0 | 2560.0 |
| | | PI(D21) | 99 | 99 | 100 | 96.3 | 100 | 475.4 | 352.2 | 641.6 | 20.0 | 7240.0 |
| | FluLD1/2 | PRE | 99 | 80 | 80.8 | 71.7 | 88.0 | 36.1 | 26.9 | 48.5 | <10.0 | 3620.0 |
| | | PI(D21) | 99 | 98 | 99.0 | 94.5 | 100 | 399.0 | 294.7 | 540.2 | <10.0 | 7240.0 |
| | Fluarix | PRE | 98 | 85 | 86.7 | 78.4 | 92.7 | 26.1 | 20.5 | 33.2 | <10.0 | 1280.0 |
| | | PI(D21) | 98 | 98 | 100 | 96.3 | 100 | 380.6 | 274.2 | 528.4 | 10.0 | 7240.0 |
| A/Wisconsin | FluLD1/1 | PRE | 99 | 61 | 61.6 | 51.3 | 71.2 | 16.8 | 13.1 | 21.5 | <10.0 | 453.0 |
| | | PI(D21) | 99 | 99 | 100 | 96.3 | 100 | 276.2 | 223.5 | 341.3 | 28.0 | 5120.0 |
| | FluLD1/2 | PRE | 99 | 66 | 66.7 | 56.5 | 75.8 | 19.9 | 15.2 | 25.9 | <10.0 | 640.0 |
| | | PI(D21) | 99 | 99 | 100 | 96.3 | 100 | 241.9 | 192.9 | 303.4 | 20.0 | 5120.0 |
| | Fluarix | PRE | 98 | 58 | 59.2 | 48.8 | 69.0 | 14.7 | 11.6 | 18.6 | <10.0 | 320.0 |
| | | PI(D21) | 98 | 97 | 99.0 | 94.4 | 100 | 172.3 | 136.4 | 217.6 | <10.0 | 5120.0 |
| B/Malaysia | FluLD1/1 | PRE | 99 | 72 | 72.7 | 62.9 | 81.2 | 20.4 | 15.9 | 26.1 | <10.0 | 453.0 |
| | | PI(D21) | 99 | 99 | 100 | 96.3 | 100 | 268.6 | 221.3 | 326.0 | 28.0 | 2560.0 |

TABLE 6-continued

Seropositivity rates and Geometric mean titers (GMTs) for anti-HA antibody at day 0 and 21 (ATP cohort for immunogenicity)

| Antibody | Group | Timing | N | n | % | ≥10 1/DIL 95% CI LL | UL | 1/DL | GMT 95% CI LL | UL | Min | Max |
|---|---|---|---|---|---|---|---|---|---|---|---|---|
| | FluLD1/2 | PRE | 99 | 76 | 76.8 | 67.2 | 84.7 | 22.2 | 17.6 | 27.9 | <10.0 | 320.0 |
| | | PI(D21) | 99 | 99 | 100 | 96.3 | 100 | 301.5 | 246.1 | 369.4 | 28.0 | 3620.0 |
| | Fluarix | PRE | 98 | 76 | 77.6 | 68.0 | 85.4 | 26.5 | 20.9 | 33.6 | <10.0 | 320.0 |
| | | PI(D21) | 98 | 97 | 99.0 | 94.4 | 100 | 219.2 | 171.4 | 280.2 | <10.0 | 5120.0 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
Fluarix = Fluarix vaccine
GMT = Geometric Mean antibody Titer
N = Number of subjects with available results
n/% = number/percentage of seropositive subjects (HI titer >= 1:10)
95% CI = 95% confidence interval,
LL = Lower Limit,
UL = Upper Limit
MIN/MAX = Minimum/Maximum
PRE = Pre-vaccination at day 0
PI (D21) = Post-vaccination at Day 21

TABLE 7

Adjusted GMT ratios between groups for each vaccine strain at day 21 (ATP cohort for immunogenicity)

| Antibody | Group description | N | Adjusted GMT | Group description | N | Adjusted GMT | Ratio order | Adjusted GMT ratio Value | 95% CI LL | UL |
|---|---|---|---|---|---|---|---|---|---|---|
| A/New Caledonia (1/DIL) | FluLD1/1 | 99 | 472.4 | FluLD1/2 | 99 | 385.0 | FluLD1/1/FluLD1/2 | 1.23 | 0.80 | 1.88 |
| | FluLD1/1 | 99 | 472.3 | Fluarix | 98 | 396.9 | FluLD1/1/Fluarix | 1.19 | 0.78 | 1.82 |
| | FluLD1/2 | 99 | 385.0 | Fluarix | 98 | 397.0 | FluLD1/2/Fluarix | 0.97 | 0.63 | 1.49 |
| A/Wisconsin (1/DIL) | FluLD1/1 | 99 | 277.3 | FluLD1/2 | 99 | 230.0 | FluLD1/1/FluLD1/2 | 1.21 | 0.90 | 1.62 |
| | FluLD1/1 | 99 | 277.5 | Fluarix | 98 | 180.8 | FluLD1/1/Fluarix | 1.54 | 1.14 | 2.06 |
| | FluLD1/2 | 99 | 230.0 | Fluarix | 98 | 180.6 | FluLD1/2/Fluarix | 1.27 | 0.95 | 1.71 |
| B/Malaysia (1/DIL) | FluLD1/1 | 99 | 275.1 | FluLD1/2 | 99 | 303.4 | FluLD1/1/FluLD1/2 | 0.91 | 0.68 | 1.22 |
| | FluLD1/1 | 99 | 275.2 | Fluarix | 98 | 212.7 | FluLD1/1/Fluarix | 1.29 | 0.96 | 1.74 |
| | FluLD1/2 | 99 | 303.4 | Fluarix | 98 | 212.6 | FluLD1/2/Fluarix | 1.43 | 1.06 | 1.92 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
Fluarix = Fluarix vaccine
Adjusted GMT = geometric mean antibody titre adjusted for baseline titre
N = Number of subjects with both pre- and post-vaccination results available
95% CI = 95% confidence interval for the adjusted GMT ratio (Ancova model: adjustment for baseline titre – pooled variance with more than 2 groups);
LL = lower limit,
UL = upper limit

III.6.2 Seroconversion Factors of Anti-HI Antibody Titres, Seroprotection Rates and Seroconversion Rates (Correlates for Protection as Established for Influenza Vaccine in Humans)

Figure 2:
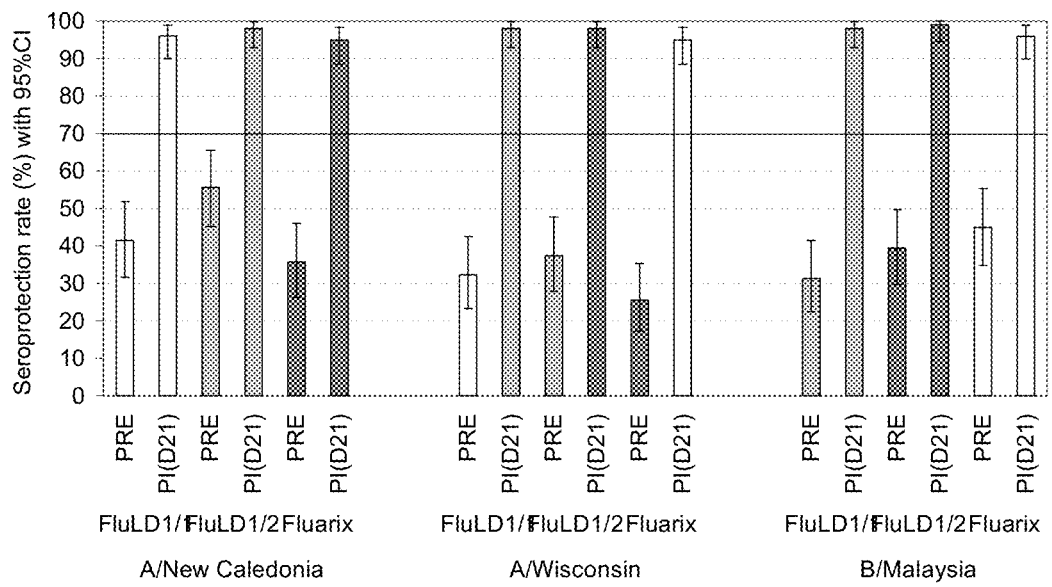
FIG. 2: Clinical trial: Seroprotection rate (SPR) for HI antibody titer with 95% confidence interval at day 0 and day 21 (ATP cohort for immunogenicity).
Figure 3:
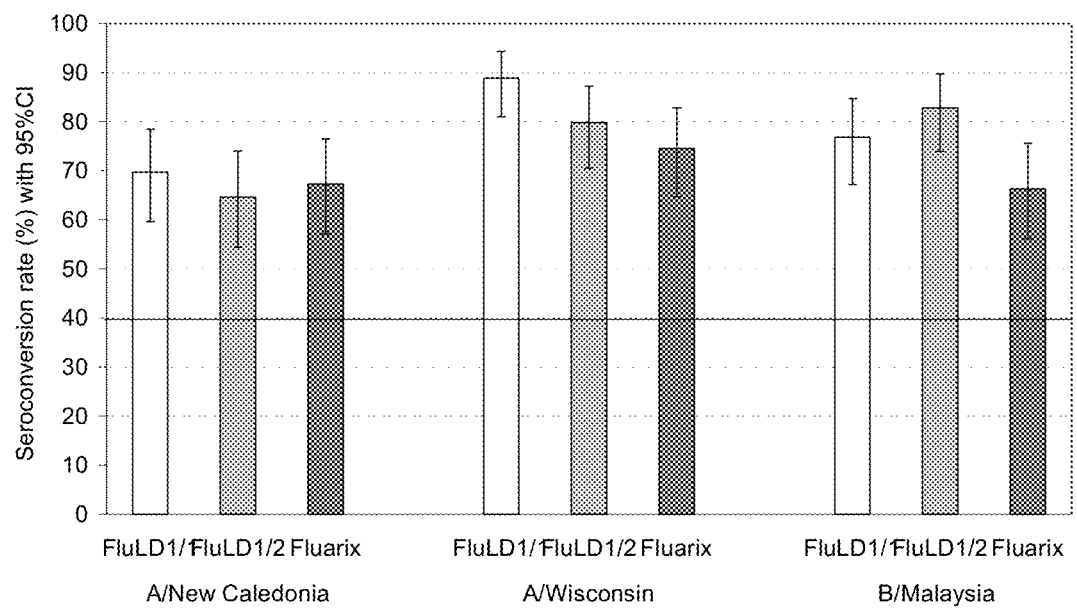
FIG. 3: Clinical trial: Seroconversion rate (SCR) for HI antibody titer with 95% confidence interval at day 21 (ATP cohort for immunogenicity).
Figure 4:
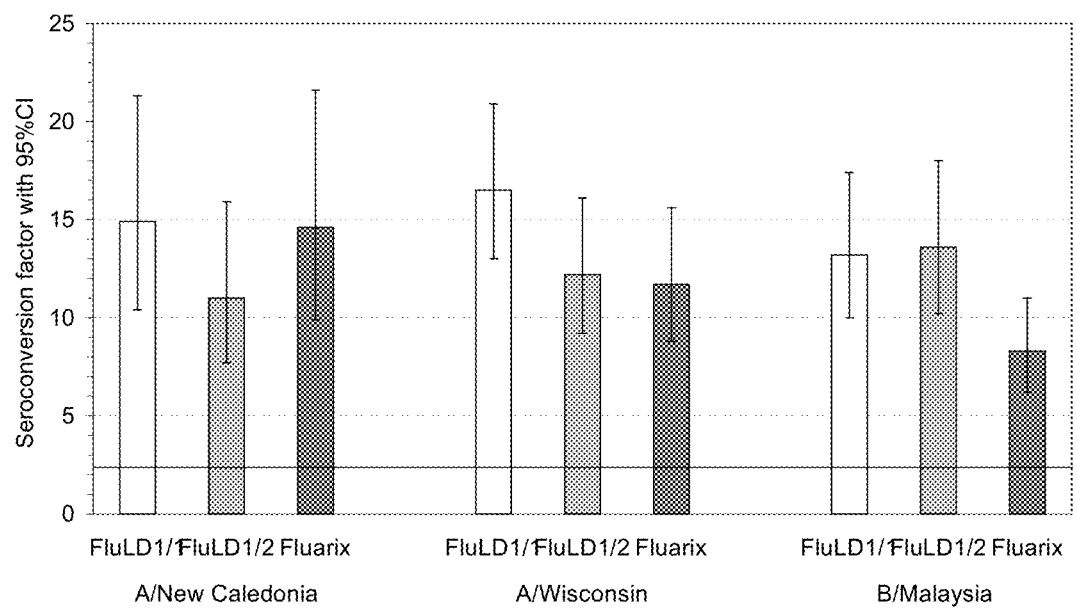
FIG. 4: Clinical trial: Seroconversion factor (SCF) for HI antibody titer with 95% confidence interval at day 21 (ATP cohort for immunogenicity).

Results are presented in Table 8-FIG. 2 for seroprotection rates, Table 9-FIG. 3 for seroconversion rates and Table 10-FIG. 4 for conversion factors.

The threshold required by the European Authorities for the seroprotection rates (70%) was reached in all groups (at least 94.9%). For each vaccine strain, the seroprotection rates at day 21 for the 3 groups were within the same range.

The threshold required by the European Authorities for the seroconversion rates (40%) was reached in all groups (at least 65%).

For the A/New Caledonia vaccine strain, the SCR at day 21 for the 3 groups were within the same range.

For the A/Wisconsin vaccine strain, the SCR at day 21 for the FluLD1/1 group tended to be higher compared to the Fluarix group. The SCR at day 21 for the FluLD½ group was within the same range compared to the Fluarix group.

For the B/Malaysia vaccine strain, the SCR at day 21 for the FluLD½ group tended to be higher compared to the Fluarix group. The SCR at day 21 for the FluLD1/1 group was within the same range compared to the Fluarix group.

The threshold required by the European Authorities for the seroconversion factors (2.5) was reached in all groups (at least 6.2).

For the A/New Caledonia vaccine strain, the SCF at day 21 for the 3 groups seemed to be within the same range. The observed value for FluLD½ group was lower than the observed value for the Fluarix group but could be explained by the higher pre-vaccination seroprotection rate in the FluLD½ group.

For the A/Wisconsin vaccine strain, the SCF at day 21 for the FluLD1/1 group tended to be higher compared to the Fluarix group. The SCF at day 21 for the FluLD½ group was within the same range compared to Fluarix group.

For the B/Malaysia vaccine strain, the SCF at day 21 for the two adjuvanted groups tended to be higher compared to the Fluarix group.

TABLE 8

Seroprotection rates (SPR) for HI antibody titer at day 0 and day 21 (ATP cohort for immunogenicity)

| Vaccine strain | Group | Timing | N | n | % | SPR 95% CI LL | UL |
|---|---|---|---|---|---|---|---|
| A/New Caledonia | FluLD1/1 | PRE | 99 | 41 | 41.4 | 31.6 | 51.8 |
| | | PI(D21) | 99 | 95 | 96.0 | 90.0 | 98.9 |
| | FluLD1/2 | PRE | 99 | 55 | 55.6 | 45.2 | 65.5 |
| | | PI(D21) | 99 | 97 | 98.0 | 92.9 | 99.8 |
| | Fluarix | PRE | 98 | 35 | 35.7 | 26.3 | 46.0 |
| | | PI(D21) | 98 | 93 | 94.9 | 88.5 | 98.3 |
| A/Wisconsin | FluLD1/1 | PRE | 99 | 32 | 32.3 | 23.3 | 42.5 |
| | | PI(D21) | 99 | 97 | 98.0 | 92.9 | 99.8 |
| | FluLD1/2 | PRE | 99 | 37 | 37.4 | 27.9 | 47.7 |
| | | PI(D21) | 99 | 97 | 98.0 | 92.9 | 99.8 |
| | Fluarix | PRE | 98 | 25 | 25.5 | 17.2 | 35.3 |
| | | PI(D21) | 98 | 93 | 94.9 | 88.5 | 98.3 |
| B/Malaysia | FluLD1/1 | PRE | 99 | 31 | 31.3 | 22.4 | 41.4 |
| | | PI(D21) | 99 | 97 | 98.0 | 92.9 | 99.8 |
| | FluLD1/2 | PRE | 99 | 39 | 39.4 | 29.7 | 49.7 |
| | | PI(D21) | 99 | 98 | 99.0 | 94.5 | 100 |
| | Fluarix | PRE | 98 | 44 | 44.9 | 34.8 | 55.3 |
| | | PI(D21) | 98 | 94 | 95.9 | 89.9 | 98.9 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
Fluarix = Fluarix vaccine
N = Number of subjects with available results
n/% = Number/percentage of seroprotected subjects (HI titer >= 40 1/DIL)
95% CI = 95% confidence interval,
LL = Lower Limit,
UL = Upper Limit
PRE = Pre-vaccination at day 0
PI (D1) = Post-vaccination at Day 21
Data source = Appendix table IIIA

TABLE 9

Seroconversion rate (SCR) for HI antibody titer at day 21 (ATP cohort for immunogenicity)

| Vaccine strain | Group | N | n | % | SCR 95% CI LL | UL |
|---|---|---|---|---|---|---|
| A/New Caledonia | FluLD1/1 | 99 | 69 | 69.7 | 59.6 | 78.5 |
| | FluLD1/2 | 99 | 64 | 64.6 | 54.4 | 74.0 |
| | Fluarix | 98 | 66 | 67.3 | 57.1 | 76.5 |
| A/Wisconsin | FluLD1/1 | 99 | 88 | 88.9 | 81.0 | 94.3 |
| | FluLD1/2 | 99 | 79 | 79.8 | 70.5 | 87.2 |
| | Fluarix | 98 | 73 | 74.5 | 64.7 | 82.8 |
| B/Malaysia | FluLD1/1 | 99 | 76 | 76.8 | 67.2 | 84.7 |
| | FluLD1/2 | 99 | 82 | 82.8 | 73.9 | 89.7 |
| | Fluarix | 98 | 65 | 66.3 | 56.1 | 75.6 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
Fluarix = Fluarix vaccine
Seroconversion defined as:
For initially seronegative subjects, antibody titre >= 40 1/DIL after vaccination
For initially seropositive subjects, antibody titre after vaccination >= 4 fold the pre-vaccination antibody titre
N = Number of subjects with pre- and post-vaccination results available
n/% = Number/percentage of seroconverted subjects
95% CI = 95% confidence interval,
LL = Lower Limit,
UL = Upper Limit

TABLE 10

Seroconversion factor (SCF) for HI antibody titer at day 21 (ATP cohort for immunogenicity)

| Vaccine strain | Group | N | Value | SCF 95% CI LL | UL |
|---|---|---|---|---|---|
| A/New Caledonia | FluLD1/1 | 99 | 14.9 | 10.4 | 21.3 |
| | FluLD1/2 | 99 | 11.0 | 7.7 | 15.9 |
| | Fluarix | 98 | 14.6 | 9.9 | 21.6 |
| A/Wisconsin | FluLD1/1 | 99 | 16.5 | 13.0 | 20.9 |
| | FluLD1/2 | 99 | 12.2 | 9.2 | 16.1 |
| | Fluarix | 98 | 11.7 | 8.8 | 15.6 |
| B/Malaysia | FluLD1/1 | 99 | 13.2 | 10.0 | 17.4 |
| | FluLD1/2 | 99 | 13.6 | 10.2 | 18.0 |
| | Fluarix | 98 | 8.3 | 6.2 | 11.0 |

FluLD1/1 = Low dose influenza vaccine (5 ug HA/strain) with full dose of AS03 adjuvant
FluLD1/2 = Low dose influenza vaccine (5 ug HA/strain) with half dose of AS03 adjuvant
Fluarix = Fluarix vaccine
N = Number of subjects with pre- and post-vaccination results available
SCF = Seroconversion Factor or geometric mean ratio (mean[log10(PI(D 21)/PRE)])
95% CI = 95% confidence interval, LL = Lower Limit, UL = Upper Limit III.7 Safety Conclusions A higher reactogenicity in terms of solicited (local/general) and unsolicited symptoms in the adjuvanted vaccine groups compared to the Fluarix Group was the global trend observed in this study. A reduction of the AS03 content in the adjuvanted vaccine has a significant impact on all the general and on the local grade 3 symptoms.

The occurrence of unsolicited symptoms tended to be higher in the adjuvanted vaccine groups (55% and 47% of subjects), compared to the Fluarix Group (35%).

From these results, it can be concluded that the reactogenicity and safety profile of the candidate vaccines is satisfactory and clinically acceptable.

III.8. Overall Conclusions

III.8.1. Immunogenicity Results

The primary objective of this study was to assess humoral immune response (anti-HI antbody titres) elicited by low dose influenza vaccine with two different concentrations of AS03 adjuvant, and by Fluarix.

At Day 21, the three vaccines exceeded the requirements of the European authorities for annual registration of split virion influenza vaccines ("Note for Guidance on Harmonisation of Requirements for influenza Vaccines" for the immuno-logical assessment of the annual strain changes-CPMP/BWP/214/96). GMTs tended to be higher in the adjuvanted groups compared to the Fluarix Group, with a statistically significant difference observed for the A/Wisconsin (FluLD1/1 vs. Fluarix) and B/Malaysia vaccine strains (FluLD½ vs. Fluarix). Similar seroprotection rates were observed in all three vaccine groups, ranging from 94.9% to 99%. Seroconversion rates and seroconversion factors were observed to be higher in the adjuvanted groups than in the Fluarix Group. Data from this trial also revealed that the immunogenicity induced by the vaccine with half the dosage of AS03 adjuvant was comparable to that induced with the full dose of adjuvant.

III.8.2. Reactogenicity and Safety Results

The administration of the low dose influenza candidate vaccine adjuvanted with AS03 was safe and clinically well tolerated in the study population, i.e. adult people aged between 18 and 59 years. The half dose adjuvanted vaccine showed a marked decrease in the incidence of solicited local and general symptoms, compared to the full dose adjuvanted vaccine.

Example IV—Preclinical Evaluation of Adjuvanted and Non-Adjuvanted Split Influenza Vaccines (Comprising Various Doses of AS03 Adjuvant) in Primed BALB/c Mice

IV.1. Experimental Design and Objective

Experiments in influenza-primed mice were performed in order to evaluate the increase in humoral responses by AS03 induced by influenza vaccines formulated with this oil-in-water adjuvant. To be closer to the human situation (people are seropositives due to repeated infection with drifted strains approximately every two years), this experiment was conducted using animals that were primed with heterosubtypic strains. The heterosubtypic priming is also a more stringent model compared to the priming with homotypic strains and is a better model to discriminate between different adjuvants.

IV.1.1. Treatment/Group (Table 11)

Groups of 27 adult female BALB/c mice were primed intranasally (20 µl volume) on day 0 with trivalent whole, formalin-inactivated influenza virus (5 µg HA for each strain). Priming strains consisted of earlier drift variants (5 µg HA whole inactivated H1N1 A/Johannesburg/82/96, H3N2 A/Sydney/5/97, B/Harbin/7/94) to those included in the vaccine. Twenty-eight days later, the mice were vaccinated with a single dose of the vaccine candidate intramuscularly in a total volume of 50 µl. Mice were immunized with formulations containing split antigens alone (trivalent split plain) or formulations containing split antigens adjuvanted with two doses of AS03 (full or ⅕). The strains used for the immunizations included H1N1 A/New Caledonia/20/99, H3N2 A/Panama/2007/99, B/Shangdong/7/97 viral antigens (1.5 µg/strain, $\frac{1}{10}^{th}$ of the human dose).

TABLE 11

| Gr | Antigen/Formulation | Other treatment |
|---|---|---|
| 1 | Trivalent split/Plain (non-adjuvanted) | Heterologous priming D0 |
| 2 | Trivalent split/AS03 | Heterologous priming D0 |
| 3 | Trivalent split/AS03 ⅕ | Heterologous priming D0 |

IV.1.2. Preparation of the Vaccine Formulations

A Premix of Tween 80, Triton X100 and Vitamin E Succinate (VES) is prepared in order to reach a final concentration into the vaccine of 750 µg/ml of Tween 80, 110 µg/ml of Triton X100 and 100 µg/ml of VES. The quantities used in the premix are calculated taking into account the quantities of detergent and VES already present in the strains.

Preparation of one liter of 10 fold concentrated Saline buffer (PBS pH 7.4): to 0.800 l of water for injection, add NaCl 80 g, KCl 2 g, $Na_2HPO_4$ 11.44 g, $KH_2PO_4$ 2 g. After solubilization, adjust to 1.0 L with water for injection. pH will be at 7.4 when 10 fold diluted.

Trivalent Split/Plain

The formulation of one 50 µl dose is prepared extemporaneously according the following sequence: Water For Injection+Saline Buffer (10 fold concentrated PBS pH 7.4)+Premix, 5 min magnetic stirring at room temperature, +1.5 µg HA H1N1 strain, 10 min magnetic stirring at room temperature, +1.5 µg HA H3N2 strain, 10 min magnetic stirring at room temperature, +1.5 µg HA B strain, 15 min magnetic stirring at room temperature. The formulations are injected within the hour following the end of their preparation.

Trivalent Split/AS03

A Premix of Tween 80, Triton X100 and Vitamin E Succinate (VES) is prepared in order to reach a final concentration into the vaccine of 750 µg/ml of Tween 80, 110 µg/ml of Triton X100 and 100 µg/ml of VES. The quantities used in the premix are calculated taking into account the quantities of detergent and VES already present in the strains. The formulation of one 50 µl dose is prepared extemporaneously according the following sequence: Water For Injection+Saline Buffer (10 fold concentrated PBS pH 7.4)+Premix, 5 min magnetic stirring at room temperature, +1.5 µg HA H1N1 strain, 10 min magnetic stirring at room temperature, +1.5 µg HA H3N2 strain, 10 min magnetic stirring at room temperature, +1.5 µgHA B strain, 15 min magnetic stirring at room temperature, +25 µl SB62 emulsion for the full dose AS03 or 5 µl SB62 emulsion for the ⅕ dose AS03, 15 min magnetic stirring at room temperature. The formulations are injected within the hour following the end of their preparation.

IV.1.3. Read-Outs (Table 12)

The humoral immune response to vaccination was measured before immunization (day 28) and 14 days after immunization (27 mice/group). Serum samples were tested by the hemagglutination inhibition (HI) test.

TABLE 12

| Read-out | Timepoint | Sample type | Analysis method |
|---|---|---|---|
| Humoral response | D28, D42 | Sera | IHA |

IV.2. Results

IV.2.1. Humoral Immunity

Figure 5A:
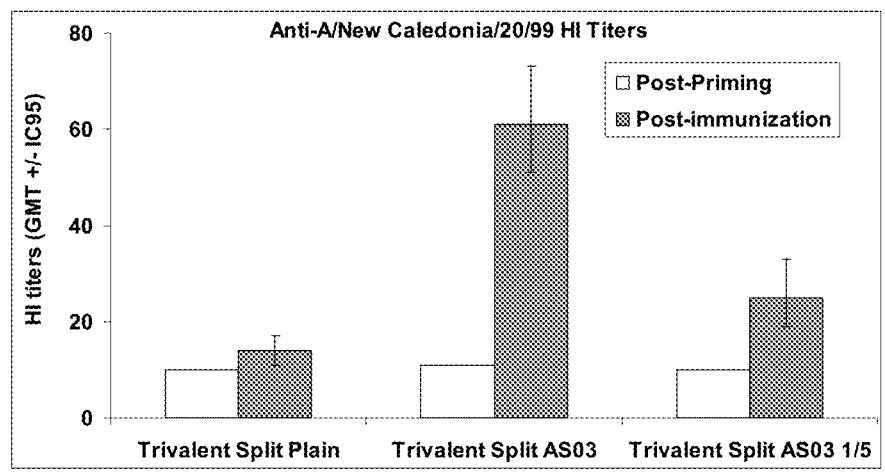
FIG. 5A: Mice study: Haemagglutinin Inhibition test (GMT+/−IC95) in BALB/c mice primed with heterosubtypic strains (dose range AS03). Anti-A/New Caledonia/20/99 HI titers.
Figure 5B:
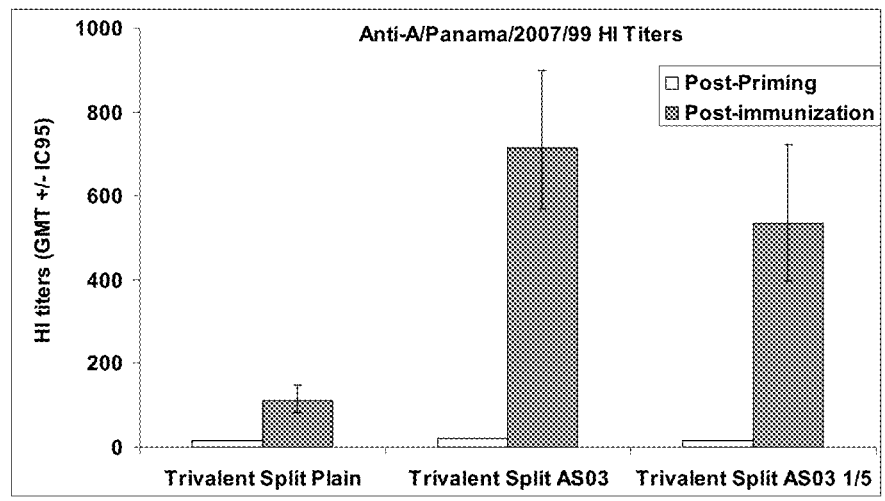
FIG. 5B: Mice study: Haemagglutinin Inhibition test (GMT+/−IC95) in BALB/c mice primed with heterosubtypic strains (dose range AS03). Anti-A/Panama/2007/99 HI titers.
Figure 5C:
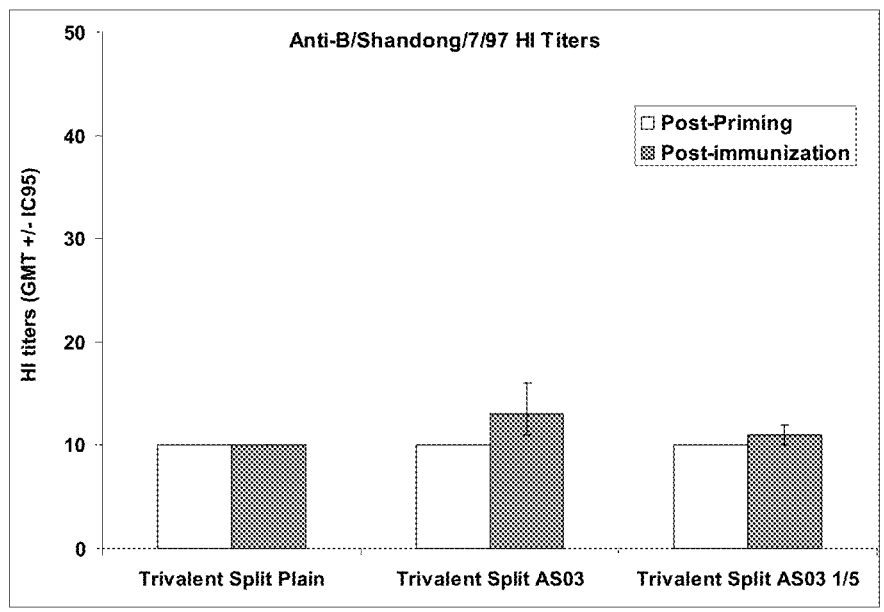
FIG. 5C: Mice study: Haemagglutinin Inhibition test (GMT+/−IC95) in BALB/c mice primed with heterosubtypic strains (dose range AS03). Anti-B/Shandong/7/97 HI titers.

Results are presented in FIGS. 5A to C. In this mouse model of heterosubtypic priming followed by single vaccination, AS03 and dilutions thereof were shown to induce higher HI titres compared to the plain vaccine. For all influenza A strains, a statistically significant increase of HI titres was observed ($p<0.05$). For the H1N1 strain, a significant difference in HI titres was also observed between AS03 and AS03 ⅕ ($p<0.05$). A reduced dose of AS03 failed to increase HI titres for the B strain compared to the plain vaccine. Very low responses were observed against the B strain (B/Shangdong); this is likely to be due to the significant antigenic drift between the B strains used for the priming and the vaccine.

IV.3. Summary of Results and Conclusions

In conclusion, an increase in HI titres was observed in animals primed with hetrosubtypic strains when using AS03 adjuvanted vaccines compared to the plain vaccine. A full dose of AS03 was optimal for obtaining robust HI titres against all three influenza vaccine strains.

Example V—Preclinical Evaluation of Adjuvanted and Non-Adjuvanted Split Influenza Vaccines (Comprising Various Doses of AS03 Adjuvant) in Primed C57Bl/6 Mice

V.1. Experimental Design and Objective

Experiments in influenza-primed mice were performed in order to evaluate the increase in humoral and cellular responses by AS03 induced influenza vaccines formulated with this oil-in-water adjuvant.

To simulate the human situation, an experiment was conducted using mice primed with heterosubtypic strains.

V.1.1. Treatment/Group (Table 13)

Groups of 25 adult female C57Bl/6 mice were primed intranasally (20 µl volume) on day 0 with trivalent whole, formalin-inactivated influenza virus (5 µg HA for each strain). Priming strains consisted of earlier drift variants (5 µg HA whole inactivated H1N1 A/Beijing/262/95, H3N2N Panama/2007/99, B/Shangdong/7/97) to those included in the vaccine. Twenty-eight days later, the mice were vaccinated with a single dose of the vaccine candidate intramuscularly in a total volume of 100 µl. Mice were immunized with formulations containing split antigens alone (trivalent split plain) or formulations containing split antigens adjuvanted with three doses of AS03 (full, ½ or ⅕). The strains used for the immunizations included H1N1 A/New Caledonia/20/99, H3N2 A/New York/55/2004, B/Jiangsu/10/2003 viral antigens (1.5 µg/strain, $\frac{1}{10}^{th}$ of the human dose).

TABLE 13

| Gr | Antigen/Formulation | Other treatment |
|---|---|---|
| 1 | Trivalent split/Plain (non-adjuvanted) | Heterologous priming D0 |
| 2 | Trivalent split/AS03 | Heterologous priming D0 |
| 3 | Trivalent split/AS03 ½ | Heterologous priming D0 |
| 4 | Trivalent split/AS03 ⅕ | Heterologous priming D0 |
| 5 | PBS | Heterologous priming D0 |

V.1.2. Preparation of the Vaccine Formulations

Trivalent Split/Plain

The formulations for a 100 µl dose are prepared extemporaneously according the following sequence: Water For Injection+Saline Buffer (10 fold concentrated PBS pH 7.4 prepared as taught in exempleIV)+Fluarix Lot DFLUA014 (1.5 µg per strain in the final dose).

Trivalent Split/AS03

The formulations for a 100 µl dose are prepared extemporaneously according the following sequence: Water For Injection+Saline Buffer (10 fold concentrated PBS pH 7.4 prepared as taught in exempleIV)+Fluarix Lot DFLUA014 (1.5 µg per strain in the final dose)+25 µl SB62 emulsion for the full dose or 12.5 µl SB62 emulsion for the ½ dose or 5 µl SB62 emulsion for the ⅕ dose. The formulations are injected within the hour following the end of the preparation.

V.1.3. Read-Outs (Table 14)

The humoral immune response to vaccination was measured 21 days after immunization (10 mice/group) and the serum samples were tested by the haemagglutination inhibition (HI) test. The cellular immune response (15 mice per group) was tested 7 days post-immunization by intracellular cytokine staining (ICS).

TABLE 14

| Read-out | Timepoint | Sample type | Analysis method |
|---|---|---|---|
| Humoral response | D49 | Sera | IHA |
| Cellular response | D35 | PBMCs | ICS |

V.2. Results

V.2.1. Humoral Immunity (10 Mice/Group)

Figure 6A:
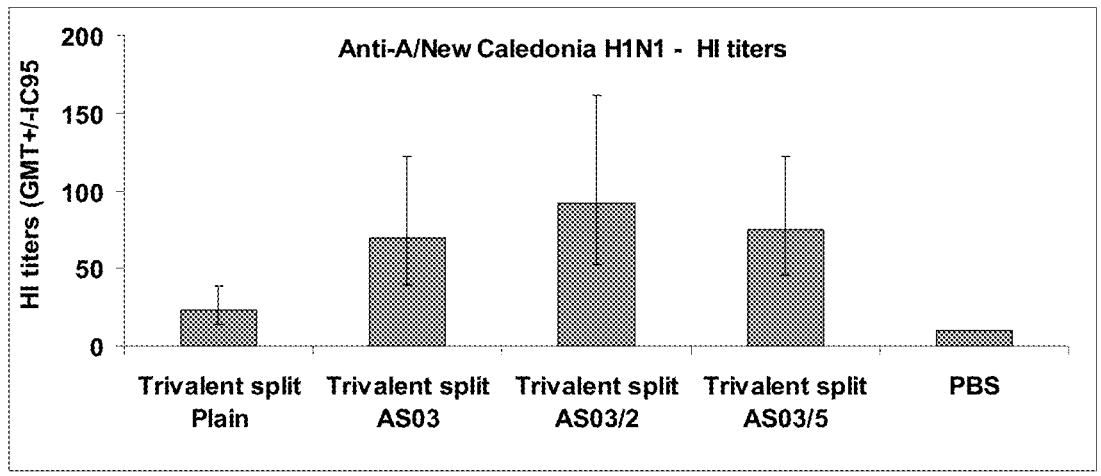
FIG. 6A: Mice study: Haemagglutinin Inhibition test (GMT+/−IC95) in C57BI/6 mice primed with heterosubtypic strains (dose range AS03). Anti-A/New Caledonia H1N1-HI titers.
Figure 6B:
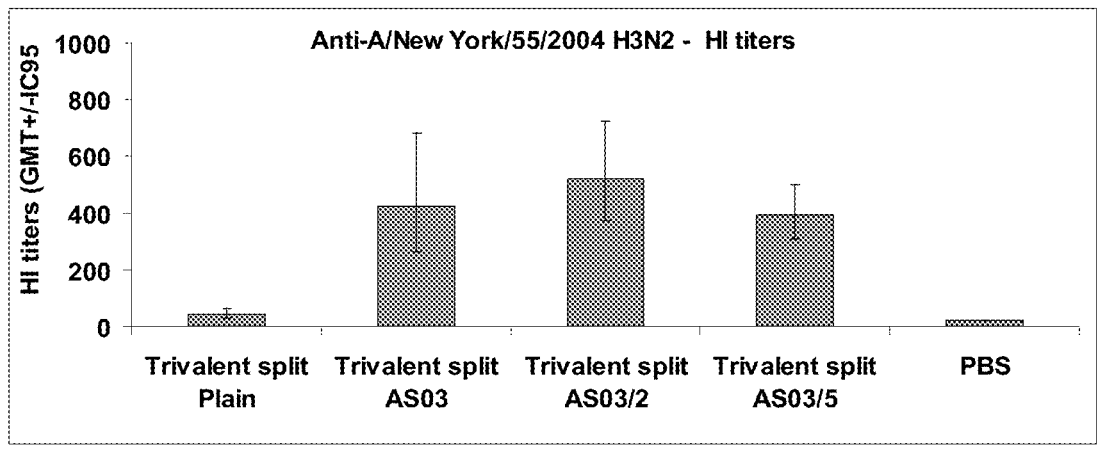
FIG. 6B: Mice study: Haemagglutinin Inhibition test (GMT+/−IC95) in C57BI/6 mice primed with heterosubtypic strains (dose range AS03). Anti-A/New York/55/2004 H3N2-HI titers.
Figure 6C:
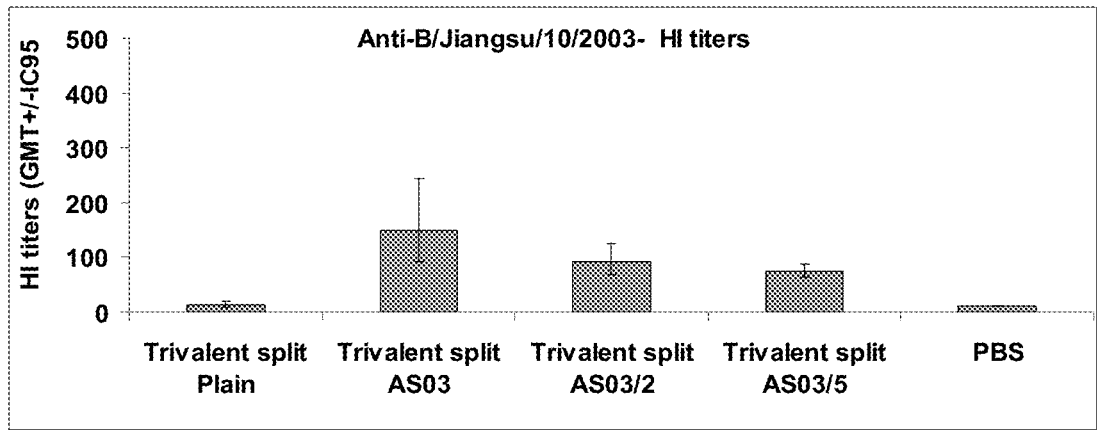
FIG. 6C: Mice study: Haemagglutinin Inhibition test (GMT+/−IC95) in C57BI/6 mice primed with heterosubtypic strains (dose range AS03). Anti-B/Jiangsu/10/2003-HI titers.

Results are presented in FIGS. 6A to C. In this mouse model of heterosubtypic priming followed by single vaccination, AS03 and dilutions (½ and ⅕) thereof were shown to induce higher HI titres compared to the plain vaccine. For all three strains, no difference of HI titres was observed between mice receiving the vaccine adjuvanted with a full dose AS03 or reduced doses AS03.

V.2.2. Cellular Immunity (15 Mice/Group)

Figure 7:
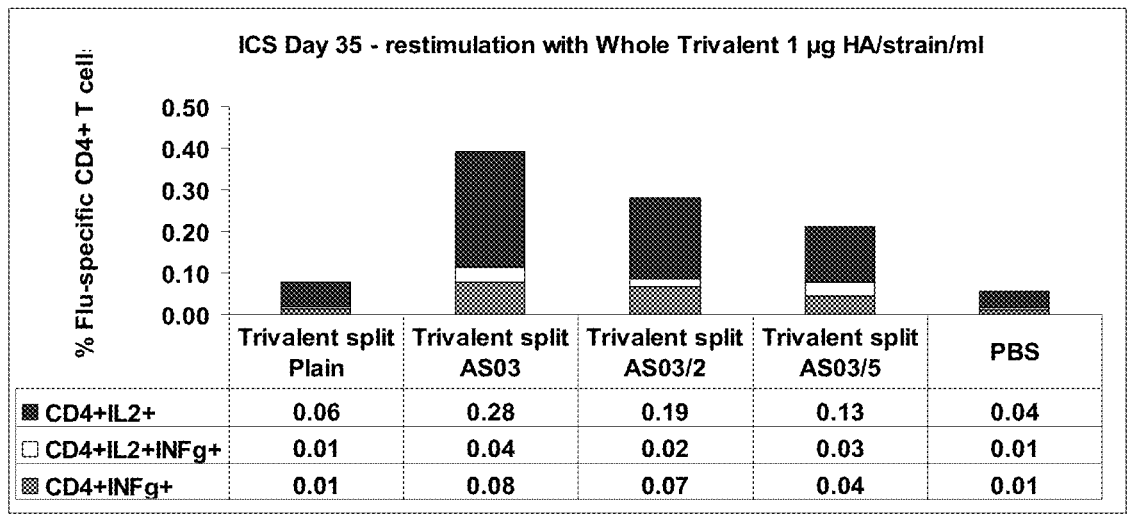
FIG. 7: Mice study: Cellular immune response (CD4+ T cell) in PBMC from C57BI/6 mice primed with heterosubtypic strains (dose range AS03).

Results are presented in FIG. 7. Whatever the dilution of AS03, higher CD4+ T cell responses were observed in mice immunized with AS03-adjuvanted trivalent split vaccine compared to mice immunized with trivalent split plain.

Compared to the response induced in mice immunized with trivalent split adjuvanted with a full dose AS03, a trend for lower cellular responses was observed when mice were immunized with trivalent split adjuvanted with lower doses of AS03.

V.3. Summary of Results and Conclusions

In conclusion, an increase in humoral and cellular responses was observed in animals primed with heterosubtypic strains when using AS03 adjuvanted vaccines compared to the plain vaccine. A similar magnitude of humoral response was observed between mice immunized with full dose or fractional doses of AS03 adjuvant. However, a reduction in adjuvant dose was associated with a trend for reduced magnitude of CD4+ T cell response.

Example VI—Preclinical Evaluation of the Cellular Immune Response Induced by Adjuvanted and Non-Adjuvanted Split Influenza Vaccines (Comprising Various Doses of AS03 Adjuvant and Low Dose Antigen) in Primed C57Bl/6 Mice

VI.1. Experimental Design and Objective

Experiments in influenza-primed mice were performed in order to evaluate the increase in cellular immune responses by AS03 induced by influenza vaccines containing low dose antigen (0.5 µg/strain, $\frac{1}{30}^{th}$ human dose) and formulated with this oil-in-water adjuvant. To simulate the human situation, an experiment was conducted using mice primed with heterosubtypic strains.

VI.1.1. Treatment/Group (Table 15)

Groups of 15 adult female C57Bl/6 mice were primed intranasally (20 µl volume) on day 0 with trivalent whole, formalin-inactivated influenza virus (5 µg HA for each strain). Priming strains consisted of earlier drift variants (5 µg HA whole inactivated H1N1 A/Beijing/262/95, H3N2N Panama/2007/99, B/Shangdong/7/97) to those included in the vaccine. Twenty-eight days later, the mice were vaccinated with a single dose of the vaccine candidate intramuscularly in a total volume of 50 µl. Mice were immunized with formulations containing split antigens alone (trivalent split plain) or formulations containing split antigens adjuvanted with three doses of AS03 (full, ½ or ⅕). The strains used for the immunizations included H1N1 A/New Caledonia/20/99, H3N2 A/New York/55/2004, B/Jiangsu/10/2003 viral antigens (0.5 µg/strain, $\frac{1}{30}^{th}$ of the human dose).

TABLE 15

| Gr | Antigen/Formulation | Other treatment |
|---|---|---|
| 1 | Trivalent split/Plain (non-adjuvanted) | Heterologous priming D0 |
| 2 | Trivalent split/AS03 | Heterologous priming D0 |
| 3 | Trivalent split/AS03 ½ | Heterologous priming D0 |
| 4 | Trivalent split/AS03 ⅕ | Heterologous priming D0 |
| 5 | PBS | Heterologous priming D0 |

VI.1.2. Preparation of the Vaccine Formulations

Trivalent Split/Plain

The formulations for a 50 µl dose are prepared extemporaneously according the following sequence: water for injection+Saline Buffer (10 fold concentrated PBS pH 7.4 prepared as taught in exempleIV)+Fluarix Lot DFLUA014 (0.5 µg per strain in the final dose).

Trivalent Split/AS03

The formulations for a 50 µl dose are prepared extemporaneously according the following sequence: Water For Injection+Saline Buffer (10 fold concentrated PBS pH 7.4 prepared as taught in exempleIV)+Fluarix Lot DFLUA014 (0.5 µg per strain in the final dose)+25 µl SB62 emulsion for the full dose or 12.5 µl SB 62 emulsion for the ½ dose or 5 µl SB62 emulsion for the ⅕ dose. The formulations are injected within the hour following the end of the preparation.

VI.1.3. Read-Outs (Table 16)

The cellular immune response was tested 7 days post-immunization by intracellular cytokine staining.

TABLE 16

| Read-out | Timepoint | Sample type | Analysis method |
|---|---|---|---|
| Cellular response | D35 | PBMCs | ICS |

VI.2. Results

VI.2.1. Cellular Immunity

Figure 8:
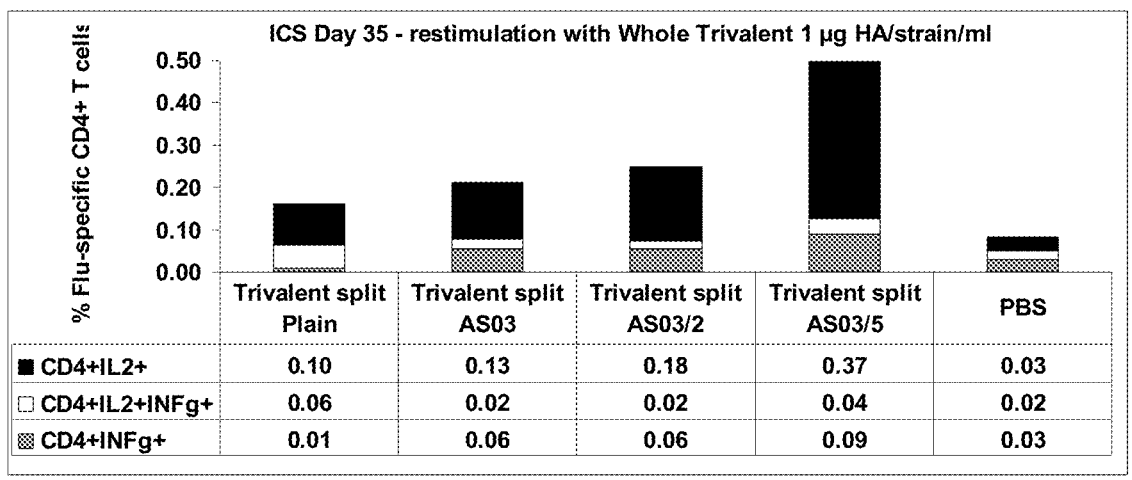
FIG. 8: Mice study: Cellular immune response (CD4+ T cell) in PBMC from C57BI/6 mice primed with heterosubtypic strains and immunized with low dose antigen (0.5 μg) adjuvanted with dose range AS03.

Results are presented in FIG. 8. Marginally higher CD4+ T cell responses were observed in mice immunized with trivalent split vaccine adjuvanted with AS03 (full or ½ dose) compared to mice immunized with trivalent split plain. Compared to the response induced in mice immunized with trivalent split plain or adjuvanted with a full dose or a half dose of AS03, higher cellular responses were observed when mice were immunized with trivalent split adjuvanted with ⅕ of AS03 dose.

VI.3. Summary of Results and Conclusions

In conclusion, a minimal increase in CD4+ T cell responses was observed in heterosubtypic primed animals when using AS03 adjuvanted vaccines compared to the plain vaccine. No adjuvant dose response was observed in this experiment and indeed a ⅕ of AS03 dose induced higher frequencies of antigen specific CD4+ T cells than was seen with higher adjuvant doses. Overall these data generated using 0.5 µg HA per strain are not similar to data from other preclinical experiments generated using 1.5 µg HA per strain.

Example VII—Preclinical Evaluation of Adjuvanted and Non-Adjuvanted Split H5N1 Vaccines (Comprising Various Doses of AS03 Adjuvant and Antigen) in Naïve C57Bl/6 Mice

VII.1. Experimental Design and Objective

Experiments in H5N1-naive mice were performed in order to evaluate the increase in humoral and cellular immune responses by AS03 induced by H5N1 split vaccines formulated with this oil-in-water adjuvant. In the case of a pandemic, it is expected that the entire world population will be immunologically naive to the newly circulating pandemic influenza strain. Due to this naive immune status a pandemic vaccine will likely require two vaccine doses to protect individuals from infection and severe illness caused by a new influenza strain. To represent this lack of previous exposure a naïve mouse model was developed to assess vaccine immunogenicity.

VII.1.1. Treatment/Group (Table 17)

Figure 9C:
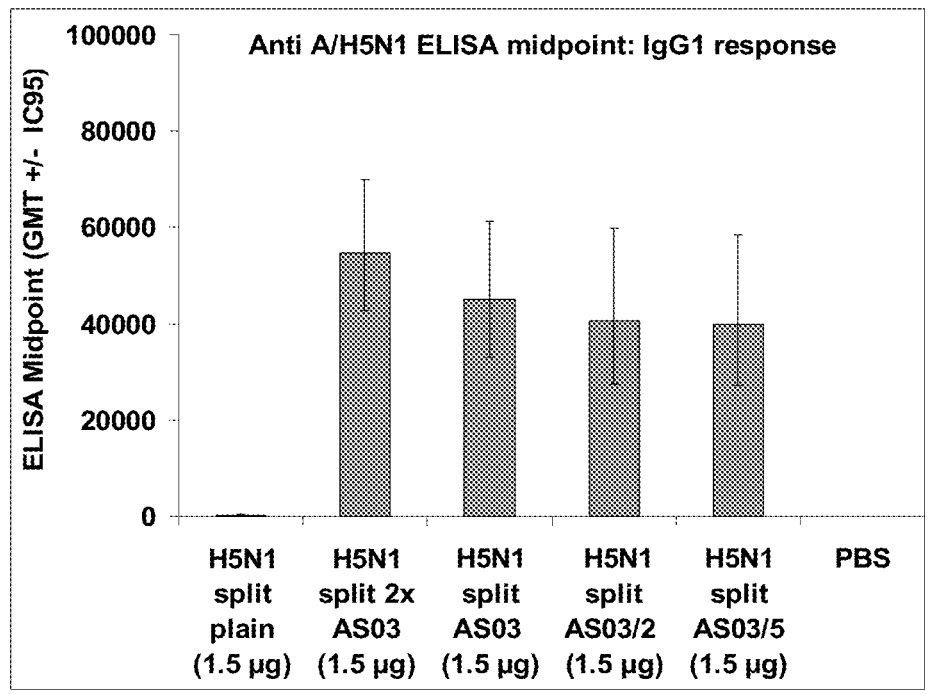
FIG. 9C: Mice study: Anti-H5N1 IgG1 isotypic responses on day 14 post-immunization (GMT+/−IC95) for 1.5 μg.
Figure 9D:
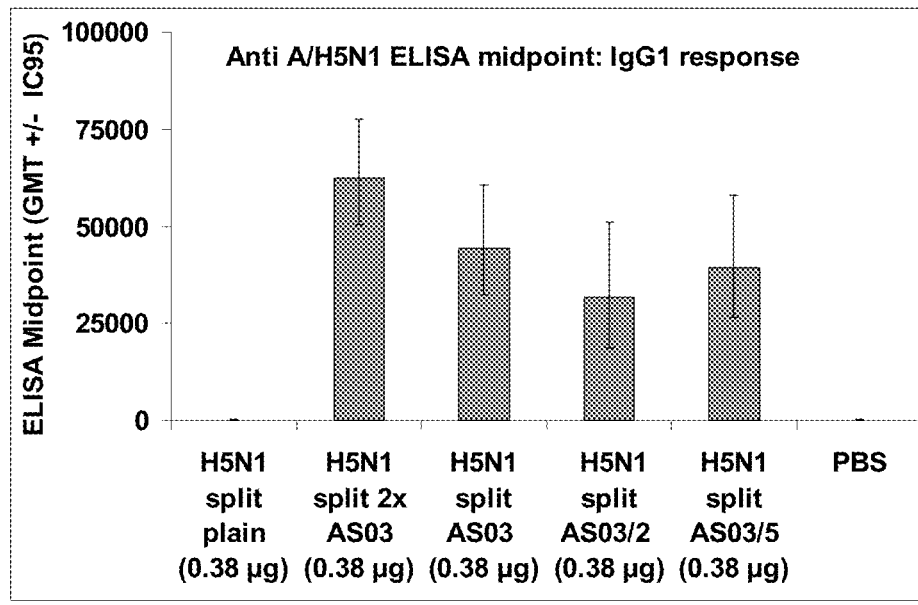
FIG. 9D: Mice study: Anti-H5N1 IgG1 isotypic responses on day 14 post-immunization (GMT+/−IC95) for 0.38 μg.

Groups of 15 adult female naïve C57Bl/6 mice were immunized on days 0 and 21 with pandemic H5N1 vaccine candidate intramuscularly in a total volume of 50 µl Mice were immunized with formulations containing split H5N1 antigens alone (H5N1 split plain) or formulations containing split antigens adjuvanted with different doses of AS03 (double, full, ½ or ⅕). The strains used for the immunizations included H5N1 A/Vietnam/1194/04 viral antigen (1.5 or 0.38 µg/strain corresponding to $1/10^{th}$ of the human dose). No formulation was done with a double AS03 dose but rather a concomitant injection of one 50 µl H5N1 split/AS03 full dose+one 50 µl dose AS03.

TABLE 17

| Gr | Antigen/Formulation | Antigen dose |
|---|---|---|
| 1 | H5N1 spilt/Plain (non-adjuvanted) | 1.5 µg |
| 2 | H5N1 split/double dose AS03 | 1.5 µg |
| 3 | H5N1 split/AS03 | 1.5 µg |
| 4 | H5N1 split/AS03 ½ | 1.5 µg |
| 5 | H5N1 split/AS03 ⅕ | 1.5 µg |
| 6 | H5N1 split/Plain (non-adjuvanted) | 0.38 µg |
| 7 | H5N1 split/double dose AS03 | 0.38 µg |
| 8 | H5N1 split/AS03 | 0.38 µg |
| 9 | H5N1 split/AS03 ½ | 0.38 µg |
| 10 | H5N1 split/AS03 ⅕ | 0.38 µg |
| 11 | PBS | |

VII.1.2. Preparation of the Vaccine Formulations

Preparation of one liter of Final Bulk Buffer (PBS pH 7.2±0.2): to 0.800 l of water for injection, add NaCl 7.699 g, KCl 0.200 g, $MgCl_2 \times 6H_2O$ 0.100 g, $Na_2HPO_4 \times 12\ H_2O$ 2.600 g, $KH_2PO_4$ 0.373 g. After solubilization, adjust to 1.0 L with water for injection H5N1 Split/Plain Preparation of a 50 µl dose:

Thiomersal (quantities taking into account its concentration in the strain) and Triton X100 are added to the Final Bulk Buffer. Tween 80 is not added as the content target in the formulation is reach by the Tween concentration of the strain. The final concentrations are of 10 µg/ml for Thiomersal, 368 µg/ml for Tween 80 and 35 µg/ml for Triton X100 in the 1.5 µg formulation dose. They are of 10 µg/ml for Thiomersal, 93 µg/ml for Tween80 and 8.9 µg/ml for Triton X100 in the 0.38 µg formulation dose. After 5-30 min magnetic stirring 1.5 or 0.38 µg of HA (H5N1 strain) are added. The formulations are stirred for 30-60 minutes. The pH is checked. Injections occur within the hour following the end of the formulation.

H5N1 Split/AS03

Preparation of a 50 µl Dose:

Thiomersal (quantities taking into account its concentration in the strain) and Triton X100 are added to the Final Bulk Buffer. Tween 80 is not added as the content target in the formulation is reach by the Tween concentration of the strain. The final concentrations are of 10 µg/ml for Thiomersal, 368 µg/ml for Tween 80 and 35 µg/ml for Triton X100 in the 1.5 µg formulation dose. They are of 10 µg/ml for Thiomersal, 93 µg/ml for Tween80 and 8.9 µg/ml for Triton X100 in the 0.38 µg formulation dose. After 5-30 min magnetic stirring 1.5 or 0.38 µg of HA (H5N1 strain) are added. After 30-60 minutes magnetic stirring, 25 or 12.5 or 5 µl of SB62 emulsion is added. The formulations are stirred for 30-60 minutes. The pH is checked. Injections occur within the hour following the end of the formulation VII.1.3. Read-Outs (Table 18A)

The humoral immune response was measured 14 days after immunization (10 mice/group) by anti-Ig, IgG1 and IgG2b antibody titers (FIGS. 9A to F). The humoral immune response was also measured 21 days after immunization (10 mice/group) by anti-H5N1 hemagglutination inhibition assay (FIGS. 10A and B).

The cellular immune response was tested 6 days post-immunization (5 pools of 3 mice per group) by intracellular cytokine staining (ICS) of antigen-specific CD4+ T cells numerated by flow cytometry (FIGS. 11A and B).

TABLE 18A

| Read-out | Timepoint | Sample type | Analysis method |
|---|---|---|---|
| Humoral response | D42 | Sera | ELISA, isotypes and HI titers |
| Cellular response | D47 | PBMCs | ICS |

VII.2. Results

VII.2.1. Humoral Immune Response: ELISA and Isotypes

Results are presented in FIGS. 9A to F and in Table 18B.

TABLE 18B

| | H5N1 Split PLAIN | H5N1 split 2 × AS03 | H5N1 spilt AS03 | H5N1 spilt AS03/2 | H5N1 spilt AS03/5 | PBS |
|---|---|---|---|---|---|---|
| Ig Response (ELISA Midpoint Titers) | | | | | | |
| 1.5 µg/Mice | 177 | 81680 | 59734 | 67772 | 57697 | 50 |
| 0.38 µg/Mice | 120 | 91319 | 76144 | 49162 | 54566 | |
| IgG1 Response (ELISA Midpoint Titers) | | | | | | |
| 1.5 µg/Mice | 124 | 54683 | 44965 | 40558 | 39854 | 50 |
| 0.38 µg/Mice | 144 | 62445 | 44381 | 31855 | 39269 | |
| IgG2b Response (ELISA Midpoint Titers) | | | | | | |
| 1.5 µg/Mice | 190 | 10928 | 10625 | 11215 | 7903 | 79 |
| 0.38 µg/Mice | 60 | 20993 | 12617 | 9352 | 9565 | |
| Ratio IgG1/IgG2b | | | | | | |
| 1.5 µg/Mice | 0.7 | 5 | 4.2 | 3.6 | 5 | 0.6 |
| 0.38 µg/Mice | 2.4 | 3 | 3.5 | 3.4 | 4.1 | |

At each dose of H5N1 split vaccine, all adjuvanted groups induced higher anti-H5N1 Ig, IgG1 and IgG2b antibody titers compared to the non-adjuvanted H5N1 split vaccine (FIGS. 9A to F). At each dose of H5N1 split vaccine; the anti-H5N1 IgG1 antibody response was 4-5-fold higher than the anti-H5N1 IgG2b antibody response (FIGS. 9C to F). With a dose of 1.5 µg HA of H5N1 split vaccine and combined with each dose of adjuvant, no difference of anti-H5N1 Ig, IgG1 and IgG2b antibody responses were observed (FIGS. 9A, C and E).

With a dose of 0.38 µg HA of H5N1 split vaccine, a trend for higher anti-H5N1 Ig titers were obtained after immunization with H5N1 split vaccine adjuvanted with 2×-full dose compared to the response induced by H5N1 split vaccine adjuvanted with AS03/2 (p=0.7315) and AS03 ⅕ (p=0.9744) (FIG. 9B). This trend was also observed for the anti-H5N1 IgG1 antibody response (FIG. 9D). However, the power was not sufficient to observe a statistically significant difference (25% power for 1.7 fold difference, or 47% for a 2 fold difference).

VII.2.2. Humoral Immune Response: HI Titers

With a Dose of 1.5 μg HA/Mice:
At each adjuvant dose, all mice immunized with AS03-adjuvanted H5N1 split vaccine induced higher HI titers compared to the response obtained in mice immunized with the non-adjuvanted H5N1 split vaccine (FIG. 10A). No statistically significant difference of HI titers were observed when H5N1 split vaccine was adjuvanted with a dose range of AS03 (FIG. 10A).

With a Dose of 0.38 μg HA/Dose
At each adjuvant dose, all mice immunized with AS03-adjuvanted H5N1 split vaccine induced higher HI titers compared to the response obtained in mice immunized with the non-adjuvanted H5N1 split vaccine (FIG. 10B).

Significantly higher HI titers were observed with H5N1 split vaccine adjuvanted with 2× full dose AS03 compared to the response obtained with H5N1 split vaccine adjuvanted with AS03/2 (p=0.032 for a 4-fold difference) (FIG. 10B).

No statistically significant difference of HI titers was observed in mice immunized with H5N1 split vaccine adjuvanted with 2× full dose AS03 or a full dose AS03 or between mice immunized with H5N1 split vaccine adjuvanted with AS03/2 or AS03/5 (FIG. 10B).

Comparison Between Antigen Doses (1.5 μg or 0.38 μg):
No statistically significant difference of HI titers were observed between mice immunized with each HA dose of H5N1 split vaccine adjuvanted with AS03, AS03/2 or AS03/5, except between mice immunized with 1.5 μg HA split H5N1 adjuvanted with AS03/5 which showed HI titer significantly lower (p=0.01) than with mice immunized with 0.38 μg HA split H5N1 adjuvanted with 2× full dose AS03 (FIGS. 10A and B).

VII.2.3. Cellular Immune Response

For the evaluation of cellular immune responses induced by a trivalent seasonal influenza vaccine, 1 μg HA of split antigen per strain was used for the re-stimulation of CD4 T cells. In order to maintain the same re-stimulating conditions for the monovalent H5N1 influenza vaccine, 3 μg HA of the monovalent split antigen was used in this experiment. This concentration was also shown to be optimal for the discrimination between different adjuvants. Results are presented in FIGS. 11A and B.

Figure 11A:
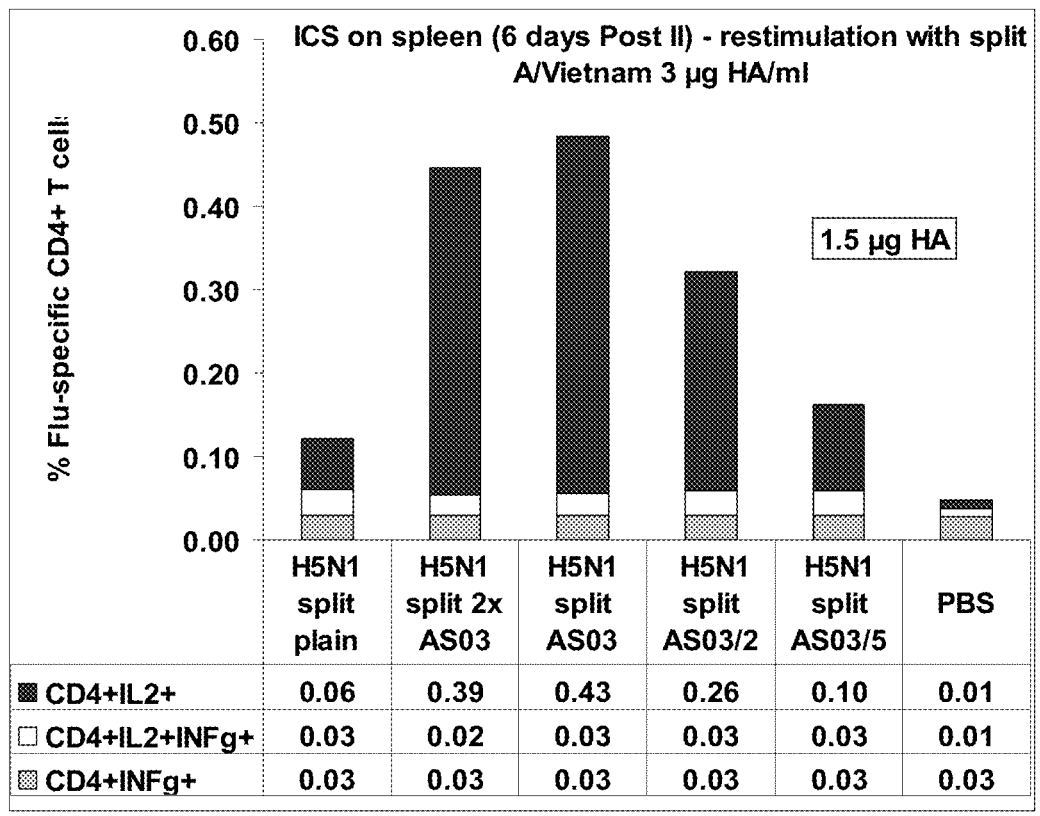
FIG. 11A: Mice study: Cellular immune response (CD4+ T cell) in naïve C57BI/6 mice immunized with different dose of H5N1 vaccine (1.5 or 0.38 μg) adjuvanted with dose range AS03: 1.5 μg HA Ag (antigen).
Figure 12A:
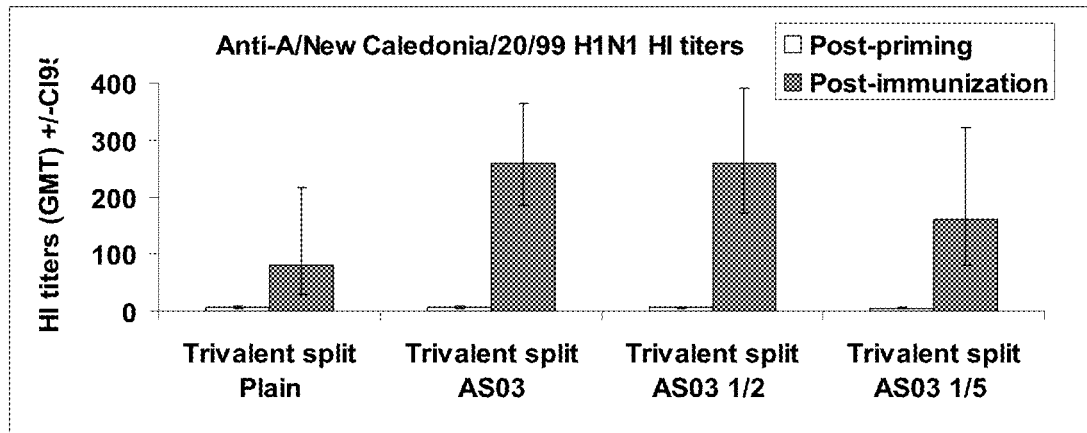
FIG. 12A: Pigs study. Haemagglutinin Inhibition test (GMT+/−IC95) in pigs primed with homologous strains (dose range AS03). Anti-A/New Caledonia/20/99 H1N1 HI titers.
Figure 12B:
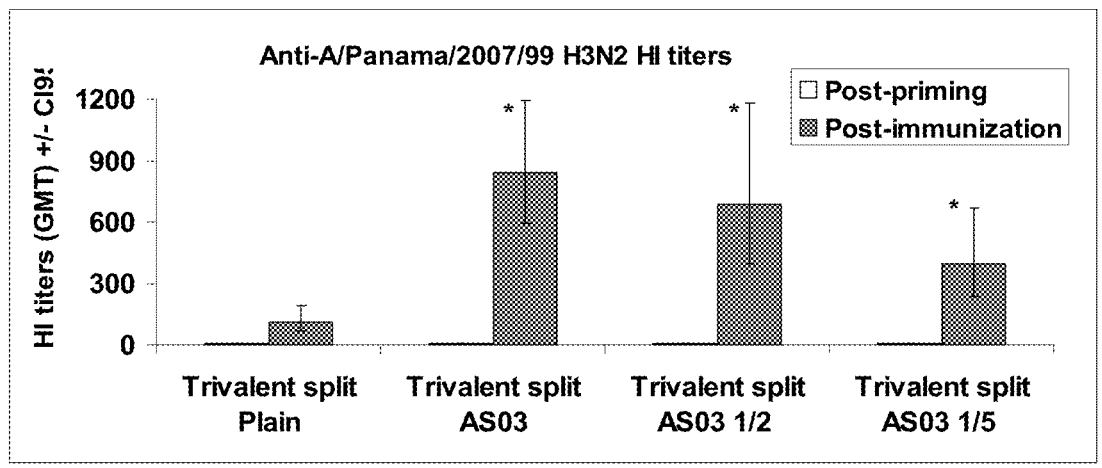
FIG. 12B: Pigs study. Haemagglutinin Inhibition test (GMT+/−IC95) in pigs primed with homologous strains (dose range AS03). Anti-A/Panama/2007/99 H3N2 HI titers.
Figure 12C:
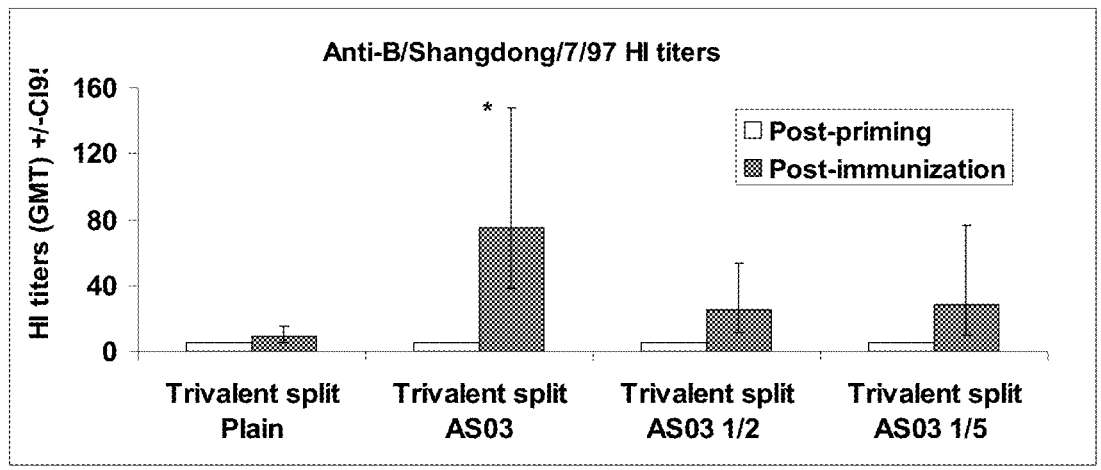
FIG. 12C: Pigs study. Haemagglutinin Inhibition test (GMT+/−IC95) in pigs primed with homologous strains (dose range AS03). Anti-B/Shangdong/7/97 HI titers.

At each dose of H5N1 split vaccine (1.5 or 0.38 μg) higher CD4+ T cell responses were observed in mice immunized with H5N1 split vaccine adjuvanted with various doses of AS03 compared to mice immunized with with the non-adjuvanted H5N1 split vaccine. At a dose of 1.5 μg H5N1 split vaccine, a reduction of the AS03 doses corresponded to a decrease in CD4+ T cell frequencies (FIG. 11A). However, at a dose of 0.38 μg H5N1 split vaccine no difference in CD4+ T cell responses was observed between different adjuvant doses in mice immunized with AS03-adjuvanted H5N1 split vaccines (FIG. 11B).

VII.3. Summary of Results and Conclusions

Immunogenicity studies in mice showed that adjuvanted H5N1 split vaccine induced significantly higher humoral (anti-H5N1 ELISA and HI titers) and cellular (CD4+ T cells) responses than those induced by the non-adjuvanted H5N1 split vaccine.

No antigen dose response effect was observed for the humoral immune response between mice immunized with 1.5 μg and 0.38 μg adjuvanted H5N1 split vaccine, except for the two groups mentioned in section VII.2.2, suggesting that in the presence of adjuvant even lower doses of HA may be required to observe a dose response effect in this model.

A strong increase in CD4+ T cell responses was observed in naïve mice when using AS03 adjuvanted H5N1 pandemic vaccines compared to the plain H5N1 vaccine. No impact of the AS03 dilution was observed when a dose of 0.38 μg of H5N1 split vaccine was used as vaccine candidate, while a decrease of CD4 T cell responses was observed when 1.5 μg H5N1 split vaccine was adjuvanted with the reduced dose AS03.

As previously observed, no difference in humoral and cellular immune responses were observed between mice immunized with H5N1 split vaccine (at either antigen dose) adjuvanted with a full dose AS03 or with AS03/2. Some enhancement in the immune response was detected when 2× full dose AS03 was used in the vaccine formulation and accordingly a decrease in the immune response was detected when AS03/5 was used in the vaccine formulation.

Overall, the data reported here support the potency of this novel adjuvant system in this vaccine formulation.

Example VIII—Preclinical Evaluation of Adjuvanted and Non-Adjuvanted Influenza Vaccines in Primed Large White Pigs VIII.1. Experimental Design and Objective Experiment in influenza-primed pigs was performed in order to evaluate the increase in humoral responses by AS03 induced influenza vaccines formulated with this oil-in-water adjuvant.

Pigs were used in order to evaluate a dose range of AS03 in an animal model close to humans. Pigs show a long list of biological analogies that establish this animal as physiologically the closest to man with very few exceptions (Douglas R., 1972). Moreover, the manifestation of influenza infection in pigs is commonly observed.

VIII.1.1. Treatment/Group (Table 19)

Groups of 10 adult Large White female pigs were primed on day 0 with trivalent whole, formalin-inactivated influenza virus (25 μg HA for each strain) intranasally in a total volume of 200 μl. Priming strains consisted of strains homologous to vaccine strains (25 μg HA whole inactivated H1N1 A/New Caledonia/20/99, H3N2 A/Panama/2007/99 and B/Shangdong/7/97). Twenty-eight days later, pigs were vaccinated with a single dose of the vaccine candidate intramuscularly in a total volume of 500 μl. Pigs were immunized with formulations containing split antigens alone (trivalent split plain) or formulations containing split antigens adjuvanted with a dose range of AS03 (full, ½ or ⅕). The strains used for the immunizations included H1N1 A/New Caledonia/20/99, H3N2 A/Panama/2007/99 and B/Shangdong/7/97 viral antigens (15 μg HA for H1N1 A/New Caledonia/20/99, H3N2 A/Panama/2007/99 strains and 17.5 μg B/Shangdong/7/97 strain as in one human dose).

TABLE 19

| Gr | Antigen/Formulation | Other treatment |
| --- | --- | --- |
| 1 | Trivalent split/Plain (non-adjuvanted) | Homologous priming D0 |
| 2 | Trivalent split/AS03 | Homologous priming D0 |
| 3 | Trivalent split/AS03 ½ | Homologous priming D0 |
| 4 | Trivalent split/AS03 ⅕ | Homologous priming D0 |

VIII.1.2. Preparation of the Vaccine Formulations

Trivalent Split/Plain

A Premix of Tween 80, Triton X100 and Vitamin E Succinate (VES) is prepared in order to reach a final concentration into the vaccine of 750 µg/ml of Tween 80, 110 µg/ml of Triton X100 and 100 µg/ml of VES. The quantities used in the premix take into account their content into the strains.

The formulation of one 500 µl dose is prepared extemporaneously according the following sequence: Water For Injection+Saline Buffer (10 fold concentrated PBS pH 7.4 prepared as taught in example IV)+Premix, 5 min magnetic stirring at room temperature, +15 µg HA H1N1 strain, 10 min magnetic stirring at room temperature, +15 µg HA H3N2 strain, 10 min magnetic stirring at room temperature, +17.5 µg HA B strain, 15 min magnetic stirring at room temperature. The formulations are injected within the hour following the end of their preparation.

Trivalent Split/AS03

A Premix of Tween 80, Triton X100 and Vitamin E Succinate (VES) is prepared in order to reach a final concentration into the vaccine of 750 μg/ml of Tween 80, 110 μg/ml of Triton X100 and 100 μg/ml of VES. The quantities used in the premix take into account their content into the strains.

The formulation of one 500 μl dose is prepared extemporaneously according the following sequence: Water For Injection+Saline Buffer (10 fold concentrated PBS pH 7.4 prepared as taught in exempleIV)+Premix, 5 min magnetic stirring at room temperature, +15 μg HA H1N1 strain, 10 min magnetic stirring at room temperature, +15 μg HA H3N2 strain, 10 min magnetic stirring at room temperature, +17.5 μg HA B strain, 15 min magnetic stirring at room temperature, +250 μl SB62 emulsion for the full dose AS03 or 125 μl SB62 emulsion for the ½ dose AS03 or 50 μl SB62 emulsion for the ⅕ dose AS03, 15 min magnetic stirring at room temperature. The formulations are injected within the hour following the end of their preparation.

VIII.1.3. Read-Outs (Table 20)

The humoral immune response to vaccination was measured before intranasal priming (day 0), before immunization (day 28) and 14 days after immunization (10 pigs/group). Serum samples were tested by the haemagglutination inhibition (HI) test.

TABLE 20

| Read-out | Timepoint | Sample type | Analysis method |
|---|---|---|---|
| Humoral response | D0, D28, D42 | Sera | IHA |

VIII.2. Results and Conclusions

VIII.2.1. Humoral Immunity

Results are presented in FIGS. 12A to C. Whatever the dilution of the adjuvant, AS03 adjuvanted trivalent split formulations induced a stronger HI response to all strains than the plain trivalent formulation in this model of homologous priming, although statistical significance was not always reached for all three strains. An adjuvant dose effect was observed with slight differences from strain to strain. For less immunogenic strains such as B/Shangdong, only the trivalent split vaccine adjuvanted with a full dose of AS03 was significantly different from the plain vaccine. In contrast to trivalent split vaccine adjuvanted with a full dose of AS03, a reduced dose of AS03 failed to increase HI titres for all three strains above those seen with the plain vaccine.

Example IX—Preclinical Evaluation of Adjuvanted and Non-Adjuvanted Split Trivalent or Quadrivalent (Containing a Second B Strain) Vaccines in Naïve and Primed C57Bl/6 Mice IX.1. Experimental Design and Objective Experiments in naïve and primed mice were performed in order to evaluate the increase in the humoral immune response induced by influenza split trivalent or quadrivalent (containing a second B strain) vaccines formulated with this oil-in-water emulsion adjuvant (AS03 or AS03 half dose). Phylogenic analysis of the HA genes of recently isolates influenza B viruses demonstrated that since the mid 1980s, this gene has evolved into two antigenically distinct lineages represented by B/Victoria/2/87-like and B/Yamagata/16/88-like viruses. These experiments evaluated the impact of the presence of a second B strain in the quadrivalent influenza vaccine (QIV) on the humoral immune response compared to the response induced by the trivalent influenza vaccine (TIV).

IX.1.1. Treatment/Group (Table 21)

These experiments were performed by using groups of 10 adult female C57Bl/6 naïve mice or mice primed with heterologous strains compared to vaccine strains.

Naïve mice were immunized on days 0 and 28 with trivalent or quadrivalent influenza vaccine candidate intramuscularly in a total volume of 1000 μl.

Primed mice received first an intranasal administration (20 μl volume) on day 0 with trivalent whole, formalin-inactivated influenza virus (5 μg HA for each strain). Priming strains consisted of drift variants (5 μg HA whole inactivated H1N1 A/Beijing/262/95, H3N2 A/Wellington/1/04 and B/Brisbane/32/02) to those included in the vaccine. Twenty-eight days later, the mice were vaccinated with a single dose of the vaccine candidate intramuscularly in a total volume of 100 μl.

Mice were immunized with formulations containing TIV or QIV alone (plain vaccine) or formulations containing TIV or QIV iadjuvanted with different doses of AS03 (full or half (½)). The strains used for the immunizations included H1N1 A/New Caledonia/20/99, H3N2 A/Wisconsin/52/05 and B/Shangdong/7/97 (B/Victoria lineage included in both TIV and QIV) and for the QIV vaccine also B/Jiangsu/10/03 (B/Yamagata lineage included only in QIV) (1.5 μg/strain corresponding to $1/10^{th}$ of the human dose).

TABLE 21

| Group | Antigen/Formulation | Antigen dose |
|---|---|---|
| 1 | TIV Plain (non-adjuvanted) | 1.5 μg |
| 2 | TIV AS03 | 1.5 μg |

TABLE 21-continued

| Group | Antigen/Formulation | Antigen dose |
|---|---|---|
| 3 | TIV AS03/2 | 1.5 μg |
| 4 | QIV Plain (non-adjuvanted) | 1.5 μg |
| 5 | QIV AS03 | 1.5 μg |
| 6 | QIV AS03/2 | 1.5 μg |
| 7 | PBS | |

IX.1.2. Preparation of the Vaccine Formulations

TIV Plain (Non-Adjuvanted)
Preparation of a 100 μl Dose:
10 fold concentrated PBS and a premixture of Tween 80, Triton X-100 and VES (quantities taking into account the detergents present in the strains) are added to water for injection. The final concentrations are 354 μg/ml for Tween 80, 52 μg/ml for Triton X-100, 47.37 μg/ml for VES in the formulation. After 5 min magnetic stirring, 1.5 μg of each strain (H1N1, H3N2, B strains) are added with 10 min magnetic stirring at between each addition. The formulation is then stirred for 15 min. The pH is checked. Injections occur within the hour following the end of the formulation.

TIV AS03 or AS03 ½
Preparation of a 100 μl Dose:
10 fold concentrated PBS and a premixture of Tween 80, Triton X-100 and VES (quantities taking into account the detergents present in the strains) are added to water for injection. The final concentrations are 354 μg/ml for Tween 80, 52 μg/ml for Triton X-100, 47.37 μg/ml for VES in the formulation. After 5 min magnetic stirring, 1.5 μg of each strain (H1N1, H3N2, B strains) are added with 10 min magnetic stirring at between each addition. After 15 min magnetic stirring, 25 μl or 12.5 μl of SB62 emulsion is added. The formulation is then stirred for 15 min. The pH is checked. Injections occur within the hour following the end of the formulation.

QIV Plain (Non-Adjuvanted)
Preparation of a 1000 Dose:
10 fold concentrated PBS and a premixture of Tween 80, Triton X-100 and VES (quantities taking into account the detergents present in the strains) are added to water for injection. The final concentrations are 472 μg/ml for Tween 80, 69.44 μg/ml for Triton X-100, 63.16 μg/ml for VES in the formulation. After 5 min magnetic stirring, 1.5 μg of each strain (H1N1, H3N2, 2 B strains) are added with 10 min magnetic stirring at between each addition. The formulation is then stirred for 15 min. The pH is checked. Injections occur within the hour following the end of the formulation.

QIV AS03 or AS03 ½
Preparation of a 100 μl Dose:
10 fold concentrated PBS and a premixture of Tween 80, Triton X-100 and VES (quantities taking into account the detergents present in the strains) are added to water for injection. The final concentrations are 472 μg/ml for Tween 80, 69.44 μg/ml for Triton X-100, 63.16 μg/ml for VES in the formulation. After 5 min magnetic stirring, 1.5 μg of each strain (H1N1, H3N2, 2 B strains) are added with 10 min magnetic stirring at between each addition. After 15 min magnetic stirring, 25 μl or 12.5 μl of SB62 emulsion is added. The formulation is then stirred for 15 min. The pH is checked. Injections occur within the hour following the end of the formulation.

IX.1.3. Read-Outs (Table 22)

Figure 13A:
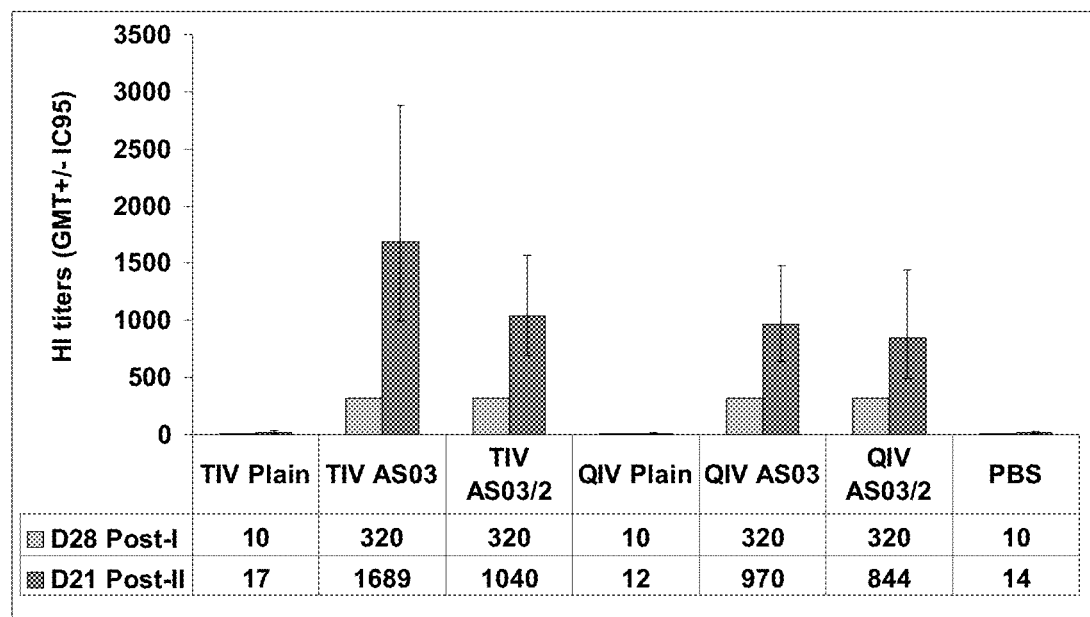
FIG. 13A: Haemagglutinin Inhibition test (GMT+/−IC95) in C57BI/6 naïve mice immunized with TIV or QIV plain or adjuvanted with AS03 or AS03/2. Anti-B/Shangdong/7/97 (B/Victoria-like virus) HI titers.

In naïve mice, the humoral immune response was measured measured 28 days after the first immunization (D28 Post-I) and 21 days after the second immunization (D21 Post-II) in 10 mice per group by hemagglutination inhibition assay (FIGS. 13A and B).

Figure 14A:
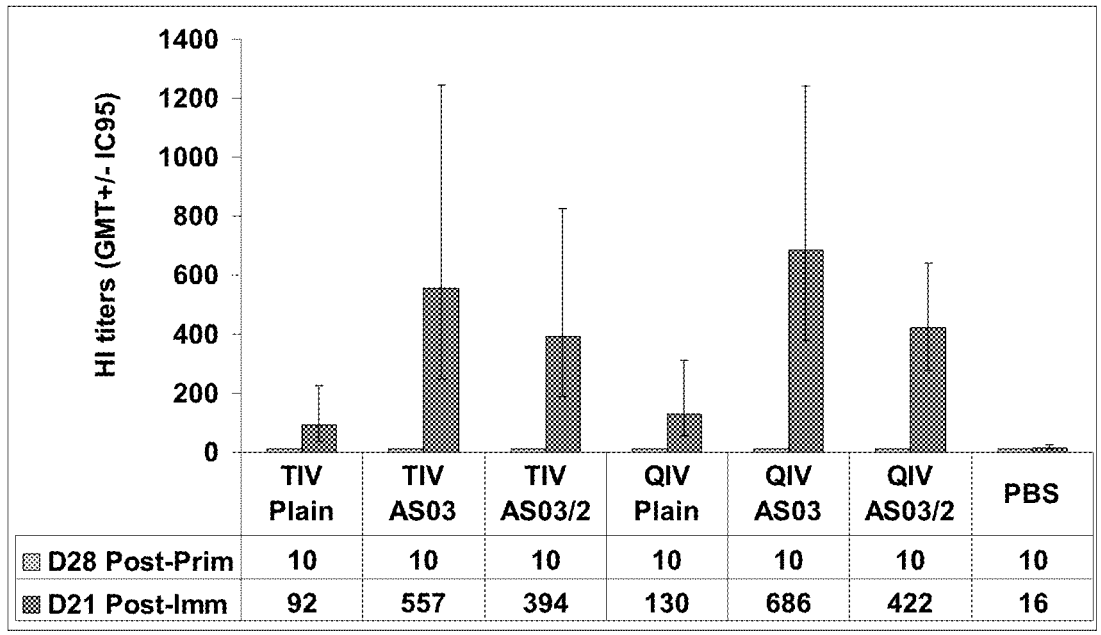
FIG. 14A: Haemagglutinin Inhibition test (GMT+/−IC95) in C57BI/6 mice primed with a B/Victoria-like virus and immunized with TIV or QIV plain or adjuvanted with AS03 or AS03/2. Anti-B/Shangdong/7/97 (B/Victoria-like virus) HI titers.

In primed mice, the humoral immune response was measured measured 28 days after the priming (Day 28 Post-Prim) and 21 days after the single immunization (D21 Post-Imm) in 10 mice per group by hemagglutination inhibition assay (FIGS. 14A and B).

In order to simplify and to focus on the objective of this experiment, only the humoral immune responses induced against the B strains were described.

TABLE 22

| Read-out | Timepoint | Sample type | Analysis method |
|---|---|---|---|
| Humoral response | Days 28 and 49 | Sera | HI titers |

IX.2. Results

IX.2.1. Humoral Immune Response in Naive Mice: HI Titers

Naïve mice immunized with adjuvanted influenza split vaccines induced higher HI titers compared to the response obtained in mice immunized with the non-adjuvanted influenza split vaccines (FIGS. 13A and B).

Whatever the adjuvant (AS03 or AS03/2), naïve mice immunized with the adjuvanted TIV or the adjuvanted QIV induced similar HI titers against B/Shangdong/7/97 (B/Victoria-like virus included in both TIV and QIV) (FIG. 13A).

Figure 13B:
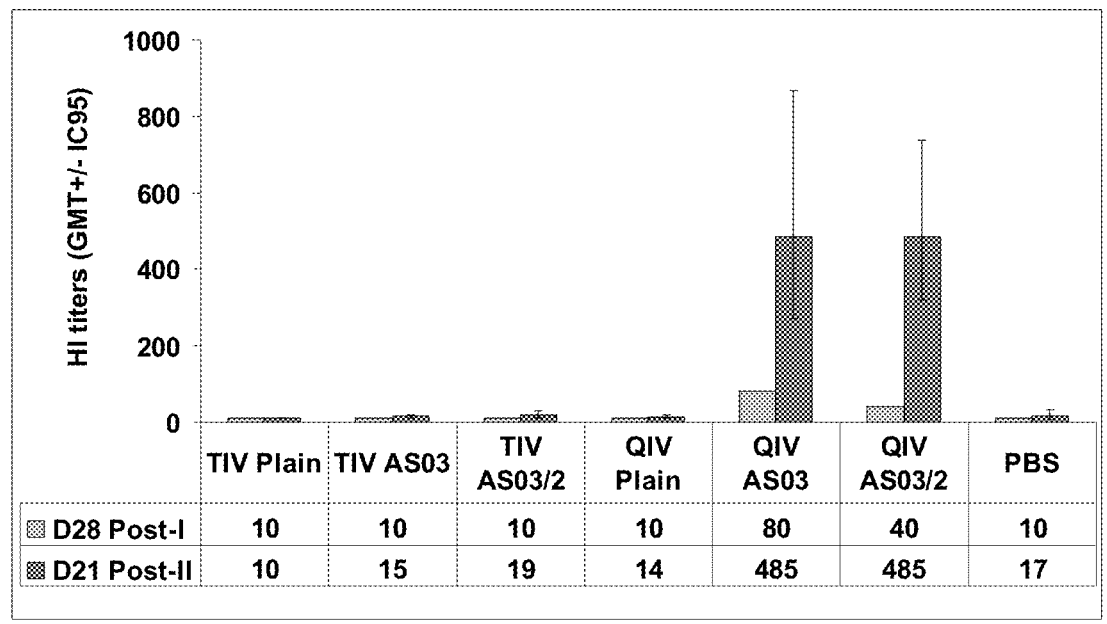
FIG. 13B: Haemagglutinin Inhibition test (GMT+/−IC95) in C57BI/6 naïve mice immunized with TIV or QIV plain or adjuvanted with AS03 or AS03/2. Anti-B/Jiangsu/10/03 (B/Yamagata-like virus) HI titers.

Whatever the adjuvant (AS03 or AS03/2), naïve mice immunized with the adjuvanted QIV induced higher HI titers against B/Jiangsu/10/03 (B/Yamagata-like virus only included in QIV) compared to the absence of HI titers observed in naïve mice immunized with the adjuvanted TIV (FIG. 13B).

IX.2.2. Humoral Immune Response in Primed Mice: HI Titers

Mice primed with a B/Victoria-like virus and immunized with adjuvanted influenza split vaccines induced higher HI titers compared to the response obtained in mice immunized with the non-adjuvanted influenza split vaccines (FIGS. 14A and B).

Figure 14B:
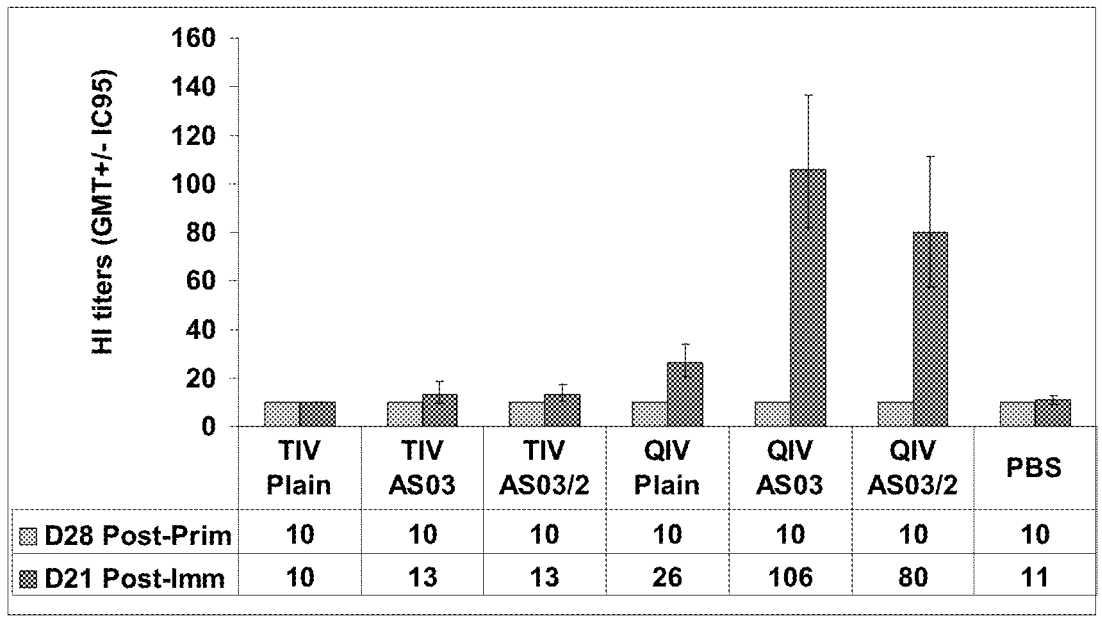
FIG. 14B: Haemagglutinin Inhibition test (GMT+/−IC95) in C57BI/6 mice primed with a B/Victoria-like virus and immunized with TIV or QIV plain or adjuvanted with AS03 or AS03/2. Anti-B/Jiangsu/10/03 (B/Yamagata-like virus) HI titers.

Whatever the adjuvant (AS03 or AS0312), mice primed with a Victoria-like virus and immunized with the adjuvanted TIV or the adjuvanted QIV induced similar HI titers against the B/Shangdong/7/97 virus (B/Victoria-like virus included in both TIV and QIV) (FIG. 14B).

Whatever the adjuvant (AS03 or AS0312), mice primed with a Victoria-like virus and immunized with the adjuvanted QIV induced higher HI titers against B/Jiangsu/10/03 (B/Yamagata-like virus only included in QIV) compared to the absence of HI titers observed in naïve mice immunized with the adjuvanted TIV (FIG. 14B).

IX.3. Summary of Results and Conclusions

Naïve mice, or mice primed with a B/Victoria-like virus, immunized with the adjuvanted (AS03 or AS0312) TIV or QIV vaccine showed cross-reactivity against the homotypic B/Victoria-like virus included in the vaccine or a hetrosubtypic virus belonging to the same B/Victoria lineage. Naïve mice, or mice primed with a B/Victoria-like virus, immunized with the adjuvanted (AS03 or AS0312) TIV vaccine did not show any cross-reactivity against a hetrosubtypic virus belonging to another lineage (B/Yamagata-like virus in this example) compared to the B virus included in the vaccine.

These experiments demonstrated that a second B strain and the adjuvant (AS03 or AS0312) are needed in order to induce a cross-reaction against a B virus belonging to both B/Victoria- and B/Yamagata-lineages.

Example X—Clinical Trial in a Population Aged 18-64 Years with a Vaccine Containing a Split Influenza Antigen Preparation and Various Doses of AS03 Adjuvant (Flu-LD-012)

X.1. Introduction

A phase II, controlled, randomized, single blind study was conducted in an adult population aged 18-64 years old in 2007 in order to evaluate the immunogenicity, safety and reactogenicity of the GlaxoSmithKline Biologicals low dose influenza candidate vaccine (i.e. containing 5 µg HA per strain) with various doses of AS03 adjuvant, administered intramuscularly, compared to Fluarix™ (GlaxoSmithKline Biologicals) used as a reference.

X.2. Study Design

Five groups of subjects (200 per group) in parallel received the following vaccines IM:
FluLD1/1: 5 µg HA/strain of flu vaccine adjuvanted with 1/1 dose of AS03
FluLD½: 5 µg HA/strain of flu vaccine adjuvanted with ½ dose of AS03
FluLD¼: 5 µg HA/strain of flu vaccine adjuvanted with ¼ dose of AS03
FluLD⅛: 5 µg HA/strain of flu vaccine adjuvanted with ⅛ dose of AS03
one group of 200 subjects receiving one full dose of Fluarix™ 15 µg HA/strain
Schedule: one IM injection of influenza vaccine at day 0, blood sample collection at day 0, day 21, and day 180 post vaccination.
The standard trivalent split influenza vaccine—Fluarix™ used in this study, is a commercial vaccine from the year 2007/2008 Northern Hemisphere developed and manufactured by GlaxoSmithKline Biologicals.

X.2. Study Objectives

X.2.1. Primary Objective: Immunogenicity

To demonstrate the immunological non-inferiority (GMT) of the low dose influenza vaccine adjuvanted with AS03 (1/1, ½, ¼, ⅛ dose of AS03) versus Fluarix 21 days following vaccination in all subjects.
Observed Variable:
At days 0 and 21: serum haemagglutination-inhibition (HI) antibody titre, against each of the three vaccine strains, in all subjects.
Derived Variable:
Geometric mean titres (GMTs) of HI antibody titres at days 0 and 21.

X.2.2. Secondary Objectives

To assess the humoral immune response in terms of antihaemagglutinin (HI) antibody titres elicited by the low dose influenza vaccine adjuvanted with AS03 (1/1, ½, ¼, ⅛ dose of AS03) and by Fluarix 21 days following vaccination in all subjects.

To assess the persistence of HI antibodies of the low dose influenza vaccine adjuvanted with AS03 (1/1, ½, ¼, ⅛ dose of AS03) and by Fluarix 180 days following vaccination in all subjects.
To assess the cell-mediated immune response induced by the low dose influenza vaccine adjuvanted with AS03 (1/1, ½, ¼, ⅛ dose of AS03) and Fluarix in terms of frequency of influenza-specific CD4/CD8 T lymphocytes, at Day 0, 21 and 180 in a subset of subjects.
To assess the humoral immune response in terms of neutralising antibody titres induced by the low dose influenza vaccine adjuvanted with AS03 (1/1, ½, ¼, ⅛ dose of AS03) and Fluarix at Day 0, 21 and 180 in a subset of subjects.
To assess the safety and reactogenicity of the low dose influenza vaccine adjuvanted with AS03 (1/1, ½, ¼, ⅛ dose of AS03) and Fluarix during the entire study period in all subjects (follow-up of solicited symptoms during 7 days, follow-up of unsolicited symptoms during 21 days, follow-up of serious adverse events and medically significant conditions during 6 month).
Observed Variables for the Humoral Response:
At day 0, 21 and 180: serum haemagglutination-inhibition (HI) antibody titre, against each of the three vaccine strains, in all subjects.
At days 0, 21 and 180: neutralising antibody titres, tested separately against each of the three influenza virus strains represented in the vaccine, in a subset of subjects.
Derived Variables:
Geometric mean titres (GMTs) of HI antibody titres at days 0, 21 and 180
Seroconversion rates* at day 21
Seroconversion factors** at day 21
Seroprotection rates*** at days 0 and 21
Seroconversion rate is defined as the percentage of vaccinees who have either a prevaccination titre <1:10 and a post-vaccination titre 1:40 or a pre-vaccination titre 1:10 and at least a four-fold increase in post-vaccination titre.
Seroconversion factor is defined as the fold increase in serum HI GMTs post-vaccination compared to day 0.
Seroprotection rate is defined as the percentage of vaccinees with a serum HI titre 1:40 that usually is accepted as indicating protection
Observed Variables for the CMI Response (in a Subset of Subjects):
At days 0, 21 and 180:
Frequency of cytokine-positive CD4/CD8 cells per $10^6$ in tests producing at least two different signal molecules (IL-2, IFN-γ, TFN-α and CD40L).
Frequency of cytokine-positive CD4/CD8 cells per $10^6$ in tests producing at least CD40L and another signal molecule (IL-2, IFN-γ, TFN-α).
Frequency of cytokine-positive CD4/CD8 cells per $10^6$ in tests producing at least IL-2 and another signal molecule (CD40L, IFN-γ, TFN-α).
Frequency of cytokine-positive CD4/CD8 cells per $10^6$ in tests producing at least TFN-α and another signal molecule (IL-2, IFN-γ, CD40L).
Frequency of cytokine-positive CD4/CD8 cells per $10^6$ in tests producing at least IFN-γ and another signal molecule (CD40L, IL-2, TFN-α).
Derived Variables
For each test, geometric mean (GM) of specific influenza CD4/CD8 T lymphocytes at day 0, 21, 180.

X.2.3. Further Objectives

To assess the humoral immune response in terms of vaccine heterologous HI titres (serum haemagglutinationinhibition (HI) antibody titer, against drifted strains), at Day 0, 21 and 180 in a subset of subjects.

To assess humoral immune response in terms of vaccine heterologous neutralising antibody titres (cross-reactive influenza specific virus strains (drifted strains)), at Day 0, 21 and 180 in a subset of subjects.

To assess the CMI response in terms of frequency of cross-reactive influenza specific CD4/CD8 T lymphocytes (heterologous strains) (drifted strains or conserved influenza epitopes), at Day 0, 21 and 180 in a subset of subjects.

The derived variables and criteria (seroprotection, seroconversion rates, and seconversion factors) are as described above.

X.3. Vaccine Composition and Administration

X.3.1. Vaccine Preparation

The AS03 adjuvanted low dose influenza vaccine used in the study is liquid mixture of equal amounts (i.e. 3×5 µg HA) of three different split inactivated influenza antigens adjuvanted with AS03. It is presented as monodose vaccine in glass (Type I) pre-filled syringes at a volume of 0.5 ml/dose. The AS03 adjuvanted low dose influenza candidate formulations contained the following strains:

A/Solomon Islands/3/2006 (H1N1)-like strain: A/Solomon Islands/03/2006 (IVR-145),
A/Wisconsin/67/2005 (H3N2)-like strain: A/Wisconsin/67/2005 (NYMCX)-161B,
B/Malaysia/2506/2004-like strain: B/Malaysia/2506/2004.

The vaccines contained 5 µg haemagglutinin (HA) of each influenza virus strain per dose, combined with a full dose, half dose, ¼th dose or ⅛th dose of the adjuvant system AS03. Influenza antigens are incorporated in the aqueous phase of the adjuvant system by simple mixing with the emulsion.

The vaccine contains the following residuals that are derived from the manufacturing process of the drug substance: thimerosal, ovalbumin, sucrose, formaldehyde and sodium deoxycholate, and residual levels of thimerosal (<1 µg per dose) from the early stages of the manufacturing process. The production of the three monovalent bulks of inactivated split virion antigens is performed following the manufacturing process of the commercial Fluarix™ vaccine. It is done as explained in section III.4.1.2. Splitting is carried out with sodium deoxycholate prior to the inactivation step, which is performed with formaldehyde.

X.3.2. Vaccine Composition

One dose of FluLD (full, half dose, ¼ dose or ⅛ dose of AS03) corresponds to 0.5 ml. The composition is provided in Table 23. The HA content per dose is about 5 µg for all formulations, the sole difference being the amount of AS03 present in the final containers.

TABLE 23

Composition of AS03 adjuvanted low dose influenza vaccine

| Component<br>Inactivated split virions | Quantity per dose (0.5 ml) | | | |
|---|---|---|---|---|
| A/Solomon Islands/03/2006 (IVR-145) | 5.0 µg HA | | | |
| A/Wisconsin/67/2005 (H3N2) NYMCX-161B | 5.0 µg HA | | | |
| B/Malaysia/2506/2004 | 5.0 µg HA | | | |
| Adjuvant | Full dose | Half dose | ¼ dose | ⅛ dose |
| SB62 emulsion (Total Volume) | 0.250 mL | 0.125 mL | 0.0625 mL | 0.0.31 mL |
| squalene | 10.70 mg | 5.35 mg | 2.675 mg | 1.337 mg |
| DL-α-tocopherol | 11.88 mg | 5.94 mg | 2.97 mg | 1.5 mg |
| Polysorbate 80 (Tween 80) | 4.85 mg | 2.425 mg | 1.21 mg | 0.6 mg |
| PBS mod | | | ad 0.250 mL | |
| Excipients (target value) | | | | |
| Polysorbate 80 (Tween-80) | 0.40 mg | | | |
| Octoxynol 10 (Triton ® X-100) | 0.05 mg | | | |
| alpha-Tocopheryl hydrogen succinate | 0.05 mg | | | |
| Sodium chloride | 4 mg | | | |
| Magnesium chloride | 0.03 mg | | | |
| Disodium phosphate | 1.30 mg | | | |
| Potassium dihydrogen phosphate | 0.19 mg | | | |
| Potassium chloride | 0.10 mg | | | |
| Water for injection | ad 0.50 mL | | | |

Abbreviations: HA = Haemagglutinin; The total content in Polysorbate 80 corresponds to 4.972 mg per dose when AS03 full dose is used, and 2.547 mg per dose when AS03 half dose is used.

X.3.3. Preparation of the Vaccine Compositions with AS03 Adjuvant

Antigen preparation ("intermediate bulk"): Tween 80, Triton X-100 and VES are added to PBS mod Na/K (132.7 mM NaCl, 2.7 mM KCl, 1.1 mM MgCl₂, 7.26 mM Na₂HPO₄, 2.72 mM KH₂PO₄, pH 7.2) in such quantities than final concentrations in the intermediate bulk were, respectively, of 952.5 µg/mL, 130.9 µg/ml and 119.1 µg/mL. After 15 to 45 minutes stirring, 35.71 µg HA per ml of each strain H1N1, 36.90 µg/mL strain H3N2 and 39.29 µg HA per ml of B strain are added.

Adjuvanted vaccine: PBS mod Na/K (132.7 mM NaCl, 2.7 mM KCl, 1.1 mM MgCl₂, 7.26 mM Na₂HPO₄, 2.72 mM KH₂PO₄, pH 7.2) is added to water for injection to achieve a final volume of 0.5 mL per human dose. After 15 to 45 min stirring, a volume of the so called "intermediate bulk" is added and mixed for 15-45 min. Then a PBS mod 20× concentrated (2.74 M NaCl, 54 mM KCl, 142.8 mM Na2HPO4, 26 mM KH2PO4, pH 6.8) is added and mixed for 15 to 45 min. This PBS mod 20× concentrated as the same composition than AS03 emulsion and amount added is function of the AS03 dose and is calculated to keep the ionic composition of vaccine constant while the emulsion content is reduced. Finally the required among of emulsion is added (31.25 or 62.5 or 125 or 250 μl/dose) and mixed for 15 to 45 min to reach the final target values illustrated in Table 23.

X.4. Immunogenicity Results—Humoral Immune Response

X.4.1 HI Geometric Mean Titres (GMT)

Figure 15:
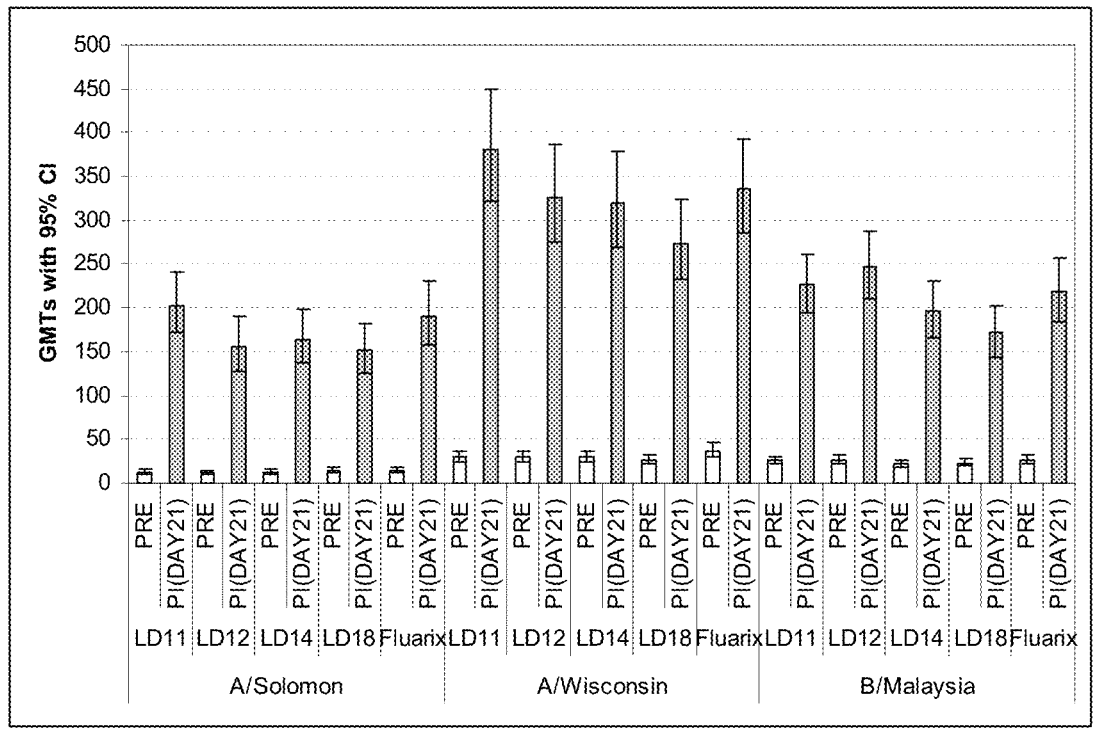
FIG. 15: Human clinical trial (adjuvant dose range): GMTs for HI antibody titer at d0 and d21.

The GMT's for HI antibodies with 95% CI are shown in Table 24 and FIG. 15. The GMT's for HI antibodies with 95% per age group (18-49y and 50-64y) are shown in Table 25.

TABLE 24

Seropositivity rates and GMTs for HI antibody titer at day 0 and day 21 (ATP cohort for immunogenicity)

| Antibody | Group | Timing | N | n | >=10 1/DIL % | 95% CI LL | 95% CI UL | GMT value | 95% CI LL | 95% CI UL | Min | Max |
|---|---|---|---|---|---|---|---|---|---|---|---|---|
| A/Solomon | FluLD11 | PRE | 187 | 94 | 50.3 | 42.9 | 57.6 | 13.0 | 10.9 | 15.5 | <10.0 | 905.0 |
| | | PI(D21) | 187 | 187 | 100 | 98.0 | 100 | 203.2 | 171.7 | 240.3 | 10.0 | 5120.0 |
| | FluLD12 | PRE | 189 | 83 | 43.9 | 36.7 | 51.3 | 12.3 | 10.2 | 14.8 | <10.0 | 1280.0 |
| | | PI(D21) | 189 | 185 | 97.9 | 94.7 | 99.4 | 155.8 | 128.2 | 189.4 | <10.0 | 2560.0 |
| | FluLD14 | PRE | 190 | 84 | 44.2 | 37.0 | 51.6 | 12.9 | 10.6 | 15.8 | <10.0 | 1280.0 |
| | | PI(D21) | 190 | 186 | 97.9 | 94.7 | 99.4 | 164.9 | 137.6 | 197.8 | <10.0 | 2560.0 |
| | FluLD18 | PRE | 192 | 100 | 52.1 | 44.8 | 59.3 | 14.9 | 12.3 | 18.2 | <10.0 | 640.0 |
| | | PI(D21) | 192 | 187 | 97.4 | 94.0 | 99.1 | 151.1 | 124.7 | 183.1 | <10.0 | 3620.0 |
| | Fluarix | PRE | 185 | 106 | 57.3 | 49.8 | 64.5 | 15.1 | 12.5 | 18.2 | <10.0 | 640.0 |
| | | PI(D21) | 185 | 183 | 98.9 | 96.1 | 99.9 | 191.0 | 158.5 | 230.2 | <10.0 | 3620.0 |
| A/Wisconsin | FluLD11 | PRE | 187 | 142 | 75.9 | 69.2 | 81.9 | 29.4 | 23.8 | 36.4 | <10.0 | 1280.0 |
| | | PI(D21) | 187 | 187 | 100 | 98.0 | 100 | 380.1 | 321.3 | 449.8 | 14.0 | 5120.0 |
| | FluLD12 | PRE | 189 | 141 | 74.6 | 67.8 | 80.6 | 30.0 | 24.3 | 37.2 | <10.0 | 1280.0 |
| | | PI(D21) | 189 | 188 | 99.5 | 97.1 | 100 | 326.4 | 275.6 | 386.7 | <10.0 | 5120.0 |
| | FluLD14 | PRE | 190 | 141 | 74.2 | 67.4 | 80.3 | 29.9 | 24.5 | 36.5 | <10.0 | 640.0 |
| | | PI(D21) | 190 | 188 | 98.9 | 96.2 | 99.9 | 319.9 | 270.0 | 379.1 | <10.0 | 20480.0 |
| | FluLD18 | PRE | 192 | 149 | 77.6 | 71.0 | 83.3 | 27.2 | 22.6 | 32.8 | <10.0 | 905.0 |
| | | PI(D21) | 192 | 191 | 99.5 | 97.1 | 100 | 273.9 | 232.0 | 323.3 | <10.0 | 5120.0 |
| | Fluarix | PRE | 185 | 155 | 83.8 | 77.7 | 88.8 | 37.4 | 30.2 | 46.4 | <10.0 | 1280.0 |
| | | PI(D21) | 185 | 185 | 100 | 98.0 | 100 | 335.3 | 286.2 | 392.7 | 20.0 | 5120.0 |
| B/Malaysia | FluLD11 | PRE | 187 | 142 | 75.9 | 69.2 | 81.9 | 25.8 | 21.3 | 31.3 | <10.0 | 2560.0 |
| | | PI(D21) | 187 | 187 | 100 | 98.0 | 100 | 225.8 | 195.3 | 261.1 | 20.0 | 2560.0 |
| | FluLD12 | PRE | 189 | 145 | 76.7 | 70.0 | 82.5 | 27.3 | 22.6 | 32.9 | <10.0 | 3620.0 |
| | | PI(D21) | 189 | 188 | 99.5 | 97.1 | 100 | 246.1 | 210.9 | 287.2 | <10.0 | 3620.0 |
| | FluLD14 | PRE | 190 | 138 | 72.6 | 65.7 | 78.8 | 22.6 | 18.8 | 27.1 | <10.0 | 1280.0 |
| | | PI(D21) | 190 | 188 | 98.9 | 96.2 | 99.9 | 195.5 | 165.1 | 231.4 | <10.0 | 2560.0 |
| | FluLD18 | PRE | 192 | 142 | 74.0 | 67.1 | 80.0 | 23.2 | 19.5 | 27.8 | <10.0 | 1280.0 |
| | | PI(D21) | 192 | 188 | 97.9 | 94.8 | 99.4 | 171.2 | 144.2 | 203.2 | <10.0 | 5120.0 |
| | Fluarix | PRE | 185 | 139 | 75.1 | 68.3 | 81.2 | 27.0 | 22.2 | 32.7 | <10.0 | 1280.0 |
| | | PI(D21) | 185 | 183 | 98.9 | 96.1 | 99.9 | 217.8 | 184.3 | 257.4 | <10.0 | 3620.0 |

FluLD11 = 5 μg HA/strain with 1/1 dose AS03;
FluLD12 = 5 μg HA/strain with 1/2 dose AS03;
FluLD14 = 5 μg HA/strain with 1/4 dose AS03;
FluLD18 = 5 μg HA/strain with 1/8 dose AS03;
Fluarix = Fluarix (15 μg HA/strain)
N = Number of subjects with available results
n/% = number/percentage of seropositive subjects (HI titer >= 1:10)
95% CI = 95% confidence interval,
LL = Lower Limit,
UL = Upper Limit
GMT = Geometric Mean antibody Titer;
PRE = Pre-vaccination at day 0;
MIN/MAX = Minimum/Maximum
PI(D21) = Post-vaccination at Day 21

TABLE 25

Seropositivity rates and GMTs for HI antibody titer at d 0 and d 21 by age category

| Antibody | Sub-group | Group | Timing | N | >=10 1/DIL n | % | 95% CI LL | 95% CI UL | GMT value | 95% CI LL | 95% CI UL | Min | Max |
|---|---|---|---|---|---|---|---|---|---|---|---|---|---|
| A/Solomon | 18-49 y | FluLD11 | PRE | 129 | 68 | 52.7 | 43.7 | 61.6 | 14.7 | 11.7 | 18.5 | <10.0 | 905.0 |
| | | | PI(D21) | 129 | 129 | 100 | 97.2 | 100 | 271.6 | 224.5 | 328.5 | 10.0 | 5120.0 |
| | | FluLD12 | PRE | 128 | 58 | 45.3 | 36.5 | 54.3 | 14.1 | 11.0 | 18.0 | <10.0 | 1280.0 |
| | | | PI(D21) | 128 | 125 | 97.7 | 93.3 | 99.5 | 195.4 | 153.3 | 249.0 | <10.0 | 2560.0 |
| | | FluLD14 | PRE | 130 | 62 | 47.7 | 38.9 | 56.6 | 15.3 | 11.7 | 20.0 | <10.0 | 1280.0 |
| | | | PI(D21) | 130 | 128 | 98.5 | 94.6 | 99.8 | 205.5 | 167.0 | 252.8 | <10.0 | 2560.0 |
| | | FluLD18 | PRE | 132 | 73 | 55.3 | 46.4 | 64.0 | 17.2 | 13.4 | 22.0 | <10.0 | 640.0 |
| | | | PI(D21) | 132 | 130 | 98.5 | 94.6 | 99.8 | 195.7 | 156.2 | 245.1 | <10.0 | 3620.0 |
| | | Fluarix | PRE | 130 | 70 | 53.8 | 44.9 | 62.6 | 15.1 | 12.0 | 19.2 | <10.0 | 640.0 |
| | | | PI(D21) | 130 | 128 | 98.5 | 94.6 | 99.8 | 247.6 | 197.7 | 310.0 | <10.0 | 3620.0 |
| A/Wisconsin | 50-64 y | FluLD11 | PRE | 58 | 26 | 44.8 | 31.7 | 58.5 | 9.9 | 7.8 | 12.5 | <10.0 | 113.0 |
| | | | PI(D21) | 58 | 58 | 100 | 93.8 | 100 | 106.5 | 80.5 | 141.0 | 10.0 | 905.0 |
| | | FluLD12 | PRE | 61 | 25 | 41.0 | 28.6 | 54.3 | 9.3 | 7.4 | 11.8 | <10.0 | 80.0 |
| | | | PI(D21) | 61 | 60 | 98.4 | 91.2 | 100 | 96.9 | 71.9 | 130.8 | <10.0 | 1810.0 |
| | | FluLD14 | PRE | 60 | 22 | 36.7 | 24.6 | 50.1 | 9.0 | 7.1 | 11.4 | <10.0 | 160.0 |
| | | | PI(D21) | 60 | 58 | 96.7 | 88.5 | 99.6 | 102.5 | 73.2 | 143.4 | <10.0 | 1280.0 |
| | | FluLD18 | PRE | 60 | 27 | 45.0 | 32.1 | 58.4 | 11.0 | 8.1 | 14.8 | <10.0 | 453.0 |
| | | | PI(D21) | 60 | 57 | 95.0 | 86.1 | 99.0 | 85.6 | 61.7 | 118.8 | <10.0 | 1280.0 |
| | | Fluarix | PRE | 55 | 36 | 65.5 | 51.4 | 77.8 | 14.9 | 11.2 | 19.9 | <10.0 | 226.0 |
| | | | PI(D21) | 55 | 55 | 100 | 93.5 | 100 | 103.5 | 77.9 | 137.3 | 20.0 | 2560.0 |
| | 18-49 y | FluLD11 | PRE | 129 | 98 | 76.0 | 67.7 | 83.1 | 28.7 | 22.2 | 37.1 | <10.0 | 1280.0 |
| | | | PI(D21) | 129 | 129 | 100 | 97.2 | 100 | 360.1 | 294.7 | 440.1 | 14.0 | 5120.0 |
| | | FluLD12 | PRE | 128 | 95 | 74.2 | 65.7 | 81.5 | 31.2 | 23.9 | 40.6 | <10.0 | 1280.0 |
| | | | PI(D21) | 128 | 127 | 99.2 | 95.7 | 100 | 335.0 | 271.4 | 413.4 | <10.0 | 5120.0 |
| | | FluLD14 | PRE | 130 | 99 | 76.2 | 67.9 | 83.2 | 32.1 | 25.2 | 41.0 | <10.0 | 640.0 |
| | | | PI(D21) | 130 | 130 | 100 | 97.2 | 100 | 334.8 | 276.0 | 406.1 | 10.0 | 20480.0 |
| | | FluLD18 | PRE | 132 | 105 | 79.5 | 71.7 | 86.1 | 27.7 | 22.2 | 34.5 | <10.0 | 905.0 |
| | | | PI(D21) | 132 | 131 | 99.2 | 95.9 | 100 | 273.2 | 223.8 | 333.6 | <10.0 | 3620.0 |
| | | Fluarix | PRE | 130 | 106 | 81.5 | 73.8 | 87.8 | 34.0 | 26.6 | 43.4 | <10.0 | 1280.0 |
| | | | PI(D21) | 130 | 130 | 100 | 97.2 | 100 | 360.7 | 299.2 | 434.8 | 20.0 | 5120.0 |
| B/Malaysia | 50-64 y | FluLD11 | PRE | 58 | 44 | 75.9 | 62.8 | 86.1 | 31.1 | 20.9 | 46.4 | <10.0 | 1280.0 |
| | | | PI(D21) | 58 | 58 | 100 | 93.8 | 100 | 428.2 | 312.7 | 587.9 | 20.0 | 2560.0 |
| | | FluLD12 | PRE | 61 | 46 | 75.4 | 62.7 | 85.5 | 27.8 | 19.2 | 40.2 | <10.0 | 640.0 |
| | | | PI(DAY 21) | 61 | 61 | 100 | 94.1 | 100 | 309.2 | 231.0 | 413.9 | 20.0 | 5120.0 |
| | | FluLD14 | PRE | 60 | 42 | 70.0 | 56.8 | 81.2 | 25.6 | 17.9 | 36.6 | <10.0 | 640.0 |
| | | | PI(D21) | 60 | 58 | 96.7 | 88.5 | 99.6 | 290.0 | 205.5 | 409.1 | <10.0 | 2560.0 |
| | | FluLD18 | PRE | 60 | 44 | 73.3 | 60.3 | 83.9 | 26.2 | 18.3 | 37.6 | <10.0 | 640.0 |
| | | | PI(D21) | 60 | 60 | 100 | 94.0 | 100 | 275.3 | 202.4 | 374.4 | 20.0 | 5120.0 |
| | | Fluarix | PRE | 55 | 49 | 89.1 | 77.8 | 95.9 | 47.1 | 30.4 | 72.9 | <10.0 | 1280.0 |
| | | | PI(D21) | 55 | 55 | 100 | 93.5 | 100 | 282.0 | 208.9 | 380.6 | 40.0 | 2560.0 |
| | 18-49 y | FluLD11 | PRE | 129 | 101 | 78.3 | 70.2 | 85.1 | 26.3 | 20.8 | 33.4 | <10.0 | 2560.0 |
| | | | PI(D21) | 129 | 129 | 100 | 97.2 | 100 | 281.2 | 237.9 | 332.4 | 40.0 | 2560.0 |
| | | FluLD12 | PRE | 128 | 98 | 76.6 | 68.3 | 83.6 | 27.2 | 21.5 | 34.4 | <10.0 | 3620.0 |
| | | | PI(D21) | 128 | 128 | 100 | 97.2 | 100 | 335.9 | 283.3 | 398.3 | 28.0 | 3620.0 |
| | | FluLD14 | PRE | 130 | 94 | 72.3 | 63.8 | 79.8 | 22.7 | 18.2 | 28.2 | <10.0 | 640.0 |
| | | | PI(D21) | 130 | 128 | 98.5 | 94.6 | 99.8 | 219.1 | 179.8 | 266.9 | <10.0 | 2560.0 |
| | | FluLD18 | PRE | 132 | 95 | 72.0 | 63.5 | 79.4 | 23.9 | 19.1 | 30.0 | <10.0 | 1280.0 |
| | | | PI(D21) | 132 | 130 | 98.5 | 94.6 | 99.8 | 203.5 | 166.7 | 248.5 | <10.0 | 5120.0 |
| | | Fluarix | PRE | 130 | 98 | 75.4 | 67.1 | 82.5 | 27.4 | 21.7 | 34.4 | <10.0 | 453.0 |
| | | | PI(D21) | 130 | 129 | 99.2 | 95.8 | 100 | 250.9 | 206.9 | 304.3 | <10.0 | 2560.0 |
| | 50-64 y | FluLD11 | PRE | 58 | 41 | 70.7 | 57.3 | 81.9 | 24.8 | 17.7 | 34.7 | <10.0 | 320.0 |
| | | | PI(D21) | 58 | 58 | 100 | 93.8 | 100 | 138.6 | 108.1 | 177.6 | 20.0 | 1280.0 |
| | | FluLD12 | PRE | 61 | 47 | 77.0 | 64.5 | 86.8 | 27.5 | 19.9 | 37.8 | <10.0 | 640.0 |
| | | | PI(D21) | 61 | 60 | 98.4 | 91.2 | 100 | 128.1 | 99.3 | 165.1 | <10.0 | 1280.0 |
| | | FluLD14 | PRE | 60 | 44 | 73.3 | 60.3 | 83.9 | 22.4 | 15.9 | 31.6 | <10.0 | 1280.0 |
| | | | PI(D21) | 60 | 60 | 100 | 94.0 | 100 | 152.7 | 110.9 | 210.3 | 10.0 | 2560.0 |
| | | FluLD18 | PRE | 60 | 47 | 78.3 | 65.8 | 87.9 | 21.8 | 16.2 | 29.2 | <10.0 | 453.0 |
| | | | PI(D21) | 60 | 58 | 96.7 | 88.5 | 99.6 | 117.0 | 85.4 | 160.3 | <10.0 | 1810.0 |
| | | Fluarix | PRE | 55 | 41 | 74.5 | 61.0 | 85.3 | 26.0 | 18.0 | 37.6 | <10.0 | 1280.0 |
| | | | PI(D21) | 55 | 54 | 98.2 | 90.3 | 100 | 155.9 | 113.0 | 215.0 | <10.0 | 3620.6 |

Intermediate Conclusion

For A/Solomon Island (H1N1) GMTs were in the same range for all study groups. All adjuvanted groups are non-inferior to the Fluarix group for all strains and all age categories. For A/Wisconsin (H3N2), a trend for a decreased immune response with decreasing AS03 concentration was shown with no statistically significant difference. For B/Malaysia, a trend for a decreased immune response with decreasing AS03 concentration was also shown but the only statistically significant difference was shown between GMT induced with FluLD½ and FluLD⅛ for this strain (see FIG. 15). Similar results were seen when data were analysed by age group. For B/Malaysia however, GMT induced with FluLD½ was statistically significantly higher than with FluLD¼ in the younger age group (18-49y).

X.4.2 Seroconversion Factors of Anti-HI Antibody Titres, Seroprotection Rates and Seroconversion Rates (Correlates for Protection as Established for Influenza Vaccine in Humans)

Figure 16:
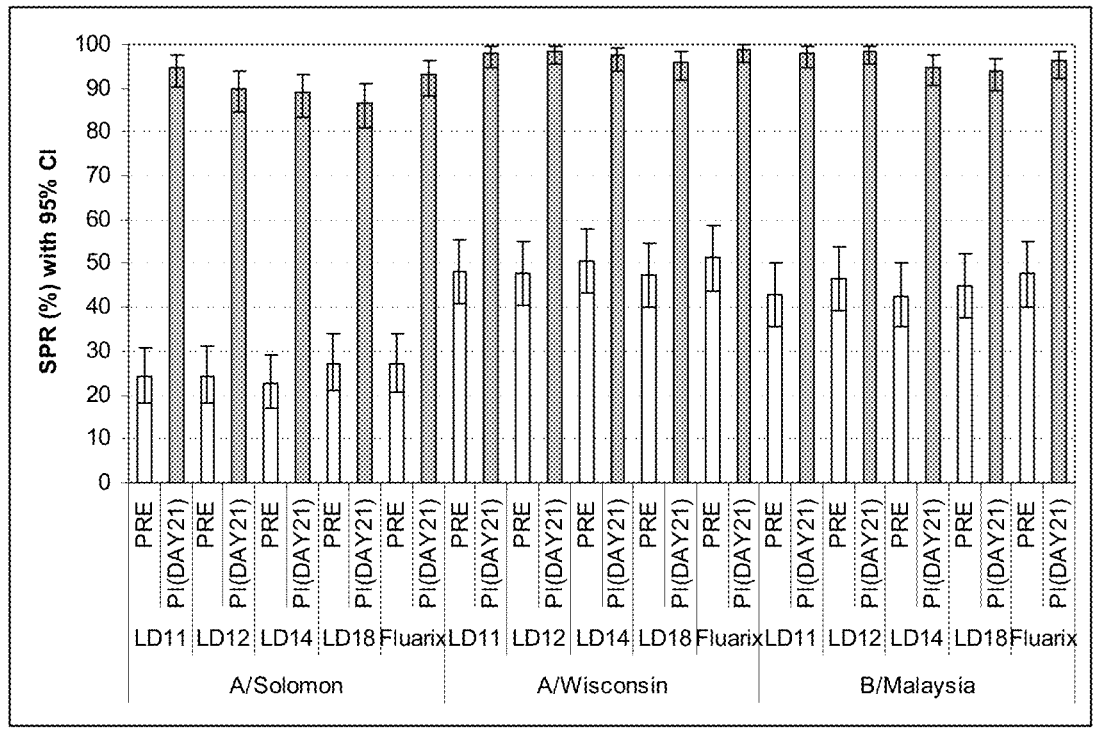
FIG. 16: Human clinical trial (adjuvant dose range in adults): Seroprotection rates (SPR) for HI antibody titer at D0 and D21.
Figure 17A:
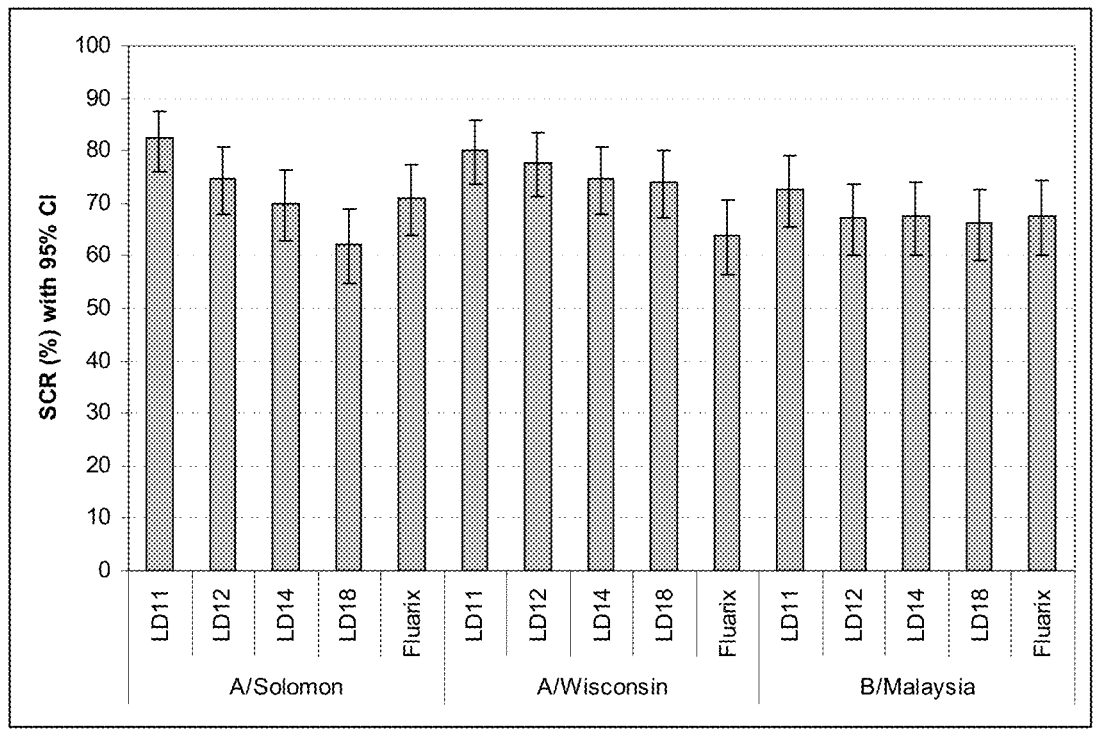
FIG. 17A: Human clinical trial (adjuvant dose range in adults): Seroconversion rate (SCR) for HI antibody titer at PI(DAY21).
Figure 17B:
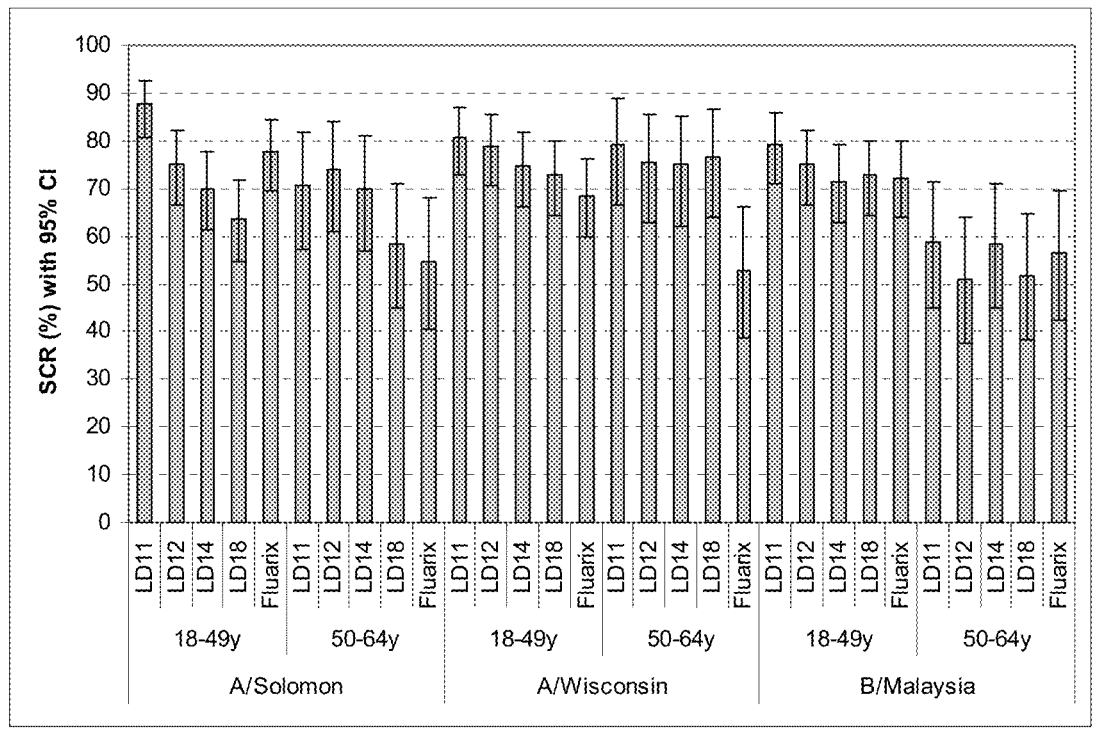
FIG. 17B: Human clinical trial (adjuvant dose range in adults): Seroconversion rate (SCR) for HI antibody titer at PI(DAY21) per age category.
Figure 18A:
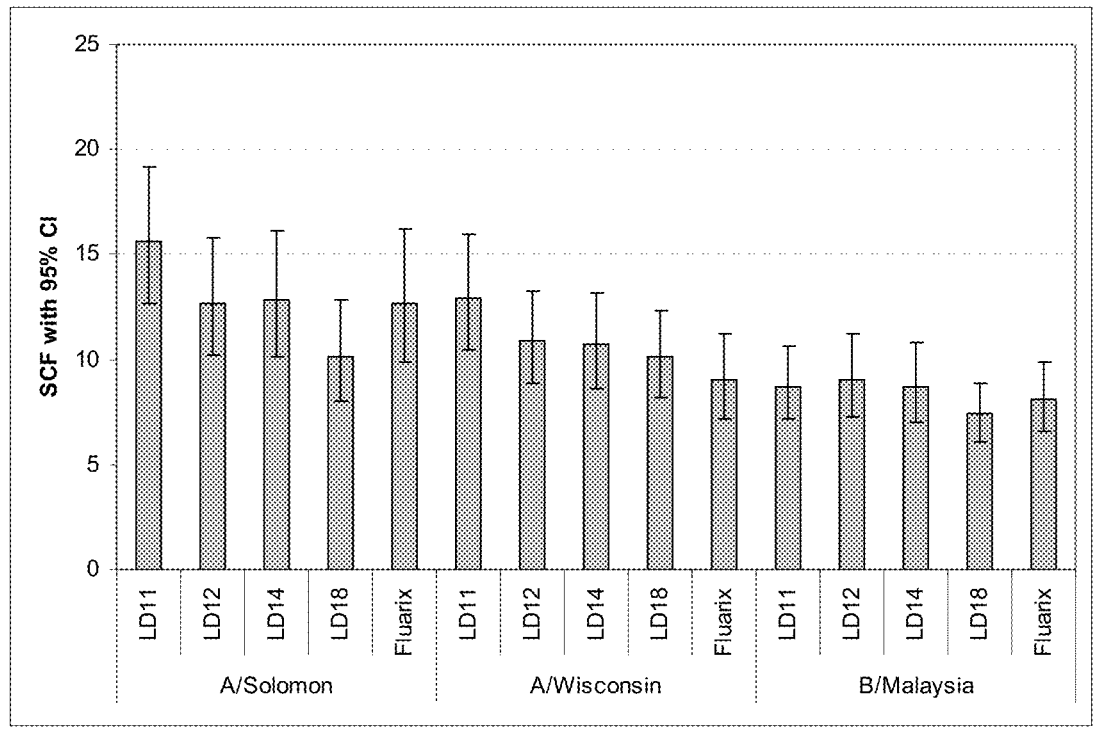
FIG. 18A: Human clinical trial (adjuvant dose range in adults): Seroconversion factor (SCF) for HI antibody titer at PI(DAY21).
Figure 18B:
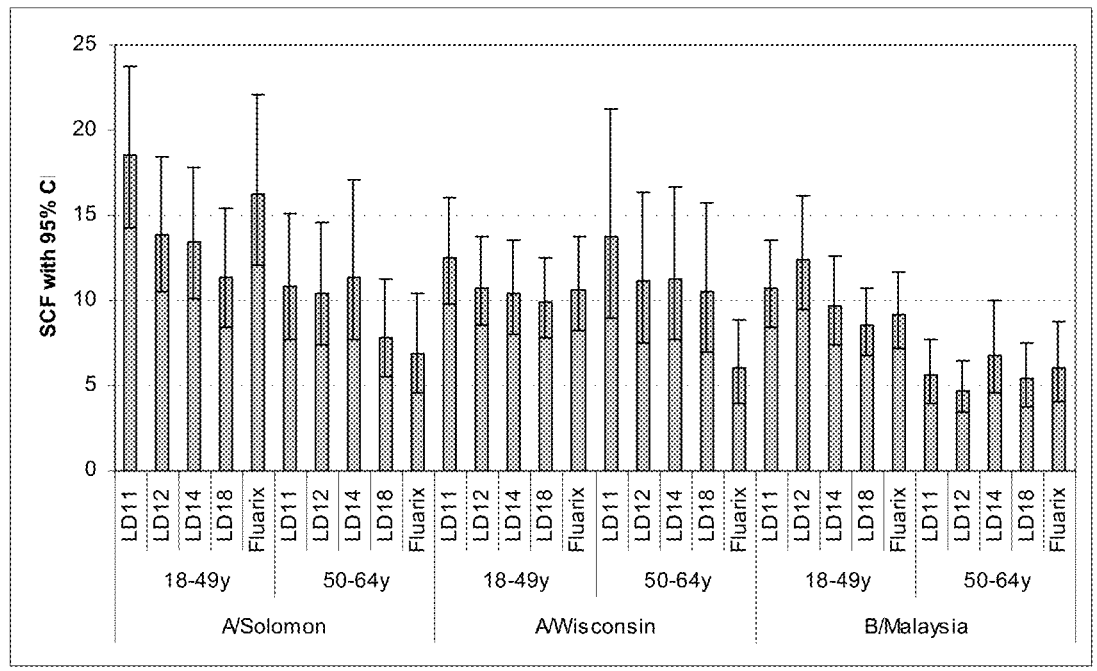
FIG. 18B: Human clinical trial (adjuvant dose range in adults): Seroconversion factor (SCF) for HI antibody titer at PI(DAY21) per age category.

Results are presented in Tables 26 and 26-FIG. 16 for seroprotection rates, Tables 28 and 29-FIGS. 17A and B for seroconversion rates and Tables 30 and 31-FIGS. 17A and B for conversion factors, and FIGS. 18A and B.

TABLE 26

Seroprotection rates (SPR) for HI antibody titer at D 0 and D 21

| Vaccine strain | Group | Timing | N | n | SPR % | 95% CI LL | 95% CI UL |
|---|---|---|---|---|---|---|---|
| A/Solomon | FluLD11 | PRE | 187 | 45 | 24.1 | 18.1 | 30.8 |
| | | PI(DAY21) | 187 | 177 | 94.7 | 90.4 | 97.4 |
| | FluLD12 | PRE | 189 | 46 | 24.3 | 18.4 | 31.1 |
| | | PI(DAY21) | 189 | 170 | 89.9 | 84.7 | 93.8 |
| | FluLD14 | PRE | 190 | 43 | 22.6 | 16.9 | 29.2 |
| | | PI(DAY21) | 190 | 169 | 88.9 | 83.6 | 93.0 |
| | FluLD18 | PRE | 192 | 52 | 27.1 | 20.9 | 34.0 |
| | | PI(DAY21) | 192 | 166 | 86.5 | 80.8 | 91.0 |
| | Fluarix | PRE | 185 | 50 | 27.0 | 20.8 | 34.0 |
| | | PI(DAY21) | 185 | 172 | 93.0 | 88.3 | 96.2 |
| A/Wisconsin | FluLD11 | PRE | 187 | 90 | 48.1 | 40.8 | 55.5 |
| | | PI(DAY21) | 187 | 183 | 97.9 | 94.6 | 99.4 |
| | FluLD12 | PRE | 189 | 90 | 47.6 | 40.3 | 55.0 |
| | | PI(DAY21) | 189 | 186 | 98.4 | 95.4 | 99.7 |
| | FluLD14 | PRE | 190 | 96 | 50.5 | 43.2 | 57.8 |
| | | PI(DAY21) | 190 | 185 | 97.4 | 94.0 | 99.1 |
| | FluLD18 | PRE | 192 | 91 | 47.4 | 40.2 | 54.7 |
| | | PI(DAY21) | 192 | 184 | 95.8 | 92.0 | 98.2 |
| | Fluarix | PRE | 185 | 95 | 51.4 | 43.9 | 58.8 |
| | | PI(DAY21) | 185 | 183 | 98.9 | 96.1 | 99.9 |
| B/Malaysia | FluLD11 | PRE | 187 | 80 | 42.8 | 35.6 | 50.2 |
| | | PI(DAY21) | 187 | 183 | 97.9 | 94.6 | 99.4 |
| | FluLD12 | PRE | 189 | 88 | 46.6 | 39.3 | 53.9 |
| | | PI(DAY21) | 189 | 186 | 98.4 | 95.4 | 99.7 |
| | FluLD14 | PRE | 190 | 81 | 42.6 | 35.5 | 50.0 |
| | | PI(DAY21) | 190 | 180 | 94.7 | 90.5 | 97.4 |
| | FluLD18 | PRE | 192 | 86 | 44.8 | 37.6 | 52.1 |
| | | PI(DAY21) | 192 | 180 | 93.8 | 89.3 | 96.7 |
| | Fluarix | PRE | 185 | 88 | 47.6 | 40.2 | 55.0 |
| | | PI(DAY21) | 185 | 178 | 96.2 | 92.4 | 98.5 |

FluLD11 = 5 µg HA/strain with 1/1 dose AS03
FluLD12 = 5 µg HA/strain with 1/2 dose AS03
FluLD14 = 5 µg HA/strain with 1/4 dose AS03
FluLD18 = 5 µg HA/strain with 1/8 dose AS03
Fluarix = Fluarix (15 µg HA/strain)
Seroprotection rate defined as the percentage of vaccinees with a serum HI titre ≥ 1:40
N = Number of subjects with pre- and post-vaccination results available
n/% = Number/percentage of seroprotected subjects
95% CI = 95% confidence interval,
LL = Lower Limit,
UL = Upper Limit
PRE = Pre-vaccination at day 0;
PI(Day21) = Post-vaccination at Day 21

TABLE 27

Seroprotection rates (SPR) for HI antibody titer at D 0 and D 21 by age category

| Vaccine strain | Sub-group | Group | Timing | N | n | SPR % | 95% CI LL | 95% CI UL |
|---|---|---|---|---|---|---|---|---|
| A/Solomon | 18-49 y | FluLD11 | PRE | 129 | 36 | 27.9 | 20.4 | 36.5 |
| | | | PI(DAY21) | 129 | 127 | 98.4 | 94.5 | 99.8 |
| | | FluLD12 | PRE | 128 | 35 | 27.3 | 19.8 | 35.9 |
| | | | PI(DAY21) | 128 | 117 | 91.4 | 85.1 | 95.6 |

TABLE 27-continued

Seroprotection rates (SPR) for HI antibody titer at D 0 and D 21 by age category

| Vaccine strain | Sub-group | Group | Timing | N | n | SPR % | 95% CI LL | 95% CI UL |
|---|---|---|---|---|---|---|---|---|
| | | FluLD14 | PRE | 130 | 35 | 26.9 | 19.5 | 35.4 |
| | | | PI(DAY21) | 130 | 119 | 91.5 | 85.4 | 95.7 |
| | | FluLD18 | PRE | 132 | 43 | 32.6 | 24.7 | 41.3 |
| | | | PI(DAY21) | 132 | 119 | 90.2 | 83.7 | 94.7 |
| | | Fluarix | PRE | 130 | 34 | 26.2 | 18.8 | 34.6 |
| | | | PI(DAY21) | 130 | 124 | 95.4 | 90.2 | 98.3 |
| A/Wisconsin | 50-64 y | FluLD11 | PRE | 58 | 9 | 15.5 | 7.3 | 27.4 |
| | | | PI(DAY21) | 58 | 50 | 86.2 | 74.6 | 93.9 |
| | | FluLD12 | PRE | 61 | 11 | 18.0 | 9.4 | 30.0 |
| | | | PI(DAY21) | 61 | 53 | 86.9 | 75.8 | 94.2 |
| | | FluLD14 | PRE | 60 | 8 | 13.3 | 5.9 | 24.6 |
| | | | PI(DAY21) | 60 | 50 | 83.3 | 71.5 | 91.7 |
| | | FluLD18 | PRE | 60 | 9 | 15.0 | 7.1 | 26.6 |
| | | | PI(DAY21) | 60 | 47 | 78.3 | 65.8 | 87.9 |
| | | Fluarix | PRE | 55 | 16 | 29.1 | 17.6 | 42.9 |
| | | | PI(DAY21) | 55 | 48 | 87.3 | 75.5 | 94.7 |
| | 18-49 y | FluLD11 | PRE | 129 | 62 | 48.1 | 39.2 | 57.0 |
| | | | PI(DAY21) | 129 | 127 | 98.4 | 94.5 | 99.8 |
| | | FluLD12 | PRE | 128 | 62 | 48.4 | 39.5 | 57.4 |
| | | | PI(DAY21) | 128 | 126 | 98.4 | 94.5 | 99.8 |
| | | FluLD14 | PRE | 130 | 68 | 52.3 | 43.4 | 61.1 |
| | | | PI(DAY21) | 130 | 128 | 98.5 | 94.6 | 99.8 |
| | | FluLD18 | PRE | 132 | 62 | 47.0 | 38.2 | 55.8 |
| | | | PI(DAY21) | 132 | 127 | 96.2 | 91.4 | 98.8 |
| | | Fluarix | PRE | 130 | 66 | 50.8 | 41.9 | 59.6 |
| | | | PI(DAY21) | 130 | 128 | 98.5 | 94.6 | 99.8 |
| B/Malaysia | 50-64 y | FluLD11 | PRE | 58 | 28 | 48.3 | 35.0 | 61.8 |
| | | | PI(DAY21) | 58 | 56 | 96.6 | 88.1 | 99.6 |
| | | FluLD12 | PRE | 61 | 28 | 45.9 | 33.1 | 59.2 |
| | | | PI(DAY21) | 61 | 60 | 98.4 | 91.2 | 100 |
| | | FluLD14 | PRE | 60 | 28 | 46.7 | 33.7 | 60.0 |
| | | | PI(DAY21) | 60 | 57 | 95.0 | 86.1 | 99.0 |
| | | FluLD18 | PRE | 60 | 29 | 48.3 | 35.2 | 61.6 |
| | | | PI(DAY21) | 60 | 57 | 95.0 | 86.1 | 99.0 |
| | | Fluarix | PRE | 55 | 29 | 52.7 | 38.8 | 66.3 |
| | | | PI(DAY21) | 55 | 55 | 100 | 93.5 | 100 |
| | 18-49 y | FluLD11 | PRE | 129 | 53 | 41.1 | 32.5 | 50.1 |
| | | | PI(DAY21) | 129 | 129 | 100 | 97.2 | 100 |
| | | FluLD12 | PRE | 128 | 59 | 46.1 | 37.2 | 55.1 |
| | | | PI(DAY21) | 128 | 127 | 99.2 | 95.7 | 100 |
| | | FluLD14 | PRE | 130 | 57 | 43.8 | 35.2 | 52.8 |
| | | | PI(DAY21) | 130 | 125 | 96.2 | 91.3 | 98.7 |
| | | FluLD18 | PRE | 132 | 61 | 46.2 | 37.5 | 55.1 |
| | | | PI(DAY21) | 132 | 128 | 97.0 | 92.4 | 99.2 |
| | | Fluarix | PRE | 130 | 61 | 46.9 | 38.1 | 55.9 |
| | | | PI(DAY21) | 130 | 126 | 96.9 | 92.3 | 99.2 |
| | 50-64 y | FluLD11 | PRE | 58 | 27 | 46.6 | 33.3 | 60.1 |
| | | | PI(DAY21) | 58 | 54 | 93.1 | 83.3 | 98.1 |
| | | FluLD12 | PRE | 61 | 29 | 47.5 | 34.6 | 60.7 |
| | | | PI(DAY21) | 61 | 59 | 96.7 | 88.7 | 99.6 |
| | | FluLD14 | PRE | 60 | 24 | 40.0 | 27.6 | 53.5 |
| | | | PI(DAY21) | 60 | 55 | 91.7 | 81.6 | 97.2 |
| | | FluLD18 | PRE | 60 | 25 | 41.7 | 29.1 | 55.1 |
| | | | PI(DAY21) | 60 | 52 | 86.7 | 75.4 | 94.1 |
| | | Fluarix | PRE | 55 | 27 | 49.1 | 35.4 | 62.9 |
| | | | PI(DAY21) | 55 | 52 | 94.5 | 84.9 | 98.9 | same legend as in Table 24

Intermediate Conclusion

SPR met CHMP (mean >70) and FDA criteria (LL of 95% CI >70) for all groups and all three strains. SPR were shown to be within the same range for all groups.

TABLE 28

Seroconversion rate (SCR) for HI antibody titer at PI(DAY21)

| Vaccine strain | Group | Timing | N | n | % | SCR 95% CI LL | UL |
|---|---|---|---|---|---|---|---|
| A/Solomon | FluLD11 | PI(DAY21) | 187 | 154 | 82.4 | 76.1 | 87.5 |
|  | FluLD12 | PI(DAY21) | 189 | 141 | 74.6 | 67.8 | 80.6 |
|  | FluLD14 | PI(DAY21) | 190 | 133 | 70.0 | 62.9 | 76.4 |
|  | FluLD18 | PI(DAY21) | 192 | 119 | 62.0 | 54.7 | 68.9 |
|  | Fluarix | PI(DAY21) | 185 | 131 | 70.8 | 63.7 | 77.2 |
| A/Wisconsin | FluLD11 | PI(DAY21) | 187 | 150 | 80.2 | 73.8 | 85.7 |
|  | FluLD12 | PI(DAY21) | 189 | 147 | 77.8 | 71.2 | 83.5 |
|  | FluLD14 | PI(DAY21) | 190 | 142 | 74.7 | 67.9 | 80.7 |
|  | FluLD18 | PI(DAY21) | 192 | 142 | 74.0 | 67.1 | 80.0 |
|  | Fluarix | PI(DAY21) | 185 | 118 | 63.8 | 56.4 | 70.7 |
| B/Malaysia | FluLD11 | PI(DAY21) | 187 | 136 | 72.7 | 65.7 | 79.0 |
|  | FluLD12 | PI(DAY21) | 189 | 127 | 67.2 | 60.0 | 73.8 |
|  | FluLD14 | PI(DAY21) | 190 | 128 | 67.4 | 60.2 | 74.0 |
|  | FluLD18 | PI(DAY21) | 192 | 127 | 66.1 | 59.0 | 72.8 |
|  | Fluarix | PI(DAY21) | 185 | 125 | 67.6 | 60.3 | 74.3 |

FluLD11 = 5 μg HA/strain with 1/1 dose AS03;
FluLD12 = 5 μg HA/strain with 1/2 dose AS03;
FluLD14 = 5 μg HA/strain with 1/4 dose AS03;
FluLD18 = 5 μg HA/strain with 1/8 dose AS03;
Fluarix = Fluarix (15 μg HA/strain)
Seroconversion defined as:
For initially seronegative subjects, antibody titre >= 40 1/DIL after vaccination
For initially seropositive subjects, antibody titre after vaccination >= 4 fold the pre-vaccination antibody titre
N = Number of subjects with pre- and post-vaccination results available
n/% = Number/percentage of seroconverted subjects
95% CI = 95% confidence interval,
LL = Lower Limit,
UL = Upper Limit
PI(DAY21)= Post-vaccination at Day 21

TABLE 29

Seroconversion rate (SCR) for HI antibody titer at PI(Day21) by age category

| Vaccine strain | Sub-group | Group | Timing | N | n | % | SCR 95% CI LL | UL |
|---|---|---|---|---|---|---|---|---|
| A/Solomon | 18-49 y | FluLD11 | PI(DAY21) | 129 | 113 | 87.6 | 80.6 | 92.7 |
|  |  | FluLD12 | PI(DAY21) | 128 | 96 | 75.0 | 66.6 | 82.2 |
|  |  | FluLD14 | PI(DAY21) | 130 | 91 | 70.0 | 61.3 | 77.7 |
|  |  | FluLD18 | PI(DAY21) | 132 | 84 | 63.6 | 54.8 | 71.8 |
|  |  | Fluarix | PI(DAY21) | 130 | 101 | 77.7 | 69.6 | 84.5 |
|  | 50-64 y | FluLD11 | PI(DAY21) | 58 | 41 | 70.7 | 57.3 | 81.9 |
|  |  | FluLD12 | PI(DAY21) | 61 | 45 | 73.8 | 60.9 | 84.2 |
|  |  | FluLD14 | PI(DAY21) | 60 | 42 | 70.0 | 56.8 | 81.2 |
|  |  | FluLD18 | PI(DAY21) | 60 | 35 | 58.3 | 44.9 | 70.9 |
|  |  | Fluarix | PI(DAY21) | 55 | 30 | 54.5 | 40.6 | 68.0 |
| A/Wisconsin | 18-49 y | FluLD11 | PI(DAY21) | 129 | 104 | 80.6 | 72.7 | 87.0 |
|  |  | FluLD12 | PI(DAY21) | 128 | 101 | 78.9 | 70.8 | 85.6 |
|  |  | FluLD14 | PI(DAY21) | 130 | 97 | 74.6 | 66.2 | 81.8 |
|  |  | FluLD18 | PI(DAY21) | 132 | 96 | 72.7 | 64.3 | 80.1 |
|  |  | Fluarix | PI(DAY21) | 130 | 89 | 68.5 | 59.7 | 76.3 |
|  | 50-64 y | FluLD11 | PI(DAY21) | 58 | 46 | 79.3 | 66.6 | 88.8 |
|  |  | FluLD12 | PI(DAY21) | 61 | 46 | 75.4 | 62.7 | 85.5 |
|  |  | FluLD14 | PI(DAY21) | 60 | 45 | 75.0 | 62.1 | 85.3 |
|  |  | FluLD18 | PI(DAY21) | 60 | 46 | 76.7 | 64.0 | 86.6 |
|  |  | Fluarix | PI(DAY21) | 55 | 29 | 52.7 | 38.8 | 66.3 |

TABLE 29-continued

Seroconversion rate (SCR) for HI antibody titer at PI(Day21) by age category

| Vaccine strain | Sub-group | Group | Timing | N | n | % | 95% CI LL | 95% CI UL |
|---|---|---|---|---|---|---|---|---|
| B/Malaysia | 18-49 y | FluLD11 | PI(DAY21) | 129 | 102 | 79.1 | 71.0 | 85.7 |
| | | FluLD12 | PI(DAY21) | 128 | 96 | 75.0 | 66.6 | 82.2 |
| | | FluLD14 | PI(DAY21) | 130 | 93 | 71.5 | 63.0 | 79.1 |
| | | FluLD18 | PI(DAY21) | 132 | 96 | 72.7 | 64.3 | 80.1 |
| | | Fluarix | PI(DAY21) | 130 | 94 | 72.3 | 63.8 | 79.8 |
| | 50-64 y | FluLD11 | PI(DAY21) | 58 | 34 | 58.6 | 44.9 | 71.4 |
| | | FluLD12 | PI(DAY21) | 61 | 31 | 50.8 | 37.7 | 63.9 |
| | | FluLD14 | PI(DAY21) | 60 | 35 | 58.3 | 44.9 | 70.9 |
| | | FluLD18 | PI(DAY21) | 60 | 31 | 51.7 | 38.4 | 64.8 |
| | | Fluarix | PI(DAY21) | 55 | 31 | 56.4 | 42.3 | 69.7 | same legend as for Table 26

Intermediate Conclusion

SCR met CHMP criteria (mean >40) and FDA criteria (LL of 95% CI >40) for all study vaccines and for all 3 strains. A trend for a decreased SCR with decreased AS03 content was shown except for B/Malaysia (where all results were shown to be within the same range). For A/Solomon Island, FluLD1/1 induced a statistically significant higher SCR compared to FluLD⅛. For all groups, SCR induced by FluLD½ and FluLD¼ were within the same range.

TABLE 30

Seroconversion factor (SCF) for HI antibody titer at D 21

| Vaccine strain | Group | Timing | N | SCF Value | 95% CI LL | 95% CI UL |
|---|---|---|---|---|---|---|
| A/Solomon (1/DIL) | FluLD11 | PI(DAY 21) | 187 | 15.6 | 12.7 | 19.2 |
| | FluLD12 | PI(DAY 21) | 189 | 12.7 | 10.2 | 15.8 |
| | FluLD14 | PI(DAY 21) | 190 | 12.8 | 10.1 | 16.1 |
| | FluLD18 | PI(DAY 21) | 192 | 10.1 | 8.0 | 12.8 |
| | Fluarix | PI(DAY 21) | 185 | 12.7 | 9.9 | 16.2 |
| A/Wisconsin (1/DIL) | FluLD11 | PI(DAY 21) | 187 | 12.9 | 10.5 | 16.0 |
| | FluLD12 | PI(DAY 21) | 189 | 10.9 | 8.9 | 13.3 |
| | FluLD14 | PI(DAY 21) | 190 | 10.7 | 8.6 | 13.2 |
| | FluLD18 | PI(DAY 21) | 192 | 10.1 | 8.2 | 12.3 |
| | Fluarix | PI(DAY 21) | 185 | 9.0 | 7.2 | 11.2 |
| B/Malaysia (1/DIL) | FluLD11 | PI(DAY 21) | 187 | 8.7 | 7.2 | 10.6 |
| | FluLD12 | PI(DAY 21) | 189 | 9.0 | 7.3 | 11.2 |
| | FluLD14 | PI(DAY 21) | 190 | 8.7 | 7.0 | 10.8 |
| | FluLD18 | PI(DAY 21) | 192 | 7.4 | 6.1 | 8.9 |
| | Fluarix | PI(DAY 21) | 185 | 8.1 | 6.6 | 9.9 |

FluLD11 = 5 μg HA/strain with ¹/₁ dose AS03; FluLD12 = 5 μg HA/strain with ½ dose AS03; FluLD14 = 5 μg HA/strain with ¼ dose AS03; FluLD18 = 5 μg HA/strain with ⅛ dose AS03; Fluarix = Fluarix (15 μg HA/strain)
N = Number of subjects with pre- and post-vaccination results available
SCF = Seroconversion Factor or geometric mean ratio (mean[log10(POST/PRE)])
95% CI = 95% confidence interval, LL = Lower Limit, UL = Upper Limit
PI(DAY 21) = Post-vaccination at Day 21

TABLE 31

Seroconversion factor (SCF) for HI antibody titer at D 21 by age category

| Vaccine strain | Sub-group | Group | Timing | N | SCF Value | 95% CI LL | 95% CI UL |
|---|---|---|---|---|---|---|---|
| A/Solomon (1/DIL) | 18-49 y | FluLD11 | PI(DAY21) | 129 | 18.5 | 14.3 | 23.8 |
| | | FluLD12 | PI(DAY21) | 128 | 13.9 | 10.5 | 18.4 |
| | | FluLD14 | PI(DAY21) | 130 | 13.4 | 10.1 | 17.8 |
| | | FluLD18 | PI(DAY21) | 132 | 11.4 | 8.4 | 15.4 |
| | | Fluarix | PI(DAY21) | 130 | 16.3 | 12.1 | 22.1 |
| | 50-64 y | FluLD11 | PI(DAY21) | 58 | 10.8 | 7.7 | 15.1 |
| | | FluLD12 | PI(DAY21) | 61 | 10.4 | 7.4 | 14.6 |
| | | FluLD14 | PI(DAY21) | 60 | 11.4 | 7.7 | 17.1 |
| | | FluLD18 | PI(DAY21) | 60 | 7.8 | 5.5 | 11.2 |
| | | Fluarix | PI(DAY21) | 55 | 6.9 | 4.6 | 10.4 |
| A/Wisconsin (1/DIL) | 18-49 y | FluLD11 | PI(DAY21) | 129 | 12.5 | 9.8 | 16.0 |
| | | FluLD12 | PI(DAY21) | 128 | 10.7 | 8.5 | 13.7 |
| | | FluLD14 | PI(DAY21) | 130 | 10.4 | 8.0 | 13.5 |
| | | FluLD18 | PI(DAY21) | 132 | 9.9 | 7.8 | 12.5 |
| | | Fluarix | PI(DAY21) | 130 | 10.6 | 8.2 | 13.8 |
| | 50-64 y | FluLD11 | PI(DAY21) | 58 | 13.8 | 9.0 | 21.2 |
| | | FluLD12 | PI(DAY21) | 61 | 11.1 | 7.5 | 16.4 |
| | | FluLD14 | PI(DAY21) | 60 | 11.3 | 7.7 | 16.7 |

TABLE 31-continued

Seroconversion factor (SCF) for HI antibody titer at D 21 by age category

| Vaccine strain | Sub-group | Group | Timing | N | SCF Value | 95% CI LL | 95% CI UL |
|---|---|---|---|---|---|---|---|
| B/Malaysia (1/DIL) | | FluLD18 | PI(DAY21) | 60 | 10.5 | 7.0 | 15.7 |
| | | Fluarix | PI(DAY21) | 55 | 6.0 | 4.0 | 8.9 |
| | 18-49 y | FluLD11 | PI(DAY21) | 129 | 10.7 | 8.4 | 13.5 |
| | | FluLD12 | PI(DAY21) | 128 | 12.4 | 9.5 | 16.1 |
| | | FluLD14 | PI(DAY21) | 130 | 9.7 | 7.4 | 12.6 |
| | | FluLD18 | PI(DAY21) | 132 | 8.5 | 6.8 | 10.7 |
| | | Fluarix | PK DAY21) | 130 | 9.2 | 7.2 | 11.7 |
| | 50-64 y | FluLD11 | PI(DAY21) | 58 | 5.6 | 4.0 | 7.7 |
| | | FluLD12 | PI(DAY21) | 61 | 4.7 | 3.4 | 6.5 |
| | | FluLD14 | PI(DAY21) | 60 | 6.8 | 4.6 | 10.0 |
| | | FluLD18 | PI(DAY21) | 60 | 5.4 | 3.8 | 7.5 |
| | | Fluarix | PI(DAY21) | 55 | 6.0 | 4.1 | 8.8 | same legend as in Table 28

Intermediate Conclusion

For all study vaccines SCF were far above the CHMP criteria (>2) for all 3 strains. SCF were within the same range for all study vaccines.

X.4.3 Non-Inferiority of the Adjuvanted Low Dose Vaccines with Respect to Fluarix (GMT)

The non-inferiority of the Adjuvanted Low Dose vaccines with respect to Fluarix in terms of GMT ratios at Day 21 for the 3 viral is shown in Table 32.

TABLE 32

Non inferiority of Adjuvanted Low Dose vaccines with respect to Fluarix in terms of GMT ratios at D 21 for the 3 viral strains

| AS03 Dose(μL) | Dose Proportion | Antibody | Flu Low Dose N | GMT | 95% CI LL | 95% CI UL | Fluarix N | GMT | 95% CI LL | 95% CI UL | LD/Fluarix Ratio | 90% CI LL | 90% CI UL |
|---|---|---|---|---|---|---|---|---|---|---|---|---|---|
| 250 | 1/1 | A/H1N1 | 187 | 202.3 | 168.3 | 243.2 | 185 | 191.0 | 158.7 | 229.9 | 1.06 | 0.85 | 1.32 |
| | | A/H3N2 | 187 | 378.6 | 320.0 | 447.8 | 185 | 335.3 | 286.5 | 392.3 | 1.13 | 0.93 | 1.37 |
| | | B | 187 | 236.0 | 206.1 | 270.4 | 185 | 217.8 | 184.5 | 257.2 | 1.08 | 0.91 | 1.30 |
| 125 | 1/2 | A/H1N1 | 189 | 160.5 | 135.7 | 189.9 | 185 | 191.0 | 158.7 | 229.9 | 0.84 | 0.68 | 1.04 |
| | | A/H3N2 | 189 | 336.0 | 288.2 | 391.8 | 185 | 335.3 | 286.5 | 392.3 | 1.00 | 0.83 | 1.20 |
| | | B | 189 | 226.2 | 204.8 | 249.7 | 185 | 217.8 | 184.5 | 257.2 | 1.04 | 0.88 | 1.22 |
| 62.5 | 1/4 | A/H1N1 | 190 | 155.5 | 139.2 | 173.7 | 185 | 191.0 | 158.7 | 229.9 | 0.81 | 0.68 | 0.98 |
| | | A/H3N2 | 190 | 302.0 | 272.9 | 334.1 | 185 | 335.3 | 286.5 | 392.3 | 0.90 | 0.77 | 1.05 |
| | | B | 190 | 205.7 | 181.9 | 232.6 | 185 | 217.8 | 184.5 | 257.2 | 0.94 | 0.79 | 1.12 |
| 31.2 | 1/8 | A/H1N1 | 192 | 156.3 | 132.8 | 183.8 | 185 | 191.0 | 158.7 | 229.9 | 0.82 | 0.67 | 1.01 |
| | | A/H3N2 | 192 | 282.9 | 244.0 | 328.1 | 185 | 335.3 | 286.5 | 392.3 | 0.84 | 0.70 | 1.01 |
| | | B | 192 | 169.4 | 145.1 | 197.7 | 185 | 217.8 | 184.5 | 257.2 | 0.78 | 0.64 | 0.94 |

N = Number of subjects with available results

95% CI = 95% confidence interval,

90% CI = 90% confidence interval,

LL = Lower Limit,

UL = Upper Limit

GMT = Geometric Mean antibody Titer

Intermediate Conclusion

FluLD1/1, ½, ¼ were shown to be non-inferior to Fluarix in terms of GMT ratios for all three strains. FluLD ⅛ was shown to be non-inferior to Fluarix for H1N1 and H3N2 strain but not for B.

X.5. Overall Conclusions

X.5.1 Safety Conclusions

A higher reactogenicity was shown with the adjuvanted vaccines, compared to that shown with the commercially available Fluarix vaccine. For the adjuvanted vaccines, a trend for decreasing reactogenicity was shown with a decreasing amount of AS03. Overall, a similar reactogenicity profile was obtained with FluDL¼ and FluDL⅛.

Unsolicited symptoms were the same for all vaccine groups.

X.5.2 Immunogenicity Conclusions

The primary objective of this stady was to assess the non-inferiority (GMT) of the LD vaccine formulations vs. Fluarix at D21.

At day 21 post vaccination with one dose of the adjuvanted vaccine FluDL1/1, FluDL½, and FluDL¼, the GMT ratios for all three strains were shown to be non-inferior to those obtained with Fluarix. In that study, the GMT ratio obtained with the vaccine FluDL⅛ was shown to be non-inferior to Fluarix for H1N1 and H3N2 strain but not for B strain. Despite a trend for decreasing immune response shown with decreasing amounts of adjuvant, all vaccines were shown to meet all 3 CHMP criteria for regulatory approval, for all strains.

Example XI—Clinical Trial in a Population Aged 65+ Years with a Vaccine Containing a Split Influenza Antigen Preparation and Various Adjuvants X1.1. Introduction The efficacy of a classical split influenza vaccine such as Fluarix™ in elderly adults is significantly lower than in an adult or young population. It is suggested that aging of the immune system (i.e. immunosenescence) is the underlying cause of the relative lack of efficacy seen in elderly adults, thus leaving room for vaccine improvement by stimulating stronger immune responses. A phase II, controlled, randomized, single blind study was therefore conducted in an elderly population aged 65+ years old in 2007 in order to evaluate the immunogenicity, safety and reactogenicity of an influenza candidate vaccine with eight different adjuvant formulations, administered intramuscularly, compared to Fluarix™ (GlaxoSmithKline Biologicals) used as a reference.

An adjuvanted influenza vaccine comprising an oil-in-water emulsion and 25 µg 3D-MPL per dose has already been tested and proved efficacious (WO 2006/100111). In that study, the quantities of each component were fixed to 250 µl of oil-in-water emulsion and 25 µg of MPL. The present study aims at determining an optimal vaccine formulation balancing the acceptability of the observed reactogenicity/safety profile with that of the immunogenicity profile.

XI.2. Study Design and Objectives

Ten groups of subjects (200 per group aged 65 years old except for the group Fluarix YNG aged 18-40 years old) in parallel received the following influenza vaccines i.m.:

FluAS03 1/1: vaccine adjuvanted with full dose of o/w emulsion (AS03 1/1)

FluAS03 ½: vaccine adjuvanted with ½ dose of o/w emulsion (AS03 ½)

FluAS03 ¼: vaccine adjuvanted with ¼ dose of o/w emulsion (AS03 ¼)

FluAS25 1/1: vaccine adjuvanted with 25 µg MPL+full dose of o/w emulsion (AS25A)

FluAS25 ½: vaccine adjuvanted with 25 µg MPL+½ dose of o/w emulsion (AS25B)

FluAS25 ¼: vaccine adjuvanted with 25 µg MPL+¼ dose of o/w emulsion (AS25C)

FluAS50 ½: vaccine adjuvanted with 50 µg MPL+½ dose of o/w emulsion (AS25E)

FluAS50 ¼: vaccine adjuvanted with 50 µg MPL+¼ dose of o/w emulsion (AS25F)

Fluarix ELD (65 years old): Fluarix™

Fluarix YNG (18-40 years old): Fluarix™

Schedule: one IM injection of influenza vaccine at day 0, blood sample collection at day 0, day 21, and day 180 post vaccination. The standard trivalent split influenza vaccine—Fluarix™ used in this study is the same as that used in Example X.

The vaccine formulations are described in Tables 31-32.

XI.2.1. Primary Objective: Immunogenicity

To identify an optimal formulation (combination of one o/w emulsion dosage and one MPL dosage) of the adjuvanted influenza vaccine compared to Fluarix, given intramuscularly in subjects aged 65 years old, based on immunogenicity (GMT) for the three vaccine strains 21 days following vaccination. The variables are as in example X.2.1 and for the subjects aged 65+(HI antibody titer and GMTs of HI antibody titers at day 21).

X.2.2. Secondary Objectives are to Evaluate the safety and reactogenicity in all subjects vaccinated with the influenza vaccines the immunogenicity (GMT, SCF, SCR and SPR) of the influenza vaccines in all subjects, 21 days following vaccination.

the persistence of HI antibodies 180 days after the first vaccination, in all subjects.

the Cell Mediated Immune (CMI) response induced by the influenza vaccines in terms of frequency of influenza-specific CD4/CD8 T lymphocytes producing at least two different cytokines (IFN-γ, IL-2, CD40L, or TNF-α), at Days 0, 21 and 180 (for a subset of subjects only).

The observed and derived variables (and definitions) are as described in Example X.

XI.3. Vaccine Composition and Administration

The adjuvanted influenza vaccine is based on the commercially available Fluarix vaccine, marketed since 1992 by GSK Bio. The candidate formulations consist of the trivalent split virion, inactivated influenza antigens composed of 3 monovalent viral antigen bulks (prepared from respectively influenza strains A/H1N1, A/H3N2 and B recommended for the 2007/2008 Northern Hemisphere, see Example X), combined with adjuvant systems based on MPL and/or an oil-in-water (o/w) emulsion.

Two families of GSK Bio proprietary adjuvant system will be tested in that trial:
- The AS03 family categorized (1/1-½-... ) by the amount of emulsion per human dose of adjuvanted vaccine;
- The AS25 family of oil-in-water emulsion supplemented with MPL and categorized (A, B, ... ) by the quantities of each component per human dose of adjuvanted vaccine.

XI.3.1. Vaccine Composition

The production of the three monobulks of split inactivated virion antigens prepared from working seeds of three influenza virus strains, type A (H1N1 and H3N2) and type B, grown individually in embryonated hens' eggs is as already described (see Example X). The clinical lots contain 15 µg haemagglutinin (HA) of each influenza virus strain per dose. The influenza antigens are adjuvanted with 3-O-desacyl-4'-monophosphoryl lipid A (MPL) and/or an oil-in-water (o/w) emulsion AS03. Eight different formulations of the AS are to be combined with the split virion influenza antigens. The method of preparation of the adjuvants is adapted from that described in Example II of WO 2006/100111, where the amount of the individual components are adapted according to the information given in Tables 31 and 32. The excipients are the following: Polysorbate 80 (Tween-80), Octoxynol 10 (Triton® X-100), α-tocopheryl hydrogen succinate, sodium chloride, magnesium chloride, disodium hydrogen phosphate, potassium dihydrogen phosphate, potassium chloride, and water for injection. The different formulations of the adjuvanted influenza vaccine are preservative-free formulations. However, they contain trace amounts of thiomersal (<1.25 µg of Hg per dose) from the early stages of the drug substance manufacturing process where it is added to reduce bioburden.

The adjuvanted influenza vaccine is a sterile whitish emulsion of adjuvanted, split purified influenza virus for injection. It is presented as a 2 component vaccine consisting of a type I glass vial containing the antigen (suspension) and a pre-filled type I glass syringe (PFS) containing the adjuvant (emulsion). The vaccine is stored at 2 to 8° C. At the time of injection, the content of the antigen pre-filled syringe is injected into the vial that contains the concentrated trivalent inactivated split vrion antigens. After mixing the content is withdrawn into the syringe and the needle is replaced by an intramuscular needle. One dose of the reconstituted adjuvanted influenza candidate vaccine corresponds to 0.7 mL (Tables 33 and 34).

TABLE 33

Vaccine formulations

| Adjuvant System | Volume of o/w emulsion | Amount of MPL | Antigens Flu NH 2007/2008 |
|---|---|---|---|
| AS25A (AS25_1_1) | 250 µl | 25 µg | A/Solomon Islands/3/2006 |
| AS25B (AS25_1_2) | 125 µl | 25 µg | (H1N1) IVR-145 A/Wisconsin/67/2005 |
| AS25C (AS25_1_4) | 62.5 µl | 25 µg | (H3N2) NYMCX-161B B/Malaysia/2506/2004 |
| AS03 1/1 (AS03_1_1) | 250 µl | 0 µg | |
| AS03 1/2 (AS03_1_2) | 125 µl | 0 µg | |
| AS03 1/4 (AS03_1_4) | 62.5 µl | 0 µg | |
| AS25E - AS50 1/2 (AS50_1_2) | 125 µl | 50 µg | |
| AS25F - AS50 1/4 (AS50_1_4) | 62.5 µl | 50 µg | |

TABLE 34

Composition of the adjuvanted influenza vaccines

| Component | Quantity per dose (0.7 mL) |
|---|---|
| ACTIVE INGREDIENTS | |

Inactivated split virions

| | |
|---|---|
| H1N1 | 15 µg HA |
| H3N2 | 15 µg HA |
| B | 15 µg HA |

| ADJUVANT | AS25A | AS25B | AS25C | AS03 1/1 | AS03 1/2 | AS03 1/4 | AS25E | AS25F |
|---|---|---|---|---|---|---|---|---|
| emulsion (µL) | 250 | 125 | 62.5 | 250 | 125 | 62.5 | 125 | 62.5 |
| squalene (mg) | 10.69 | 5.34 | 2.67 | 10.69 | 5.34 | 2.67 | 5.34 | 2.67 |
| DL-α-tocopherol (mg) | 11.86 | 5.93 | 2.97 | 11.86 | 5.93 | 2.97 | 5.93 | 2.97 |
| Polysorbate 80 (Tween-80) (mg) | 4.86 | 2.43 | 1.22 | 4.86 | 2.43 | 1.22 | 2.43 | 1.22 |
| MPL | 25 µg | 25 µg | 25 µg | / | / | / | 50 µg | 50 µg |

| EXCEPIENTS (TARGET VALUES) | |
|---|---|
| Polysorbate 80 (Tween-80) | 0.40 mg |
| Octoxynol 10 (Triton ® X-100) | 0.05 mg |
| α-Tocopheryl hydrogen succinate | 0.05 mg |
| Sodium chloride | 3.92 mg |
| Magnesium chloride | 0.03 mg |
| Disodium phosphate | 0.54 mg |
| Potassium dihydrogen phosphate | 0.16 mg |
| Potassium chloride | 0.10 mg |
| Water for injection | ad 0.70 mL |

XI.3.2. Vaccine Preparation

The AS03 formulations are prepared by diluting the phosphate buffer (Na/K 191.4 mM $PO_4^{3-}$, 2.74 mM NaCl, 54 mM KCL, pH 6.8, ad 9.57 mM $PO_4^{3-}$) with Water for Injection (stirring for 15-45 min at RT until homogeneity). The appropriate amount of oil-in-water emulsion bulk is then added. The mixture is stirred for 15-45 minutes at room temperature, and the pH is measured. The mixture is then sterilised by filtration through a 0.2 µm membrane. Sterile inert gas (nitrogen) flushing is performed to produce inert head space in the filled containers during minimum 1 minute. The sterile AS03 adjuvant is stored at +2-8° C. until aseptical filling into 1.25-ml sterile Type I (Ph. Eur.) glass syringes. Each syringe contains a volume overage of 60 µl+60 µl overfill).

The AS25 formulations are prepared by diluting the phosphate buffer with Water for Injection (stirring for 15-45 min at RT until homogeneity). The appropriate amounts of SB62 bulk and MPL liquid bulk are then added. The rest of the procedure is as described above.

One dose of the reconstituted adjuvanted influenza vaccine corresponds to 0.7 mL. The final HA concentration is 21.4 µg of each monovalent bulk per mL of trivalent final bulk. The final bulk of antigens (Ags) is filled in 3-ml glass vials, one dose of trivalent flu antigens corresponding to a volume of 0.42 ml. The adjuvant final bulk is filled in 1.25-ml glass PFS, one dose corresponding to a volume of 0.28 ml. The final vaccine dose after reconstitution will be of 0.7 ml.

To allow injection of the nominal volume (0.7 mL) after reconstitution, each Ags vial is filled with a target volume of 0.51 ml and each AS syringe is filled with a target volume of 0.34 ml.

XI.4. Immunogenicity Results—Humoral Immune Response

XI.4.1 HI Geometric Mean Titres (GMT)

Figure 19A:
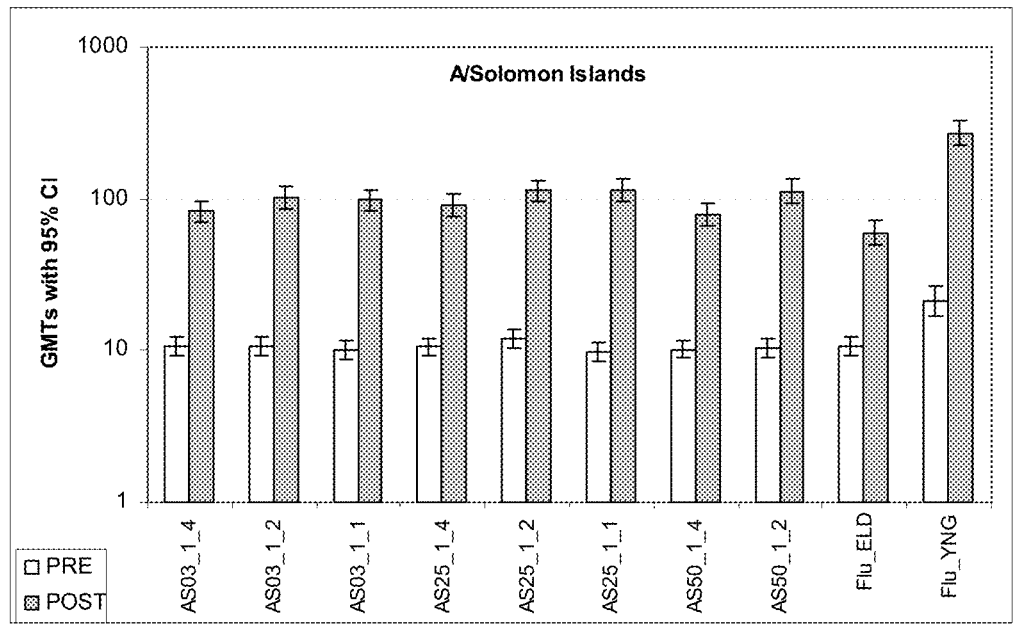
FIG. 19A: Human clinical trial (adjuvant dose range in elderly): GMTs for HI antibody titer at d0 and d21. A/Solomon Islands.
Figure 19B:
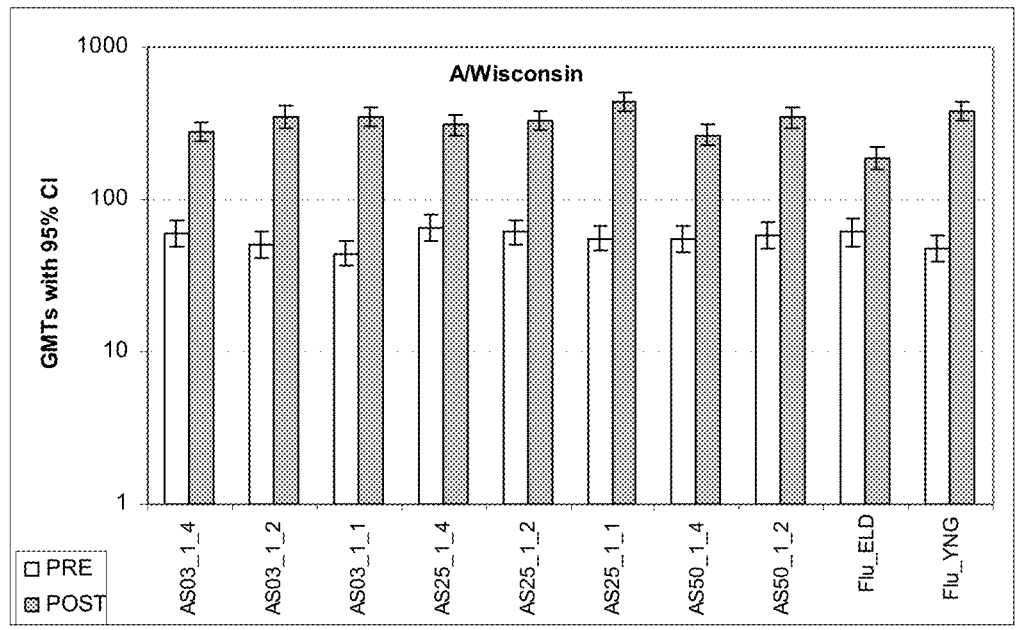
FIG. 19B: Human clinical trial (adjuvant dose range in elderly): GMTs for HI antibody titer at d0 and d21. A/Wisconsin.
Figure 19C:
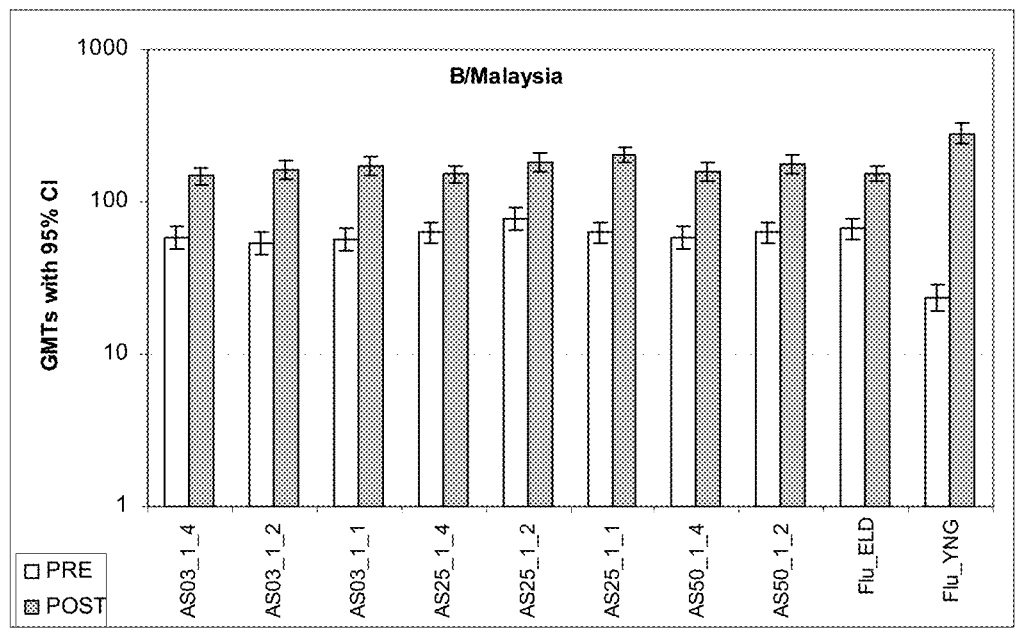
FIG. 19C: Human clinical trial (adjuvant dose range in elderly): GMTs for HI antibody titer at d0 and d21. B/Malaysia.

The GMT's for HI antibodies with 95% CI are shown in Table 35 and FIGS. 19A to C.

TABLE 35

Seropositivity rates and GMTs for HI antibody titer at days 0 and 21 (ATP cohort for immunogenicity HI)

| Antibody | Group | Timing | N | n | >=10 1/DIL % | 95% CI LL | 95% CI UL | GMT value | 95% CI LL | 95% CI UL | Min | Max |
|---|---|---|---|---|---|---|---|---|---|---|---|---|
| A/Solomon Islands | AS03_1_4 | PRE | 191 | 97 | 50.8 | 43.5 | 58.1 | 10.6 | 9.3 | 12.2 | <10.0 | 453.0 |
| | | PI(D21) | 191 | 184 | 96.3 | 92.6 | 98.5 | 82.3 | 69.7 | 97.1 | <10.0 | 2560.0 |
| | AS03_1_2 | PRE | 191 | 91 | 47.6 | 40.4 | 55.0 | 10.8 | 9.4 | 12.4 | <10.0 | 226.0 |
| | | PI(D21) | 192 | 188 | 97.9 | 94.8 | 99.4 | 102.2 | 87.0 | 119.9 | <10.0 | 1280.0 |
| | AS03_1_1 | PRE | 189 | 86 | 45.5 | 38.3 | 52.9 | 10.1 | 8.8 | 11.5 | <10.0 | 320.0 |
| | | PI(D21) | 189 | 185 | 97.9 | 94.7 | 99.4 | 98.2 | 84.3 | 114.3 | <10.0 | 3620.0 |
| | AS25_1_4 | PRE | 194 | 97 | 50.0 | 42.8 | 57.2 | 10.6 | 9.3 | 12.1 | <10.0 | 226.0 |
| | | PI(D21) | 194 | 189 | 97.4 | 94.1 | 99.2 | 91.7 | 76.9 | 109.3 | <10.0 | 1810.0 |
| | AS25_1_2 | PRE | 192 | 97 | 50.5 | 43.2 | 57.8 | 12.0 | 10.3 | 14.0 | <10.0 | 320.0 |
| | | PI(D21) | 192 | 190 | 99.0 | 96.3 | 99.9 | 113.2 | 96.0 | 133.6 | <10.0 | 2560.0 |
| | AS25_1_1 | PRE | 193 | 88 | 45.6 | 38.4 | 52.9 | 9.9 | 8.6 | 11.3 | <10.0 | 320.0 |
| | | PI(D21) | 193 | 188 | 97.4 | 94.1 | 99.2 | 114.4 | 97.1 | 134.8 | <10.0 | 1810.0 |
| | AS50_1_4 | PRE | 192 | 87 | 45.3 | 38.1 | 52.6 | 10.2 | 8.9 | 11.7 | <10.0 | 160.0 |
| | | PI(D21) | 192 | 183 | 95.3 | 91.3 | 97.8 | 78.5 | 65.9 | 93.5 | <10.0 | 1280.0 |
| | AS50_1_2 | PRE | 189 | 91 | 48.1 | 40.8 | 55.5 | 10.3 | 9.0 | 11.9 | <10.0 | 640.0 |
| | | PI(D21) | 189 | 183 | 96.8 | 93.2 | 98.8 | 111.8 | 93.3 | 134.0 | <10.0 | 1280.0 |
| | Flu_ELD | PRE | 187 | 88 | 47.1 | 39.7 | 54.5 | 10.7 | 9.2 | 12.4 | <10.0 | 2560.0 |
| | | PI(D21) | 188 | 177 | 94.1 | 89.8 | 97.0 | 59.6 | 49.6 | 71.7 | <10.0 | 3620.0 |
| | Flu_YNG | PRE | 197 | 122 | 61.9 | 54.8 | 68.7 | 21.3 | 17.1 | 26.5 | <10.0 | 1810.0 |
| | | PI(D21) | 197 | 195 | 99.0 | 96.4 | 99.9 | 271.6 | 224.6 | 328.4 | <10.0 | 5120.0 |
| A/Wisconsin | AS03_1_4 | PRE | 191 | 176 | 92.1 | 87.4 | 95.5 | 59.9 | 49.5 | 72.4 | <10.0 | 1280.0 |
| | | PI(D21) | 191 | 190 | 99.5 | 97.1 | 100 | 276.2 | 238.8 | 319.6 | <10.0 | 5120.0 |
| | AS03_1_2 | PRE | 191 | 168 | 88.0 | 82.5 | 92.2 | 51.2 | 41.9 | 62.4 | <10.0 | 905.0 |
| | | PI(D21) | 192 | 192 | 100 | 98.1 | 100 | 350.2 | 298.0 | 411.4 | 14.0 | 14480.0 |
| | AS03_1_1 | PRE | 189 | 168 | 88.9 | 83.5 | 93.0 | 44.4 | 36.5 | 54.0 | <10.0 | 2560.0 |
| | | PI(D21) | 189 | 189 | 100 | 98.1 | 100 | 351.3 | 304.8 | 404.8 | 28.0 | 5120.0 |
| | AS25_1_4 | PRE | 194 | 175 | 90.2 | 85.1 | 94.0 | 65.7 | 53.7 | 80.4 | <10.0 | 2560.0 |
| | | PI(D21) | 194 | 194 | 100 | 98.1 | 100 | 309.2 | 264.9 | 361.0 | 10.0 | 5120.0 |
| | AS25_1_2 | PRE | 192 | 174 | 90.6 | 85.6 | 94.3 | 61.1 | 50.6 | 73.8 | <10.0 | 1280.0 |
| | | PI(D21) | 192 | 192 | 100 | 98.1 | 100 | 331.1 | 289.6 | 378.6 | 40.0 | 5120.0 |
| | AS25_1_1 | PRE | 193 | 173 | 89.6 | 84.4 | 93.6 | 55.8 | 46.2 | 67.4 | <10.0 | 1280.0 |
| | | PI(D21) | 193 | 192 | 99.5 | 97.1 | 100 | 438.1 | 379.7 | 505.4 | <10.0 | 3620.0 |
| | AS50_1_4 | PRE | 192 | 168 | 87.5 | 82.0 | 91.8 | 54.6 | 44.5 | 67.0 | <10.0 | 2560.0 |
| | | PI(D21) | 192 | 191 | 99.5 | 97.1 | 100 | 263.3 | 225.3 | 307.7 | <10.0 | 5120.0 |
| | AS50_1_2 | PRE | 189 | 166 | 87.8 | 82.3 | 92.1 | 57.8 | 47.1 | 70.9 | <10.0 | 2560.0 |
| | | PI(D21) | 189 | 188 | 99.5 | 97.1 | 100 | 347.5 | 296.4 | 407.3 | <10.0 | 2560.0 |
| | Flu_ELD | PRE | 187 | 169 | 90.4 | 85.2 | 94.2 | 61.0 | 49.8 | 74.7 | <10.0 | 1810.0 |
| | | PI(D21) | 188 | 188 | 100 | 98.1 | 100 | 186.7 | 158.0 | 220.7 | 10.0 | 2560.0 |
| | Flu_YNG | PRE | 197 | 166 | 84.3 | 78.4 | 89.1 | 47.8 | 39.2 | 58.4 | <10.0 | 1280.0 |
| | | PI(D21) | 197 | 197 | 100 | 98.1 | 100 | 380.2 | 331.6 | 435.9 | 40.0 | 5120.0 |
| B/Malaysia | AS03_1_4 | PRE | 191 | 178 | 93.2 | 88.6 | 96.3 | 58.6 | 49.8 | 68.9 | <10.0 | 2560.0 |
| | | PI(D21) | 191 | 190 | 99.5 | 97.1 | 100 | 147.1 | 129.1 | 167.6 | <10.0 | 2560.0 |
| | AS03_1_2 | PRE | 191 | 180 | 94.2 | 89.9 | 97.1 | 53.7 | 45.7 | 63.2 | <10.0 | 640.0 |
| | | PI(D21) | 192 | 192 | 100 | 98.1 | 100 | 163.1 | 142.5 | 186.6 | 14.0 | 2560.0 |

TABLE 35-continued

Seropositivity rates and GMTs for HI antibody titer at days 0 and 21 (ATP cohort for immunogenicity HI)

| Antibody | Group | Timing | N | n | % | >=10 1/DIL 95% CI LL | >=10 1/DIL 95% CI UL | GMT value | GMT 95% CI LL | GMT 95% CI UL | Min | Max |
|---|---|---|---|---|---|---|---|---|---|---|---|---|
| | AS03_1_1 | PRE | 189 | 177 | 93.7 | 89.2 | 96.7 | 57.0 | 48.2 | 67.5 | <10.0 | 2560.0 |
| | | PI(D21) | 189 | 189 | 100 | 98.1 | 100 | 172.1 | 149.9 | 197.6 | 14.0 | 2560.0 |
| | AS25_1_4 | PRE | 194 | 183 | 94.3 | 90.1 | 97.1 | 62.6 | 53.3 | 73.4 | <10.0 | 1810.0 |
| | | PI(D21) | 194 | 194 | 100 | 98.1 | 100 | 152.4 | 134.4 | 172.7 | 20.0 | 2560.0 |
| | AS25_1_2 | PRE | 192 | 184 | 95.8 | 92.0 | 98.2 | 77.8 | 66.0 | 91.7 | <10.0 | 1280.0 |
| | | PI(D21) | 192 | 192 | 100 | 98.1 | 100 | 181.4 | 158.9 | 207.1 | 10.0 | 2560.0 |
| | AS25_1_1 | PRE | 193 | 186 | 96.4 | 92.7 | 98.5 | 62.9 | 53.9 | 73.4 | <10.0 | 2560.0 |
| | | PI(D21) | 193 | 193 | 100 | 98.1 | 100 | 202.0 | 179.7 | 227.1 | 20.0 | 3620.0 |
| | AS50_1_4 | PRE | 192 | 179 | 93.2 | 88.7 | 96.3 | 58.2 | 49.0 | 69.1 | <10.0 | 1280.0 |
| | | PI(D21) | 192 | 192 | 100 | 98.1 | 100 | 155.7 | 134.8 | 179.8 | 20.0 | 5120.0 |
| | AS50_1_2 | PRE | 189 | 176 | 93.1 | 88.5 | 96.3 | 62.6 | 53.0 | 74.0 | <10.0 | 1280.0 |
| | | PI(D21) | 189 | 189 | 100 | 98.1 | 100 | 174.6 | 152.0 | 200.7 | 10.0 | 2560.0 |
| | Flu_ELD | PRE | 187 | 179 | 95.7 | 91.7 | 98.1 | 66.5 | 56.5 | 78.3 | <10.0 | 905.0 |
| | | PI(D21) | 188 | 188 | 100 | 98.1 | 100 | 153.0 | 135.2 | 173.1 | 20.0 | 1280.0 |
| | Flu_YNG | PRE | 197 | 135 | 68.5 | 61.5 | 74.9 | 23.4 | 19.1 | 28.7 | <10.0 | 1280.0 |
| | | PI(D21) | 197 | 197 | 100 | 98.1 | 100 | 281.9 | 241.7 | 328.7 | 20.0 | 5120.0 |

Flu_ELD = Fluarix elderly (aged >= 65 years);
Flu_YNG = Fluarix young (aged 18-40 years)
GMT = geometric mean antibody titre calculated on all subjects
N = number of subjects with available results
n/% = number/percentage of subjects with titre within the specified range
95% CI = 95% confidence interval;
LL = Lower Limit,
UL = Upper Limit;
MIN/MAX = Minimum/Maximum
PRE = Pre-vaccination dose 1 (Day 0);
PI(D21) = Post-vaccination dose 1 (Day 21)

Intermediate Conclusion

The influenza vaccine adjuvanted with one full dose of AS03 and 25 µg of MPL (AS25_1_1) elicits a statistically significantly better HI response for the B/Malaysia strain compared to Fluarix in subjects aged ≥65 years. For the other two strains all adjuvanted vaccines, except the ones with one-quarter of a dose of AS03, did well compared to Fluarix in subjects aged ≥65 years in this study.

XI.4.2 Seroconversion Factors of Anti-HI Antibody Titres, Seroprotection Rates and Seroconversion Rates (Correlates for Protection as Established for Influenza Vaccine in Humans)

Figure 20A:
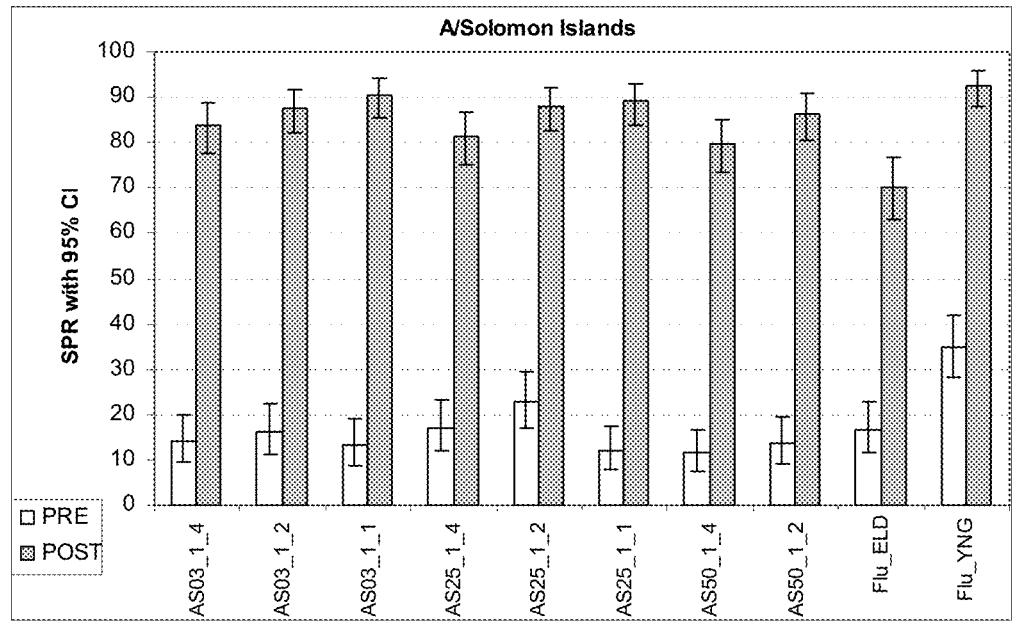
FIG. 20A: Human clinical trial (adjuvant dose range in elderly): Seroprotection rates (SPR) for HI antibody titer with 95% confidence interval at days 0 and 21. A/Solomon Islands.
Figure 20B:
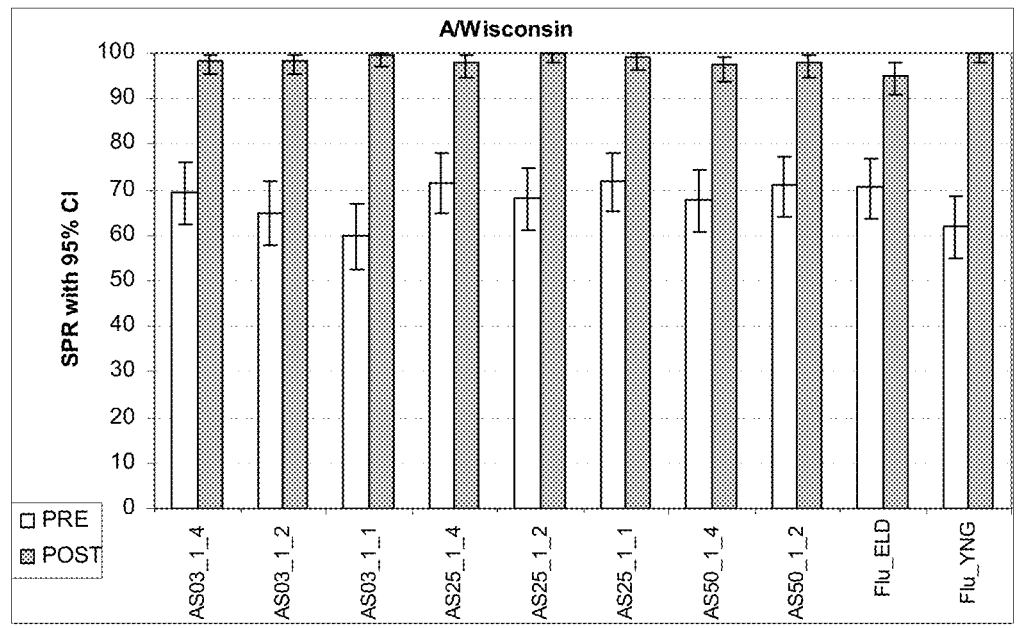
FIG. 20B: Human clinical trial (adjuvant dose range in elderly): Seroprotection rates (SPR) for HI antibody titer with 95% confidence interval at days 0 and 21. A/Wisconsin.
Figure 20C:
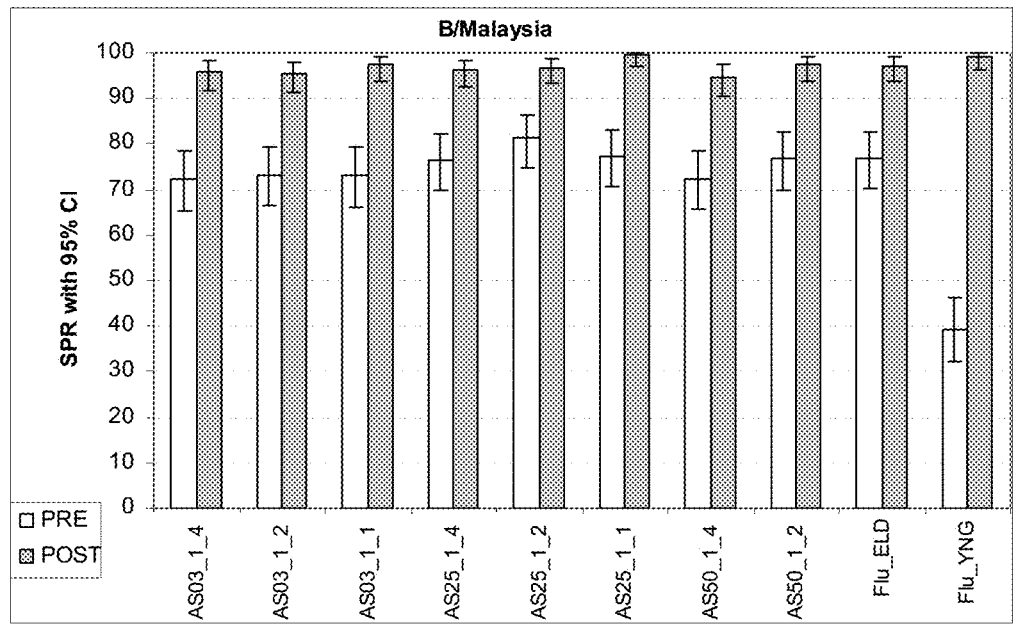
FIG. 20C: Human clinical trial (adjuvant dose range in elderly): Seroprotection rates (SPR) for HI antibody titer with 95% confidence interval at days 0 and 21. B/Malaysia.
Figure 21:
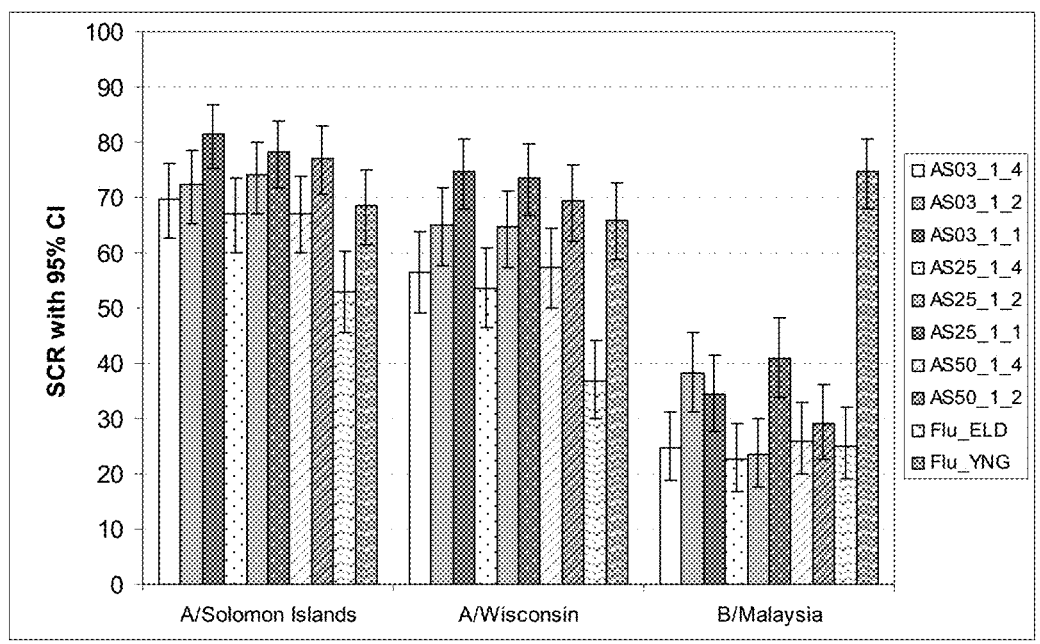
FIG. 21: Human clinical trial (adjuvant dose range in elderly): Seroconversion rate (SCR) for HI antibody titer at PI(DAY21).
Figure 22:
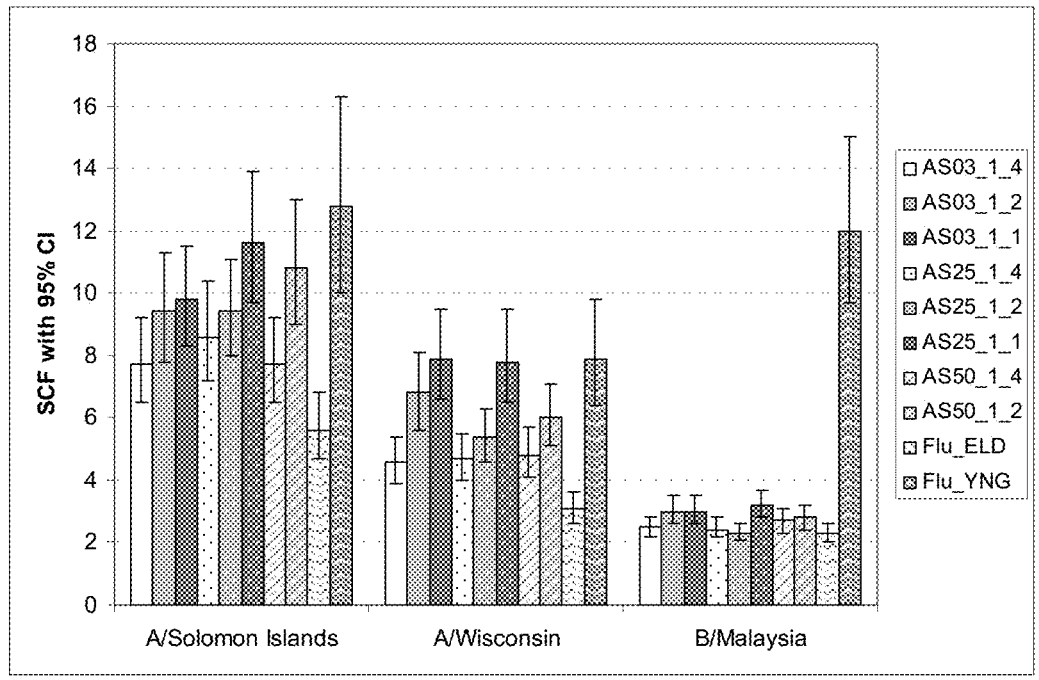
FIG. 22: Human clinical trial (adjuvant dose range in elderly): SCF for HI antibody titer with 95% CI at day 21 (ATP cohort for immunogenicity HI).

Results are presented in Tables 36-FIGS. 20A to C (one per strain) for seroprotection rates, Table 37-FIG. 21 for seroconversion rates, and Table 38-FIG. 22 for seroconversion factors.

TABLE 36

SPR for HI antibody titer at D 0 and D 21 (ATP cohort for HI)

| Vaccine strain | Group | Timing | N | n | % | SPR 95% CI LL | SPR 95% CI UL |
|---|---|---|---|---|---|---|---|
| A/Solomon Islands | AS03_1_4 | PRE | 191 | 27 | 14.1 | 9.5 | 19.9 |
| | | PI(D21) | 191 | 160 | 83.8 | 77.8 | 88.7 |
| | AS03_1_2 | PRE | 191 | 31 | 16.2 | 11.3 | 22.2 |
| | | PI(D21) | 192 | 168 | 87.5 | 82.0 | 91.8 |
| | AS03_1_1 | PRE | 189 | 25 | 13.2 | 8.7 | 18.9 |
| | | PI(D21) | 189 | 171 | 90.5 | 85.4 | 94.3 |
| | AS25_1_4 | PRE | 194 | 33 | 17.0 | 12.0 | 23.1 |
| | | PI(D21) | 194 | 158 | 81.4 | 75.2 | 86.7 |
| | AS25_1_2 | PRE | 192 | 44 | 22.9 | 17.2 | 29.5 |
| | | PI(D21) | 192 | 169 | 88.0 | 82.6 | 92.3 |

TABLE 36-continued

SPR for HI antibody titer at D 0 and D 21 (ATP cohort for HI)

| Vaccine strain | Group | Timing | N | n | % | 95% CI LL | 95% CI UL |
|---|---|---|---|---|---|---|---|
| | AS25_1_1 | PRE | 193 | 23 | 11.9 | 7.7 | 17.3 |
| | | PI(D21) | 193 | 172 | 89.1 | 83.8 | 93.1 |
| | AS50_1_4 | PRE | 192 | 22 | 11.5 | 7.3 | 16.8 |
| | | PI(D21) | 192 | 153 | 79.7 | 73.3 | 85.1 |
| | AS50_1_2 | PRE | 189 | 26 | 13.8 | 9.2 | 19.5 |
| | | PI(D21) | 189 | 163 | 86.2 | 80.5 | 90.8 |
| | Flu_ELD | PRE | 187 | 31 | 16.6 | 11.6 | 22.7 |
| | | PI(D21) | 188 | 132 | 70.2 | 63.1 | 76.6 |
| | Flu_YNG | PRE | 197 | 69 | 35.0 | 28.4 | 42.1 |
| | | PI(D21) | 197 | 182 | 92.4 | 87.8 | 95.7 |
| A/Wisconsin | AS03_1_4 | PRE | 191 | 133 | 69.6 | 62.6 | 76.1 |
| | | PI(D21) | 191 | 188 | 98.4 | 95.5 | 99.7 |
| | AS03_1_2 | PRE | 191 | 124 | 64.9 | 57.7 | 71.7 |
| | | PI(D21) | 192 | 189 | 98.4 | 95.5 | 99.7 |
| | AS03_1_1 | PRE | 189 | 113 | 59.8 | 52.4 | 66.8 |
| | | PI(D21) | 189 | 188 | 99.5 | 97.1 | 100 |
| | AS25_1_4 | PRE | 194 | 139 | 71.6 | 64.8 | 77.9 |
| | | PI(D21) | 194 | 190 | 97.9 | 94.8 | 99.4 |
| | AS25_1_2 | PRE | 192 | 131 | 68.2 | 61.1 | 74.7 |
| | | PI(D21) | 192 | 192 | 100 | 98.1 | 100 |
| | AS25_1_1 | PRE | 193 | 139 | 72.0 | 65.1 | 78.2 |
| | | PI(D21) | 193 | 191 | 99.0 | 96.3 | 99.9 |
| | AS50_1_4 | PRE | 192 | 130 | 67.7 | 60.6 | 74.3 |
| | | PI(D21) | 192 | 187 | 97.4 | 94.0 | 99.1 |
| | AS50_1_2 | PRE | 189 | 134 | 70.9 | 63.9 | 77.3 |
| | | PI(D21) | 189 | 185 | 97.9 | 94.7 | 99.4 |
| | Flu_ELD | PRE | 187 | 132 | 70.6 | 63.5 | 77.0 |
| | | PI(D21) | 188 | 179 | 95.2 | 91.1 | 97.8 |
| | Flu_YNG | PRE | 197 | 122 | 61.9 | 54.8 | 68.7 |
| | | PI(D21) | 197 | 197 | 100 | 98.1 | 100 |
| B/Malaysia | AS03_1_4 | PRE | 191 | 138 | 72.3 | 65.3 | 78.5 |
| | | PI(D21) | 191 | 183 | 95.8 | 91.9 | 98.2 |
| | AS03_1_2 | PRE | 191 | 140 | 73.3 | 66.4 | 79.4 |
| | | PI(D21) | 192 | 183 | 95.3 | 91.3 | 97.8 |
| | AS03_1_1 | PRE | 189 | 138 | 73.0 | 66.1 | 79.2 |
| | | PI(D21) | 189 | 184 | 97.4 | 93.9 | 99.1 |
| | AS25_1_4 | PRE | 194 | 148 | 76.3 | 69.7 | 82.1 |
| | | PI(D21) | 194 | 187 | 96.4 | 92.7 | 98.5 |
| | AS25_1_2 | PRE | 192 | 156 | 81.3 | 75.0 | 86.5 |
| | | PI(D21) | 192 | 186 | 96.9 | 93.3 | 98.8 |
| | AS25_1_1 | PRE | 193 | 149 | 77.2 | 70.6 | 82.9 |
| | | PI(D21) | 193 | 192 | 99.5 | 97.1 | 100 |
| | AS50_1_4 | PRE | 192 | 139 | 72.4 | 65.5 | 78.6 |
| | | PI(D21) | 192 | 182 | 94.8 | 90.6 | 97.5 |
| | AS50_1_2 | PRE | 189 | 145 | 76.7 | 70.0 | 82.5 |
| | | PI(D21) | 189 | 184 | 97.4 | 93.9 | 99.1 |
| | Flu_ELD | PRE | 187 | 144 | 77.0 | 70.3 | 82.8 |
| | | PI(D21) | 188 | 183 | 97.3 | 93.9 | 99.1 |
| | Flu_YNG | PRE | 197 | 77 | 39.1 | 32.2 | 46.3 |
| | | PI(D21) | 197 | 195 | 99.0 | 96.4 | 99.9 |

TABLE 37

SCR for HI antibody titer at day 21 (ATP cohort for immunogenicity HI)

| Vaccine strain | Group | N | n | % | 95% CI LL | 95% CI UL |
|---|---|---|---|---|---|---|
| A/Solomon Islands | AS03_1_4 | 191 | 133 | 69.6 | 62.6 | 76.1 |
| | AS03_1_2 | 191 | 138 | 72.3 | 65.3 | 78.5 |
| | AS03_1_1 | 189 | 154 | 81.5 | 75.2 | 86.7 |
| | AS25_1_4 | 194 | 130 | 67.0 | 59.9 | 73.6 |
| | AS25_1_2 | 192 | 142 | 74.0 | 67.1 | 80.0 |
| | AS25_1_1 | 193 | 151 | 78.2 | 71.7 | 83.8 |
| | AS50_1_4 | 192 | 129 | 67.2 | 60.1 | 73.8 |
| | AS50_1_2 | 189 | 146 | 77.2 | 70.6 | 83.0 |
| | Flu_ELD | 187 | 99 | 52.9 | 45.5 | 60.3 |
| | Flu_YNG | 197 | 135 | 68.5 | 61.5 | 74.9 |
| A/Wisconsin | AS03_1_4 | 191 | 108 | 56.5 | 49.2 | 63.7 |
| | AS03_1_2 | 191 | 124 | 64.9 | 57.7 | 71.7 |
| | AS03_1_1 | 189 | 141 | 74.6 | 67.8 | 80.6 |
| | AS25_1_4 | 194 | 104 | 53.6 | 46.3 | 60.8 |

TABLE 37-continued

SCR for HI antibody titer at day 21
(ATP cohort for immunogenicity HI)

| Vaccine strain | Group | N | n | % | 95% CI LL | 95% CI UL |
|---|---|---|---|---|---|---|
| | AS25_1_2 | 192 | 124 | 64.6 | 57.4 | 71.3 |
| | AS25_1_1 | 193 | 142 | 73.6 | 66.8 | 79.6 |
| | AS50_1_4 | 192 | 110 | 57.3 | 50.0 | 64.4 |
| | AS50_1_2 | 189 | 131 | 69.3 | 62.2 | 75.8 |
| | Flu_ELD | 187 | 69 | 36.9 | 30.0 | 44.2 |
| | Flu_YNG | 197 | 130 | 66.0 | 58.9 | 72.6 |
| B/Malaysia | AS03_1_4 | 191 | 47 | 24.6 | 18.7 | 31.3 |
| | AS03_1_2 | 191 | 73 | 38.2 | 31.3 | 45.5 |
| | AS03_1_1 | 189 | 65 | 34.4 | 27.6 | 41.6 |
| | AS25_1_4 | 194 | 44 | 22.7 | 17.0 | 29.2 |
| | AS25_1_2 | 192 | 45 | 23.4 | 17.6 | 30.1 |
| | AS25_1_1 | 193 | 79 | 40.9 | 33.9 | 48.2 |
| | AS50_1_4 | 192 | 50 | 26.0 | 20.0 | 32.9 |
| | AS50_1_2 | 189 | 55 | 29.1 | 22.7 | 36.1 |
| | Flu_ELD | 187 | 47 | 25.1 | 19.1 | 32.0 |
| | Flu_YNG | 197 | 147 | 74.6 | 67.9 | 80.5 |

Seroconversion defined as:
For initially seronegative subjects, antibody titre >= 40 1/DIL after vaccination
For initially seropositive subjects, antibody titre after vaccination >= 4 fold the pre-vaccination antibody titre
N = Number of subjects with pre- and post-vaccination results available
n/% = Number/percentage of seroconverted subjects
95% CI = 95% confidence interval,
LL = Lower Limit,
UL = Upper Limit

TABLE 38

SCF for HI antibody titer at day 21
(ATP cohort for immunogenicity HI)

| Vaccine strain | Group | N | Value | 95% CI LL | 95% CI UL |
|---|---|---|---|---|---|
| A/Solomon Islands | AS03_1_4 | 191 | 7.7 | 6.5 | 9.2 |
| | AS03_1_2 | 191 | 9.4 | 7.8 | 11.3 |
| | AS03_1_1 | 189 | 9.8 | 8.3 | 11.5 |
| | AS25_1_4 | 194 | 8.6 | 7.2 | 10.4 |
| | AS25_1_2 | 192 | 9.4 | 8.0 | 11.1 |
| | AS25_1_1 | 193 | 11.6 | 9.7 | 13.9 |
| | AS50_1_4 | 192 | 7.7 | 6.5 | 9.2 |
| | AS50_1_2 | 189 | 10.8 | 9.0 | 13.0 |
| | Flu_ELD | 187 | 5.6 | 4.7 | 6.8 |
| | Flu_YNG | 197 | 12.8 | 10.0 | 16.3 |
| A/Wisconsin | AS03_1_4 | 191 | 4.6 | 3.9 | 5.4 |
| | AS03_1_2 | 191 | 6.8 | 5.6 | 8.1 |
| | AS03_1_1 | 189 | 7.9 | 6.6 | 9.5 |
| | AS25_1_4 | 194 | 4.7 | 4.0 | 5.5 |
| | AS25_1_2 | 192 | 5.4 | 4.6 | 6.3 |
| | AS25_1_1 | 193 | 7.8 | 6.5 | 9.5 |
| | AS50_1_4 | 192 | 4.8 | 4.1 | 5.7 |
| | AS50_1_2 | 189 | 6.0 | 5.1 | 7.1 |
| | Flu_ELD | 187 | 3.1 | 2.6 | 3.6 |
| | Flu_YNG | 197 | 7.9 | 6.4 | 9.8 |
| B/Malaysia | AS03_1_4 | 191 | 2.5 | 2.2 | 2.8 |
| | AS03_1_2 | 191 | 3.0 | 2.6 | 3.5 |
| | AS03_1_1 | 189 | 3.0 | 2.6 | 3.5 |
| | AS25_1_4 | 194 | 2.4 | 2.2 | 2.8 |
| | AS25_1_2 | 192 | 2.3 | 2.1 | 2.6 |
| | AS25_1_1 | 193 | 3.2 | 2.8 | 3.7 |
| | AS50_1_4 | 192 | 2.7 | 2.3 | 3.1 |
| | AS50_1_2 | 189 | 2.8 | 2.4 | 3.2 |
| | Flu_ELD | 187 | 2.3 | 2.0 | 2.6 |
| | Flu_YNG | 197 | 12.0 | 9.7 | 15.0 |

N = Number of subjects with pre- and post-vaccination results available
SCF = Seroconversion Factor or geometric mean ratio (mean[log10(POST/PRE)])
95% CI = 95% confidence interval, LL = Lower Limit, UL = Upper Limit
Data source = Appendix table IIIA Intermediate Conclusion for the Humoral Immune Response A clear dose effect of the AS03 (oil-in-water emulsion) is visible in the HI data. The GMTs were statistically significantly higher in the adjuvanted influenza vaccine groups compared to the Flu_ELD group for the A/Solomon Islands strain (except for AS03_1_4 and AS50_1_4) and A/Wisconsin strain. For the B/Malaysia strain, the GMTs were statistically significantly higher in the AS25_1_1 group compared to the Flu_ELD group. For the H3N2 strain (A/Wisconsin), the humoral response is increased to the level seen in young adults for all adjuvanted influenza vaccine groups, except in the groups where a ¼ dose of the emulsion was used.

The SCRs were statistically significantly higher in the adjuvanted influenza vaccine groups compared to the Flu_ELD group for the A/Solomon Islands strain (except for AS25_1_4 and AS50_1_4) and the A/Wisconsin strain. For the B/Malaysia strain, the SCRs were statistically significantly higher in the AS25_1_1 group compared to the Flu_ELD group.

XI.5. Analysis of Cell Mediated Immune Response

Figure 23:
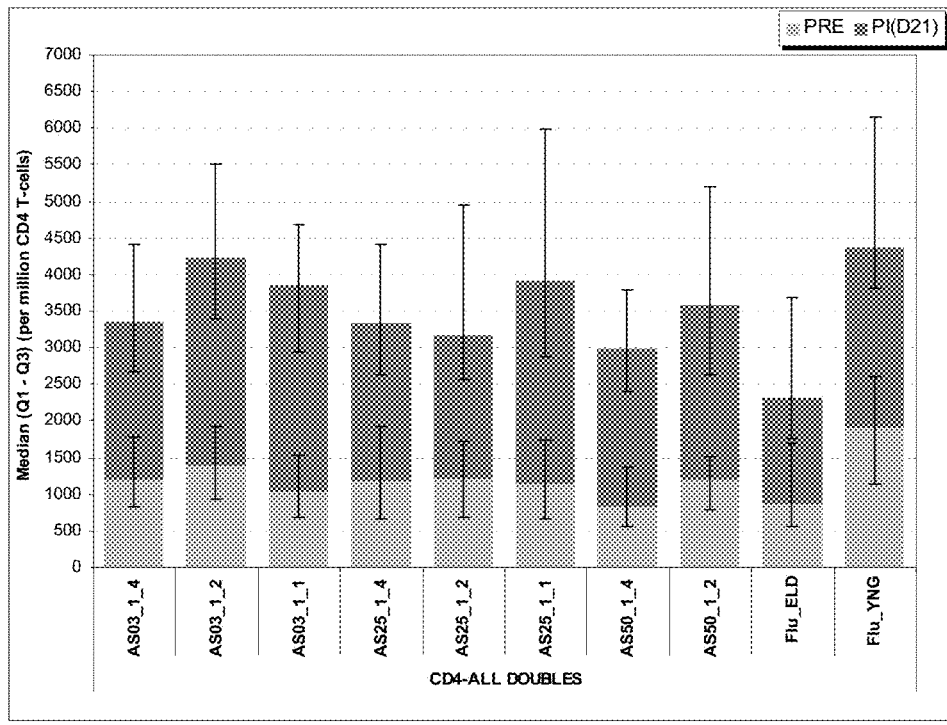
FIG. 23: Human clinical trial (adjuvant dose range in elderly): Cytokine-positive CD4 T-cells for pooled strains at D0 and D21 (ATP cohort for CMI).

The frequencies of influenza specific CD4 T-cells producing at least two cytokines (all doubles) at day 0 and day 21 are presented in Table 39 and FIG. 23 for cells re-stimulated with pooled vaccine strains.

TABLE 39

Frequency cytokine-positive CD4 T-cells (per million CD4 T-cells) for pooled strains at days 0 and 21 (ATP cohort for immunogenicity CMI)

| Test description | Group | Timing | N | Nmiss | GM | SD | Min | Q1 | Median | Q3 | Max |
|---|---|---|---|---|---|---|---|---|---|---|---|
| CD4-ALL DOUBLES | AS03_1_4 | PRE | 42 | 1 | 1013.57 | 679.94 | 1.00 | 819.00 | 1202.00 | 1790.00 | 2841.00 |
| | | PI(D21) | 43 | 0 | 2038.17 | 1508.79 | 422.00 | 1479.00 | 2156.00 | 3215.00 | 6834.00 |
| | AS03_1_2 | PRE | 38 | 1 | 1085.68 | 912.10 | 1.00 | 939.00 | 1382.50 | 1921.00 | 3502.00 |
| | | PI(D21) | 39 | 0 | 2780.75 | 1529.68 | 426.00 | 2023.00 | 2851.00 | 4126.00 | 8108.00 |
| | AS03_1_1 | PRE | 48 | 1 | 870.96 | 1342.41 | 1.00 | 685.00 | 1035.50 | 1534.50 | 6956.00 |
| | | PI(D21) | 49 | 0 | 2563.84 | 1840.16 | 280.00 | 1907.00 | 2826.00 | 3636.00 | 8830.00 |

TABLE 39-continued

Frequency cytokine-positive CD4 T-cells (per million CD4 T-cells) for pooled strains at days 0 and 21 (ATP cohort for immunogenicity CMI)

| Test description | Group | Timing | N | Nmiss | GM | SD | Min | Q1 | Median | Q3 | Max |
|---|---|---|---|---|---|---|---|---|---|---|---|
| | AS25_1_4 | PRE | 47 | 0 | 1089.72 | 853.67 | 139.00 | 664.00 | 1177.00 | 1933.00 | 3321.00 |
| | | PI(D21) | 47 | 0 | 2186.84 | 1776.15 | 506.00 | 1447.00 | 2155.00 | 3234.00 | 9385.00 |
| | AS25_1_2 | PRE | 41 | 2 | 1124.53 | 1071.90 | 384.00 | 674.00 | 1194.00 | 1717.00 | 4917.00 |
| | | PI(D21) | 43 | 0 | 2153.42 | 1871.41 | 348.00 | 1383.00 | 1978.00 | 3751.00 | 8426.00 |
| | AS25_1_1 | PRE | 44 | 0 | 1106.74 | 3071.01 | 140.00 | 669.00 | 1140.50 | 1731.00 | 20615.00 |
| | | PI(D21) | 44 | 0 | 2771.86 | 2784.80 | 526.00 | 1742.00 | 2773.50 | 4855.00 | 15247.00 |
| | AS50_1_4 | PRE | 41 | 2 | 867.17 | 666.69 | 77.00 | 559.00 | 835.00 | 1364.00 | 2671.00 |
| | | PI(D21) | 43 | 0 | 2067.82 | 1008.33 | 303.00 | 1560.00 | 2142.00 | 2949.00 | 5044.00 |
| | AS50_1_2 | PRE | 41 | 6 | 1067.79 | 1038.58 | 169.00 | 794.00 | 1192.00 | 1512.00 | 6122.00 |
| | | PI(D21) | 47 | 0 | 2421.78 | 6581.38 | 202.00 | 1447.00 | 2389.00 | 4010.00 | 46387.00 |
| | Flu_ELD | PRE | 42 | 3 | 960.35 | 998.67 | 189.00 | 561.00 | 863.50 | 1706.00 | 4356.00 |
| | | PI(D21) | 45 | 0 | 1509.05 | 2074.14 | 211.00 | 897.00 | 1452.00 | 2818.00 | 11117.00 |
| | Flu_YNG | PRE | 40 | 6 | 1681.05 | 1196.39 | 225.00 | 1144.00 | 1907.50 | 2611.00 | 5110.00 |
| | | PI(D21) | 46 | 0 | 2687.64 | 2151.90 | 830.00 | 1900.00 | 2459.50 | 4241.00 | 11758.00 |
| CD4-CD40L | AS03_1_4 | PRE | 42 | 1 | 967.13 | 664.97 | 1.00 | 842.00 | 1186.50 | 1742.00 | 2748.00 |
| | | PI(D21) | 43 | 0 | 1916.56 | 1502.81 | 168.00 | 1353.00 | 2102.00 | 3122.00 | 6538.00 |
| | AS03_1_2 | PRE | 38 | 1 | 1060.88 | 878.50 | 1.00 | 891.00 | 1384.00 | 1921.00 | 3398.00 |
| | | PI(D21) | 39 | 0 | 2714.74 | 1519.80 | 486.00 | 1957.00 | 2829.00 | 4076.00 | 8038.00 |
| | AS03_1_1 | PRE | 48 | 1 | 762.13 | 1329.02 | 1.00 | 645.00 | 1022.50 | 1541.00 | 6797.00 |
| | | PI(D21) | 49 | 0 | 2428.54 | 1856.48 | 210.00 | 1862.00 | 2733.00 | 3589.00 | 8809.00 |
| | AS25_1_4 | PRE | 47 | 0 | 994.17 | 865.71 | 35.00 | 579.00 | 1076.00 | 1912.00 | 3340.00 |
| | | PI(D21) | 47 | 0 | 1982.33 | 1801.26 | 73.00 | 1293.00 | 2055.00 | 3159.00 | 9312.00 |
| | AS25_1_2 | PRE | 41 | 2 | 1039.63 | 1062.10 | 116.00 | 596.00 | 1152.00 | 1715.00 | 4899.00 |
| | | PI(D21) | 43 | 0 | 1998.69 | 1842.77 | 309.00 | 1396.00 | 1946.00 | 3459.00 | 8149.00 |
| | AS25_1_1 | PRE | 44 | 0 | 1048.77 | 1485.48 | 145.00 | 674.00 | 1108.50 | 1632.50 | 8844.00 |
| | | PI(D21) | 44 | 0 | 2529.59 | 2189.87 | 102.00 | 1599.50 | 2763.00 | 4419.50 | 9999.00 |
| | AS50_1_4 | PRE | 41 | 2 | 847.56 | 663.49 | 95.00 | 549.00 | 842.00 | 1350.00 | 2588.00 |
| | | PI(D21) | 43 | 0 | 1673.39 | 1043.51 | 1.00 | 1413.00 | 2062.00 | 2880.00 | 4884.00 |
| | AS50_1_2 | PRE | 41 | 6 | 1037.41 | 982.61 | 171.00 | 799.00 | 1168.00 | 1492.00 | 5650.00 |
| | | PI(D21) | 47 | 0 | 2268.52 | 6584.73 | 117.00 | 1447.00 | 2245.00 | 3739.00 | 46410.00 |
| | Flu_ELD | PRE | 42 | 3 | 923.98 | 976.85 | 110.00 | 607.00 | 816.50 | 1597.00 | 4296.00 |
| | | PI(D21) | 45 | 0 | 1299.05 | 2034.85 | 1.00 | 896.00 | 1545.00 | 2818.00 | 10836.00 |
| | Flu_YNG | PRE | 40 | 6 | 1636.72 | 1186.79 | 233.00 | 1068.00 | 1878.50 | 2418.00 | 5088.00 |
| | | PI(D21) | 46 | 0 | 2575.50 | 2169.43 | 456.00 | 1862.00 | 2331.50 | 4178.00 | 11718.00 |
| CD4-IFNγ | AS03_1_4 | PRE | 42 | 1 | 721.19 | 483.64 | 114.00 | 475.00 | 772.00 | 1142.00 | 2052.00 |
| | | PI(D21) | 43 | 0 | 1394.52 | 1096.51 | 347.00 | 898.00 | 1305.00 | 2261.00 | 5075.00 |
| | AS03_1_2 | PRE | 38 | 1 | 712.34 | 598.18 | 1.00 | 566.00 | 936.50 | 1412.00 | 2422.00 |
| | | PI(D21) | 39 | 0 | 1894.63 | 1156.37 | 581.00 | 1297.00 | 2083.00 | 3016.00 | 6342.00 |
| | AS03_1_1 | PRE | 48 | 1 | 527.46 | 1053.96 | 1.00 | 395.00 | 544.00 | 985.50 | 6583.00 |
| | | PI(D21) | 49 | 0 | 1623.21 | 1383.09 | 104.00 | 1208.00 | 1652.00 | 2380.00 | 6983.00 |
| | AS25_1_4 | PRE | 47 | 0 | 741.88 | 643.41 | 36.00 | 430.00 | 770.00 | 1401.00 | 2602.00 |
| | | PI(D21) | 47 | 0 | 1433.90 | 1206.49 | 246.00 | 861.00 | 1374.00 | 2301.00 | 5754.00 |
| | AS25_1_2 | PRE | 41 | 2 | 670.69 | 656.68 | 218.00 | 380.00 | 596.00 | 1151.00 | 3664.00 |
| | | PI(D21) | 43 | 0 | 1279.87 | 1279.29 | 173.00 | 617.00 | 1330.00 | 2402.00 | 5385.00 |
| | AS25_1_1 | PRE | 44 | 0 | 597.78 | 2794.11 | 1.00 | 372.50 | 652.50 | 1226.00 | 18946.00 |
| | | PI(D21) | 44 | 0 | 1802.95 | 2189.25 | 258.00 | 1133.50 | 1970.00 | 3238.00 | 13164.00 |
| | AS50_1_4 | PRE | 41 | 2 | 571.79 | 448.58 | 134.00 | 335.00 | 597.00 | 945.00 | 1901.00 |
| | | PI(D21) | 43 | 0 | 1325.52 | 769.76 | 188.00 | 936.00 | 1428.00 | 1959.00 | 3841.00 |
| | AS50_1_2 | PRE | 41 | 6 | 601.27 | 513.44 | 32.00 | 485.00 | 743.00 | 1025.00 | 2283.00 |
| | | PI(D21) | 47 | 0 | 1550.79 | 6051.21 | 41.00 | 1016.00 | 1624.00 | 2710.00 | 42697.00 |
| | Flu_ELD | PRE | 42 | 3 | 584.91 | 588.62 | 77.00 | 396.00 | 598.00 | 955.00 | 2680.00 |
| | | PI(D21) | 45 | 0 | 980.97 | 1396.79 | 137.00 | 614.00 | 876.00 | 1662.00 | 6633.00 |
| | Flu_YNG | PRE | 40 | 6 | 1156.67 | 945.24 | 126.00 | 731.50 | 1248.00 | 2152.50 | 3774.00 |
| | | PI(D21) | 46 | 0 | 1811.65 | 1618.60 | 411.00 | 1162.00 | 1813.00 | 2524.00 | 8432.00 |
| CD4-IL2 | AS03_1_4 | PRE | 42 | 1 | 805.41 | 572.67 | 1.00 | 683.00 | 971.50 | 1429.00 | 2562.00 |
| | | PI(D21) | 43 | 0 | 1563.40 | 1203.93 | 296.00 | 1116.00 | 1509.00 | 2516.00 | 5786.00 |
| | AS03_1_2 | PRE | 38 | 1 | 881.32 | 713.88 | 1.00 | 727.00 | 1191.50 | 1605.00 | 2791.00 |
| | | PI(D21) | 39 | 0 | 2057.58 | 1251.53 | 205.00 | 1522.00 | 2184.00 | 3140.00 | 7019.00 |
| | AS03_1_1 | PRE | 48 | 1 | 640.10 | 1098.72 | 1.00 | 513.50 | 813.50 | 1240.50 | 6391.00 |
| | | PI(D21) | 49 | 0 | 1955.75 | 1528.09 | 232.00 | 1407.00 | 2088.00 | 2874.00 | 7173.00 |
| | AS25_1_4 | PRE | 47 | 0 | 864.60 | 696.78 | 117.00 | 557.00 | 896.00 | 1612.00 | 2771.00 |
| | | PI(D21) | 47 | 0 | 1629.80 | 1344.02 | 330.00 | 1080.00 | 1595.00 | 2504.00 | 6819.00 |
| | AS25_1_2 | PRE | 41 | 2 | 887.73 | 863.40 | 275.00 | 554.00 | 924.00 | 1431.00 | 4256.00 |
| | | PI(D21) | 43 | 0 | 1656.36 | 1486.45 | 316.00 | 1128.00 | 1617.00 | 2760.00 | 6311.00 |
| | AS25_1_1 | PRE | 44 | 0 | 834.27 | 755.62 | 131.00 | 537.00 | 877.00 | 1457.50 | 4105.00 |
| | | PI(D21) | 44 | 0 | 2028.18 | 1595.73 | 325.00 | 1334.00 | 2044.50 | 3624.00 | 7175.00 |
| | AS50_1_4 | PRE | 41 | 2 | 690.38 | 574.37 | 35.00 | 466.00 | 730.00 | 1132.00 | 2423.00 |
| | | PI(D21) | 43 | 0 | 1533.43 | 780.68 | 194.00 | 1145.00 | 1477.00 | 2269.00 | 3752.00 |
| | AS50_1_2 | PRE | 41 | 6 | 831.91 | 720.68 | 102.00 | 620.00 | 879.00 | 1221.00 | 3918.00 |
| | | PI(D21) | 47 | 0 | 1862.37 | 5848.13 | 158.00 | 1154.00 | 1852.00 | 3278.00 | 41253.00 |
| | Flu_ELD | PRE | 42 | 3 | 729.05 | 856.17 | 177.00 | 369.00 | 716.00 | 1299.00 | 3514.00 |
| | | PI(D21) | 45 | 0 | 1191.28 | 1688.15 | 145.00 | 620.00 | 1301.00 | 2414.00 | 9166.00 |
| | Flu_YNG | PRE | 40 | 6 | 1210.88 | 920.74 | 138.00 | 747.00 | 1308.50 | 1909.50 | 3925.00 |
| | | PI(D21) | 46 | 0 | 2033.00 | 1700.20 | 684.00 | 1429.00 | 1940.50 | 3296.00 | 9375.00 |

TABLE 39-continued

Frequency cytokine-positive CD4 T-cells (per million CD4 T-cells) for
pooled strains at days 0 and 21 (ATP cohort for immunogenicity CMI)

| Test description | Group | Timing | N | Nmiss | GM | SD | Min | Q1 | Median | Q3 | Max |
|---|---|---|---|---|---|---|---|---|---|---|---|
| CD4-TNFα | AS03_1_4 | PRE | 42 | 1 | 652.51 | 499.99 | 1.00 | 538.00 | 778.00 | 1141.00 | 2037.00 |
| | | PI(D21) | 43 | 0 | 1147.97 | 942.25 | 126.00 | 677.00 | 1251.00 | 2054.00 | 4142.00 |
| | AS03_1_2 | PRE | 38 | 1 | 755.02 | 646.69 | 1.00 | 607.00 | 985.00 | 1429.00 | 2844.00 |
| | | PI(D21) | 39 | 0 | 1596.30 | 975.22 | 295.00 | 1113.00 | 1695.00 | 2577.00 | 4927.00 |
| | AS03_1_1 | PRE | 48 | 1 | 550.23 | 1016.73 | 1.00 | 343.50 | 605.50 | 1001.00 | 5709.00 |
| | | PI(D21) | 49 | 0 | 1445.35 | 1172.61 | 132.00 | 989.00 | 1578.00 | 2128.00 | 5107.00 |
| | AS25_1_4 | PRE | 47 | 0 | 673.18 | 622.76 | 91.00 | 352.00 | 673.00 | 1460.00 | 2299.00 |
| | | PI(D21) | 47 | 0 | 1172.10 | 1122.07 | 193.00 | 722.00 | 1122.00 | 1987.00 | 6086.00 |
| | AS25_1_2 | PRE | 41 | 2 | 708.33 | 761.85 | 191.00 | 447.00 | 730.00 | 1004.00 | 3592.00 |
| | | PI(D21) | 43 | 0 | 1228.68 | 1330.12 | 171.00 | 671.00 | 1224.00 | 2452.00 | 6334.00 |
| | AS25_1_1 | PRE | 44 | 0 | 693.62 | 2910.36 | 116.00 | 358.00 | 615.00 | 1077.00 | 19515.00 |
| | | PI(D21) | 44 | 0 | 1435.67 | 2242.66 | 13.00 | 908.50 | 1490.00 | 3017.00 | 13332.00 |
| | AS50_1_4 | PRE | 41 | 2 | 538.80 | 433.49 | 37.00 | 331.00 | 655.00 | 935.00 | 1648.00 |
| | | PI(D21) | 43 | 0 | 1204.59 | 698.67 | 364.00 | 814.00 | 1295.00 | 1934.00 | 3219.00 |
| | AS50_1_2 | PRE | 41 | 6 | 658.48 | 764.82 | 75.00 | 440.00 | 810.00 | 1078.00 | 4501.00 |
| | | PI(D21) | 47 | 0 | 1349.54 | 4822.50 | 39.00 | 895.00 | 1297.00 | 2514.00 | 33798.00 |
| | Flu_ELD | PRE | 42 | 3 | 558.80 | 704.36 | 40.00 | 326.00 | 627.00 | 1189.00 | 2767.00 |
| | | PI(D21) | 45 | 0 | 819.29 | 1407.45 | 1.00 | 543.00 | 969.00 | 1694.00 | 7960.00 |
| | Flu_YNG | PRE | 40 | 6 | 1056.84 | 852.19 | 221.00 | 633.00 | 1129.50 | 1724.50 | 3947.00 |
| | | PI(D21) | 46 | 0 | 1426.37 | 1615.23 | 385.00 | 852.00 | 1505.00 | 2355.00 | 9378.00 |

N = number of subjects with available results
Nmiss = number of subjects with missing results
GM = Geometric Mean
SD = Standard Deviation
Q1, Q3 = First and third quartiles
Min/Max = Minimum/Maximum Intermediate Conclusion for the Cell Mediated Immune Response Five adjuvanted vaccines (AS03_1_1, AS03_1_2, AS25_1_1, AS50_1_2 and AS50_1_4) induced a significantly higher CMI response to pooled strains compared to Fluarix in subjects aged ≥65 years for all cytokine combinations in terms of individual differences (D21-D0). Three of these adjuvanted vaccines (AS03_1_1, AS03_1_2 and AS25_1_1) also induced a significantly higher CMI response to pooled strains compared to Fluarix in younger adults for all cytokine combinations in terms of individual differences (Day 21-Day 0).

XI.6. Reactogenicity

Local Symptoms

The percentage of subjects reporting solicited local symptoms (any grade/grade 3) during the 7-day post-vaccination period has been assessed using the EMEA and FDA grading for quantifiable symptoms.

EMEA grading: ecchymosis (any grade [>0 mm] and grade 3 [>50 mm]); pain (any grade); grade 3 pain; redness (any grade [>0 mm] and grade 3 [>50 mm]) and swelling (any grade [>0 mm]); grade 3 swelling (>50 mm). FDA grading: ecchymosis (any grade [≥25 mm] and grade 3 [>100 mm]), grade 3 redness (>100 mm); grade 3 swelling (>100 mm), redness (any grade [≥25 mm]); swelling (any grade [≥25 mm]).

General Symptoms

EMEA grading: fever (≥37.5° C.), grade 3 fever (>39.0° C.). FDA grading: fever (≥38° C.) and grade 3 fever (>40° C.).

Figure 24:
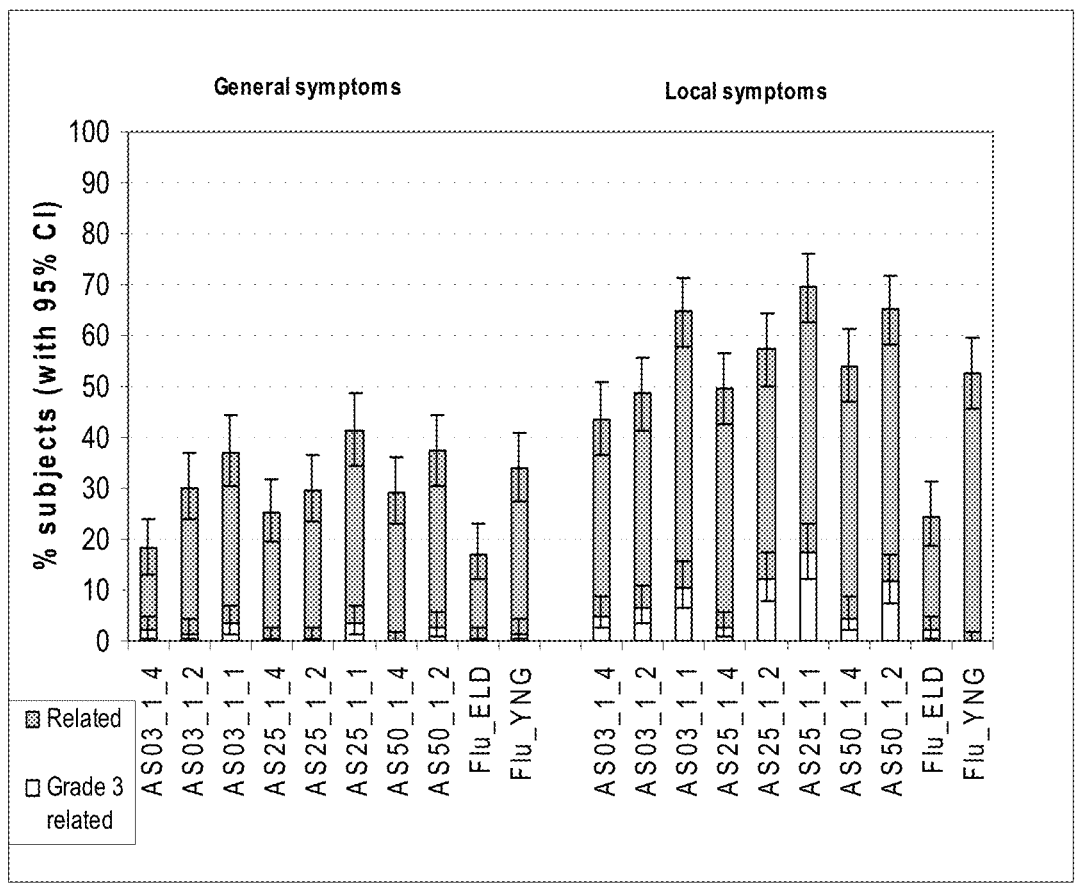
FIG. 24: Human clinical trial (adjuvant dose range in elderly): Percentage of subjects reporting related solicited and unsolicited symptoms (all grades/grade 3) during the 7-day (Days 0-6) post-vaccination period (Total vaccinated cohort).

The overall incidence and nature of any and grade 3 solicited and unsolicited symptoms reported during the 7-day (Days 0-6) post-vaccination period is presented in FIG. 24.

Conclusion

The percentage of subjects reporting at least one general symptom was statistically significantly higher in the adjuvanted influenza vaccine groups compared to the Flu_ELD group, but in the same range as for the Flu_YNG group (except for AS03_1_4). The percentage of subjects reporting at least one grade 3 general symptom are in the same range for all groups.

The percentage of subjects reporting at least one local symptom was statistically significantly higher in the adjuvanted influenza vaccine groups compared to the Flu_ELD group and in the AS25_1_1 group compared to the Flu_YNG group.

The percentage of subjects reporting at least one grade 3 local symptom was statistically significantly higher in the AS03_1_1, AS25_1_2, AS25_1_1 and AS50_1_2 groups compared to the Flu_ELD and Flu_YNG groups.

XI.7. General conclusion

These data are important to appropriately balance the immune response/adverse effect in a human population.

In terms of HI immunogenicity, a clear adjuvant effect was demonstrated, with in particular a significant increase for H1N1 and H3N2 for with all adjuvant dosages. A significant increase was obtained for the B strain mainly with AS25 1/1, but also with AS03 1/1, AS03 ½ and AS50 ½. A dose-effect was shown with the oil-in-water emulsion component of the adjuvant, and also for the MPL component of the adjuvant, although the latter was less clearly marked.

In terms of cell mediated immune response, an adjuvant effect was also demonstrated with a significant difference compared to Fluarix in the Elderly for pooled strains (frequency, all measures) for AS03 1/1, AS03 ½, AS25 1/1 and AS50 ½. Highest responses were obtained with AS25 1/1, AS03 1/1 and AS03 ½.

In terms of reactogenicity, the adjuvanted vaccines are more reactogenic than Fluarix, associated with the oil-in-water emulsion component of the vaccine; a dose effect of MPL also present, though less pronounced. AS03 ½ is less reactogenic than AS03 1/1 whilst exhibiting a satisfactory immogenicity profile in this elderly population.

What is claimed is:

1. An immunogenic composition in a dose volume suitable for human use comprising an influenza virus antigen or antigenic preparation prepared in the presence of less than or equal to 5 µg/ml thiomersal in combination with an oil-in-water emulsion adjuvant, wherein the oil-in-water emulsion adjuvant consists of an aqueous carrier, squalene and one or two emulsifying agents, and wherein the squalene is present in an amount from 0.5 mg to 9 mg and the one or two emulsifying agents are present in a total amount from 0.1 mg to 5 mg per human dose, wherein the dose volume is between 0.25 ml and 1.5 ml; and wherein the influenza virus antigen or antigenic preparation comprises 7.5 µg of haemagglutinin (HA) per dose per influenza strain.

2. The immunogenic composition of claim 1, wherein one or two of the one or two emulsifying agents is a non-ionic surfactant.

3. The immunogenic composition of claim 2, wherein the one or two emulsifying agents is a polyoxyethylene sorbitan monooleate or a sorbitan trioleate or a mixture of both.

4. The immunogenic composition of claim 1, wherein the one or two emulsifying agents are present at a total amount of 0.5-4 mg, per human dose.

5. The immunogenic composition of claim 1, wherein the composition is a monovalent composition comprising a virus antigen or antigenic preparation from an influenza virus strain.

6. The immunogenic composition of claim 5, wherein the influenza virus strain is selected from the group consisting of: H2, H5, H9, H7, or H6.

7. The immunogenic composition of claim 5, wherein the influenza virus strain is selected from the group consisting of: H5N1, H9N2, H5N8, H5N9, H7N4, H7N7, H2N2, H10N7, H5N2, H7N2, H7N1, and H7N3.

8. The immunogenic composition of claim 1, wherein the influenza virus antigen or antigenic preparation thereof is from influenza virus grown in eggs or in cell culture.

9. The immunogenic composition of claim 8, wherein the influenza virus antigen or antigenic preparation thereof is from influenza virus grown in eggs and wherein the antigen or antigenic preparation thereof is depleted from egg-contaminating proteins.

10. The immunogenic composition of claim 1, wherein the influenza virus antigen or antigenic preparation thereof comprises a whole virus, a split virus, a virosome or one or more purified antigens selected from the group consisting of: HA, NA, M1, and M2.

11. The immunogenic composition of claim 10, wherein the purified antigen is recombinantly produced.

12. The immunogenic composition of claim 10, wherein the split virus comprises one or more of neuraminidase, matrix protein, and nucleoprotein.

13. The immunogenic composition of claim 1, wherein the oil-in-water emulsion comprises oil droplets of less than 1 micron in size.

14. The immunogenic composition of claim 1, wherein the dose volume is between 1 ml and 1.5 ml.

15. The immunogenic composition of claim 1, wherein the dose volume is between 0.5 ml and 1.5 ml.

16. The immunogenic composition of claim 1, wherein the dose volume is 0.25 ml.

* * * * *